US008344028B2

(12) United States Patent
Xu et al.

(10) Patent No.: US 8,344,028 B2
(45) Date of Patent: Jan. 1, 2013

(54) GAMMA-AMINO-BUTYRIC ACID DERIVATIVES AS GABA$_B$ RECEPTOR LIGANDS

(75) Inventors: Feng Xu, Palo Alto, CA (US); Mark A. Gallop, Santa Clara, CA (US); Ge Peng, Mountain View, CA (US); Thu Phan, Fremont, CA (US); Usha Dilip, Sunnyvale, CA (US); David J. Wustrow, Saratoga, CA (US)

(73) Assignee: XenoPort, Inc., Santa Clara, CA (US)

( * ) Notice: Subject to any disclaimer, the term of this patent is extended or adjusted under 35 U.S.C. 154(b) by 302 days.

(21) Appl. No.: 12/762,152

(22) Filed: Apr. 16, 2010

(65) Prior Publication Data

US 2010/0267676 A1 Oct. 21, 2010
US 2012/0035139 A9 Feb. 9, 2012

Related U.S. Application Data

(60) Provisional application No. 61/170,511, filed on Apr. 17, 2009.

(51) Int. Cl.
*A61K 31/19* (2006.01)
*A61K 31/135* (2006.01)
*A61K 31/03* (2006.01)
*C07C 211/00* (2006.01)
*C07C 22/00* (2006.01)

(52) U.S. Cl. ........ 514/568; 514/649; 514/751; 564/374; 570/182

(58) Field of Classification Search .................. 514/568, 514/649, 751; 564/374; 570/182
See application file for complete search history.

(56) References Cited

U.S. PATENT DOCUMENTS

| | | | |
|---|---|---|---|
| 4,126,684 | A | 11/1978 | Robson et al. |
| 5,006,560 | A | 4/1991 | Kreutner et al. |
| 5,719,185 | A | 2/1998 | Bountra et al. |
| 6,117,908 | A | 9/2000 | Andrews et al. |
| 6,818,787 | B2 | 11/2004 | Gallop et al. |
| 6,972,341 | B2 | 12/2005 | Gallop et al. |
| 7,109,239 | B2 | 9/2006 | Gallop et al. |
| 7,227,028 | B2 | 6/2007 | Gallop et al. |
| 2003/0176398 | A1 | 9/2003 | Gallop et al. |
| 2005/0187196 | A1 | 8/2005 | Madrid et al. |
| 2008/0206332 | A1 | 8/2008 | Kidney et al. |
| 2009/0197958 | A1 | 8/2009 | Sastry et al. |

FOREIGN PATENT DOCUMENTS

| | | |
|---|---|---|
| WO | WO 01/08675 | 2/2001 |
| WO | WO 01/26638 | 4/2001 |
| WO | WO 02/096404 | 12/2002 |
| WO | WO 2008/056257 A2 | 5/2008 |
| WO | WO 2009/041904 A1 | 4/2009 |

OTHER PUBLICATIONS

Berthelot P, Vaccher C, Musadad A, Flouquet N, Debaert M, Luyckx M. Synthesis and pharmacological evaluation of gamma-aminobutyric acid analogues. New ligand for GABAB sites. J Med Chem. Apr. 1987;30(4):743-6.*
Addolorato et al., Baclofen efficacy in reducing alcohol craving and intake: a preliminary double-blind randomized controlled study, *Alcohol Alcohol* 2002, 37(5), 504-8.
Addolorato et al., Rapid suppression of alcohol withdrawal syndrome by baclofen, *Am J. Med* 2002, 112, 226-9.
Ahmadi-Abhari et al., Baclofen versus clonidine in the treatment of opiates withdrawal, side-effects aspect: a double-blind study randomized controlled trial, *J Clin Pharm Therapeutics* 2001, 26(1), 67-71.
Anghinah et al., Effect of baclofen on pain in diabetic neuropathy, *Muscle Nerve* 1994, 958-9.
Assadi et al., Baclofen for maintenancr treatment of opioid dependence: A randomized doube-blind placebo-contolled clinical trial [ISRCTN32121581], *BMC Psychiatry* 2003, 3(16).
Balerio and Rubio, Baclofen analgesia: involvement of the GABAergic system, *Pharmacol Res* 2002, 46, 281-6.
Becker et al., Intrathecal baclofen alleviates autonomic dysfunction in severe brain injury, *J Clin Neurosci* 2000, 7, 316-319.
Bennett and Xie, A peripheral mononeuropathy in rat that produces disorders of pain sensation like those seen in man, *Pain* 1988, 33, 87-107.
Blackshaw et al., Inhibition of transient LES relaxations and reflux in ferrets by GABA$_B$ receptor agonists, *Am. J. Physiol.* 1999, 277, G867-874.
Bowery et al., International Union of Pharmacology. XXXIII. Mammalian γ-Aminobutyric acid receptors: structure and function, *Pharmacol Rev* 2002, 54, 247-64.
Bowery, GABA$_B$ receptor: a site of therapeutic benefit. *Current Opinion Pharmacology* 2006, 6, 37-43.
Bowsher, Neurogenic pain syndromes and their management, *Br Med Bull* 1991, 47, 655-66.
Brebner et al., A potential role for GABA$_B$ agonists in the treatment of psychostimulant addiction, *Alcohol Alcohol* 2002, 37(5), 478-84.
Brennan et al., Characterization of a rat model of incisional pain, *Pain* 1996, 64, 493-501.
Chai et al., Influence of aminooxyacetic acid, a γ-aminobutyrate transaminase inhibitor, on hereditary spastic defect in the mouse, *Proc. Soc. Exptl. Biol. Med.* 1962, 109, 491.
Chan et al., Action of anti-tussive drugs on the emetic reflex of *Suncus murinus* (house musk shrew), *Eur J Pharmacology* 2007, 559(2-3), 196-201.
Chaplan et al., Quantitative assessment of tactile allodynia in the rat paw, *J Neurosci Methods* 1994, 53, 55-63.
Ciccaglione et al., Effect of acute and chronic administration of the GABA$_B$ agonist baclofen on 24 hour pH metry and symptoms in control subjects and in patients with gastro-oesophageal reflux disease, *Gut* 2003, 52, 464-470.
Colombo et al., Ability of baclofen in reducing alcohol intake and withdrawal severity: I-preclinical evidence, *Alcohol Clin Exp Res* 2000, 24, 58-66.

(Continued)

*Primary Examiner* — Paul Zarek
(74) *Attorney, Agent, or Firm* — Kilpatrick Townsend & Stockton LLP

(57) ABSTRACT

Gamma-amino-butyric acid derivatives that are GABA$_B$ receptor ligands, pharmaceutical compositions comprising such derivatives, and methods of using such derivatives and pharmaceutical compositions thereof for treating diseases are disclosed.

28 Claims, No Drawings

OTHER PUBLICATIONS

Colombo et al., Baclofen suppresses motivation to consume alcohol in rats, *Psychopharmacology* 2003, 167, 221-224.

Cousins et al., $GABA_B$ receptor agonists for the treatment of drug addiction: a review of recent findings, *Drug Alcohol Dependence* 2002, 65(3), 209-20.

Cryan and Kaupmann, Assessing antidepressant activity in rodents: recent developments and future needs, *Trends Pharmacol Sci* 2005, 26, 36-43.

Cryan et al., Behavioral characterization of the novel $GABA_B$ receptor-positive modulator GS39783 (N,N-dicyclopentyl-2-methylsulfanyl-5-nitro-pyrimidine-4,6-diamine): Anxiolytic-like activity without side effects associated with baclofen or benzodiazepines, *J Pharmacol Exp Ther* 2004, 310, 952-963.

Dapas et al., Baclofen for the treatment of acute low-back syndrome a double-blind comparison with placebo, *Spine* 1985, 10(4), 345-349.

Dicpinigaitis and Dobkin. Antitussive effect on the GABA-agonist baclofen, *Chest* 1997, 111(4), 996-9.

Dicpinigaitis and Rauf, Treatment of chronic, refractory cough with baclofen, *Respiration* 1998, 65(1), 86-8.

Dicpinigaitis et al., Inhibition of capsaicin-induced cough by the gamma-aminobutyric acid agonist baclofen, *J Clin Pharmacol* 1998, 38(4), 364-7.

Dixon, Efficient analysis of experimental observations, *Ann Rev Pharmacol Toxicol* 1980, 20, 441-462.

Dubuisson and Dennis, The formalin test: A Quantitative study of the analgesic effects of morphine, meperidine, and brain stem stimulation in rats and cats, *Pain* 1977, 4, 161-174.

Fattore et al., Baclofen antagonizes intravenous self-administration of nicotine in mice and rats, *Alcohol Alcohol* 2002, 37, 496-498.

Flannery et al., Baclofen for Alcohol Dependence: A preliminary open-label study, *Alcohol Clin Exp Res* 2004, 28(10), 1517-23.

Freitag, Preventative Treatment for migraine and tension-type headaches do drugs having effects on muscle spasm and tone have a role?, *CNS Drugs* 2003, 17(6), 373-381.

Froestl et al., SGS742: The first $GABA_B$ receptor antagonist in clinical trials, *Biochem Pharmacol* 2005, 68(8), 1479-87.

Fromm et al., Baclofen in the treatment of trigeminal neuralga: double-blind study and long-term follow-up, *Ann Neurol* 1984, 15, 240-244.

Fromm et al., Role of inhibitory mechanisms in trigeminal neuralgia, *Neurology* 1981, 31, 683-687.

Gatscher et al., Combined intrathecal baclofen and morphine infusion for the treatment of spasticity related pain and central deafferentiation pain, *Acta Neurochir Suppl* 2002, 79, 75-76.

Getova and Bowery, Effects of high-affinity $GABA_B$ receptor antagonists on active and passive avoidance responding in rodents with gamma-hydroxybutyrolactone-induced absence syndrome, *Psychopharmaoclogy* 2001, 157, 89-95.

Goadsby et al., Adenosine $A_1$ receptor agonists inhibit trigeminovascular nociceptive transmission, *Brain* 2002, 125, 1392-1401.

Haney et al., Effects of baclofen on cocaine self-administration: Opioid- and nonopioid-dependent volunteers, *Neuropsychopharmacology* 2006, 31, 1814-21.

Heinzerling et al., Randomized, placebo-controlled trial of baclofen and gabapentin for the treatment of methamphetamine dependence, *Drug Alcohol Depend* 2006, 85(3), 177-84.

Hering-Hanit and Gadoth, Baclofen in cluster headache, *Headache* 2000, 40(1), 48-51.

Hering-Hanit, Baclofen for prevention of migraine, *Cephalalgia* 1999, 19(6), 589-91.

Herman et al., Intrathecal Baclofen Suppresses Central Pain in Patients with Spinal lesions, *Clin J Pain* 1992, 12, 241-247.

Hwang and Yaksh, The effect of spinal GABA receptor agonists on tactile allodynia in a surgically-induced neuropathic pain model in the rat, *Pain* 1997, 70, 15-22.

Johnson et al., Safety and efficacy of GABAergic medications for treating alcoholism, *Alcoholism Clin Exp Res* 2005, 29, 248-254.

Kim et al., An experimental model for peripheral neuropathy produced by segmental spinal nerve ligation in the rat, *Pain* 1992, 50, 355-363.

Lam and Hilas. Pharmacologic management of overactive bladder, *Clinical Interventions in Aging* 2007, 2, 337-345.

Lehmann et al., Activation of the $GABA_B$ receptor inhibits transient lower esophageal sphincter relaxations in dogs, *Gastroenterol* 1999, 117, 1147-1154.

Lidums et al., Control of transient lower esophageal sphincter relaxations and reflux by the $GABA_B$ agonist baclofen in normal subjects, *Gastroenterol.* 2000, 18, 7-13.

Ling et al., Baclofen as a cocaine anti-craving medication: a preliminary clinical study, *Neuropsychopharmacology* 1998, 18, 403-404.

Malcangio and Bowery. GABA and its receptors in the spinal cord, *Trends Pharmacol Sci* 1996, 17, 457-462.

Markou et al., Role of γ-aminobutyric acid (GABA) and metabotropic glutamate receptors in nicotine Reinforcement, *Ann N.Y. Acad Sci* 2004, 1025, 491-503.

Mason et al., Effect of oral acamprosate on abstinence in patients with alcohol dependence in a double-blind, placebo-controlled trial: The role of patient motivation, *J Psychiatric Res* 2006, 40, 383-393.

Meleger and Krivickas. Neck and back pain: musculoskeletal disorders, *Neurol Clin* 2007, 25, 419-438.

Mombereau et al., Genetic and pharmacological evidence of a role for $GABA_B$ receptors in the modulation of anxiety- and antidepressant behavior, *Neuropsychopharmacology* 2004, 29, 1050-1062.

Mondadori et al., CGP 36742: The first orally active $GABA_B$ blocker improves the cognitive performance of mice, rats, and rhesus monkeys, *Behav Neural Biol* 1993, 60, 62-8.

Nakagawa and Takashima, The $GABA_B$ receptor antagonist CGP36742 attenuates the baclofen- and scopolamine-induced deficit in Morris water maze task in rats, *Brain Res* 1997, 766, 101-6.

Nakagawa et al., The $GABA_B$ receptor antagonist CGP36742 improves learned helplessness in rats, *Eur J Pharmacology* 1999, 381, 1-7.

Nowak et al., Antidepressant-like activity of CGP 36742 and CGP 51176, selective $GABA_B$ receptor antagonists, in rodents, *British J Pharmacology* 2006, 149, 581-590.

Ong and Kerr, Clinical potential of $GABA_B$ receptor modulators, *CNS Drug Reviews* 2005, 11(3), 317-334.

Ong et al., Comparative potentcies of CGP 47654A and CGP 46165A as $GABA_B$ receptor antagonists in rat brain, *Eur J Pharmacology* 1999, 374, 351-4.

Patel et al., The effects of $GABA_B$ agonists and gabapentin on mechanical hyperalgesia in models of neuropathic and inflammatory pain in the rat, *Pain* 2001, 90, 217-226.

Paterson et al., Repeated administration of the GABAB receptor agonist CGP44532 decreased nicotine self-administration, and acute administration decreased cue-induced reinstatement of nicotine-seeking in rats, *Neuropsychopharmacology* 2005, 30, 119-128.

Paterson et al., The $GABA_B$ receptor agonists baclofen and CGP44532 decreased nicotine self-administration in the rat, *Psychopharmacology* 2004, 172, 179-186.

Pellow and File, Anxiolytic and anxiogenic drug effects on exploratory activity in an elevated Plus-Maze: a Novel test of anxiety in the rat, *Pharmacol Biochem Behav* 1986, 24, 524-529.

Quéva et al., Effects of GABA agonists on body temperature regulation in $GABA_{B(1)}$ mice, *Br. J. Pharmacology* 2003, 140, 315-322.

Raphael et al., Long-term experience with implanted intrathecal drug administration systems for failed back syndrome and chronic mechanical low back pain, *BMC Musculoskeletal Disorders* 2002, 3(17), EPub Jun. 20.

Raphael et al., Efficacy and adverse effects of intravenous lignocaine therapy in fibromyalgia syndrome, *BMC Musculoskeletal Disorders* 2002, 3917.

Reis and Duarte, Baclofen, an agonist at peripheral $GABA_B$ receptors, induces antinociception via activation of TEA-sensitive potassium channels, *Br J Pharmacol* 2006, 149(6), 733-9.

Ringel and Roy, Glossopharyngeal neuralgia: successful treatment with baclofen, *Ann Neurol* 1987, 21, 514-515.

Sampathkumar et al., Baclofen withdrawal presenting as multiorgan system failure *Anesth. Analg.* 1998, 87, 562-563.

Scott et al., Acamprosate A review of its Use in the maintenance of abstinence in patients with alcohol dependence *CNS Drugs* 2005, 19(5), 445-464.

Slattery et al., $GABA_B$ receptor antagonist-mediated antidepressant-Like behavior is serotonin-dependent, *J Pharmacology Experimental Therapeutics* 2005, 312, 290-6.

Smith et al., Increased sensitivity to the antinociceptive activity of (+)-baclofen in an animal model of chronic neuropathic, but not chronic inflammatory, hyperalgesia, *Neuropharmacology* 1994, 33, 1103-1108.

Stakeberg and Lehmann, Influence of different intragastric stimuli on triggering of transient lower oesophageal sphincter relaxation in the dog, *Neurogastroenterol. Mot.* 1999, 11, 125-132.

Suzuki et al., Effect of a selective $GABA_B$ receptor agonist baclofen on the μ-opioid receptor agonist-induced antinociceptive, emetic and rewarding effects. *Neuropharmacology* 2005, 49(8), 1121-31.

Taira et al., A new approach to control central deafferentation pain: spinal intrathecal baclofen, *Stereotactic Funct Neurosurg* 1995, 65, 101-105.

Taylor and Bates. A double-blind crossover trial of baclofen—a new treatment for the unstable bladder syndrome, *British J Urology* 1979, 51, 504-505.

Van Herwaarden et al., The effect of baclofen on gastro-oesophageal reflux, lower oesophageal sphincter function and reflux symptoms in patients with reflux disease, *Aliment. Pharmacol. Ther.* 2002, 6, 1655-1662.

Van Hilten et al., Intrathecal baclofen for the treatment of dystonia in patients with reflex sympathetic dystrophy, *N Engl J Med* 2000, 343, 625-630.

Van Schoor and Pauwels, Effect of inhaled fluticasone on bronchial responsiveness to neurokinin A in asthma, *Eur Respir J* 2002, 19, 997-1002.

Vatine et al., Effect of intrathecal baclofen in low back pain with root compression syndromes, *Pain Clin* 1989, 2, 207-217.

Xi et al., Baclofen inhibits heroin self-administration behavior and mesolimbic dopamine release, *J Pharmacol Exp Ther* 1999, 290, 1369-74.

Zhang et al., Control of transient lower oesophageal sphincter relaxations and reflux by the $GABA_B$ agonist baclofen in patients with gastro-oesophageal reflux disease, *Gut* 2002, 50, 19-24.

Zuniga et al., Intrathecal baclofen Is analgesic in patients with chronic pain, *Anesthesiology* 2000, 92, 876-880.

Zuniga et al., Intrathecal baclofen: A useful Agent in the Treatment of well-established complex regional pain syndrome, *Reg Anesth Pain Med* 2002, 27, 90-93.

Carpes, M.J.S., et al., "Heck Arylations of N-acyl-3-pyrroline and N-acyl-1,2,5,6-tetrahydropy Ridine With Aryldiazonium Salts. Short Syntheses of Aryl Gamma- and Delta-lactams, Baclofen, Homobaclofen and Analogues", Tetrahedron Letters, Elsevier, Amsterdam, NL, vol. 43, No. 5, Jan. 28, 2002, pp. 741-744.

Froestel, W. et al., "Phosphinic Acid Analogues of GABA. 2. Selective, Orally Active GABAB Antagonists", Journal of Medicinal Chemistry, American Chemical Society, Washington, U.S., vol. 38, No. 17, Jan. 1, 1995, pp. 3313-3331.

Kerr, D.I.B., et al., "Benzofuran Analogues of Baclofen: a New Class of Central and Peripheral GABAB-Receptor Antagonists", European Journal of Pharmacology, Elsevier BV, NL, vol. 164, No. 2, May 19, 1989, pp. 361-364.

Davies, S., "SGS-742", Drugs of the Future, vol. 30, No. 3, Mar. 2005, pp. 248-253.

International Search Report and Written Opinion of the International Searching Authority mailed Nov. 24, 2010, for PCT International Application No. PCT/US2010/001128 filed Apr. 16, 2010.

* cited by examiner

GAMMA-AMINO-BUTYRIC ACID DERIVATIVES AS GABA$_B$ RECEPTOR LIGANDS

This application claims the benefit under 35 U.S.C. §119 (e) of U.S. Provisional Application Ser. No. 61/170,511, filed Apr. 17, 2009, which is incorporated by reference in its entirety.

Disclosed herein are γ-amino-butyric acid derivatives that are GABA$_B$ receptor ligands, pharmaceutical compositions comprising such derivatives, and methods of using such derivatives and pharmaceutical compositions thereof for treating diseases.

GABA is the major inhibitory neurotransmitter in the central nervous system, acting via stimulation of GABA$_A$, GABA$_B$, and GABA$_C$ receptors. GABA$_A$ and GABA$_C$ receptors are coupled to chloride ion channels and mediate fast synaptic inhibition. GABA$_B$ receptors are coupled through G proteins to neuronal potassium and calcium channels and mediate slow synaptic inhibition by increasing potassium and decreasing calcium conductance. The GABA$_B$ receptor exists as a heterodimer formed by dimerization of two homologous subunits, GABA$_{B1}$ and GABA$_{B2}$. The GABA$_{B1}$ subunit binds the endogenous ligand, whereas the GABA$_{B2}$ subunit is responsible for the trafficking of the GABA$_{B1}$ subunit to the cell surface and is responsible for interaction with G proteins. On the subcellular level, most GABA$_B$ receptors are extrasynaptic, sometimes localized in close proximity to glutamatergic synapses. Postsynaptic GABA$_B$ receptors activate inwardly rectifying potassium channels. Activation of presynaptic GABA$_B$ receptors, acting as heteroreceptors or autoreceptors, causes an inhibition of neurotransmitter release by depressing Ca$^{2+}$ influx via calcium channels.

The therapeutic potential of GABA$_B$ receptor modulators including agonists, antagonists and allosteric modulators has been widely investigated (Bowery, *Current Opinion Pharmacology* 2006, 6, 37-43; and Ong and Kerr, *CNS Drug Reviews* 2005, 11(3), 317-334).

GABA$_B$ agonists such as baclofen are known to be useful in treating spasticity, controlling gastro-esophageal reflux disease (van Herwaarden et al., *Aliment. Pharmacol. Ther.* 2002, 6, 1655-1662; Ciccaglione et al., *Gut* 2003, 52, 464-470; Andrews et al., U.S. Pat. No. 6,117,908; and Fara et al., Patent Cooperation Treaty Publication No. WO 02/096404); in promoting alcohol abstinence in alcoholics (Gessa et al., Patent Cooperation Treaty Publication No. WO 01/26638); in promoting smoking cessation (Gessa et al., Patent Cooperation Treaty Publication No. WO 01/08675); in reducing addiction liability of narcotic agents (Robson et al., U.S. Pat. No. 4,126,684); in the treatment of emesis (Bountra et al., U.S. Pat. No. 5,719,185); and as an anti-tussive for the treatment of cough (Kreutner et al., U.S. Pat. No. 5,006,560), overactive bladder (Taylor and Bates, *British J. Urology* 1979, 51, 504-505), anxiety (Cryan et al., *J Pharmacol Exp Ther* 2004, 310, 952-963; and Mombereau et al., *Neuropsychopharmacology* 2004, 29, 1050-1062), migraine (Hering-Hanit, *Cephalalgia* 1999, 19(6), 589-91; and Hering-Hanit and Gadoth, *Headache* 2000, 40(1), 48-51), and pain (Anghinah et al., *Muscle Nerve* 1994, 958-59; Fromm et al., *Ann Neurol* 1984, 15, 240-244; and Dapas et al., *Spine* 1985, 10(4), 345-349).

When certain GABA$_B$ agonists such as baclofen are given orally, sedation is an adverse effect, particularly at elevated doses. Impairment of cognitive function, confusion, memory loss, dizziness, muscle weakness, ataxia, hallucinations, nausea, drowsiness, respiratory depression, and tolerance that develops during prolonged use, are other commonly encountered adverse effects of GABA$_B$ agonist therapy.

Intrathecal administration is often recommended for patients who find the adverse effects of oral baclofen intolerable. For example, the intrathecal use of baclofen permits effective treatment of spasticity with doses less than $\frac{1}{100}^{th}$ of those required orally, because administration directly into the spinal subarachnoid space permits immediate access to the GABA$_B$ receptor sites in the dorsal horn of the spinal cord. Surgical implantation of a pump is, however, inconvenient and a variety of mechanical and medical complications may arise (e.g., catheter displacement, kinking or blockage, pump failure, sepsis, and deep vein thrombosis). Acute discontinuation of baclofen therapy (e.g., in cases of mechanical failure) may cause serious withdrawal symptoms such as hallucinations, confusion, agitation, and seizures (Sampathkumar et al., *Anesth. Analg.* 1998, 87, 562-563).

GABA$_B$ receptor antagonists have been shown to modulate the inhibitory action of GABA and are believed to amplify neurotransmission. GABA$_B$ antagonists have been shown to be potentially useful in improving attention (Madrid et al., U.S. Patent Application Publication No. 2005/0187196), enhancing cognitive function (Froestl et al., *Biochem Pharmacol* 2004, 68, 1479-87; Mondadori et al., *Behav Neural Biol* 1993, 60, 62-8; and Nakagawa and Takashima, *Brain Res* 1997, 766, 101-6), and as antidepressants (see e.g., Nowak et al., *British J Pharmacology* 2006, 149, 581-590; Slattery et al., *J Pharmacology Experimental Therapeutics* 2005, 312, 290-6; and Cryan and Kaupmann, *Trends Pharmacol Sci* 2005, 26, 36-43). However, at high doses, certain GABA$_B$ receptor antagonists induce convulsions. GABA$_B$ receptor antagonists that exhibit a move favorable therapeutic profile are expected to enhance the utility for treating these and other disorders.

Positive allosteric modulators of the GABA$_B$ receptor have been shown to be active in animal models of anxiety (Cryan et al., *J Pharmacol Exp Ther* 2004, 310, 952-963; and Mombereau et al., *Neuropsychopharmacology* 2004, 29, 1050-1062).

Thus, there is a need for new GABA$_B$ receptor ligands that do not exhibit the adverse side effects of currently known compounds and that exhibit useful pharmacokinetic profiles.

In a first aspect, compounds of Formula (I) are provided:

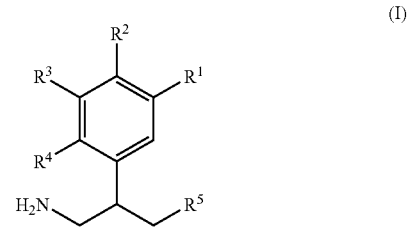

(I)

or a pharmaceutically acceptable salt thereof, wherein:

$R^1$ and $R^2$ are independently chosen from hydrogen, halogen, —CN, —CF$_3$, C$_{1-4}$ alkyl, —OR$^6$, and —N(R$^6$)$_2$ wherein each R$^6$ is independently chosen from hydrogen and C$_{1-4}$ alkyl;

one of $R^3$ and $R^4$ is —X—Y, and the other of $R^3$ and $R^4$ is hydrogen, wherein:

X is chosen from a covalent bond, C$_{1-3}$ alkyldiyl, substituted C$_{1-3}$ alkyldiyl, C$_{1-3}$ heteroalkyldiyl, and substituted C$_{1-3}$ heteroalkyldiyl; and Y is chosen from C$_{6-12}$ aryl, substituted C$_{6-12}$ aryl, C$_{6-12}$ heteroaryl, and substituted C$_{6-12}$ heteroaryl; and $R^5$ is chosen from —COOH, —SOOH, and —P(O)(OH) $R^5$ wherein $R^5$ is chosen from hydrogen and C$_{1-4}$ alkyl.

In a second aspect, pharmaceutical compositions are provided comprising a compound chosen from Formula (I) and at least one pharmaceutically acceptable vehicle.

In a third aspect, methods of treating a disease in a patient are provided comprising administering to a patient in need of such treatment a pharmaceutical composition comprising a compound of Formula (I). In certain embodiments, the disease is chosen from spasticity, gastro-esophageal reflux disease, emesis, cough, overactive bladder, a substance abuse disorder, an attention disorder, an anxiety disorder, a mood disorder, a cognitive disorder, migraine, and pain.

In a fourth aspect, methods of modulating $GABA_B$ receptor function in a patient are provided comprising administering to a patient a compound of Formula (I).

A dash ("-") that is not between two letters or symbols is used to indicate a point of attachment for a moiety or substituent. For example, —$CONH_2$ is attached through the carbon atom.

"Alkyl" by itself or as part of another substituent refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Alkoxy" by itself or as part of another substituent refers to a radical —$OR^{11}$ where $R^{11}$ is chosen from alkyl, heteroalkyl, cycloalkyl, heterocycloalkyl, cycloalkylalkyl, heterocycloalkylalkyl, aryl, heteroaryl, arylalkyl, and heteroarylalkyl, as defined herein. Examples of alkoxy groups include, but are not limited to, methoxy, ethoxy, propoxy, butoxy, cyclohexyloxy, and the like. In certain embodiments, an alkoxy group is $C_{1-18}$ alkoxy, in certain embodiments, $C_{1-12}$ alkoxy, in certain embodiments, $C_{1-6}$ alkoxy, in certain embodiments, $C_{1-4}$ alkoxy, and in certain embodiments, $C_{1-3}$ alkoxy.

"Alkyldiyl" refers to a divalent hydrocarbon radical derived by the removal of a single hydrogen atom from a single carbon atom of a $C_2$ or greater alkyl, other than the alkyl radical carbon atom; or derived by the removal of a single hydrogen atom from a $C_1$ alkyl radical carbon atom; where alkyl is as defined herein. Examples of alkyldiyl groups include —$CH_2$—, —$CH_2$—$CH_2$—, —CH=CH—, —$CH_2$—$CH_2$—$CH_2$—, and the like.

"Aryl" by itself or as part of another substituent refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), and in certain embodiments, from 6 to 10 carbon atoms ($C_{8-10}$). Aryl, however, does not encompass or overlap in any way with heteroaryl, separately defined herein. In certain embodiments, aryl is phenyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{7-18}$ arylalkyl, e.g., the alkanyl, alkenyl or alkynyl moiety of the arylalkyl group is $C_{1-8}$ and the aryl moiety is $C_{8-10}$. In certain embodiments an arylalkyl group is $C_{7-6}$ arylalkyl, wherein the alkyl moiety is $C_{1-3}$ alkyl and the aryl moiety is phenyl.

"Compounds" of Formula (I) disclosed herein include any specific compounds within these formulae. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds of Formula (I) include, but are not limited to, optical isomers of compounds of Formula (I), racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds of Formula (I) include Z- and E-forms (or cis- and trans-forms) of compounds with double bonds.

Compounds of Formula (I) may also exist in several tautomeric forms including the enol form, the keto form, and mixtures thereof. Accordingly, the chemical structures depicted herein encompass all possible tautomeric forms of the illustrated compounds. Compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, etc. Compounds may exist in unsolvated forms as well as solvated forms, including hydrated forms and as N-oxides. In general, compounds may be hydrated, solvated, or N-oxides. Certain compounds may exist in multiple crystalline, co-crystalline, or amorphous forms. Compounds of Formula (I) include pharmaceutically acceptable salts thereof, or pharmaceutically acceptable solvates of the free acid form of any of the foregoing, as well as crystalline forms of any of the foregoing. Compound of Formula (I) encompass compounds of Formula (II).

Further, when partial structures of the compounds are illustrated, an asterisk (*) indicates the point of attachment of the partial structure to the rest of the molecule.

"Cycloalkyl" by itself or as part of another substituent refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-5}$ cycloalkyl. In certain embodiments, cycloalkyl is chosen from cyclopropyl, cyclopentyl, and cyclohexyl.

"Cycloalkylalkyl" by itself or as part of another substituent refers to an acyclic alkyl radical in which one of the hydrogen atoms bonded to a carbon atom, typically a terminal or sp$^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{4-20}$ cycloalkylalkyl, e.g., the alkanyl, alkenyl, or alkynyl moiety of the cycloalkylalkyl group is $C_{1-8}$ and the cycloalkyl moiety is $C_{3-12}$. In certain embodiments, cycloalkylalkyl is $C_{4-6}$ cycloalkylalkyl, wherein the alkyl moiety is $C_{1-3}$ alkyl, and the cycloalkyl moiety is $C_{3-6}$ cycloalkyl.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . ."

"Halogen" refers to a fluoro, chloro, bromo, or iodo group. In certain embodiments, halogen refers to a chloro group.

"Heteroalkyl" by itself or as part of another substituent refer to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{10}$, =N—N=, —N|N—, —N|N—NR$^{10}$, —PR$^{10}$—, —P(O)$_2$—, —POR$^{10}$—, —O—P(O)$_2$—, —SO—, —SO$_2$—, —Sn(R$^{10}$)$_2$—, and the like, where each R$^{37}$ is independently chosen from hydrogen, $C_{1-8}$ alkyl, substituted $C_{1-8}$ alkyl, $C_{8-12}$ aryl, substituted $C_{8-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{8-12}$ heteroaryl, substituted $C_{8-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-8}$ alkyl group in which at least one of the carbon atoms (and certain associated hydrogen atoms) is replaced with a heteroatom. For example $C_{1-6}$ heteroalkyl includes groups having five carbon atoms and one heteroatoms, groups having four carbon atoms and two heteroatoms, etc. In certain embodiments, each R$^{10}$ is independently chosen from hydrogen and $C_{1-3}$ alkyl. In certain embodiments, a heteroatomic group is chosen from, —O—, —S—, —NH—, —N(CH$_3$)—, and —SO$_2$—.

"Heteroalkyldiyl" by itself or as part of another substituent refers to an alkyldiyl group in which one or more of the carbon atoms (and any associated hydrogen atoms) are independently replaced with the same or different heteroatomic groups, where alkyldiyl is as defined herein. Examples of heteroatomic group include those disclosed for "heteroalkyl" herein. For example, in certain embodiments, $C_{1-3}$ heteroalkyldiyl is chosen from —O—, —NH—, —O—CH$_2$—, —O(CH$_2$)$_2$—, —NH—CH$_2$—, —NH(CH$_2$)$_2$—, —CH$_2$—O—, —(CH$_2$)$_2$—O—, —CH$_2$—O—CH$_2$—, —CH$_2$—NH—, and —(CH$_2$)$_2$—NH—, —CH$_2$—NH—CH$_2$—.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

Examples of heteroaryl groups include, but are not limited to, groups derived from acridine, arsindole, carbazole, ▢-chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, heteroaryl is $C_5$ heteroaryl and is chosen from furyl, thienyl, pyrrolyl, imidazolyl, pyrazolyl, isothiazolyl, isoxazolyl. In certain embodiments, heteroaryl is $C_6$ heteroaryl, and is chosen from pyridinyl, pyrazinyl, pyrimidinyl, and pyridazinyl.

"Heteroarylalkyl" by itself or as part of another substituent refers to an acyclic alkyl radical in which one of the hydrogen atoms bonded to a carbon atom, is replaced with a heteroaryl group. Typically a terminal or $sp^3$ carbon atom is the atom replaced with the heteroaryl group. In certain embodiments, a heteroarylalkyl group is a 6- to 30-membered heteroarylalkyl ($C_{6-30}$), e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, heterocycloalkyl is $C_5$ heterocycloalkyl and is chosen from pyrrolidinyl, tetrahydrofuranyl, tetrahydrothiophenyl, imidazolidinyl, oxazolidinyl, thiazolidinyl, doxolanyl, and dithiolanyl. In certain embodiments, heterocycloalkyl is $C_6$ heterocycloalkyl and is chosen from piperidinyl, tetrahydropyranyl, piperizinyl, oxazinyl, dithianyl, and dioxanyl.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt. The term "pharmaceutically acceptable salt" includes hydrates and other solvates, as well as salts in crystalline or non-crystalline form. Where a particular pharmaceutically acceptable salt is disclosed, it is understood that the particular salt (e.g. a hydrochloride salt) is an exemplary salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) and at least one pharmaceutically acceptable vehicle, with which the compound of Formula (I) is administered to a patient.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecule is water.

"Substituted" refers to a group in which one or more hydrogen atoms are independently replaced with the same or different substituent(s). In certain embodiments, each substituent group is independently chosen from halogen, —OH, —CN, —CF$_3$, =O, —NO$_2$, C$_{1-3}$ alkoxy, C$_{1-3}$ alkyl, —COOR$^{12}$ wherein R$^{12}$ is chosen from hydrogen and C$_{1-3}$ alkyl, and —NR$^{12}$$_2$ wherein each R$^{12}$ is independently chosen from hydrogen and C$_{1-3}$ alkyl. In certain embodiments, each substituent is independently chosen from halogen, —OH, —CN, —CF$_3$, —OCF$_3$, =O, —NO$_2$, C$_{1-6}$ alkoxy, C$_{1-6}$ alkyl, —COOR$^{13}$, —NR$^{13}$$_2$, and —CONR$^{13}$$_2$; wherein each R$^{13}$ is independently chosen from hydrogen and C$_{1-6}$ alkyl. In certain embodiments, each substituent is independently chosen from halogen, —NH$_2$, —OH, C$_{1-3}$ alkoxy, and C$_{1-3}$ alkyl.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Certain embodiments provide a compound of Formula (I):

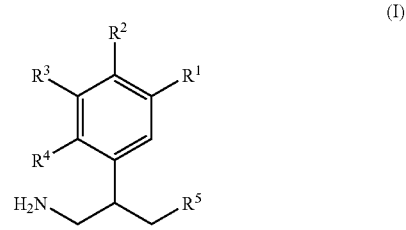

(I)

or a pharmaceutically acceptable salt thereof, wherein:
R$^1$ and R$^2$ are independently chosen from hydrogen, halogen, —CN, —CF$_3$, C$_{1-4}$ alkyl, —OR$^6$, and —N(R$^6$)$_2$ wherein each R$^6$ is independently chosen from hydrogen and C$_{1-4}$ alkyl;
one of R$^3$ and R$^4$ is —X—Y, and the other of R$^3$ and R$^4$ is hydrogen, wherein:
  X is chosen from a covalent bond, C$_{1-3}$ alkyldiyl, substituted C$_{1-3}$ alkyldiyl, C$_{1-3}$ heteroalkyldiyl, and substituted C$_{1-3}$ heteroalkyldiyl; and
  Y is chosen from C$_{6-12}$ aryl, substituted C$_{6-12}$ aryl, C$_{5-12}$ heteroaryl, and substituted C$_{5-12}$ heteroaryl; and
R$^5$ is chosen from —COOH, —SOOH, and —P(O)(OH)R$^8$ wherein R$^8$ is chosen from hydrogen and C$_{1-4}$ alkyl.

In certain embodiments of a compound of Formula (I), the compound is a compound of Formula (II):

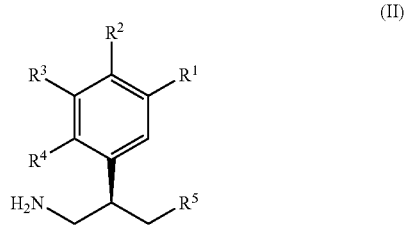

(II)

or a pharmaceutically acceptable salt thereof, wherein:
R$^1$ and R$^2$ are independently chosen from hydrogen, halogen, —CN, —CF$_3$, C$_{1-4}$ alkyl, —OR$^6$, and —N(R$^6$)$_2$ wherein each R$^6$ is independently chosen from hydrogen and C$_{1-4}$ alkyl;
one of R$^3$ and R$^4$ is —X—Y, and the other of R$^3$ and R$^4$ is hydrogen, wherein:
  X is chosen from a covalent bond, C$_{1-3}$ alkyldiyl, substituted C$_{1-3}$ alkyldiyl, C$_{1-3}$ heteroalkyldiyl, and substituted C$_{1-3}$ heteroalkyldiyl; and Y is chosen from $C_{6-12}$ aryl, substituted $C_{6-12}$ aryl, $C_{5-12}$ heteroaryl, and substituted $C_{5-12}$ heteroaryl; and
$R^5$ is chosen from —COON, —SOON, and —P(O)(OH)$R^8$ wherein $R^8$ is chosen from hydrogen and $C_{1-4}$ alkyl.

In certain embodiments of a compound of Formula (I) or Formula (II), $R^1$ and $R^2$ are independently chosen from halogen.

In certain embodiments of a compound of Formula (I) or Formula (II), $R^1$ is hydrogen; and $R^2$ is chloro.

In certain embodiments of a compound of Formula (I) or Formula (II),
$R^3$ is —X—Y; and $R^4$ is hydrogen.

In certain embodiments of a compound of Formula (I) or Formula (II), $R^3$ is hydrogen; and $R^4$ is —X—Y.

In certain embodiments of a compound of Formula (I) or Formula (II), $R^5$ is —COOH. In certain embodiments of Formula (I) or Formula (II), $R^5$ is —SOON. In certain embodiments a compound of Formula (I) or Formula (II), $R^5$ is —P(O)(OH)$R^8$ wherein $R^8$ is chosen from hydrogen and $C_{1-4}$ alkyl. In certain embodiments of a compound of Formula (I) or Formula (II), $R^5$ is —P(O)(OH)$R^8$ wherein $R^8$ is hydrogen. In certain embodiments of a compound of Formula (I) or Formula (II), $R^5$ is —P(O)(OH)$R^8$ wherein $R^8$ is $C_{1-4}$ alkyl.

In certain embodiments of a compound of Formula (I) or Formula (II), $C_{1-3}$ heteroalkyldiyl is chosen from —NH(CHR$^7$)$_n$—, —O(CHR$^7$)$_n$—, and —NH—SO$_2$—; wherein n is chosen from 0, 1, and 2; and each $R^7$ is independently chosen from hydrogen, $C_{1-4}$ alkyl, $C_{1-4}$ heteroalkyl, phenyl, substituted phenyl, $C_{5-6}$ heteroaryl, and substituted $C_{5-6}$ heteroaryl. In certain embodiments, each $R^7$ is independently chosen from hydrogen and $C_{1-4}$ alkyl, and in certain embodiments, each $R^7$ is hydrogen.

In certain embodiments of a compound of Formula (I) or Formula (II), each of the one or more substituents of substituted $C_{1-3}$ alkyldiyl and substituted $C_{1-3}$ heteroalkyldiyl is independently chosen from —OH, —NH$_2$, $C_{1-4}$ alkyl, $C_{1-4}$ alkoxy, and =O.

In certain embodiments of a compound of Formula (I) or Formula (II), each of the one or more substituents of substituted $C_{6-12}$ aryl and substituted $C_{5-12}$ heteroaryl is independently chosen from halogen, —OH, —NH$_2$, —NO$_2$, —CN, —COOH, —CF$_3$, —OCF$_3$, $C_{1-4}$ alkyl, substituted $C_{1-4}$ alkyl, $C_{1-4}$ heteroalkyl, and substituted $C_{1-4}$ heteroalkyl.

In certain embodiments of a compound of Formula (I) or Formula (II), each of the one or more substituents of substituted $C_{1-4}$ alkyl is chosen from —OH, =O, —OCH$_3$, —SCH$_3$, —N(CH$_3$)$_2$, and —OCH$_2$CH$_3$; and substituted $C_{1-4}$ heteroalkyl is chosen from —C(O)NH$_2$, —CH$_2$COOH, —COOCH$_3$, —COOCH$_2$CH$_3$, —SO$_2$CH$_3$.

In certain embodiments of a compound of Formula (I) or Formula (II), Y is chosen from phenyl, substituted phenyl, $C_5$ heteroaryl, substituted $C_5$ heteroaryl, $C_6$ heteroaryl, and substituted $C_6$ heteroaryl.

In certain embodiments of a compound of Formula (I) or Formula (II), Y is chosen from phenyl, substituted phenyl, thienyl, substituted thienyl, furyl, substituted furyl, imidazolyl, substituted imidazolyl, thiazole, substituted thiazole, oxazole, substituted oxazole, oxazolidine, substituted oxazolidine, thiazolidine, substituted thiazolidine, oxadiazole, substituted oxadiazole, thiadiazole, substituted thiadiazole, pyridyl, substituted pyridyl, indazolyl, substituted indazolyl, isoquinolyl, and substituted isoquinolyl.

In certain embodiments of a compound of Formula (I) or Formula (II), $R^1$ is hydrogen; $R^2$ is chloro; $R^3$ is hydrogen; $R^5$ is chosen from —COOH, —SOOH, and —P(O)(OH)$R^8$ wherein $R^8$ is chosen from hydrogen and $C_{1-4}$ alkyl; and $R^4$ is —X—Y wherein: X is chosen from a covalent bond, $C_{1-3}$ alkyldiyl, substituted $C_{1-3}$ alkyldiyl, —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl; and Y is chosen from phenyl, substituted phenyl, $C_5$ heteroaryl, substituted $C_5$ heteroaryl, $C_6$ heteroaryl, and substituted $C_6$ heteroaryl. In certain embodiments of a compound of Formula (I) or Formula (II), $R^1$ is hydrogen; $R^2$ is chloro; $R^3$ is hydrogen; $R^5$ is —COOH; and $R^4$ is —X—Y wherein: X is chosen from a covalent bond, $C_{1-3}$ alkyldiyl, substituted $C_{1-3}$ alkyldiyl, —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl; and Y is chosen from phenyl, substituted phenyl, $C_5$ heteroaryl, substituted $C_5$ heteroaryl, $C_6$ heteroaryl, and substituted $C_6$ heteroaryl. In certain of the preceding embodiments of a compound of Formula (I) or Formula (II), Y is chosen from phenyl, substituted phenyl, thienyl, substituted thienyl, furyl, substituted furyl, imidazolyl, substituted imidazolyl, thiazole, substituted thiazole, oxazole, substituted oxazole, oxazolidine, substituted oxazolidine, thiazolidine, substituted thiazolidine, oxadiazole, substituted oxadiazole, thiadiazole, substituted thiadiazole, pyridyl, and substituted pyridyl; wherein each of the one or more substituent groups is independently chosen from halogen, —OH, —NH$_2$, —NO$_2$, —CN, —COOH, —CF$_3$, —OCF$_3$, $C_{1-4}$ alkyl, substituted $C_{1-4}$ alkyl, $C_{1-4}$ heteroalkyl, and substituted $C_{1-4}$ heteroalkyl.

In certain embodiments of a compound of Formula (I) or Formula (II), $R^1$ is hydrogen; $R^2$ is chloro; $R^5$ is —COOH; $R^3$ is —X—Y wherein: X is chosen from a covalent bond, $C_{1-3}$ alkyldiyl, substituted $C_{1-3}$ alkyldiyl, —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl; and Y is chosen from phenyl, substituted phenyl, $C_5$ heteroaryl, substituted $C_5$ heteroaryl, $C_6$ heteroaryl, and substituted $C_6$ heteroaryl; and $R^4$ is hydrogen. In certain of the preceding embodiments of a compound of Formula (I) or Formula (II), Y is chosen from phenyl, substituted phenyl, thienyl, substituted thienyl, furyl, substituted furyl, imidazolyl, substituted imidazolyl, thiazole, substituted thiazole, oxazole, substituted oxazole, oxazolidine, substituted oxazolidine, thiazolidine, substituted thiazolidine, oxadiazole, substituted oxadiazole, thiadiazole, substituted thiadiazole, pyridyl, and substituted pyridyl; wherein each of the one or more substituent groups is independently chosen from halogen, —OH, —NH$_2$, —NO$_2$, —CN, —COOH, —CF$_3$, —OCF$_3$, $C_{1-4}$ alkyl, substituted $C_{1-4}$ alkyl, $C_{1-4}$ heteroalkyl, and substituted $C_{1-4}$ heteroalkyl.

In certain embodiments of a compound of Formula (II), each of $R^1$ and $R^4$ is hydrogen; $R^2$ is chloro; $R^5$ is —COOH; and $R^3$ is —X—Y wherein X is a bond; and Y is substituted phenyl wherein the substituents are independently chosen from halogen, —COOH, —CN, and —NO$_2$.

In certain embodiments of a compound of Formula (II), each of $R^1$ and $R^4$ is hydrogen; $R^2$ is chloro; $R^5$ is —COOK and $R^3$ is —X—Y wherein X is a bond; and Y is substituted thienyl wherein the substituents are independently chosen from halogen, —COOK —CN, —NO$_2$, and —C(O)N(CH$_3$)$_2$.

In certain embodiments of a compound of Formula (II), each of $R^1$ and $R^4$ is hydrogen; $R^2$ is chloro; $R^5$ is —COOH; and $R^3$ is —X—Y wherein X is a bond; and Y is substituted pyridinyl wherein the substituents are independently chosen from halogen, —COOH, —CN, and —NO$_2$.

In certain embodiments of a compound of Formula (II), the compound is chosen from:

(3R)-4-amino-3-[4-chloro-3-(phenylcarbonylamino)phenyl]butanoic acid;
(3R)-4-amino-3-[2-(3,4-dichlorophenyl)-4-chlorophenyl]butanoic acid hydrochloride;
4-{2-[(1R)-2-amino-1-(carboxymethyl)ethyl]-5-chlorophenyl}benzoic acid hydrochloride;
(3R)-4-amino-3-(4-chloro-2-(3-thienyl)phenyl)butanoic acid hydrochloride;
(3R)-4-amino-3-[4-chloro-2-(4-chlorophenyl)phenyl]butanoic acid hydrochloride;
2-({5-[(1R)-2-amino-1-(carboxymethyl)ethyl]-2-chlorophenyl}amino)benzoic acid;
3-({5-[(1R)-2-amino-1-(carboxymethyl)ethyl]-2-chlorophenyl}amino)benzoic acid;
4-({5-[(1R)-2-amino-1-(carboxymethyl)ethyl]-2-chlorophenyl}amino)benzoic acid;
(3R)-4-amino-3-(4-chloro-2-(3-pyridyl)phenyl)butanoic acid hydrochloride;
(3R)-4-amino-3-(4-chloro-2-phenoxyphenyl)butanoic acid hydrochloride;
(3R)-4-amino-3-{3-[(3,4-dichlorophenyl)amino]-4-chlorophenyl}butanoic acid hydrochloride;
(3R)-4-amino-3-[4-chloro-2-(phenylcarbonyl)phenyl]butanoic acid hydrochloride;
(3R)-4-amino-3-[4-chloro-2-(2-phenylethyl)phenyl]butanoic acid hydrochloride;
(3R)-4-amino-3-[3-({[3-(3,4-dichlorophenoxy)phenyl]methyl}amino)-4-chlorophenyl]butanoic acid hydrochloride;
(3R)-4-amino-3-[3-({[4-(tert-butoxy)phenyl]methyl}amino)-4-chlorophenyl]butanoic acid hydrochloride;
(3R)-4-amino-3-(4-chloro-3-{[(2-fluorophenyl)methyl]amino}phenyl)butanoic acid hydrochloride;
(3R)-4-amino-3-(3-{[(2,4-dichlorophenyl)methyl]amino}-4-chlorophenyl)butanoic acid hydrochloride;
(3R)-4-amino-3-(4-chloro-3-{[(3-phenoxyphenyl)methyl]amino}phenyl)butanoic acid hydrochloride;
4-amino-3-[4-chloro-3-(phenylamino)phenyl]butanoic acid hydrochloride;
(3R)-4-amino-3-{4-chloro-3-[(2-pyridylmethyl)amino]phenyl}butanoic acid hydrochloride;
(3R)-4-amino-3-{4-chloro-3-[(3-furylmethyl)amino]phenyl}butanoic acid hydrochloride;
(3R)-4-amino-3-{4-chloro-3-[(imidazol-5-ylmethyl)amino]phenyl}butanoic acid hydrochloride;
3-{5-[(1R)-2-amino-1-(carboxymethyl)ethyl]-2-chlorophenyl}benzoic acid hydrochloride;
(3R)-4-amino-3-{4-chloro-3-[3-(ethoxycarbonyl)phenyl]phenyl}butanoic acid hydrochloride;
(3R)-4-amino-3-(4-chloro-3-(3-pyridyl)phenyl)butanoic acid hydrochloride;
(3R)-4-amino-3-[4-chloro-3-(3-cyanophenyl)phenyl]butanoic acid hydrochloride;
(3R)-4-amino-3-{3-[3-(carboxymethyl)phenyl]-4-chlorophenyl}butanoic acid hydrochloride;
(3R)-4-amino-3-[4-chloro-3-(3-hydroxyphenyl)phenyl]butanoic acid hydrochloride;
3-{3-[(1R)-2-amino-1-(carboxymethyl)ethyl]phenyl}benzoic acid hydrochloride;
(3R)-4-amino-3-[4-chloro-3-(3-methoxyphenyl)phenyl]butanoic acid hydrochloride;
(3R)-4-amino-3-(3-benzimidazol-6-yl-4-chlorophenyl)butanoic acid hydrochloride;
(3R)-4-amino-3-[4-chloro-3-(4-cyanophenyl)phenyl]butanoic acid hydrochloride;
(3R)-4-amino-3-[3-(3-carbamoylphenyl)-4-chlorophenyl]butanoic acid hydrochloride;
(3R)-4-amino-3-{4-chloro-3-[3-(hydroxymethyl)phenyl]phenyl}butanoic acid hydrochloride;
3-{5-[(1R)-2-amino-1-(carboxymethyl)ethyl]-2-chlorophenyl}-4-chlorobenzoic acid hydrochloride;
(3R)-4-amino-3-[4-chloro-3-(3-nitrophenyl)phenyl]butanoic acid hydrochloride;
(3R)-4-amino-3-[4-chloro-3-(4-nitrophenyl)phenyl]butanoic acid hydrochloride;
5-{5-[(1R)-2-amino-1-(carboxymethyl)ethyl]-2-chlorophenyl}pyridine-3-carboxylic acid hydrochloride;
3-{5-[(1R)-1-(aminomethyl)-3-hydroxypropyl]-2-chlorophenyl}benzenecarbonitrile hydrochloride;
4-{5-[(1R)-2-amino-1-(carboxymethyl)ethyl]-2-chlorophenyl}thiophene-2-carboxylic acid;
(3R)-4-amino-3-{4-chloro-3-[(4-pyridylmethyl)amino]phenyl}butanoic acid hydrochloride;
(3R)-4-amino-3-[4-chloro-3-(3-methylthiophenyl)phenyl]butanoic acid hydrochloride;
(3R)-4-amino-3-{4-chloro-3-[3-(methylsulfonyl)phenyl]phenyl}butanoic acid hydrochloride;
5-{5-[(1R)-2-amino-1-(carboxymethyl)ethyl]-2-chlorophenyl}thiophene-2-carboxylic acid hydrochloride;
(3R)-4-amino-3-(4-chloro-3-phenylphenyl)butanoic acid hydrochloride;
3-{5-[(1R)-2-amino-1-(carboxymethyl)ethyl]-2-chlorophenyl}-5-nitrobenzoic acid hydrochloride;
(3R)-4-amino-3-[4-chloro-3-(4-chloro-3-cyanophenyl)phenyl]butanoic acid hydrochloride;
(3R)-4-amino-3-{3-[3-(dimethylamino)phenyl]-4-chlorophenyl}butanoic acid hydrochloride;
3-{5-[(1R)-2-amino-1-(carboxymethyl)ethyl]-2-chlorophenyl}-5-fluorobenzoic acid hydrochloride;
4-{5-[(1R)-2-amino-1-(carboxymethyl)ethyl]-2-chlorophenyl}-3-chlorobenzoic acid hydrochloride;
(3R)-4-amino-3-[4-chloro-3-(4-pyridylmethoxy)phenyl]butanoic acid hydrochloride;
(3R)-4-amino-3-{4-chloro-3-[(3-chlorophenyl)carbonylamino]phenyl}butanoic acid;
(3R)-4-amino-3-(2-{[(3,4-dichlorophenyl)sulfonyl]amino}-4-chlorophenyl)butanoic acid hydrochloride;
(3R)-4-amino-3-{2-[(3,4-dichlorophenyl)carbonylamino]-4-chlorophenyl}butanoic acid hydrochloride;
(3R)-4-amino-3-[4-chloro-3-(2-pyridylamino)phenyl]butanoic acid;
(3R)-4-amino-3-{4-chloro-3-[(4-methoxyphenyl)amino]phenyl}butanoic acid;
(3R)-4-amino-3-[4-chloro-3-(4-pyridylamino)phenyl]butanoic acid;
4-{3-[(1R)-2-amino-1-(carboxymethyl)ethyl]-4-chlorophenoxy}benzoic acid hydrochloride;
3-{5-[(1R)-2-amino-1-(carboxymethyl)ethyl]-2-chlorophenoxy}benzoic acid;
(3R)-4-amino-3-(4-chloro-3-phenoxyphenyl)butanoic acid;
(3R)-4-amino-3-(3-{[(3,4-dichlorophenyl)sulfonyl]amino}-4-chlorophenyl)butanoic acid;
4-{5-[(1R)-2-amino-1-(carboxymethyl)ethyl]-2-chlorophenyl}benzoic acid hydrochloride;
3-({2-[(1R)-2-amino-1-(carboxymethyl)ethyl]-4-chlorophenyl}hydroxymethyl)benzoic acid hydrochloride;
4-[({5-[(1R)-2-amino-1-(carboxymethyl)ethyl]-2-chlorophenyl}amino)methyl]benzoic acid hydrochloride;
(3R)-4-amino-3-(4-chloro-3-{[(1-methylimidazol-5-yl)methyl]amino}phenyl)butanoic acid;

(3R)-4-amino-3-[4-chloro-3-(5-cyano(2-thienyl))phenyl]butanoic acid;
(3R)-4-amino-3-[4-chloro-3-(2-methylpyrimidin-5-yl)phenyl]butanoic acid hydrochloride;
2-{5-[(1R)-2-Amino-1-(carboxymethyl)ethyl]-2-chlorophenyl}-1,3-thiazole-4-carboxylic acid hydrochloride;
2-{5-[(1R)-2-amino-1-(carboxymethyl)ethyl]-2-chlorophenyl}-1,3-oxazole-4-carboxylic acid hydrochloride;
4-{5-[(1R)-2-amino-1-(carboxymethyl)ethyl]-2-chlorophenyl}-1,3-thiazole-2-carboxylic acid hydrochloride;
5-{5-[(1R)-2-amino-1-(carboxymethyl)ethyl]-2-chlorophenyl}furan-3-carboxylic acid;
(3R)-4-amino-3-[4-chloro-3-(4-pyridylethoxy)phenyl]butanoic acid;
(3R)-4-amino-3-{4-chloro-3-[(3-chloro(4-pyridyl))methoxy]phenyl}butanoic acid;
5-{5-[(1R)-2-amino-1-(carboxymethyl)ethyl]-2-chlorophenyl}thiophene-3-carboxylic acid;
(3R)-4-amino-3-[4-chloro-3-(1,3-thiazol-5-ylmethoxy)phenyl]butanoic acid;
2-{5-[(1R)-2-amino-1-(carboxymethyl)ethyl]-2-chlorophenyl}-4-methyl-1,3-thiazole-5-carboxylic acid; and
a pharmaceutically acceptable salt of any of the foregoing.

The following compounds of Formula (II) exhibited GABA$_B$ receptor agonist or partial agonist activity as determined using the binding, electrophysiology, cAMP, and/or Ca$^{2+}$ assay methods described in Examples 83-86:
2-({5-[(1R)-2-amino-1-(carboxymethyl)ethyl]-2-chlorophenyl}amino)benzoic acid;
3-{2-[(1R)-2-amino-1-(carboxymethyl)ethyl]-5-chlorophenyl}benzoic acid hydrochloride;
(3R)-4-amino-3-(4-chloro-2-(3-pyridyl)phenyl)butanoic acid hydrochloride;
(3R)-4-amino-3-[4-chloro-2-(phenylcarbonyl)phenyl]butanoic acid hydrochloride;
(3R)-4-amino-3-{4-chloro-3-[(2-phenylethyl)amino]phenyl}butanoic acid;
(3R)-4-amino-3-[3-({[4-(tert-butoxy)phenyl]methyl}amino)-4-chlorophenyl]butanoic acid hydrochloride;
(3R)-4-amino-3-(4-chloro-3-{[(3-fluorophenyl)methyl]amino}phenyl)butanoic acid hydrochloride;
(3R)-4-amino-3-(4-chloro-3-{[(4-fluorophenyl)methyl]amino}phenyl)butanoic acid hydrochloride;
(3R)-4-amino-3-{4-chloro-3-[methylbenzylamino]phenyl}butanoic acid hydrochloride;
(3R)-4-amino-3-[4-chloro-3-(N-methylphenylcarbonylamino)phenyl]butanoic acid hydrochloride;
(3R)-4-amino-3-[3-({[3,5-bis(trifluoromethyl)phenyl]methyl}amino)-4-chlorophenyl]butanoic acid hydrochloride;
(3R)-4-amino-3-(4-chloro-3-{[(4-nitrophenyl)methyl]amino}phenyl)butanoic acid hydrochloride;
(3R)-4-amino-3-{4-chloro-3-[(2-pyridylmethyl)amino]phenyl}butanoic acid hydrochloride;
(3R)-4-amino-3-{4-chloro-3-[(3-furylmethyl)amino]phenyl}butanoic acid hydrochloride;
(3R)-4-amino-3-{4-chloro-3-[(2-furylmethyl)amino]phenyl}butanoic acid hydrochloride;
(3R)-4-amino-3-{4-chloro-3-[(imidazol-5-ylmethyl)amino]phenyl}butanoic acid hydrochloride;
3-{5-[(1R)-2-amino-1-(carboxymethyl)ethyl]-2-chlorophenyl}benzoic acid hydrochloride;
(3R)-4-amino-3-(4-chloro-3-(3-pyridyl)phenyl)butanoic acid hydrochloride;
(3R)-4-amino-3-[4-chloro-3-(3-cyanophenyl)phenyl]butanoic acid hydrochloride;
(3R)-4-amino-3-{3-[3-(carboxymethyl)phenyl]-4-chlorophenyl}butanoic acid hydrochloride;
(3R)-4-amino-3-[4-chloro-3-(3-hydroxyphenyl)phenyl]butanoic acid hydrochloride;
3-{3-[(1R)-2-amino-1-(carboxymethyl)ethyl]phenyl}benzoic acid hydrochloride;
(3R)-4-amino-3-[4-chloro-3-(3-methoxyphenyl)phenyl]butanoic acid hydrochloride;
(3R)-4-amino-3-[4-chloro-2-(3-cyanophenyl)phenyl]butanoic acid hydrochloride;
(3R)-4-amino-3-(3-benzimidazol-6-yl-4-chlorophenyl)butanoic acid hydrochloride;
(3R)-4-amino-3-[3-(3-carbamoylphenyl)-4-chlorophenyl]butanoic acid hydrochloride;
(3R)-4-amino-3-{4-chloro-3-[3-(hydroxymethyl)phenyl]phenyl}butanoic acid hydrochloride;
3-{5-[(1R)-2-amino-1-(carboxymethyl)ethyl]-2-chlorophenyl}-4-chlorobenzoic acid hydrochloride;
(3R)-4-amino-3-[4-chloro-3-(3-nitrophenyl)phenyl]butanoic acid hydrochloride;
5-{5-[(1R)-2-amino-1-(carboxymethyl)ethyl]-2-chlorophenyl}pyridine-3-carboxylic acid hydrochloride;
3-{5-[(1R)-1-(aminomethyl)-3-hydroxypropyl]-2-chlorophenyl}benzenecarbonitrile hydrochloride;
4-{5-[(1R)-2-amino-1-(carboxymethyl)ethyl]-2-chlorophenyl}thiophene-2-carboxylic acid;
(3R)-4-amino-3-{4-chloro-3-[(3-pyridylmethyl)amino]phenyl}butanoic acid;
(3R)-4-amino-3-{4-chloro-3-[(4-pyridylmethyl)amino]phenyl}butanoic acid hydrochloride;
(3R)-4-amino-3-{4-chloro-3-[3-(methylsulfonyl)phenyl]phenyl}butanoic acid hydrochloride;
3-{5-[(1R)-2-amino-1-(carboxymethyl)ethyl]-3-bromo-2-chlorophenyl}benzoic acid hydrochloride;
5-{5-[(1R)-2-amino-1-(carboxymethyl)ethyl]-2-chlorophenyl}thiophene-2-carboxylic acid hydrochloride;
(3R)-4-amino-3-(4-chloro-3-phenylphenyl)butanoic acid hydrochloride;
(3R)-4-amino-3-{3-[3-(aminomethyl)phenyl]phenyl}butanoic acid hydrochloride;
(3R)-4-amino-3-[4-chloro-3-(4-chloro-3-cyanophenyl)phenyl]butanoic acid hydrochloride;
(3R)-4-amino-3-{3-[3-(dimethylamino)phenyl]-4-chlorophenyl}butanoic acid hydrochloride;
3-{5-[(1R)-2-amino-1-(carboxymethyl)ethyl]-2-chlorophenyl}-5-fluorobenzoic acid hydrochloride;
3-{5-[(1R)-2-amino-1-(carboxymethyl)ethyl]-3-bromo-2-chlorophenyl}-5-chlorobenzoic acid;
4-{5-[(1R)-2-amino-1-(carboxymethyl)ethyl]-2-chlorophenyl}-3-chlorobenzoic acid hydrochloride;
4-amino-3-[4-chloro-3-(5-methoxy(3-pyridyl))phenyl]butanoic acid hydrochloride;
(3R)-4-amino-3-[4-chloro-3-(3-cyano-4-fluorophenyl)phenyl]butanoic acid hydrochloride;
5-{5-[(1R)-2-amino-1-(carboxymethyl)ethyl]-2-chlorophenyl}-2-fluorobenzoic acid hydrochloride;
6-{5-[(1R)-2-amino-1-(carboxymethyl)ethyl]-2-chlorophenyl}pyridine-2-carboxylic acid hydrochloride;
(3R)-4-amino-3-[4-chloro-3-(5-chloro-3-cyanophenyl)phenyl]butanoic acid hydrochloride;
(3R)-4-amino-3-[4-chloro-3-(3-chloro-4-hydroxyphenyl)phenyl]butanoic acid hydrochloride;
(3R)-4-amino-3-[4-chloro-3-(4-chloro-3-methylphenyl)phenyl]butanoic acid hydrochloride;
(3R)-4-amino-3-(4-chloro-3-{[(3-chloro(4-pyridyl))methyl]amino}phenyl)butanoic acid hydrochloride;

3-[({5-[(1R)-2-amino-1-(carboxymethyl)ethyl]-2-chlorophenyl}amino)methyl]benzoic acid hydrochloride;
(3R)-4-amino-3-(4-chloro-3-{[(2-cyanophenyl)methyl]amino}phenyl)butanoic acid hydrochloride;
3-((1E)-2-{5-[(1R)-2-amino-1-(carboxymethyl)ethyl]-2-chlorophenyl}vinyl)benzoic acid hydrochloride;
(3R)-4-amino-3-(4-chloro-3-(4-pyridyl)phenyl)butanoic acid hydrochloride;
(3R)-4-amino-3-{4-chloro-3-[(3-fluorophenyl)carbonylamino]phenyl}butanoic acid;
(3R)-4-amino-3-{4-chloro-3-[(4-nitrophenyl)carbonylamino]phenyl}butanoic acid;
(3R)-4-amino-3-{4-chloro-3-[(2-pyridyl)carbonylamino]phenyl)carbonylamino]phenyl}butanoic acid;
(3R)-4-amino-3-{3-[(1,3-dimethylpyrazol-5-yl)carbonylamino]-4-chlorophenyl}butanoic acid;
(3R)-4-amino-3-{3-[4-(carboxymethyl)phenyl]-4-chlorophenyl}butanoic acid hydrochloride;
(3R)-4-amino-3-[4-chloro-3-(3-cyano-6-methylphenyl)phenyl]butanoic acid hydrochloride;
(3R)-4-amino-3-[4-chloro-3-(6-cyano(2-pyridyl))phenyl]butanoic acid hydrochloride;
(3R)-4-amino-3-[4-chloro-3-(3-cyano-5-hydroxyphenyl)phenyl]butanoic acid hydrochloride;
3-{5-[(1R)-2-amino-1-(carboxymethyl)ethyl]-2-chlorophenyl}-4-cyanobenzoic acid hydrochloride;
(3R)-4-amino-3-[4-chloro-3-(5-cyano(3-pyridyl))phenyl]butanoic acid hydrochloride;
4-({5-[(1R)-2-amino-1-(carboxymethyl)ethyl]-2-chlorophenyl}methyl)benzoic acid hydrochloride;
(3R)-4-amino-3-[4-chloro-3-(3-cyano-5-fluorophenyl)phenyl]butanoic acid hydrochloride;
(3R)-4-amino-3-[4-chloro-3-(4-methyl(3-pyridyl))phenyl]butanoic acid hydrochloride;
(3R)-4-amino-3-[4-chloro-3-(2-(2-pyridyl)ethyl)phenyl]butanoic acid hydrochloride;
(3R)-4-amino-3-[4-chloro-3-(3-cyano-6-fluorophenyl)phenyl]butanoic acid hydrochloride;
(3R)-4-amino-3-[4-chloro-3-(6-chloro-3-cyanophenyl)phenyl]butanoic acid hydrochloride;
(3R)-4-amino-3-[4-chloro-3-(4-chloro(2-pyridyl))phenyl]butanoic acid hydrochloride;
(3R)-4-amino-3-[4-chloro-3-(3-cyano-6-hydroxyphenyl)phenyl]butanoic acid hydrochloride;
5-{5-[(1R)-2-amino-1-(carboxymethyl)ethyl]-2-chlorophenyl}pyridine-2-carboxylic acid hydrochloride;
(3R)-4-amino-3-[4-chloro-3-(4-pyridylmethoxy)phenyl]butanoic acid hydrochloride;
(3R)-4-amino-3-[4-chloro-3-(3-cyano-4-methylphenyl)phenyl]butanoic acid hydrochloride;
(3R)-4-amino-3-{4-chloro-3-[(4-cyanophenyl)methoxy]phenyl}butanoic acid hydrochloride;
(3R)-4-amino-3-[4-chloro-3-(3-pyridylmethoxy)phenyl]butanoic acid hydrochloride;
3-{5-[(1S)-2-amino-1-(carboxymethyl)ethyl]-2-chlorophenyl}benzoic acid hydrochloride;
(3S)-4-amino-3-[4-chloro-3-(3-cyanophenyl)phenyl]butanoic acid hydrochloride;
(3S)-4-amino-3-(4-chloro-3-(3-pyridyl)phenyl)butanoic acid hydrochloride;
(3R)-4-amino-3-(4-chloro-3-(4-pyridyloxy)phenyl)butanoic acid hydrochloride;
3-({5-[(1R)-2-amino-1-(carboxymethyl)ethyl]-2-chlorophenoxy}methyl)benzoic acid hydrochloride;
(3R)-4-amino-3-{4-chloro-3-[(3-cyanophenyl)methoxy]phenyl}butanoic acid hydrochloride;
(3R)-4-amino-3-[4-chloro-3-(phenylmethoxy)phenyl]butanoic acid hydrochloride;
(3S)-4-amino-3-{4-chloro-3-[(4-pyridylmethyl)amino]phenyl}butanoic acid hydrochloride;
(3R)-4-amino-3-[4-chloro-3-(4-pyridylmethyl)phenyl]butanoic acid hydrochloride;
3-{5-[(1R)-2-amino-1-(carboxymethyl)ethyl]-2-chlorophenyl}-4-methylbenzoic acid hydrochloride;
(3R)-4-amino-3-{4-chloro-3-[(2-cyanophenyl)methoxy]phenyl}butanoic acid hydrochloride;
(3R)-4-amino-3-[4-chloro-3-(2-pyridylmethoxy)phenyl]butanoic acid hydrochloride;
(3R)-4-amino-3-[4-chloro-3-(3,4-dichlorophenyl)phenyl]butanoic acid hydrochloride;
(3R)-4-amino-3-[4-chloro-3-(2,4-dichlorophenyl)phenyl]butanoic acid hydrochloride;
(3R)-4-amino-3-[4-chloro-3-(3,4,5-trifluorophenyl)phenyl]butanoic acid hydrochloride;
(3R)-4-amino-3-[4-chloro-3-(3-thienyl)phenyl]butanoic acid;
4-{5-[(1R)-2-amino-1-(carboxymethyl)ethyl]-2-chlorophenyl}butanoic acid;
3-{5-[(1R)-2-amino-1-(carboxymethyl)ethyl]-2-chlorophenoxy}benzoic acid;
4-{5-[(1R)-2-amino-1-(carboxymethyl)ethyl]-2-chlorophenyl}benzoic acid hydrochloride;
4-[({5-[(1R)-2-amino-1-(carboxymethyl)ethyl]-2-chlorophenyl}amino)methyl]benzoic acid hydrochloride;
(3R)-4-amino-3-(4-chloro-3-{[(4-methylphenyl)methyl]amino}phenyl)butanoic acid hydrochloride;
4-{5-[(1R)-2-amino-1-(carboxymethyl)ethyl]-2-chlorophenyl}-3-chlorobenzoic acid hydrochloride;
(3R)-4-amino-3-(4-chloro-3-{[(1-methylimidazol-5-yl)methyl]amino}phenyl)butanoic acid;
(3R)-4-amino-3-[4-chloro-3-(5-cyano(2-thienyl))phenyl]butanoic acid;
3-{5-[(1R)-2-amino-1-(carboxymethyl)ethyl]-3-bromo-2-chlorophenyl}benzoic acid;
(3R)-4-amino-3-[4-chloro-3-(2-methylpyrimidin-5-yl)phenyl]butanoic acid hydrochloride;
(3R)-4-amino-3-(5-bromo-4-chloro-3-(3-pyridyl)phenyl)butanoic acid;
(3R)-4-amino-3-[3-bromo-4-chloro-5-(3-cyanophenyl)]butanoic acid hydrochloride;
(3R)-4-amino-3-[4-chloro-3-(2-(4-pyridyl)ethyl)phenyl]butanoic acid hydrochloride;
(3R)-4-amino-3-{4-chloro-3-[(3-nitrophenyl)methyl]phenyl}butanoic acid hydrochloride;
(3R)-4-amino-3-{4-chloro-3-[(3-cyanophenyl)carbonylamino]phenyl}butanoic acid;
(3R)-4-amino-3-[4-chloro-3-(2-pyridylcarbonylamino)phenyl]butanoic acid;
2-{5-[(1R)-2-amino-1-(carboxymethyl)ethyl]-2-chlorophenyl}benzoic acid hydrochloride;
(3R)-4-amino-3-[4-chloro-3-(5-cyano(3-pyridyl))phenyl]butanoic acid hydrochloride;
(3R)-4-amino-3-{4-chloro-3-[5-(trifluoromethyl)(3-pyridyl)]phenyl}butanoic acid;
3-[3-((1E)-2-(2-pyridyl)vinyl)-4-chlorophenyl](3R)-4-aminobutanoic acid hydrochloride;
3-[2-((1E)-2-phenylvinyl)-4-chlorophenyl](3R)-4-aminobutanoic acid hydrochloride;
(3R)-4-amino-3-(4-chloro-3-(4-isoquinolyl)phenyl)butanoic acid hydrochloride;
(3R)-4-amino-3-{4-chloro-3-[(2-pyridylsulfonyl)amino]phenyl}butanoic acid hydrochloride;

3-{5-[(1R)-2-amino-1-(carboxymethyl)ethyl]-2-chlorophenyl}pyridine-4-carboxylic acid hydrochloride;
(3R)-4-amino-3-[4-chloro-3-(3-cyano-2-fluorophenyl)phenyl]butanoic acid hydrochloride; and
(3R)-4-amino-3-{3-[6-(dimethylamino)(2-pyridyl)]-4-chlorophenyl}butanoic acid hydrochloride.

In certain embodiments of a compound of Formula (II), the compound is chosen from:
3-{5-[(1R)-2-amino-1-(carboxymethyl)ethyl]-2-chlorophenyl}hexanoic acid hydrochloride;
(3R)-4-amino-3-[4-chloro-3-(3-nitrophenyl)phenyl]butanoic acid hydrochloride;
(3R)-4-amino-3-[4-chloro-3-(3-cyanophenyl)phenyl]butanoic acid hydrochloride;
(3R)-4-amino-3-[4-chloro-3-(3-cyano-5-fluorophenyl)phenyl]butanoic acid,
hydrochloride;
5-{5-[(1R)-2-amino-1-(carboxymethyl)ethyl]-2-chlorophenyl}thiophene-2-carboxylic acid;
(3R)-4-amino-3-{3-[5-(N,N-dimethylcarbamoyl)(2-thienyl)]-4-chlorophenyl}butanoic acid hydrochloride;
(3R)-4-amino-3-[4-chloro-3-(5-cyano(2-thienyl))phenyl]butanoic acid;
4-{5-[(1R)-2-amino-1-(carboxymethyl)ethyl]-2-chlorophenyl}thiophene-2-carboxylic acid;
(3R)-4-amino-3-[4-chloro-3-(5-cyano(3-thienyl))phenyl]butanoic acid hydrochloride;
(3R)-4-amino-3-(4-chloro-3-(3-pyridyl)phenyl)butanoic acid, hydrochloride;
(3R)-4-amino-3-{4-chloro-3-[(4-pyridylmethyl)amino]phenyl}butanoic acid hydrochloride;
(3R)-4-amino-3-[4-chloro-3-(3-cyano-6-methylphenyl)phenyl]butanoic acid hydrochloride;
(3R)-4-amino-3-[4-chloro-3-(6-chloro-3-cyanophenyl)phenyl]butanoic acid hydrochloride;
(3R)-4-amino-3-[4-chloro-3-(4-pyridylmethoxy)phenyl]butanoic acid hydrochloride;
(3R)-4-amino-3-[4-chloro-3-(2-(4-pyridyl)ethoxy)phenyl]butanoic acid hydrochloride;
(3R)-3-[3-((1R)-1-(4-pyridyl)ethoxy)-4-chlorophenyl]-4-aminobutanoic acid hydrochloride;
(3R)-4-amino-3-{4-chloro-3-[(2-methyl(4-pyridyl))methoxy]phenyl}butanoic acid hydrochloride; and
methyl (3R)-4-amino-3-[4-chloro-3-(4-pyridyl methoxy)phenyl]butanoate hydrochloride.

In certain embodiments of a compound of Formula (II), the compound is chosen from:
3-({5-[(1R)-2-amino-1-(carboxymethyl)ethyl]-2-chlorophenyl}amino)benzoic acid;
3-{5-[(1R)-2-Amino-1-(carboxymethyl)ethyl]-2-chlorophenyl}benzoic acid;
(3R)-4-amino-3-{4-chloro-3-[(imidazol-5-ylmethyl)amino]phenyl}butanoic acid;
(3R)-4-amino-3-(4-chloro-3-(3-pyridyl)phenyl)butanoic acid;
(3R)-4-amino-3-[4-chloro-3-(3-cyanophenyl)phenyl]butanoic acid;
(3R)-4-amino-3-[3-(3-carbamoylphenyl)-4-chlorophenyl]butanoic acid;
3-{5-[(1R)-2-amino-1-(carboxymethyl)ethyl]-2-chlorophenyl}-4-chlorobenzoic acid;
(3R)-4-amino-3-[4-chloro-3-(3-nitrophenyl)phenyl]butanoic acid;
4-{5-[(1R)-2-amino-1-(carboxymethyl)ethyl]-2-chlorophenyl}thiophene-2-carboxylic acid
(3R)-4-amino-3-{4-chloro-3-[(4-pyridylmethyl)amino]phenyl}butanoic acid;
5-{5-[(1R)-2-amino-1-(carboxymethyl)ethyl]-2-chlorophenyl}thiophene-2-carboxylic acid;
3-{5-[(1R)-2-amino-1-(carboxymethyl)ethyl]-2-chlorophenyl}-5-fluorobenzoic acid;
(3R)-4-amino-3-[4-chloro-3-(4-pyridylmethoxy)phenyl]butanoic acid;
(3R)-4-amino-3-[4-chloro-3-(5-cyano(2-thienyl))phenyl]butanoic acid;
5-{5-[(1R)-2-amino-1-(carboxymethyl)ethyl]-2-chlorophenyl}-2-fluorobenzoic acid;
(3R)-4-amino-3-[4-chloro-3-(3-cyano-6-methylphenyl)phenyl]butanoic acid;
(3R)-4-amino-3-[4-chloro-3-(3-cyano-5-fluorophenyl)phenyl]butanoic acid;
(3R)-4-amino-3-[4-chloro-3-(4-methyl(3-pyridyl))phenyl]butanoic acid;
(3R)-4-amino-3-[4-chloro-3-(3-cyano-6-fluorophenyl)phenyl]butanoic acid;
(3R)-4-amino-3-[4-chloro-3-(6-chloro-3-cyanophenyl)phenyl]butanoic acid;
methyl (3R)-4-amino-3-[4-chloro-3-(4-pyridyl methoxy)phenyl]butanoate;
(3R)-4-amino-3-[4-chloro-3-(3-pyridylmethoxy)phenyl]butanoic acid;
5-{5-[(1R)-2-amino-1-(carboxymethyl)ethyl]-2-chlorophenyl}furan-3-carboxylic acid;
(3R)-4-amino-3-[4-chloro-3-(2-(4-pyridyl)ethoxy)phenyl]butanoic acid;
(3R)-4-amino-3-[4-chloro-3-(4-pyridylethoxy)phenyl]butanoic acid;
(3R)-3-[3-((1R)-1-(4-pyridyl)ethoxy)-4-chlorophenyl]-4-aminobutanoic acid;
(3R)-4-amino-3-[4-chloro-3-(5-cyano(3-thienyl))phenyl]butanoic acid;
(3R)-4-amino-3-{4-chloro-3-[(2-methyl(4-pyridyl))methoxy]phenyl}butanoic acid;
(3R)-4-amino-3-{4-chloro-3-[(3-chloro(4-pyridyl))methoxy]phenyl}butanoic acid;
5-{5-[(1R)-2-amino-1-(carboxymethyl)ethyl]-2-chlorophenyl}thiophene-3-carboxylic acid;
(3R)-4-amino-3-[4-chloro-3-(2-(4-pyridyl)ethyl)phenyl]butanoic acid;
(3R)-4-amino-3-[4-chloro-3-(1,3-thiazol-5-ylmethoxy)phenyl]butanoic acid;
(3R)-4-amino-3-{3-[5-(N,N-dimethylcarbamoyl)(2-thienyl)]-4-chlorophenyl}butanoic acid;
2-{4-Chloro-3-(4-pyridylmethoxy)phenyl}-3-(hydroxydroxyphosphoryl)propylamine; and
a pharmaceutically acceptable salt of any of the foregoing.

In certain embodiments, a compound of Formula (I) is chosen from any of the compounds in the preceding paragraphs, and a pharmaceutically acceptable salt thereof.

Compounds disclosed herein may be obtained via the synthetic methods illustrated in Schemes 1-26. General synthetic methods useful in the synthesis of compounds described herein are available in the art. Starting materials useful for preparing compounds and intermediates thereof, and/or practicing methods described herein, are commercially available or may be prepared by well-known synthetic methods. Other methods for the synthesis of $GABA_B$ ligands described herein are either described in the art or will be readily apparent to the skilled artisan in view of the references provided herein. Accordingly, the methods presented in the schemes provided by the present disclosure are illustrative rather than comprehensive.

The substructure
as used for example in Schemes 1-23 means arylene or heteroarylene where arylene is a bivalent group derived from aryl by removal of a hydrogen atom from two ring carbon atoms, and heteroarylene is a bivalent group derived from a heteroaryl group by removal of a hydrogen atom from two ring atoms.
Scheme 1
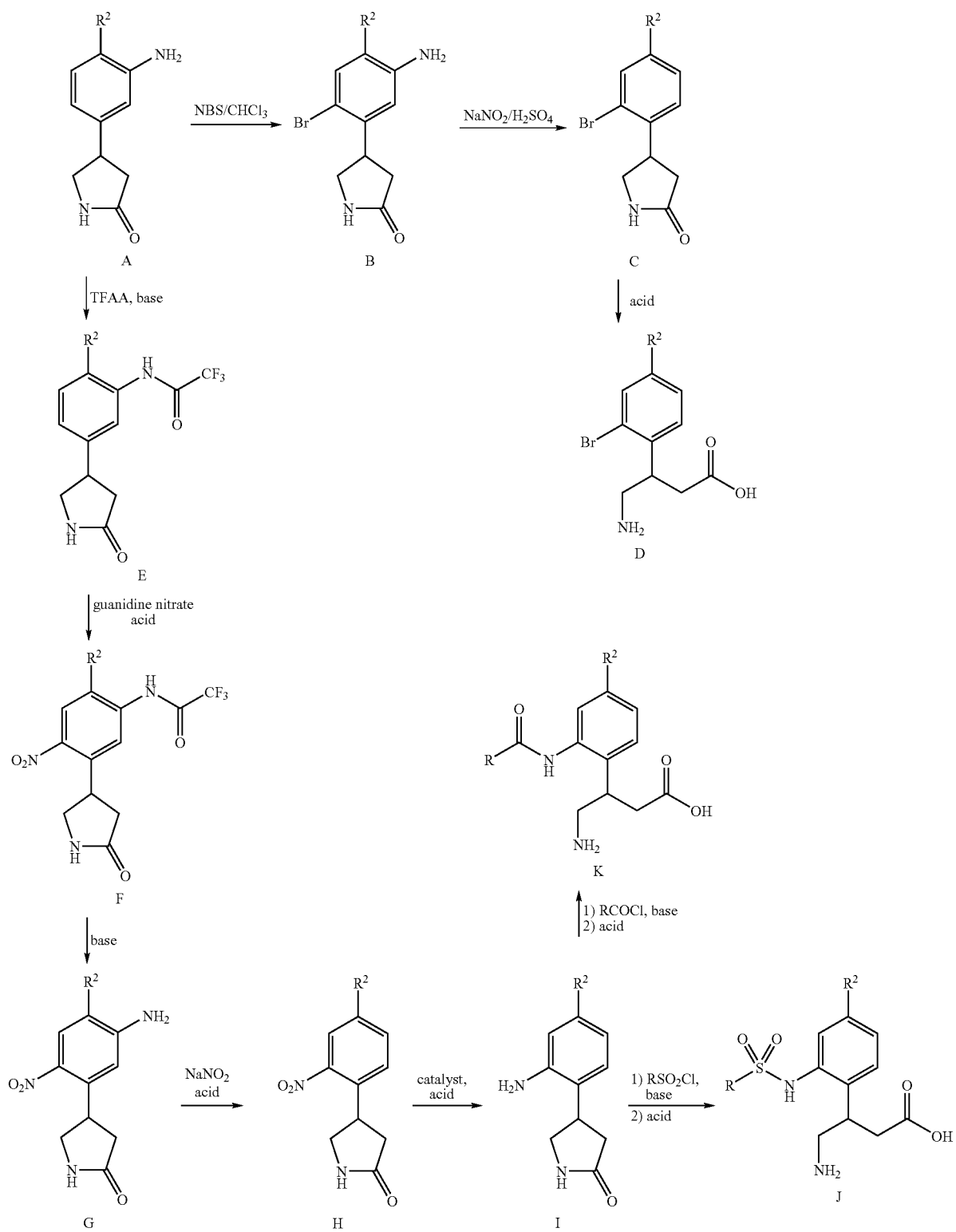

Precursors for compounds of Formula (I) in which R³ is hydrogen and R⁴ is —X—Y, i.e. 2-substituted phenyl derivatives, may be synthesized following the methods shown in Schemes 1-8.

Synthesis of 2-sulfonamide substituted phenyl and 2-amide substituted phenyl derivatives is shown in Scheme 1.

To prepare 2-bromo substituted phenyl derivatives, 3-amino substituted phenyl lactam (A) may be treated with N-bromosuccinimide (NBS) to provide 2-bromo, 5-amino substituted phenyl lactam (B). The amino group may be removed by diazotization to provide lactam (C). Opening of the lactam ring in the presence of an acid at elevated temperature provides the corresponding 2-bromo substituted phenyl derivative (D).

Precursors of 2-sulfonamide substituted phenyl and 2-amide substituted phenyl derivatives may be prepared by first treating 3-amino substituted phenyl lactam (A) in an organic solvent and in the presence of an organic base such as triethylamine, with trifluoroacetic anhydride (TFAA) to provide the corresponding 3-trifluoroacetamide substituted phenyl lactam (E). Lactam (E) may then be treated with guanidine nitrate in the presence of an acid to provide 3-trifluoroacetamide-2-nitro substituted phenyl lactam (F). The amide may be deprotected by treating lactam (F) with sodium hydroxide to provide 2-nitro-5-amino substituted phenyl lactam (G), and the amino group then removed by treating with sodium nitrite in the presence of a strong acid to provide 2-nitro substituted phenyl lactam (H). The nitro group may be converted to an amine by treating lactam (H) under reducing conditions to provide the corresponding 2-amino substituted lactam (I).

2-Sulfonamide substituted phenyl derivatives may be prepared by reacting lactam (I) with an appropriate sulfonyl chloride in the presence of an organic base to provide, after acid-catalyzed ring opening, the corresponding 2-sulfonamide substituted phenyl derivative (J).

2-Amide substituted phenyl derivatives may be prepared by reacting lactam (I) and an appropriate acid chloride in the presence of an organic base to provide the corresponding 2-amide substituted phenyl derivative (K).

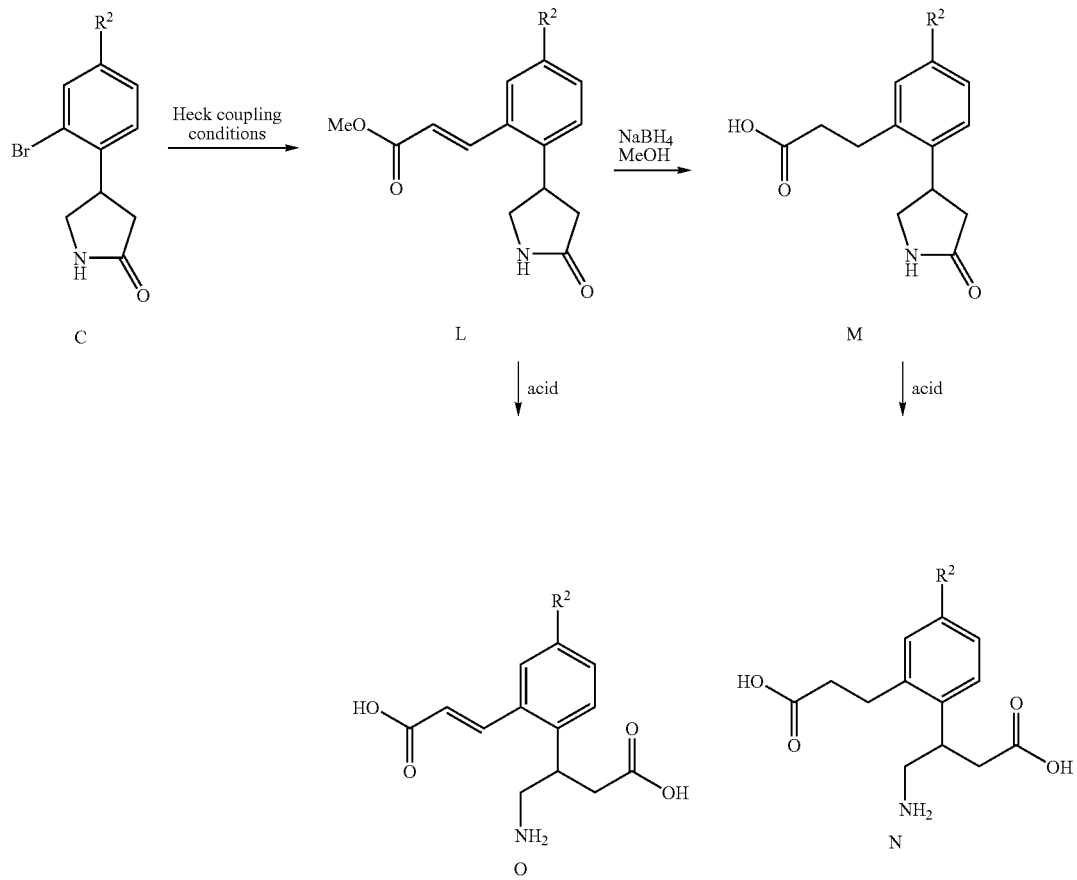

2-Carboxyalkyl substituted phenyl derivatives may be synthesized following the methods described in Scheme 2. Using Heck coupling conditions 2-bromo substituted lactam (C) may be converted to the corresponding 2-alkyloxycarbonylalkyl substituted phenyl lactam (L). Following treatment of lactam (L) with acid at elevated temperatures to simultaneously convert the ester to a carboxyl group and open the lactam ring provides the corresponding 2-carboxyalkyl substituted derivative (O). Treating lactam (L) with a reducing agent such as NaBH$_4$ in methanol provides the corresponding 2-carboxylalkyl substituted phenyl lactam (M). Treatment of lactam (M) with a strong acid at elevated temperature to open the lactam ring provides the corresponding 2-carboxylalkyl substituted phenyl derivative (N).

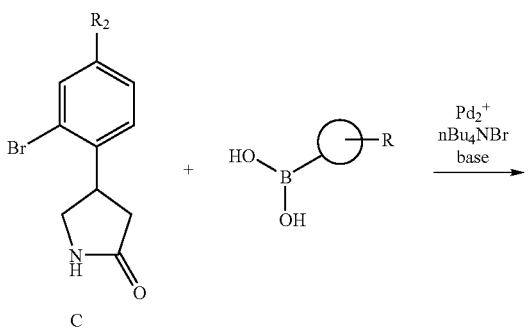

Scheme 4

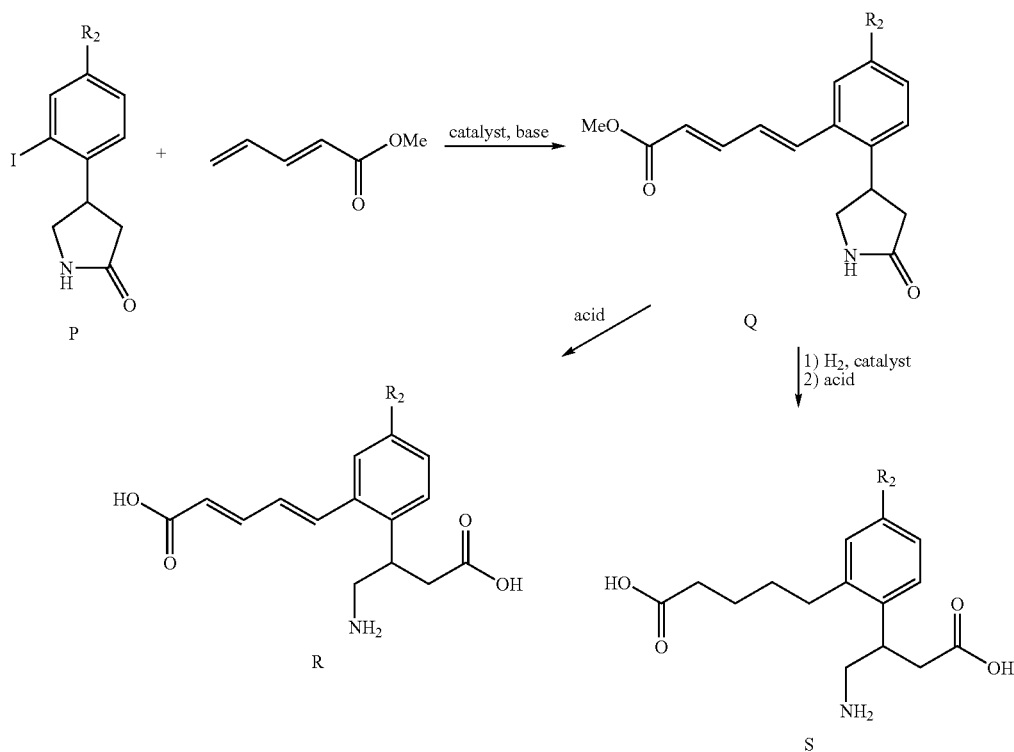

Scheme 3

Other 2-substituted carboxylalkyl derivatives may be synthesized following the methods shown in Scheme 3 using 3-iodo substituted phenyl lactam (P) prepared as described for the preparation of the corresponding 2-bromo substituted phenyl lactam (C) according to Scheme 1. 2-Iodo substituted phenyl lactam (P) may be reacted with an unsaturated carboxymethyl ester in the presence of an inorganic and organic, catalyst, and an organic base at elevated temperature to provide the corresponding 2-methylesteralkyl substituted lactam (O). Lactam ring opening and removal of the terminal methyl group followed by treatment with an acid at elevated temperature provides the corresponding 2-carboxyalkenyl derivative (R). Reducing lactam (O) in the presence of a platinum catalyst and hydrogen followed by lactam ring opening provides the corresponding 2-carboxyalkyl substituted phenyl derivative (S).

-continued

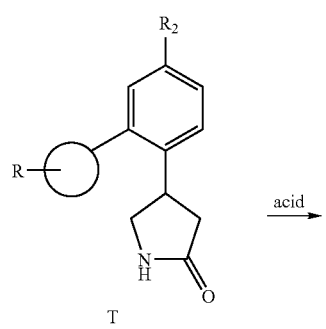

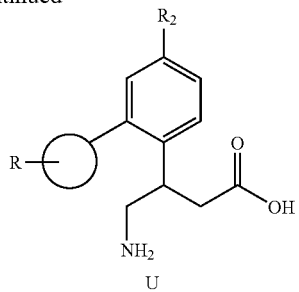

2-Aryl, 2-substituted aryl, 2-heteroaryl, and 2-substituted heteroaryl substituted phenyl derivatives may be synthesized following the palladium catalyzed Suzuki cross-coupling reaction shown in Scheme 4.

2-Bromo substituted phenyl lactam (C) and an appropriate boronic acid may be reacted in the presence of $Pd^{2+}$ (such as a provided by $Pd(OAc)_2$), tetrabutylammonium bromide, and an alkali phosphate such as $K_3PO_4$ at elevated temperature to provide the corresponding 2-substituted lactam (T). Treating an aqueous solution of lactam (T) with a strong acid at elevated temperature to open the lactam ring provides the corresponding 2-aryl, 2-substituted aryl, 2-heteroaryl, and 2-substituted heteroaryl substituted phenyl derivative (U).

2-Aryl-, 2-(substituted aryl), 2-heteroaryl, and 2-(substituted heteroaryl) oxy-substituted phenyl derivatives may be synthesized following the methods shown in Scheme 5. Reacting 2-bromo substituted phenyl lactam (C) with an appropriate hydroxy-aryl, -substituted aryl, -heteroaryl, or -substituted heteroaryl in the presence of CuI and a base such as cesium carbonate ($Cs_2CO_3$) provides the corresponding 2-aryloxy, -substituted aryloxy-, heteroaryloxy- or substituted heteroaryloxy-lactam (V), which following lactam ring opening provides the corresponding 2-substituted 2-aryl-, 2-(substituted aryl), 2-heteroaryl, and 2-(substituted heteroaryl) oxy substituted phenyl derivative (W).

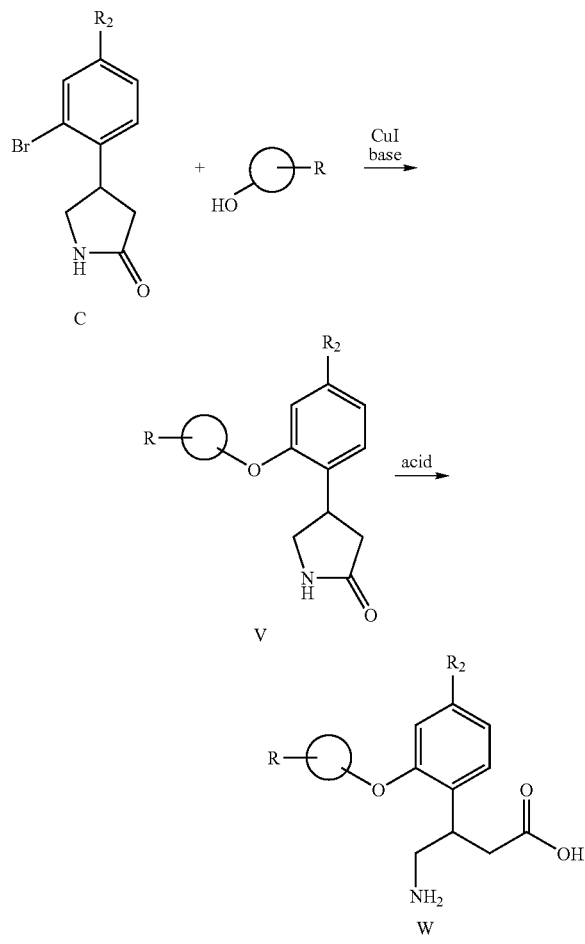

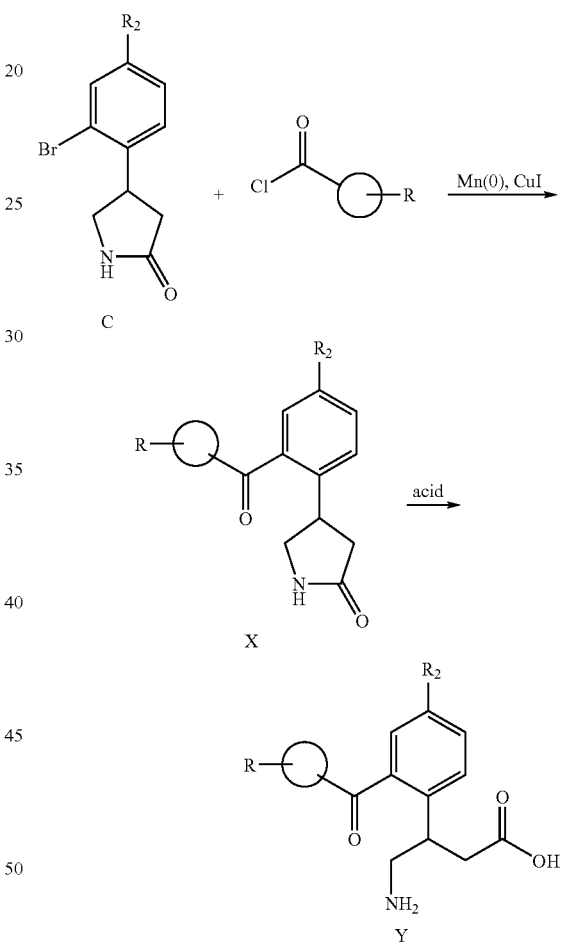

2-Aryl-, 2-(substituted aryl), 2-heteroaryl, and 2-(substituted heteroaryl) carbonyl substituted phenyl derivatives may be synthesized following the methods shown in Scheme 6. Reacting 2-bromo substituted phenyl lactam (C) with an appropriate aroyl-substituted aroyl-, heteroaroyl-, or substituted heteroaroyl-chloride in the presence of CuI and a Mn(0) catalyst provides the corresponding 2-substituted lactam (X), which following lactam ring opening provides the corresponding 2-aryl-, 2-(substituted aryl), 2-heteroaryl, and 2-(substituted heteroaryl) carbonyl substituted phenyl derivative (Y).

Scheme 7

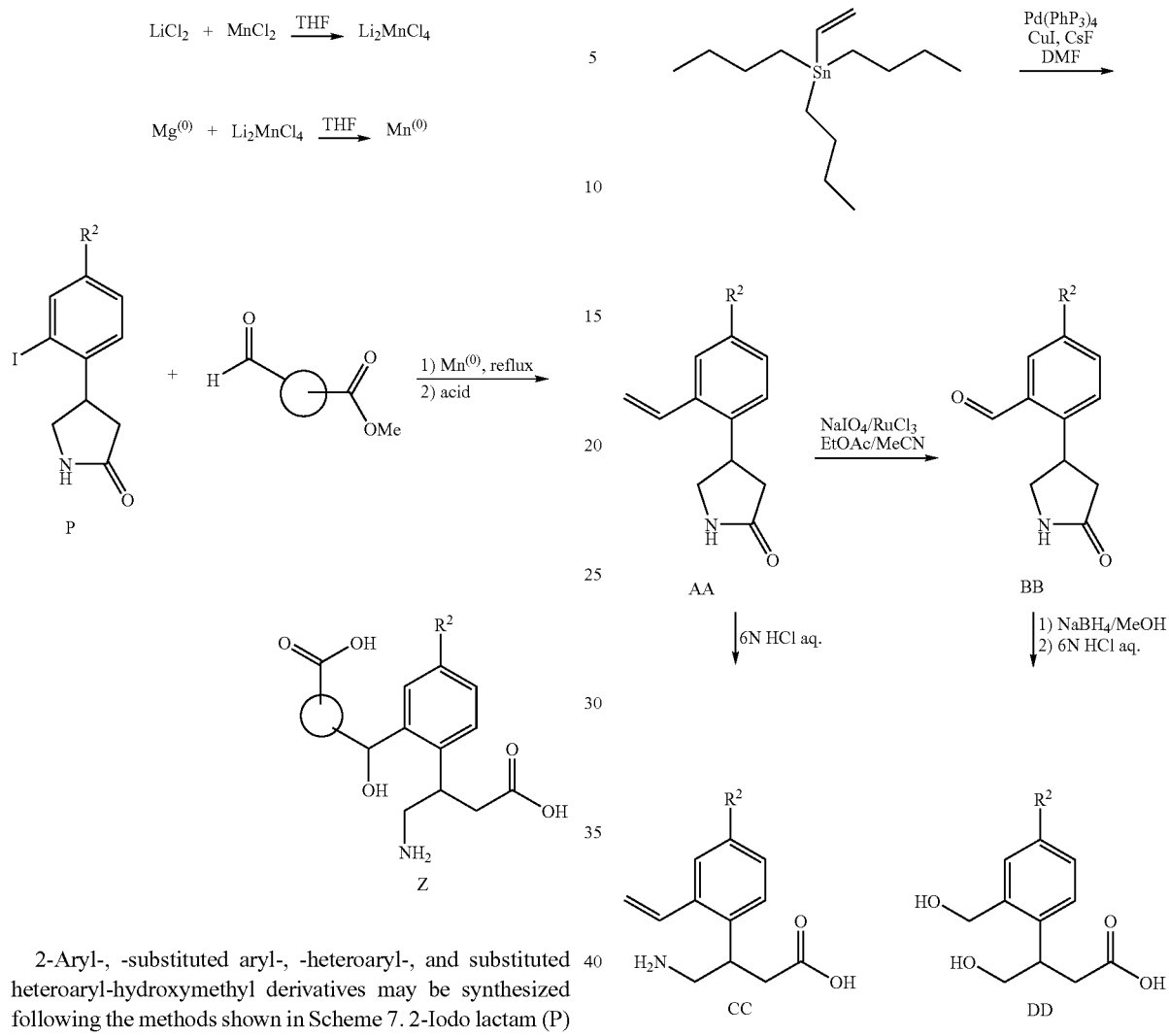

2-Aryl-, -substituted aryl-, -heteroaryl-, and substituted heteroaryl-hydroxymethyl derivatives may be synthesized following the methods shown in Scheme 7. 2-Iodo lactam (P) may be reacted with an appropriate formyl substituted aryl, substituted aryl, heteroaryl, or substituted heteroaryl in the presence of Mn(0) under reflux conditions followed by lactam ring opening to provide the corresponding 2-aryl-, -substituted aryl-, -heteroaryl-, and substituted heteroaryl-hydroxymethyl substituted phenyl derivative (Z).

Scheme 8

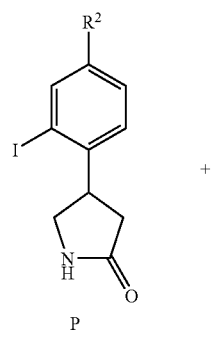

Methods of synthesizing useful intermediates are shown in Scheme 8. 2-Iodo substituted phenyl lactam (P) may be reacted with Pd(PhP$_3$)$_4$, Pd2+, CuI, and CsF in an organic solvent to provide 2-vinyl substituted phenyl lactam (AA). 2-Vinyl substituted phenyl lactam (AA) may be treated with aqueous 6N HCl at elevated temperature to open the lactam ring to provide 2-vinyl substituted phenyl intermediate (CC), which may be used to synthesize a variety of 2-substituted phenyl derivatives. Alternatively, 2-vinyl lactam (AA) may be treated with an oxidizing agent such as NaIO$_4$ in the presence of a catalyst such as ruthenium trichloride (RuCl$_3$) to provide 2-acyl substituted phenyl intermediate (BB), which following reduction to the 2-hydroxymethyl lactam and lactam ring opening provides the 2-hydroxymethyl substituted phenyl intermediate (DD).

Compounds of Formula (I) in which R$^3$ is —X—Y and R$^4$ is hydrogen, i.e., 3-substituted phenyl derivatives, may be synthesized following to the methods described in Schemes 9-21.

Scheme 9

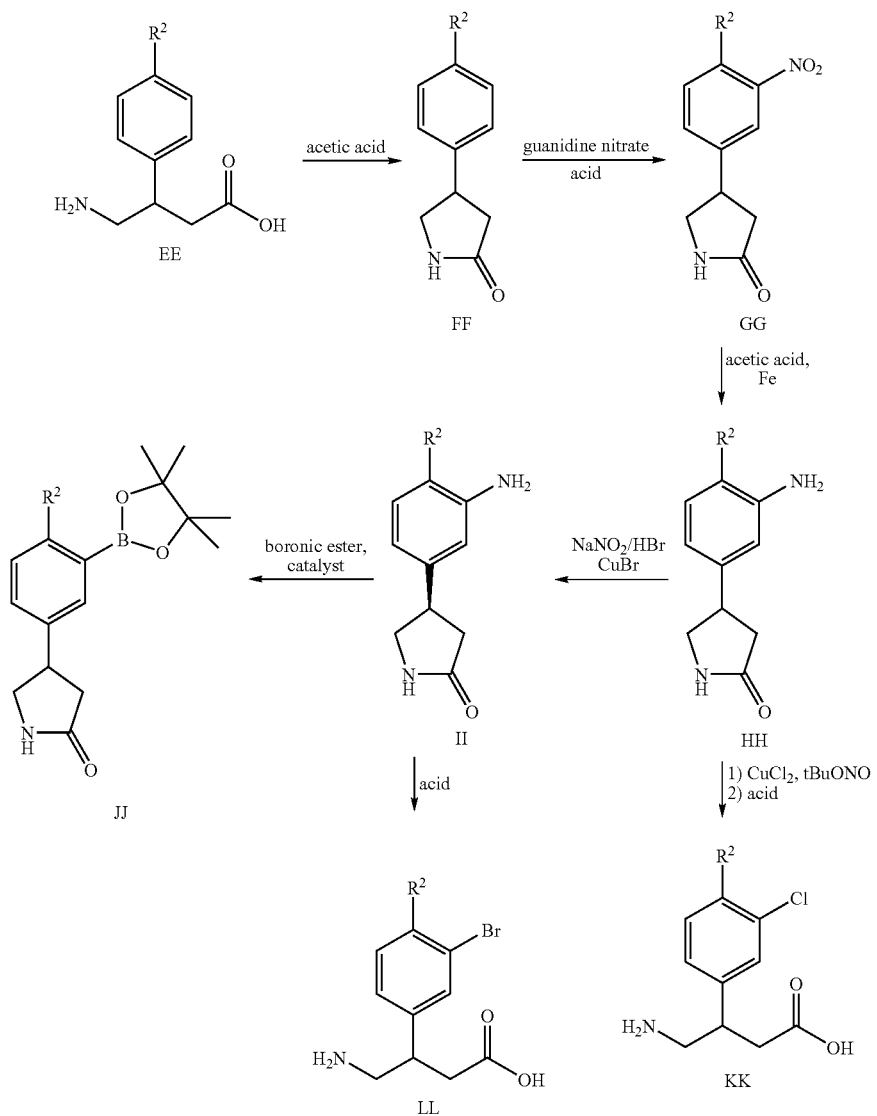

Methods of synthesizing precursors for 3-substituted phenyl derivatives are shown in Scheme 9. For example, 4-amino-3-(4-chlorophenyl)butanoic acid (EE), where $R^2$ is chloro, may be treated with acetic acid under reflux conditions to provide 4-chlorophenyl lactam (FF). Reacting lactam (FF) with guanidine nitrate under acidic conditions provides 3-nitro substituted lactam (GG), which may be converted to the 3-amino substituted phenyl lactam (HH) upon treatment with acetic acid and Fe(0). Treatment of 3-amino lactam (HH) with an aqueous solution of HBr and sodium nitrite ($NaNO_2$) in the presence of CuBr provides 3-bromo substituted phenyl lactam (GG). The 3-boronic ester (JJ) may be synthesized by treating lactam (II) with bis(pinalcolato)diboron, 1,1-bis(diphenylphosphino)ferrocene)dichloro palladium and potassium acetate at elevated temperature.

Treating lactam (II) with an acid at elevated temperature to open the lactam ring provides 3-bromo substituted phenyl derivative (LL). Treating lactam (HH) with tert-butyl nitrite (tert-$BuNO_2$) and Cu(II) chloride in the presence of an organic catalyst followed by lactam ring opening provides 3-chloro substituted phenyl derivative (KK).

Scheme 10

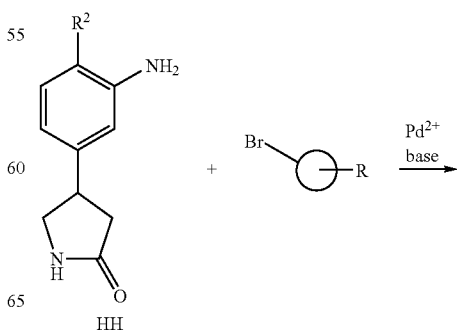

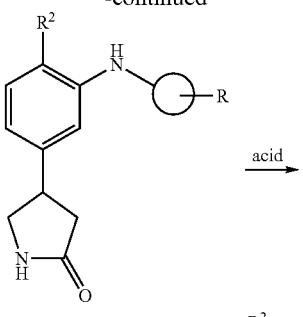

MM

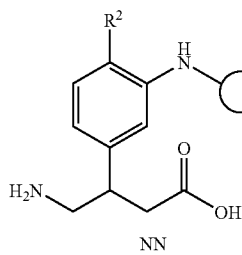

NN 3-(Arylamine-, -substituted arylamine-, heteroarylamine, and substituted heteroarylamine) substituted phenyl derivatives (NN) may be prepared according to the methods shown in Scheme 10. 3-Amino substituted phenyl lactam (HH) and an appropriate bromo-substituted aryl, substituted aryl, heteroaryl, or substituted heteroaryl may be treated with $Pd^{2+}$ (for example, palladium acetate $(Pd(OAc)_2)$, and a base such as an alkali carbonate to provide the corresponding lactam (MM), which following ring opening in the presence of an acid at elevated temperature provides the corresponding 3-arylamine-, -substituted arylamine-, heteroarylamine, or substituted heteroarylamine) substituted phenyl derivative (NN).

Scheme 11

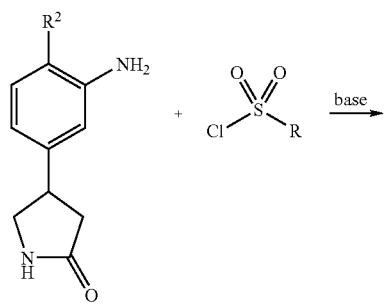

HH

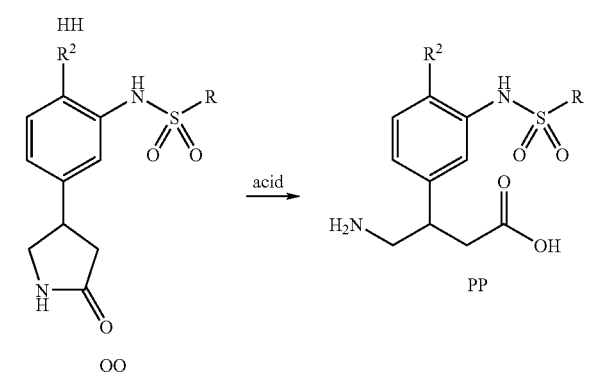

OO

PP 3-(Substituted sulfonamide) substituted phenyl derivatives (PP) may be synthesized according to the methods shown in Scheme 11. 3-Amino substituted phenyl lactam (HH) in methylene chloride may be treated with an appropriate sulfonyl chloride in the presence of an organic base to provide the corresponding 3-sulfonamide substituted phenyl lactam (OO), which following ring opening provides 3-(substituted sulfonamide) substituted phenyl derivative (PP).

Scheme 12

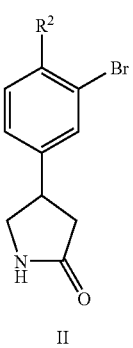

II

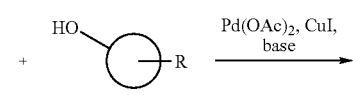

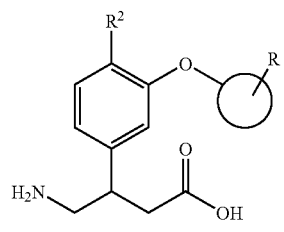

QQ

RR 3-(Aryloxy, substituted aryloxy, heteroaryloxy, and substituted heteroaryloxy) substituted phenyl derivatives (RR) may be synthesized according to the methods shown in Scheme 12. 3-Bromo substituted phenyl lactam (II) and an appropriate hydroxyl-substituted aryl, substituted aryl, heteroaryl, or substituted heteroaryl may be treated with $Pd^{2+}$, CuI, and a base at elevated temperature to provide the corresponding 3-substituted phenyl lactam (QQ), which following lactam ring opening provides 3-(substituted aryloxy, substituted aryloxy, heteroaryloxy, or substituted heteroaryloxy phenyl) substituted phenyl derivative (RR).

Scheme 13

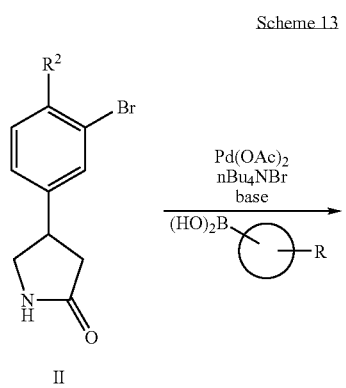

Scheme 14

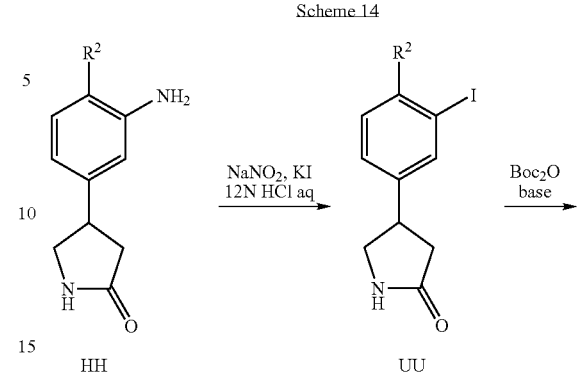

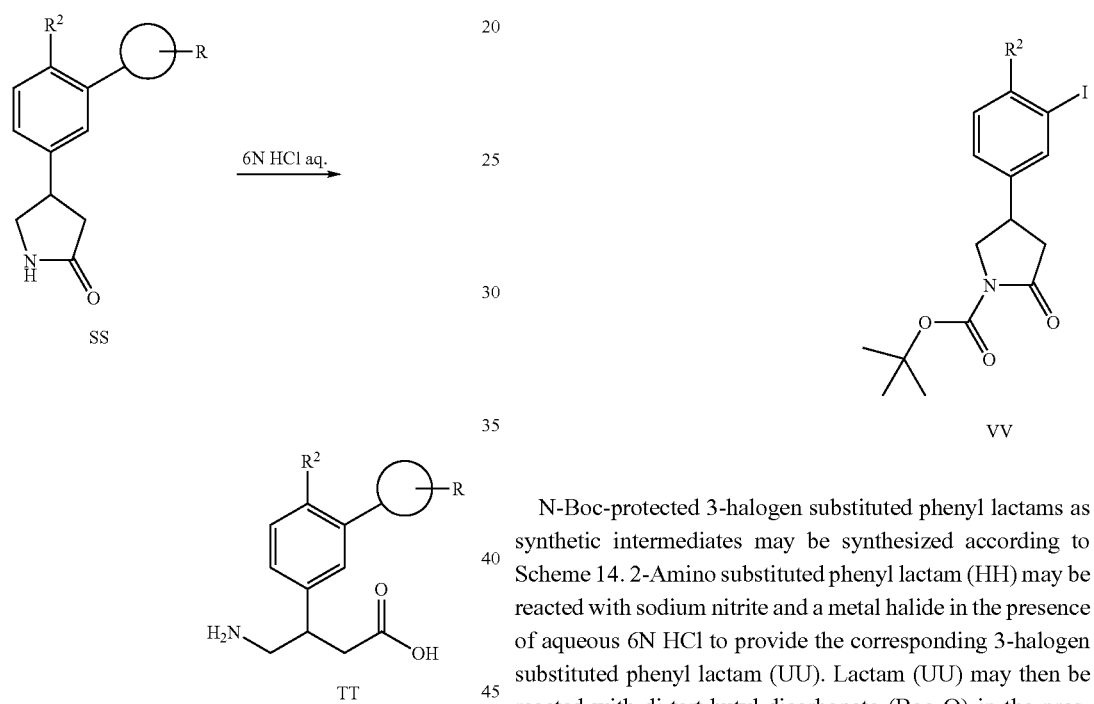

3-(Aryl, substituted aryl, heteroaryl, and substituted heteroaryl) substituted phenyl derivatives (TT) may be synthesized according to the methods shown in Scheme 13. 3-Bromo substituted phenyl lactam (II) and an appropriate 3-aryl, substituted aryl, heteroaryl, or substituted heteroaryl boronic acid may be reacted with palladium acetate (Pd(OAc)$_2$), a reducing agent such as nBu$_4$NBr, and a base such as an alkali phosphate to provide the corresponding 3-substituted phenyl lactam (SS), which following lactam ring opening using an aqueous solution of 6N HCl provides the corresponding 3-(aryl, substituted aryl, heteroaryl, and substituted heteroaryl) I substituted phenyl derivative (TT).

Alternatively, 3-aryl, substituted aryl, heteroaryl, and substituted heteroaryl substituted phenyl derivatives (TT) may be synthesized according to the methods shown in Schemes 14-15.

N-Boc-protected 3-halogen substituted phenyl lactams as synthetic intermediates may be synthesized according to Scheme 14. 2-Amino substituted phenyl lactam (HH) may be reacted with sodium nitrite and a metal halide in the presence of aqueous 6N HCl to provide the corresponding 3-halogen substituted phenyl lactam (UU). Lactam (UU) may then be reacted with di-tert-butyl-dicarbonate (Boc$_2$O) in the presence of an organic base to provide N-Boc protected 3-halogen substituted phenyl lactam (VV).

Scheme 15

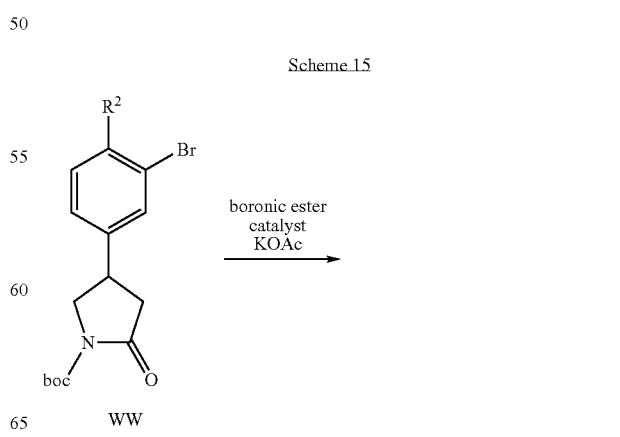

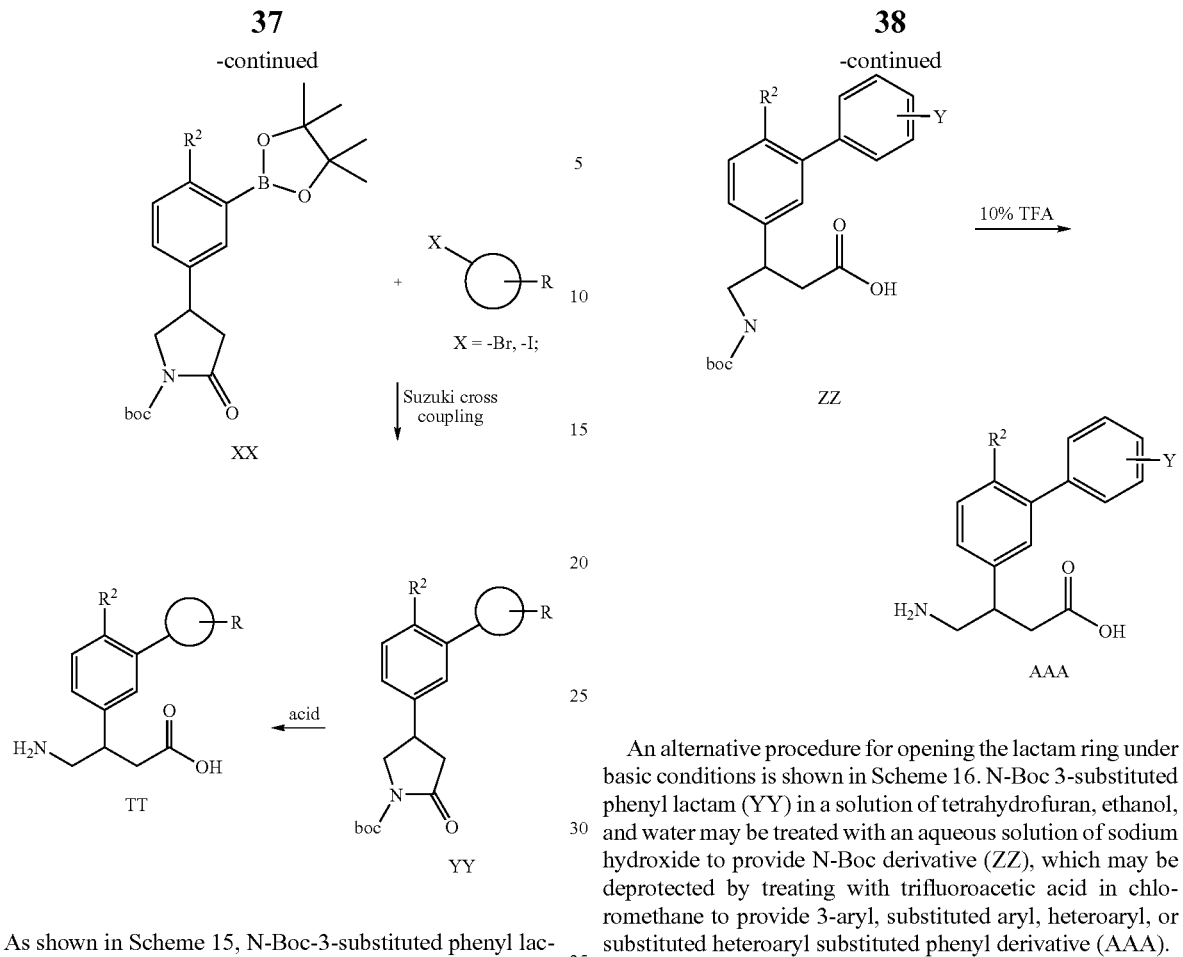

As shown in Scheme 15, N-Boc-3-substituted phenyl lactam (WW) and 1,1-bis(diphenyl)phosphino)ferrocene) dichloro palladium (II) (boronic ester) may be reacted at elevated temperature under a nitrogen atmosphere to provide N-Boc-3-(4,4,5,5-tetramethyl)1,3,2-dioxaborolan-2-yl) substituted lactam (XX). Reacting lactam (XX) with a halo-substituted 3-aryl, substituted aryl, heteroaryl, or substituted heteroaryl substituted phenyl using Suzuki cross-coupling reaction conditions provides the corresponding 3-substituted phenyl lactam (YY), which following ring lactam opening provides the 3-aryl, substituted aryl, heteroaryl, or substituted heteroaryl substituted phenyl derivative (TT).

An alternative procedure for opening the lactam ring under basic conditions is shown in Scheme 16. N-Boc 3-substituted phenyl lactam (YY) in a solution of tetrahydrofuran, ethanol, and water may be treated with an aqueous solution of sodium hydroxide to provide N-Boc derivative (ZZ), which may be deprotected by treating with trifluoroacetic acid in chloromethane to provide 3-aryl, substituted aryl, heteroaryl, or substituted heteroaryl substituted phenyl derivative (AAA).

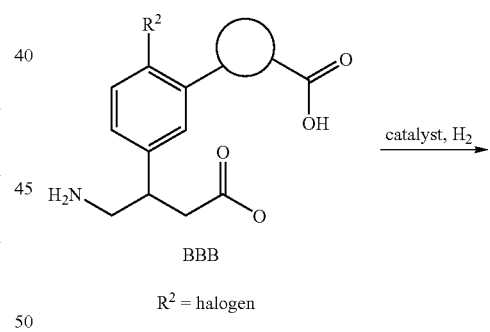

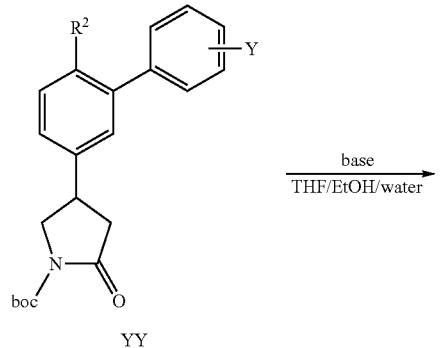

Dehalogenation of $R^2$ may be accomplished according to the procedure shown in Scheme 17. Using hydrogenolysis conditions, 3-substituted phenyl derivative (BBB) may be reacted with a hydrogenation catalyst such as 5% Pd/C and hydrogen gas to provide the corresponding derivative (CCC) in which $R^2$ is hydrogen.

Scheme 18

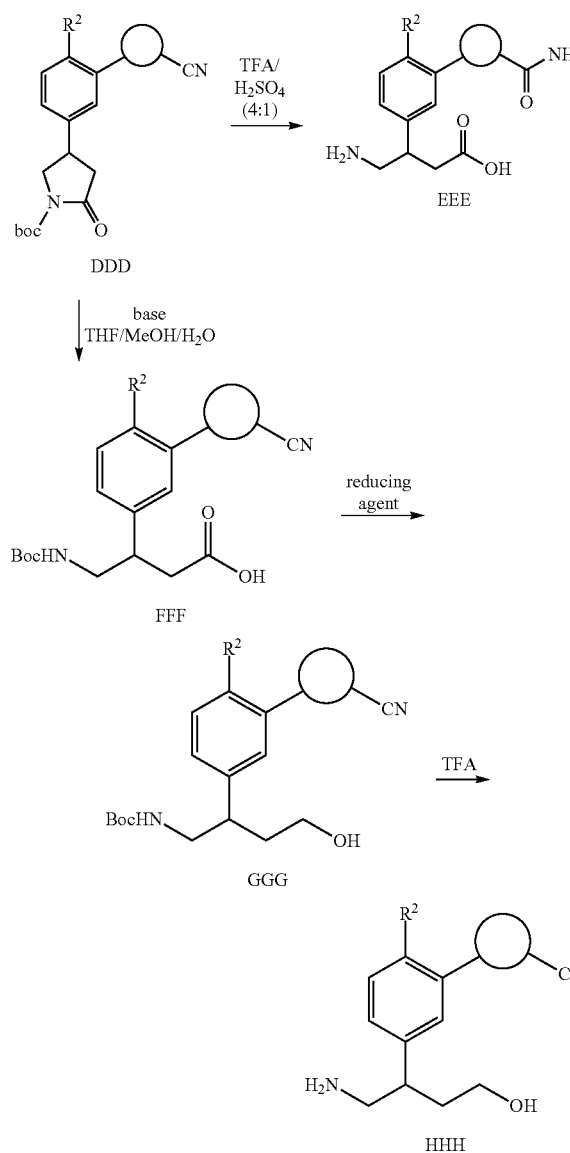

Scheme 19

Methods for synthesizing other 3-aryl and heteroaryl substituted phenyl derivatives are shown in Scheme 18. 3-Cyanophenyl substituted phenyl lactam (DDD) synthesized using the Suzuki cross-coupling method may be treated with trifluoroacetic acid and sulfuric acid ($H_2SO_4$) in a ratio of 4:1 to simultaneously open the lactam ring, deprotect the amino group, and exchange the amide group to provide the corresponding 3-amidophenyl substituted phenyl derivative (EEE).

Butanol derivatives of substituted phenyl derivatives may be synthesized as shown in Scheme 18 by treating phenyl substituted Boc-protected lactam (DDD) in a solution of THF, methanol, and water in the presence of a base to open the lactam ring to provide lactam (FFF). The carbonyl group may be reduced by treating lactam (FFF) with a reducing agent to provide (GGG), which may then be deprotected by treating with TFA to provide the corresponding butanol derivative (HHH).

3-Sulfonylaryl and sulfonyl heteroaryl substituted phenyl-derivatives may be synthesized according to the methods shown in Scheme 19. 3-Thiophenyl substituted phenyl boc-protected lactam (III) synthesized according the Suzuki cross-coupling method described in Scheme 4, in dichloromethane may be treated with an oxidizing agent such as 3-chloroperoxybenzoic acid (mCPBA) to provide the corresponding sulfonyl Boc-protected lactam (JJJ), which following ring opening under acidic conditions provides the corresponding 3-sulfonylaryl or sulfonylheteroaryl substituted phenyl derivative (KKK).

Scheme 20

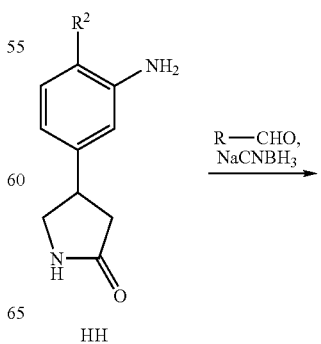

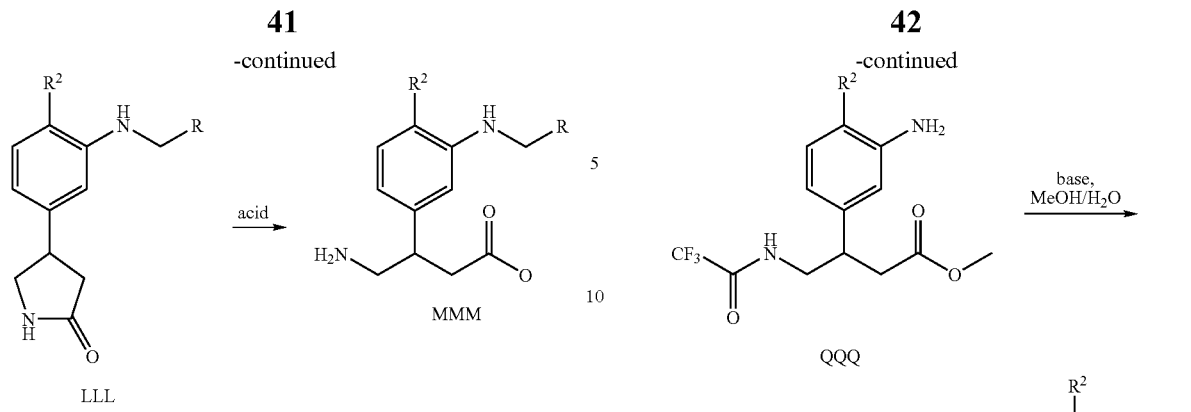

3-(Alkylamine) substituted derivatives may be synthesized according to the methods shown in Scheme 20. 3-Amino substituted phenyl lactam (HH) may be reacted with an aldehyde in the presence of sodium cyanoborohydride (NaCNBH$_3$) to provide the corresponding 3-(alkylamine) substituted phenyl lactam (LLL), which following lactam ring opening under acidic conditions provides the corresponding 3-(alkylamine) substituted phenyl derivative (MMM).

3-Amino substituted phenyl derivatives may be synthesized according to the procedure shown in Scheme 21. Methyl (3R)-4-amino-3-(4-substituted phenyl)butanoate hydrochloride (NNN) may be reacted with trifluoroacetic anhydride (TFAA) in the presence of an organic base to provide the corresponding N-trifluoroacetyl protected intermediate (OOO). Intermediate (OOO) may be treated with concentrated sulfuric acid and nitric acid to provide the corresponding 3-nitro substituted phenyl intermediate (PPP), which may be converted to the corresponding 3-amino substituted intermediate (QQQ) upon treatment with acetic acid (AcOH) in the presence of an inorganic catalyst such as Fe. 3-Amino substituted intermediate (QQQ) may then be deprotected following treatment with a sodium base to provide the corresponding 3-amino substituted phenyl derivative (RRR).

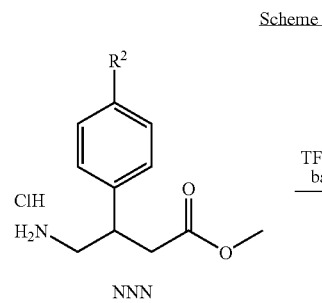

Scheme 21

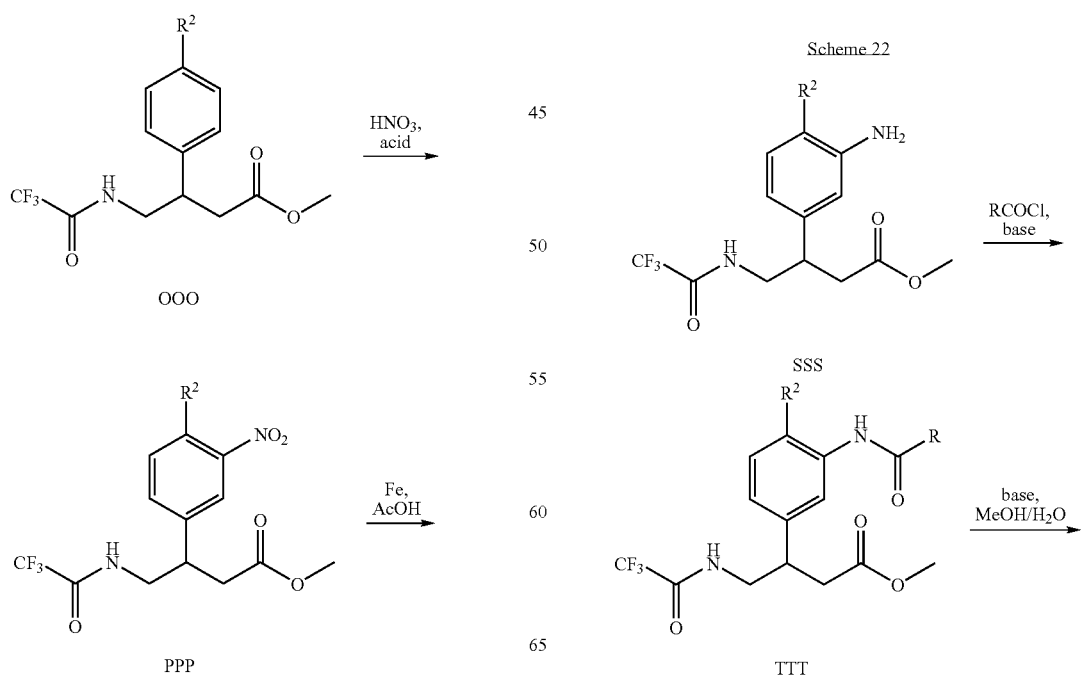

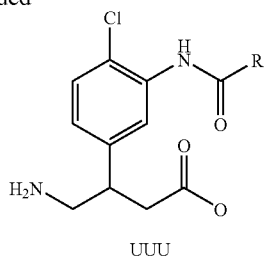

UUU

3-Amide substituted phenyl derivatives may be synthesized according to the procedure shown in Scheme 22. 3-Amino substituted phenyl intermediate (SSS), prepared according to the method shown in Scheme 21, may be reacted with an acylchloride in the presence of an organic base to provide the corresponding 3-amide substituted phenyl intermediate (UT), which following deprotection with a sodium base provides 3-amide substituted phenyl derivative (UUU).

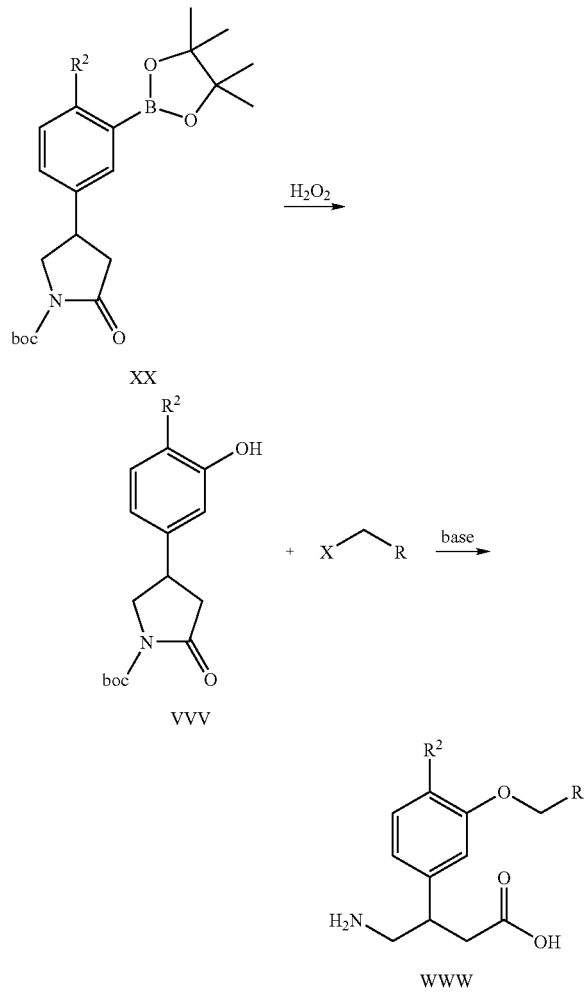

Scheme 23

3-Alkoxy substituted phenyl derivatives may be synthesized according to the methods shown in Scheme 23. 3-[4,4,5,5-Tetramethyl(1,3,2-dioxaborrolan-2-yl)] Boc-protected lactam (XX), prepared according to the method shown in Scheme 15, may be treated with hydrogen peroxide to form the corresponding lactam (VVV). Lactam (VVV) may then be reacted with an appropriate electrophile (X—CH$_2$—R) in the presence of a base such as an alkali carbonate to provide the corresponding 3-alkoxy substituted phenyl lactam, which following opening of the lactam ring under acidic conditions provides 3-alkoxy substituted phenyl derivative (WWW).

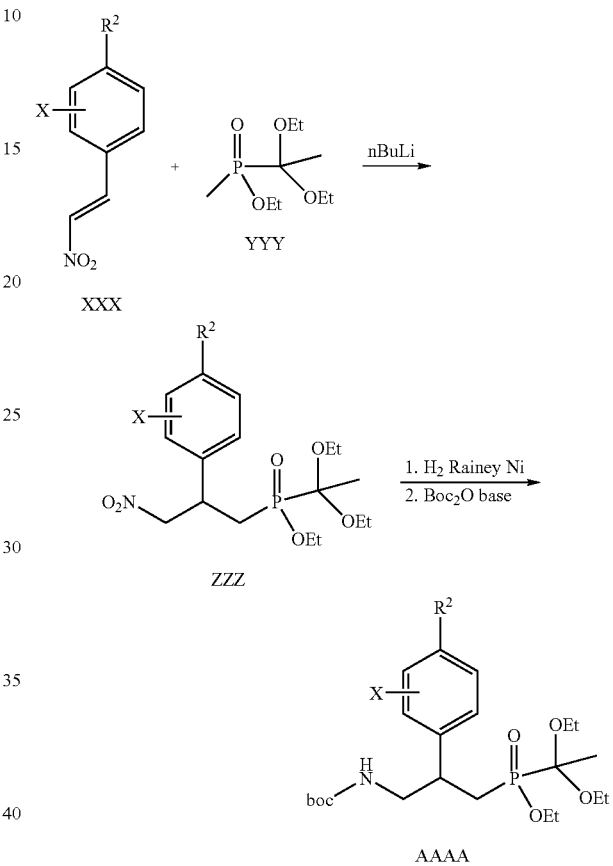

Scheme 24

Preparation of amino-phosphinic acid embodiments of Formula I can be accomplished using the methodology disclosed in Schemes 24-26. Treatment of substituted nitrostyrene (XXX) with the anion of (1,1-dethyloxoethyl)ethoxymethylphosphino-1-one YYY to provide the nitro-phosphin-1-one (ZZZ), as shown in Scheme 24. Reduction of the nitro group with hydrogen and Rainey nickel catalyst followed by protection of the resulting amine to give the corresponding Boc protected amine (AAAA).

Scheme 25

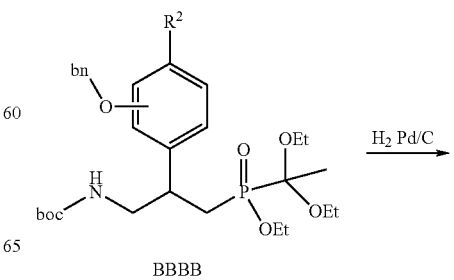

BBBB

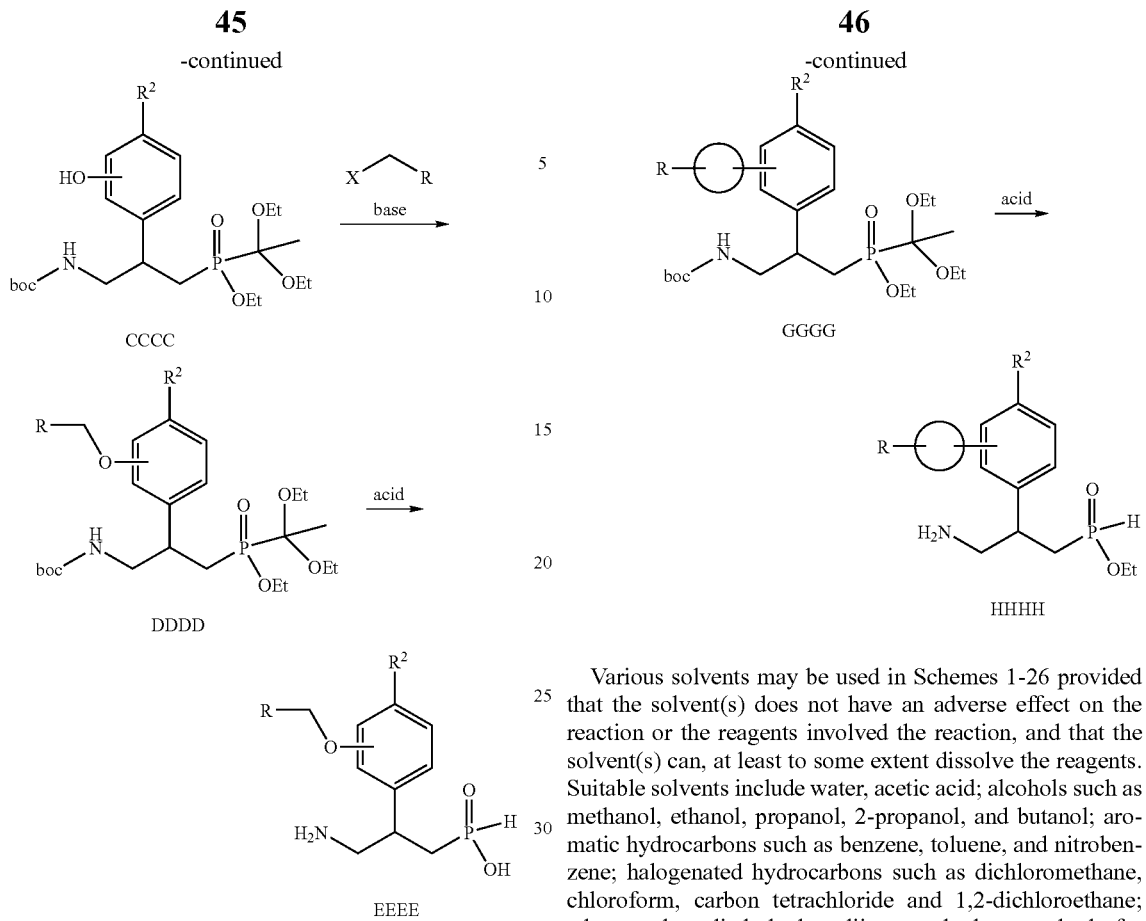

In the cases where X is an O-benzyl group (BBBB) it can be selectively removed by hydrogenation in the presence of a palladium on charcoal catalyst to the corresponding phenols (CCCC) which could be reacted with an alkyl halide in the presence of a base to give the corresponding phenyl ethers (DDDD). These can subsequently be deprotected under acidic conditions to give the corresponding phosphinic acids (FFFF) as shown in Scheme 25.

As shown in Scheme 26, in the case where the X group of AAAA is equal to iodine or bromine (compound FFFF) can be reacted with an arylboronic acid under Suzuki coupling conditions to give the substituted aryl-phosphin-1-one (GGGG) which can be treated with acid to give the desired amino-phosphinic acid HHHH. Alternatively protected phosphonate GGGG may be reacted first with TMSCl followed by acid to produce the desired amino phosphinic acids (HHHH).

Scheme 26

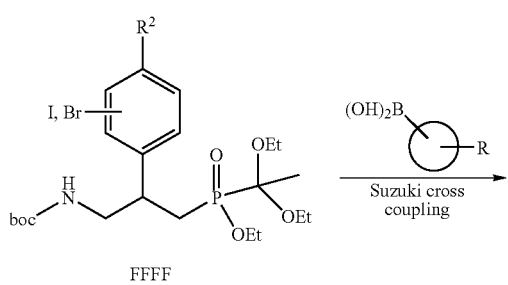

FFFF

Various solvents may be used in Schemes 1-26 provided that the solvent(s) does not have an adverse effect on the reaction or the reagents involved the reaction, and that the solvent(s) can, at least to some extent dissolve the reagents. Suitable solvents include water, acetic acid; alcohols such as methanol, ethanol, propanol, 2-propanol, and butanol; aromatic hydrocarbons such as benzene, toluene, and nitrobenzene; halogenated hydrocarbons such as dichloromethane, chloroform, carbon tetrachloride and 1,2-dichloroethane; ethers such as diethyl ether, diisopropyl ether, tetrahydrofuran and dioxane; amines such as N-methylmorpholine, triethylamine, tripropylamine, tributylamine, diisopropylethylamine, dicyclohexylamine, N-methylpiperidine, N-methylpyrrolidine, pyridine, 4-pyrrolidinopyridine, N,N-dimethylaniline, and N,N-diethylaniline; amides such as N,N-dimethylformamide and N,N-dimethylacetamide; sulfoxides such as dimethyl sulfoxide; and combinations of any of the foregoing.

Certain methods shown in Schemes 1-26 may be carried out in the presence of a suitable base. Examples of useful organic bases include amines such as N-methylmorpholine, triethylamine, tripropylamine, tributylamine, diisopropylethylamine, dicyclohexylamine, N-methyl-piperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene, 1,4-diazabicyclo[2.2.2]octane, and 1,8-diazabicyclo[5.4.0]undec-7-ene. Examples of other useful bases include alkali metal hydroxides such as lithium hydroxide, sodium hydroxide, and potassium hydroxide; alkali metal alkoxides such as sodium methoxide, sodium ethoxide, and potassium tert-butoxide; alkali metal carbonates such as lithium carbonate, sodium carbonate, potassium carbonate, and cesium carbonate; and alkali metal hydrides such as lithium hydride, sodium hydride and potassium hydrate.

Certain methods shown in Schemes 1-26 may be carried out in the presence of a suitable acid. Examples of suitable acids include hydrochloric acid, trifluoroacetic acid, sulfuric acid, acetic acid, and p-toluenesulfonic acid.

Certain methods shown in Schemes 1-26 may be carried out in the presence of a reducing agent. Examples of suitable reducing agents include metal borohydrides such as sodium borohydride, sodium cyanoborohydride, and sodium triacetoxyborohydride; hydrides such as lithium aluminum hydride and diisobutyl aluminum; and combinations of hydrogen gas and a catalyst such as palladium-carbon, platinum, or Raney nickel.

Reactions shown in Schemes 1-26 may take place over a wide range of temperatures. An appropriate reaction temperature can depend upon such factors as the nature of the solvent and the starting materials. It is generally convenient to carry out a reaction at a temperature of from about 0° C. to about 120° C., although other appropriate temperatures may be employed. The time required for a reaction to complete may also vary depending on factors such as the reaction temperature, the nature of the starting materials, and the solvent used. Reaction times can be, for example, from about 5 minutes to about 48 hours.

Certain compounds of Formula (I) are $GABA_B$ receptor ligands, which are capable of modulating $GABA_B$ receptors. $GABA_B$ receptor ligands may exhibit agonist, partial agonist, antagonist, and/or inverse agonist activity at $GABA_B$ receptors, or may be allosteric modulators of $GABA_B$ receptors. Compounds of Formula (I) may exhibit competitive or non-competitive interaction kinetics with substrates for $GABA_B$ receptors.

Full $GABA_B$ receptor agonists bind to the binding site of endogenous $GABA_B$ receptor agonist and display full efficacy. Partial $GABA_B$ agonists also bind at the $GABA_B$ receptor at the endogenous agonist binding site and activate the receptor but exhibit only partial efficacy relative to a full agonist. Partial agonists can also be considered ligands that exhibit both agonistic and antagonistic effects, e.g., the presence of a partial agonist will reduce the receptor activation of a full agonist. $GABA_B$ receptor antagonists bind to the $GABA_B$ receptor but do not exhibit efficacy, and will inhibit the function of a $GABA_B$ receptor agonist. $GABA_B$ receptor antagonists also bind to the $GABA_B$ receptor and will partially inhibit the function of a $GABA_B$ receptor agonist relative to a full antagonist.

In general it is believed that $GABA_B$ receptor antagonists do not potentiate the stimulation by noradrenalin of adenylate cyclase on sections of the cerebral cortex of rats but act as antagonists of the baclofen action. $GABA_B$ receptor antagonists can increase the release of rapid stimulant amino acid transmitters such as glutamate and aspartate and are believed to permit faster nerve impulse transmission. Compounds of Formula (I) that exhibit $GABA_B$ receptor antagonist activity are suitable for use in the treatment of diseases characterized by stimulation of $GABA_B$ receptors, including, for example, use as nootropics, antidepressants, and anxiolytics.

Allosteric modulators are compounds able to regulate the activity of a receptor by binding at a site distinct from that at which endogenous ligands bind. Negative allosteric modulators act as non-competitive antagonists and can have inverse agonist properties (ability to inhibit constitutive activity of the receptor). Positive allosteric modulators can directly activate the receptor, although such activity is usually partial, and can potentiate either the potency of the efficacy, or both, of orthosteric agonists. Positive allosteric $GABA_B$ receptor modulators have little or no intrinsic activity of their own, but interact synergistically with GABA or other $GABA_B$ agonists to enhance its effects, thus producing pharmacological activity in systems where GABA is already present.

The functional activity of compounds of Formula (I) as $GABA_B$ receptor ligands may be determined using in vitro assays and animal models.

The capacity for a compound of Formula (I) to function as a partial $GABA_B$ receptor agonist may be assessed by determining the maximal response in a $GABA_B$ receptor agonist activity assay. A $GABA_B$ receptor agonist will demonstrate a response equal to or nearly equal to that of a known reference $GABA_B$ receptor agonist such as GABA or R-baclofen. A partial agonist will demonstrate a response less than that of a full response. In vitro assays for $GABA_B$ agonist and partial agonist activity include the cAMP assay, $Ca^{2+}$ assay, and electrophysiology assay disclosed in Examples 83-86.

The following compounds exhibited a binding $IC_{50}$ in a [$^3$H]CGP54626 rat brain binding assay of less than 25 μM, a cAMP $EC_{50}$ less than 100 nm, and a $Ca^{2+}$ $EC_{50}$ less than 700 nM in cells expressing recombinant human $GABA_BR1a2$: (3R)-4-Amino-3-{4-chloro-3-[(imidazol-5-ylmethyl) amino]phenyl}butanoic acid hydrochloride, 3-{5-[(1R)-2-Amino-1-(carboxymethyl)ethyl]-2-chlorophenyl}benzoic acid hydrochloride, (3R)-4-Amino-3-(4-chloro-3-(3-pyridyl)phenyl)butanoic acid hydrochloride, (3R)-4-Amino-3-[4-chloro-3-(3-cyanophenyl)phenyl]butanoic acid hydrochloride, (3R)-4-Amino-3-[3-(3-carbamoylphenyl)-4-chlorophenyl]butanoic acid hydrochloride, 3-{5-[(1R)-2-Amino-1-(carboxymethyl)ethyl]-2-chlorophenyl}-4-chlorobenzoic acid hydrochloride, (3R)-4-Amino-3-[4-chloro-3-(3-nitrophenyl)phenyl]butanoic acid hydrochloride, (3R)-4-Amino-3-[4-chloro-3-(4-nitrophenyl) phenyl]butanoic acid hydrochloride, 4-{5-[(1R)-2-Amino-1-(carboxymethyl)ethyl]-2-chlorophenyl}thiophene-2-carboxylic acid hydrochloride, (3R)-4-Amino-3-{4-chloro-3-[(4-pyridylmethyl)amino]phenyl}butanoic acid hydrochloride, 5-{5-[(1R)-2-Amino-1-(carboxymethyl) ethyl]-2-chlorophenyl}thiophene-2-carboxylic acid, 5-{5-[(1R)-2-amino-1-(carboxymethyl)ethyl]-2-chlorophenyl}-2-fluorobenzoic acid hydrochloride, (3R)-4-amino-3-[4-chloro-3-(3-cyano-6-methylphenyl)phenyl]butanoic acid hydrochloride, (3R)-4-amino-3-[4-chloro-3-(3-cyano-5-fluorophenyl)phenyl]butanoic acid hydrochloride, (3R)-4-amino-3-[4-chloro-3-(4-methyl(3-pyridyl))phenyl]butanoic acid hydrochloride, (3R)-4-amino-3-[4-chloro-3-(3-cyano-6-fluorophenyl)phenyl]butanoic acid hydrochloride, (3R)-4-amino-3-[4-chloro-3-(6-chloro-3-cyanophenyl)phenyl]butanoic acid hydrochloride, (3R)-4-Amino-3-[4-chloro-3-(4-pyridylmethoxy)phenyl]butanoic acid hydrochloride, methyl (3R)-4-amino-3-[4-chloro-3-(4-pyridylmethoxy)phenyl]butanoate hydrochloride, (3R)-4-amino-3-[4-chloro-3-(3-pyridylmethoxy)phenyl]butanoic acid hydrochloride, 5-{5-[(1R)-2-amino-1-(carboxymethyl)ethyl]-2-chlorophenyl}furan-3-carboxylic acid hydrochloride, (3R)-4-amino-3-[4-chloro-3-(2-(4-pyridyl)ethoxy)phenyl] butanoic acid hydrochloride, (3R)-4-amino-3-[4-chloro-3-(4-pyridylethoxy)phenyl]butanoic acid hydrochloride, (3R)-3-[3-((1R)-1-(4-pyridyl)ethoxy)-4-chlorophenyl]-4-aminobutanoic acid hydrochloride, (3R)-4-amino-3-[4-chloro-3-(5-cyano(3-thienyl))phenyl]butanoic acid hydrochloride, (3R)-4-amino-3-{4-chloro-3-[(2-methyl(4-pyridyl))methoxy]phenyl}butanoic acid hydrochloride, (3R)-4-amino-3-{4-chloro-3-[(3-chloro(4-pyridyl))methoxy]phenyl}butanoic acid hydrochloride, 5-{5-[(1R)-2-amino-1-(carboxymethyl)ethyl]-2-chlorophenyl}thiophene-3-carboxylic acid hydrochloride, (3R)-4-Amino-3-[4-chloro-3-(5-cyano-2-thienyl))phenyl]butanoic acid hydrochloride, 3-{5-[(1R)-2-Amino-1-(carboxymethyl) ethyl]-2-chlorophenyl}-5-fluorobenzoic acid hydrochloride, (3R)-4-amino-3-[4-chloro-3-(2-(4-pyridyl)ethyl)phenyl]butanoic acid hydrochloride, (3R)-4-amino-3-[4-chloro-3-(1,3-thiazol-5-ylmethoxy)phenyl]butanoic acid hydrochloride, 2-{4-Chloro-3-(4-pyridylmethoxy)phenyl]-3-(hydrohydroxyphosphoryl)propylamine, and (3R)-4-amino-3-{3-[5-

(N,N-dimethylcarbamoyl)(2-thienyl)]-4-chlorophenyl}butanoic acid hydrochloride.

Animal models useful in determining $GABA_B$ receptor agonist and partial agonist activity include the hypothermia model disclosed in Example 88.

A functional assay for $GABA_B$ receptor antagonist activity using spontaneously discharging rat neocortical slices is disclosed in Example 87.

Pharmaceutical compositions provided by the present disclosure may comprise a therapeutically effective amount of a compound of Formula (I) together with a suitable amount of one or more pharmaceutically acceptable vehicles so as to provide a composition for proper administration to a patient. Suitable pharmaceutical vehicles are described in the art.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such oral compositions may be prepared in a manner known in the pharmaceutical art and comprise a compound of Formula (I) and at least one pharmaceutically acceptable vehicle. Oral pharmaceutical compositions may include a therapeutically effective amount of a compound of Formula (I) and a suitable amount of a pharmaceutically acceptable vehicle, so as to provide an appropriate form for administration to a patient.

Compounds of Formula (I) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formula (I) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formula (I) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formula (I) the stability of a compound of Formula (I) in the gastrointestinal tract, the pharmacokinetics of a compound of Formula (I) and the intended therapeutic profile. An appropriate controlled release oral dosage form may be selected for a particular compound of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formula (I) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formula (I) or pharmaceutical composition comprising a compound of Formula (I) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Compounds of Formula (I) may be adapted as prodrugs to achieve desirable pharmacokinetic properties following oral administration.

For example, prodrugs of the GABA analog, R-baclofen, that exhibit high bioavailability as R-baclofen when dosed either orally or directly into the colon of a mammal have been disclosed (Gallop et al., U.S. Pat. No. 7,109,239, U.S. Pat. No. 6,972,341, U.S. Pat. No. 6,818,787 and U.S. Pat. No. 7,227,028). Prodrugs of compounds of Formula (I) include the prodrug systems disclosed by Gallop et al. as well as others known in the art. Sustained release oral dosage forms comprising R-baclofen prodrugs are disclosed in Kidney et al., U.S. Patent Application Publication No. 2008/0206332, Sastry et al., U.S. application Ser. No. 12/024,830, and Karaborni et al., U.S. Provisional Application No. 61/157,114.

In certain embodiments, a prodrug of a compound of Formula (I) has Formula (III):

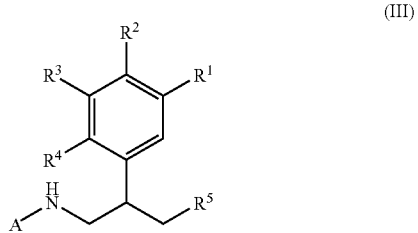

(III)

or a pharmaceutically acceptable salt thereof, wherein:

$R^1$ and $R^2$ are independently chosen from hydrogen, halogen, —CN, —CF$_3$, $C_{1-4}$ alkyl, —OR$^6$, and —N(R$^6$)$_2$ wherein each $R^6$ is independently chosen from hydrogen and $C_{1-4}$ alkyl; and one of $R^3$ and $R^4$ is —X—Y, and the other of $R^3$ and $R^4$ is hydrogen, wherein:

X is chosen from a covalent bond, $C_{1-3}$ alkyldiyl, substituted $C_{1-3}$ alkyldiyl, $C_{1-3}$ heteroalkyldiyl, and substituted $C_{1-3}$ heteroalkyldiyl; and Y is chosen from $C_{6-12}$ aryl, substituted $C_{6-12}$ aryl, $C_{5-12}$ heteroaryl, and substituted $C_{5-12}$ heteroaryl;

$R^5$ is chosen from —COOH, —SOOH, and —P(O)(OH) $R^8$ wherein $R^8$ is chosen from hydrogen and $C_{1-4}$ alkyl; and A is an amino acid.

In certain embodiments, a compound of Formula (III) is chosen from:

5-(5-{(1R)-1-[2S-amino-4-carbamoylbutanoylamino)methyl]-2-carboxyethyl}-2-chlorophenyl)thiophene-2-carboxylic acid hydrochloride;

(3R)-4-(2S)-2-aminopropanoylamino)-3-[4-chloro-3-(4-pyridylmethoxy)phenyl]butanoic acid hydrochloride; and (3R)-4-((2S)-2-amino-3-methylbutanoylamino)-3-[4-chloro-3-(4-pyridylmethoxy)phenyl]butanoic acid hydrochloride.

In certain embodiments, a prodrug of a compound of Formula (I) has Formula (IV):

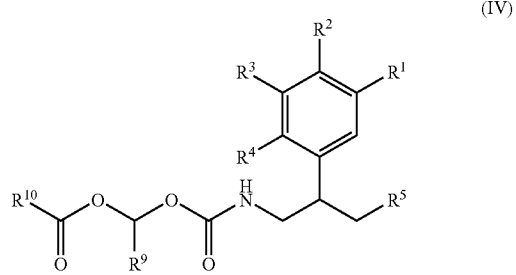

(IV)

or a pharmaceutically acceptable salt thereof, wherein:

$R^1$ and $R^2$ are independently chosen from hydrogen, halogen, —CN, —CF$_3$, $C_{1-4}$ alkyl, —OR$^6$, and —N(R$^6$)$_2$ wherein each $R^6$ is independently chosen from hydrogen and $C_{1-4}$ alkyl; and one of $R^3$ and $R^4$ is —X—Y, and the other of $R^3$ and $R^4$ is hydrogen, wherein:

X is chosen from a covalent bond, $C_{1-3}$ alkyldiyl, substituted $C_{1-3}$ alkyldiyl, $C_{1-3}$ heteroalkyldiyl, and substituted $C_{1-3}$ heteroalkyldiyl; and Y is chosen from $C_{6-12}$ aryl, substituted $C_{6-12}$ aryl, $C_{5-12}$ heteroaryl, and substituted $C_{5-12}$ heteroaryl;

$R^5$ is chosen from —COOH, —SOOH, and —P(O)(OH) $R^8$ wherein $R^8$ is chosen from hydrogen and $C_{1-4}$ alkyl; and each of $R^9$ and $R^{19}$ are independently chosen from hydrogen, $C_{1-4}$ alkyl, cyclohexyl, and phenyl In certain embodiments, a prodrug of a compound of Formula (I) has Formula (IV):

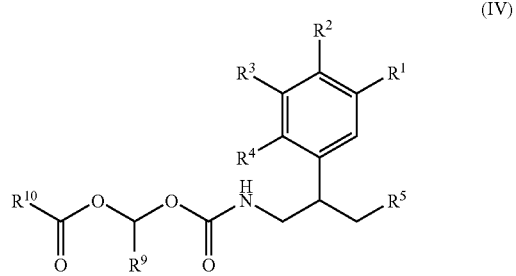

(IV)

or a pharmaceutically acceptable salt thereof, wherein:

$R^1$ and $R^2$ are independently chosen from hydrogen, halogen, —CN, —CF$_3$, $C_{1-4}$ alkyl, —OR$^6$, and —N(R$^6$)$_2$ wherein each $R^6$ is independently chosen from hydrogen and $C_{1-4}$ alkyl; and one of $R^3$ and $R^4$ is —X—Y, and the other of $R^3$ and $R^4$ is hydrogen, wherein:

X is chosen from a covalent bond, $C_{1-3}$ alkyldiyl, substituted $C_{1-3}$ alkyldiyl, $C_{1-3}$ heteroalkyldiyl, and substituted $C_{1-3}$ heteroalkyldiyl; and Y is chosen from $C_{6-12}$ aryl, substituted $C_{6-12}$ aryl, $C_{6-12}$ heteroaryl, and substituted $C_{6-12}$ heteroaryl;

$R^5$ is chosen from —COOH, —SOOH, and —P(O)(OH) $R^8$ wherein $R^8$ is chosen from hydrogen and $C_{1-4}$ alkyl; and each of $R^9$ is chosen from hydrogen, $C_{1-4}$ alkyl, cyclohexyl, and phenyl; and $R^{10}$ is chosen from $C_{1-4}$ alkyl, cyclohexyl and phenyl.

In certain embodiments, a compound of Formula (IV) is (3R)-3-{4-chloro-3-{5-methoxycarbonyl)(2-thienyl)}phenyl}-4-{[(2-methylpropanoyloxy)ethoxy]carbonylamino}butanoic acid.

Compounds of Formula (I) are $GABA_B$ receptor ligands. Thus, compounds of Formula (I) and pharmaceutical compositions thereof may be administered to a patient suffering from any disease including a disorder, condition, or symptom for which a $GABA_B$ receptor ligand is known or hereafter discovered to be therapeutically effective. Indications for which $GABA_B$ ligands have been prescribed, and hence for which a compound of Formula (I) or pharmaceutical composition thereof are also expected to be effective, include spasticity, gastro-esophageal reflux disease, emesis, cough, overactive bladder, substance abuse disorders, attention disorders, anxiety disorders, mood disorders, cognitive disorders, migraine, and pain.

Methods of treating a disease in a patient provided by the present disclosure comprise administering to a patient in need of such treatment a therapeutically effective amount of a compound of Formula (I). Compounds of Formula (I) or pharmaceutical compositions thereof may provide therapeutic or prophylactic plasma and/or blood concentrations of the compound following administration to a patient.

Compounds of Formula (I) may be included in a pharmaceutical composition and/or dosage form adapted for oral administration, although compounds of Formula (I) may also be administered by any other appropriate route, such as for example, by injection, infusion, inhalation, transdermal, or absorption through epithelial or mucosal membranes (e.g., oral, rectal, and/or intestinal mucosa).

Compounds of Formula (I) may be administered in an amount and using a dosing schedule as appropriate for treatment of a particular disease. Daily doses of a compound of Formula (I) can range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, compounds of Formula (I) may be administered at a dose over time from about 1 mg to about 5 g per day, from about 10 mg to about 4 g per day, and in certain embodiments from about 20 mg to about 2 g per day. An appropriate dose of a compound of Formula (I) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to one skilled in the art.

Compounds of Formula (I) may be assayed in vitro and in vivo for the desired therapeutic or prophylactic activity prior to use in humans. In vivo assays, for example using appropriate animal models, may also be used to determine whether administration of a compound of Formula (I) is therapeutically effective. In certain embodiments, a therapeutically effective dose of a compound of Formula (I) may provide therapeutic benefit without causing substantial toxicity including adverse side effects. Toxicity of compounds of Formula (I) prodrugs, and/or metabolites thereof may be determined using standard pharmaceutical procedures and may be ascertained by one skilled in the art. The dose ratio between toxic and therapeutic effect is the therapeutic index. A dose of a compound of Formula (I) may be within a range capable of establishing and maintaining a therapeutically effective circulating plasma and/or blood concentration of a compound of Formula (I) that exhibits little or no toxicity.

Compounds of Formula (I) may be used to treat diseases, disorders, conditions, and symptoms of any of the foregoing for which $GABA_B$ receptor ligands are shown to provide therapeutic benefit. $GABA_B$ receptor ligands achieving $GABA_B$ receptor agonist or partial agonist activity are known to be effective in treating gastro-esophageal reflux disease, emesis, cough, overactive bladder, substance abuse disorders, anxiety, migraine, pain, and spasticity. $GABA_B$ receptor ligands having $GABA_B$ receptor antagonist activity are known to be effective in treating attention disorders, cognitive disorders, and mood disorders. Hence, compounds of Formula (I) may be used to treat any of the foregoing diseases and disorders. The underlying etiology of any of the foregoing diseases being treated may have a multiplicity of origins.

Further, in certain embodiments, a therapeutically effective amount of one or more compounds of Formula (I) may be administered to a patient, such as a human, as a preventative measure against various diseases or disorders. Thus, a therapeutically effective amount of one or more compounds of Formula (I) may be administered as a preventative measure to a patient having a predisposition for and/or history of spasticity, gastro-esophageal reflux disease, emesis, cough, overactive bladder, a substance abuse disorder, an attention disorder, an anxiety disorder, a mood disorder, a cognitive disorder, migraine, and pain.

Gastro-esophageal reflux disease (GERD) is the most common ailment in the upper gastrointestinal tract. Gastro-esophageal reflux disease (GERD) is defined as chronic symptoms or mucosal damage produced by the abnormal reflux in the esophagus. Symptoms of GERD include heartburn, esophagitis, strictures, dysphagia, chronic chest pain, cough, hoarseness, voice changes, chronic ear ache, burning chest pains, nausea, and sinusitis. A major factor responsible for GERD is an incompetence of the lower esophageal sphincter that opens transiently and allows passage of acidic material from the stomach into the esophagus. This motor event referred to as transient lower esophageal sphincter relaxation (TLESR) occurs more often in patients suffering from GERD than in healthy subjects and in infants with regurgitation. Frequent exposure of the esophageal mucosa to acid can trigger pain, often perceived as heartburn, and lead to erosions in the esophagus.

$GABA_B$ receptor agonists can reduce TLESRs. $GABA_B$ receptor agonists such as baclofen play a key role in nervous circuitries mediating TLESR and have been shown to reduce the sensitivity of vagal afferent and efferent fibers.

Administration of baclofen has been shown to reduce the frequency of TLESR in animal models (Blackshaw et al., *Am. J. Physiol.* 1999, 277, G867-874; and Lehmann et al., *Gastroenterol* 1999, 117, 1147-1154) and in human patients (Zhang et al., Gut 2002, 50, 19-24; and Lidums et al., *Gastroenterol.* 2000, 18, 7-13). Efficacy for treating GERD may be assessed using animal models and in clinical trials.

Nausea, vomiting, and retching are basic human protective reflexes against the absorption of toxins as well as responses to certain stimuli. Nausea is a subjectively unpleasant wave-like sensation in the back of the throat or epigastrium associated with pallor or flushing, tachycardia, and an awareness of the urge to vomit. Sweating, excess salivation, and a sensation of being cold or hot may also occur. Vomiting is characterized by contraction of the abdominal muscles, descent of the diaphragm, and opening of the gastric cardia, resulting in forceful expulsion of stomach contents from the mouth. Retching involves spasmodic contractions of the diaphragm and the muscles of the thorax and abdominal wall without expulsion of gastric contents. Emesis is used herein to refer to nausea, vomiting, and/or retching.

Chemotherapy-induced nausea and vomiting (CINV) and post-operative nausea and vomiting (PONV) are two of the most significant targets of anti-emetic therapy. Chemotherapeutic agents used, for example, in cancer therapy can stimulate enterochromaffin cells in the gastrointestinal tract to release serotonin, which activates serotonin receptors. Activation of serotonin receptors subsequently activates the vagal afferent pathway, which in turn activates the vomiting center and causes an emetic response. The emetic potential of a chemotherapeutic agent can be the major stimulus for emesis in chemotherapy-induced emesis. Chemotherapeutic agents are rated according to their emetic potential.

Methods provided by the present disclosure may be used to treat emesis of any etiology. Emesis may be induced by factors including, but not limited to, cancer chemotherapeutic agents such as alkylating agents, e.g., cyclophosphamide, carmustine, lomustine, and chlorambucil; cytotoxic antibiotics, e.g., dactinomycin, doxorubicin, mitomycin-C, and bleomycin; anti-metabolites, e.g., cytarabine, methotrexate, and 5-fluorouracil; vinca alkaloids, e.g., etoposide, vinblastine, and vincristine; and other chemotherapeutic agents such as cisplatin, dacarbazine, procarbazine, and hydroxyurea; and combinations thereof; radiation sickness; radiation therapy, e.g., irradiation of the thorax or abdomen, such as in the treatment of cancer; poisons; toxins such as toxins caused by metabolic disorders or by infection, e.g., gastritis, or released during bacterial or viral gastrointestinal infection; pregnancy; vestibular disorders, such as motion sickness, vertigo, dizziness, and Meniere's disease; post-operative sickness; gastrointestinal obstruction; reduced gastrointestinal motility; visceral pain, such as myocardial infarction or peritonitis; headache; migraine; increased intracranial pressure; decreased intracranial pressure (e.g., altitude sickness); opioid analgesics such as morphine; drugs that cause gastric irritation such as nonsteroidal anti-inflammatory drugs, selective serotonin reuptake inhibitors, antibiotics, and antiparasitics; drugs that indirectly stimulate the vomiting center such as morphine, digitoxin, alcohol, ipecac, and chemotherapy drugs; olfactory, visual, vestibular, and psychogenic stimuli; anesthetics; pancreatitis; diabetic ketoacidosis; meningitis; heart failure; hepatobiliary causes; cerebrovascular trauma; hypotension; peridonitis; hyponatremia; brain tumors; myocardial infarction; gastrointestinal bleeding; uremia; hypercalcemia; gastroesophageal reflux disease; acid indigestion; over-indulgence of food or drink; acid stomach; sour stomach; regurgitation; heartburn such as episodic heartburn, nocturnal heartburn and meal-induced heartburn; and dyspepsia.

Emesis may also be caused by conditions, disorders, or diseases of the gastrointestinal tract such as cholecystitis, choledocholithiasis, intestinal obstruction, acute gastroenteritis, perforated viscus, dyspepsia resulting from, for example, gastroesophageal reflux disease, peptic ulcer disease, gastroparesis, gastric or esophageal neoplasms, infiltrative gastric disorders such as Menetrier's syndrome, Crohn's disease, eosinophilic gastroenteritis, sarcoidosis and amuloidosis, gastric infections such as CMV, fungal, TB, and syphilis, parasites such as *Giardia lamblia* and *Strongyloides stercoralis*, chronic gastric volvulus, chronic intestinal ischemia, altered gastric motility and/or food intolerance, or Zollinger-Ellison syndrome.

$GABA_B$ agonists such as baclofen have been shown to suppress the retching and vomiting induced by morphine, thereby indicating the involvement of the $GABA_B$ receptor in the emetic control pathway (Suzuki et al., *Neuropharmacology* 2005, 49(8), 1121-31). Baclofen has also been shown to antagonize emesis induced by nicotine and motion in animal models (Chan et al., *Eur J Pharmacology* 2007, 559(2-3), 196-201). Efficacy in treating emesis can be assessed using appropriate animal models and using clinical trials.

Cough reflex, elicited by activation of cough receptors located in the respiratory tract, clears inhaled irritants and foreign substances from the respiratory tract and in conjunction with the mucociliary system can expel excessive airway secretion produced under abnormal conditions from the respiratory tract. Cough can be caused by mild acute upper respiratory tract infections, allergies, asthma, chronic obstructive pulmonary disease, lung cancer, gastro-esophageal reflux disease, post-nasal drip, and heart or ear disorders. However, chronic non-productive cough having no identifiable cause accounts for a significant percent of patients presenting with cough. Chronic cough is associated with exacerbation of asthmatic symptoms, rib fractures, breathlessness, ruptured abdominal muscles, pneumothorax, syncope, second and third degree heart block, and loss of consciousness. Persistent and uncontrollable cough can lead to morbidity and severely impairs the quality of life of these patients. Cough includes acute and chronic cough of any type, etiology, or pathogenesis, and in particular cough associated with laryngeal sensory neuropathy.

The anti-tussive effects of baclofen are well-known (Dicpinigaitis and Dobkin, *Chest* 1997, 111(4), 996-9; Dicpinigaitis and Rauf, *Respiration* 1998, 65(1), 86-8; Dicpinigaitis et al., *J Clin Pharmacol* 1998, 38(4), 364-7; and Kreutner of al., U.S. Pat. No. 5,006,560.

Efficacy in treating cough can be assessed using appropriate animal models and using clinical trials.

Attention disorders are conditions characterized by impaired ability to concentrate on selected features of the environment to the relative exclusion of others. Attention disorders include attention deficit disorder (ADD) and attention-deficit/hyperactivity disorder (ADHD). Patients affected by ADD typically have difficulty concentrating, listening, learning, and completing tasks, and are restless, fidgety, impulsive and easily distracted. ADHD includes the symptoms of ADD as well as a high level of activity, e.g., restlessness and movement. The diagnostic criteria for ADD and ADHD are provided in the DSM-IV.

$GABA_B$ receptor antagonists such as 3-aminopropyl-(n-butyl)-phosphinic acid have been shown to improve attention in animal models and in clinical trials (Madrid et al., U.S. Application Publication No. 2005/0187196). The efficacy of a $GABA_B$ receptor ligands for treating a attention disorders can be determined using animal models and clinical trials.

Cognitive disorders are abnormalities of thinking and memory that are associated with temporary or permanent brain dysfunction. The main symptoms of cognitive disorders include problems with memory, orientation, language, information processing, and the ability to focus and sustain attention on a task. Examples of central nervous system (CNS) disorders or conditions that fall within the scope of cognitive disorders include, age-associated memory impairment, mild cognitive impairment, delirium, dementia, Alzheimer's disease, Parkinson's disease, Huntington's disease, mental retardation, cerebrovascular disease, affective disorders, psychotic disorders, Asperger's disorder, autism, neurotic disorders, attention deficit disorders, oppositional defiant disorder, conduct disorder, subdural hematoma, normal-pressure hydrocephalus, brain tumor, head trauma, and brain trauma (DSM IV). Cognitive disorders may be associated with other conditions. For example, memory impairment can be associated with depression or anxiety, psychosis, Down's syndrome, stroke, traumatic brain injury, Huntington's disease AIDS associated dementia, schizophrenia, and attention deficit disorders.

Cognitive impairment is typically manifested by one or more cognitive deficits. Memory impairment is a cognitive deficit characterized by the inability to learn new information or recall previously learned information. Aphasia is a cognitive deficit characterized by a language and/or speech disturbance. Apraxia is a cognitive deficit characterized by the impaired ability to carry out motor activities despite intact motor function. Agnosia is a cognitive deficit characterized by the failure to recognize or identify objects despite intact sensory functions. Cognitive impairment may also be manifested by a disturbance in executive functioning, i.e., planning, organizing, sequencing, and abstracting.

In certain embodiments, a cognitive disorder is a learning disorder. Such learning disorders are known in the art and include autism, dyslexia, Asperger's syndrome, a neurobiological disorder similar to autism and characterized by serious deficits in social and communication skills; specific learning disability, a disorder in one or more of the basic psychological processes involved in understanding or in using spoken or written language, which may manifest itself in an imperfect ability to listen, think, speak, read, write, spell or to do mathematical calculations; dysgraphia, a disorder that causes difficulty with forming letters or writing within a defined space; dyscalculia, a disorder that causes people to have problems doing arithmetic and grasping mathematical concepts; dyspraxia, a problem with the body's system of motion that interferes with a person's ability to make a controlled or coordinated physical response in a given situation; visual perceptual deficit, difficulty receiving and/or processing accurate information from the sense of sight, although there is nothing wrong with vision; and auditory perceptual deficit, difficulty receiving accurate information through auditory means, even though there is no problem with hearing.

Methods provided by the present disclosure can be useful for improving cognitive function, including "promoting" cognitive function (affecting impaired cognitive function in a subject so that it more closely resembles the function of an aged-matched normal, unimpaired subject, including affecting states in which cognitive function is reduced compared to a normal subject) and "reserving" cognitive function (affecting normal or impaired cognitive function such that it does not decline or does not fall below that observed in the subject upon first presentation or diagnosis).

$GABA_B$ receptor antagonists have been found to improve cognitive performance in a variety of animal models (Bowery et al., *Pharmacol Rev* 2002, 54, 247-64) as well as in clinical trial of patients with mild cognitive impairment (Froestl et al., *Biochem Pharmacol* 2004, 68, 1479-87; Mondadori et al., *Behav Neural Biol* 1993, 60, 62-8; and Nakagawa and Takashima, *Brain Res* 1997, 766, 101-6) and in clinical trials (Froestl et al., *Biochem Pharmacol* 2005, 68(8), 1479-87). $GABA_B$ receptor antagonists have also been shown to improve learning behavior in animal models (Getova and Bowery, *Psychopharmaoclogy* 2001, 157, 89-95; and Nakagawa et al., *Eur J Pharmacology* 1999, 381, 1-7).

The efficacy of a $GABA_B$ receptor ligand for treating a cognitive disorder can be determined using animal models such as disclosed in the references cited in the preceding paragraph and in clinical trials.

Substance abuse disorders refer to disorders related to taking a drug of abuse, to the side effects of a medication, and to toxin exposure. Drugs of abuse include alcohol, amphetamines, caffeine, *cannabis*, cocaine, hallucinogens, inhalants, nicotine, opioids, phencyclidine, or similarly acting arylcyclohexylamines, sedatives, hypnotics, and anxiolytics.

Alcoholism or alcohol dependence is a chronic disorder with genetic, psychosocial, and environmental causes. Alcoholism refers to "maladaptive alcohol use with clinically significant impairment as manifested by at least three of the following within any one-year period: tolerance; withdrawal; taken in greater amounts or over longer time course than intended; desire or unsuccessful attempts to cut down or control use; great deal of time spent obtaining, using, or recovering from use; social, occupational, or recreational activities given up or reduced; continued use despite knowledge of physical or psychological sequelae." (Diagnostic and Statistical Manual of Mental Disorders, Fourth Edition, Text Revision, Washington D.C., American Psychiatric Association, 2000 (DSM-IV)). Alcohol use disorders include alcohol dependence and alcohol abuse. Screening tests useful for identifying alcoholism include the Alcohol Dependence Data Questionnaire, the Michigan Alcohol Screening Test, the Alcohol Use Disorders Identification Test, and the Paddington Alcohol Test, and other generally recognized tests for diagnosing alcohol dependence.

Treatment for alcoholism generally includes psychological, social, and pharmacotherapeutic interventions aimed at reducing alcohol-associated problems and usually involves detoxification and rehabilitation phases.

$GABA_B$ receptor agonists such as baclofen have been shown to suppress alcohol consumption in alcohol-preferring rats (Colombo et al., *Psychopharmacology* 2003, 167, 221-224), and in clinical studies shown to maintain alcohol abstinence, reduce alcohol intake, suppress obsessive and compulsive symptoms of craving, and reduce the symptoms of alcohol withdrawal (Addolorato et al., *Am J. Med* 2002, 112, 226-9; and Johnson et al., *Alcoholism Clin Exp Res* 2005, 29, 248-254). The efficacy of compounds of Formula (I) and compositions thereof for treating alcohol dependency may be assessed using animal models of alcoholism and using clinical studies.

Baclofen has also been shown to limit self-administration of a variety of addictive substance in animal models including, alcohol, cocaine, heroine, and nicotine (Colombo et al., *Alcohol Clin Exp Res* 2000, 24, 58-66; and Fattore et al., *Alcohol Alcohol* 2002, 37, 496-498) and early human trials suggest efficacy of baclofen in reducing cocaine craving (Ling et al., *Neuropsychopharmacology* 1998, 18, 403-404).

In clinical trials, the $GABA_B$ receptor agonist R-baclofen and other $GABA_B$ receptor agonists have been shown to be effective in treating cocaine addiction (Brebner et al., *Alcohol Alcohol* 2002, 37(5), 478-84; and Haney et al., *Neuropsychopharmacology* 2006, 31, 1814-21); methamphetamine dependence (Heinzerling et al., *Drug Alcohol Depend* 2006, 85(3), 177-84); opioid dependence (Assadi et al., *BMC Psychiatry* 2003, 3(16); and Ahmadi-Abhari et al., *J Clin Pharm Therapeutics* 2001, 26(1), 67-71); heroin self-administration (Xi and Stein, *J Pharmacol Exp Ther* 1999, 290, 1369-74); alcohol craving and intake (Addolorato et al., *Alcohol Alcohol* 2002, 37(5), 504-8; and Flannery et al., *Alcohol Clin Exp Res* 2004, 28(10), 1517-23); nicotine use (Markou et al., *Ann N.Y. Acad Sci* 2004, 1025, 491-503; Paterson et al., *Psychopharmacology* 2004, 172, 179-186; and Paterson et al., *Neuropsychopharmacology* 2005, 30, 119-128); and drug addiction generally (Cousins et al., *Drug Alcohol Dependence* 2002, 65(3), 209-20). Efficacy for treating substance addiction and abuse can be assessed using animal models and in clinical trials.

In certain embodiments, compounds of Formula (I) or pharmaceutical compositions thereof can be used to treat spasticity. Spasticity is an involuntary, velocity-dependent, increased resistance to stretch. Spasticity is characterized by muscle hypertonia in which there is increased resistance to externally imposed movement with increasing speed of stretch. Spasticity is associated with damage to the corticospinal tract and is a common complication of neurological disease. Spasticity can be caused by lack of oxygen to the brain before, during, or after birth (cerebral palsy); physical trauma (brain or spinal cord injury); blockage of or bleeding from a blood vessel in the brain (stroke); certain metabolic diseases; adrenolekodystrophy; phenylketonuria; neurodegenerative diseases such as Parkinson's disease and amyotrophic lateral sclerosis; and neurological disorders such as multiple sclerosis. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient.

Symptoms of spasticity include hypertonia (increased muscle tone), clonus (a series of rapid muscle contractions), exaggerated deep tendon reflexes, muscle spasms, scissoring (involuntary crossing of the legs), deformities with fixed joints, stiffness, and/or fatigue caused by trying to force the limbs to move normally. Other complications include urinary tract infections, chronic constipation, fever or other systemic illnesses, and/or pressure sores. The degree of spasticity can vary from mild muscle stiffness to severe, painful, and uncontrollable muscle spasms. Spasticity may coexist with other conditions but is distinguished from rigidity (involuntary bidirectional non-velocity-dependent resistance to movement), clonus (self-sustaining oscillating movements secondary to hypertonicity), dystonia (involuntary sustained contractions resulting in twisting abnormal postures), athetoid movement (involuntary irregular confluent writhing movements), chorea (involuntary, abrupt, rapid, irregular, and unsustained movements), ballisms (involuntary flinging movements of the limbs or body), and tremor (involuntary rhythmic repetitive oscillations, not self-sustaining). Spasticity can lead to orthopedic deformity such as hip dislocation, contractures, or scoliosis; impairment of daily living activities such as dressing, bathing, and toileting; impairment of mobility such as inability to walk, roll, or sit; skin breakdown secondary to positioning difficulties and shearing pressure; pain or abnormal sensory feedback; poor weight gain secondary to high caloric expenditure; sleep disturbance; and/or depression secondary to lack of functional independence.

$GABA_B$ receptor agonists such as baclofen are currently approved for the treatment of spasticity.

Efficacy for the treatment of spasticity can be assessed using animal models of spasticity and in clinically relevant studies of spasticity of different etiologies.

In certain embodiments, $GABA_B$ receptor ligands of Formula (I) or pharmaceutical compositions thereof can be used to treat mood disorders such as, for example, a bipolar disorder or a depressive disorder. Mood disorders include depressive disorders, which include major depressive disorder, dysthymic disorder, bipolar depression and/or bipolar mania, bipolar I with or without manic, depressive or mixed episodes, bipolar II, cyclothymic disorder, mood disorder due to a general medical condition, manic episodes associated with bipolar disorder, mixed episodes associated with bipolar disorder, and the like. Mood disorders are classified and defined in the American Psychiatric Association: Diagnostic and Statistical Manual of Mental Disorders, Fourth Edition, Text Revision, Washington, D.C., American Psychiatric Association, 2000.

Bipolar disorder is a psychiatric condition characterized by periods of extreme mood. The moods can occur on a spectrum ranging from depression (e.g., persistent feelings of sadness, anxiety, guilt, anger, isolation, and/or hopelessness, disturbances in sleep and appetite, fatigue and loss of interest in usually enjoyed activities, problems concentrating, loneliness, self-loathing, apathy or indifference, depersonalization, loss of interest in sexual activity, shyness or social anxiety, irritability, chronic pain, lack of motivation, and morbid/suicidal ideation) to mania (e.g., elation, euphoria, irritation, and/or suspicious). Bipolar disorder includes bipolar I disorder, bipolar II disorder, cyclothymia, and bipolar disorder not otherwise specified. Patients afflicted with bipolar disorder typically alternate between episodes of depression (depressed mood, hopelessness, anhedonia, varying sleep disturbances, difficulty in concentration, psychomotor retardation and often, suicidal ideation) and episodes of mania (grandiosity, euphoria, racing thoughts, decreased need for sleep, increased energy, risk taking behavior).

Treatment of bipolar disorder can be assessed in clinical trials using rating scales such as the Montgomery-Asberg Depression Rating Scale, the Hamilton Depression Scale, the Raskin Depression Scale, Feighner criteria, and/or Clinical Global Impression Scale Score.

Depressive disorders include major depressive disorder, dysthymic disorder, premenstrual dysphoric disorder, minor depressive disorder, recurrent brief depressive disorder, and postpsychotic depressive disorder of schizophrenia. Depressive disorders and their diagnosis are described in Am. Psychiatric Assoc.: Diagnostic and Statistical Manual of Mental Disorders (DSM-IV), Fourth Ed, Text Revision, Washington, D.C., Am. Psychiatric Assoc., 2000, p. 369-382).

Several studies support antidepressant activity of $GABA_B$ receptor antagonists in animal models of depression (Nowak et al., *British J Pharmacology* 2006, 149, 581-590; Slattery et al., *J Pharmacology Experimental Therapeutics* 2005, 312, 290-6; and Cryan and Kaupmann, *Trends Pharmacol Sci* 2005, 26, 36-43).

The efficacy of compounds provided by the present disclosure for treating depression can be evaluated in animal models of depression such as the forced swim test, the tail suspension test, chronic mild stress rat model, and others.

Anxiety is defined and classified in DSM-IV-TR. Anxiety disorders include panic attack, agoraphobia, panic disorder without agoraphobia, agoraphobia without history of panic disorder with or without agoraphobia, agoraphobia specific phobia, social phobia, social anxiety disorder, obsessive-compulsive disorder, posttraumatic stress disorder, acute stress disorder, generalized anxiety disorder, anxiety disorder due to a general medical condition, substance-induced anxiety disorder, and anxiety disorder not otherwise specified.

Dysfunction of GABA-mediated neurotransmission has been implicated in the pathophysiology of anxiety (Cryan and Kaupmann, *Trends Pharmacol Sci* 2005, 26, 36-43). $GABA_B$ agonists such as baclofen demonstrate anxiolytic effects in preclinical studies (Momnereau et al., *Neuropsychopharmacology* 2004, 29, 1050-1062), and positive allosteric modulators of the $GABA_B$ receptor have been shown to be active in animal models of anxiety (Cryan et al., *J Pharmacol Exp Ther* 2004, 310, 952-963; and Mombereau et al., *Neuropsychopharmacology* 2004, 29, 1050-1062).

Useful animal models for assessing treatment of anxiety include fear-potentiated startle; elevated plus-maze; fear-potentiated behavior in the elevated plus-maze test; X-maze test of anxiety; and rat social interaction test. Genetic animal models of anxiety are known as are other animal models sensitive to anti-anxiety agents.

In clinical trials, efficacy can be evaluated using psychological procedures for inducing experimental anxiety applied to healthy volunteers and patients with anxiety disorders (or by selecting patients based on the Structured Clinical interview for DSM-IV Axis I Disorders as described by First et al., Structured Clinical Interview for DSM-IV Axis I Disorders, Patient Edition (SCIDIP), Version 2. Biometrics Research, New York State Psychiatric Institute, New York, 1995. One or more scales can be used to evaluate anxiety and the efficacy of treatment including, for example, the Penn State Worry Questionnaire, the Hamilton Anxiety and Depression Scales, the Spielberger State-Trait Anxiety Inventory, and the Liebowitz Social Anxiety Scale.

Migraine is a neurological disorder that is characterized by recurrent attacks of headache, with pain most often occurring on one side of the head, accompanied by various combinations of symptoms such as nausea, vomiting, and sensitivity to light, sound, and odors. Migraine is recognized as a chronic illness, not simply as a headache.

The exact mechanism of migraine initiation and progress is not known. Migraine can occur at any time of day or night, but occurs most frequently on arising in the morning. Migraine can be triggered by various factors, such as hormonal changes, stress, foods, lack of sleep, excessive sleep, or visual, auditory, olfactory, or somatosensory stimulation. In general, there are four phases to a migraine: the prodrome, auras, the attack phase, and postdrome. The prodrome phase is a group of vague symptoms that may precede a migraine attack by several hours, or even a few days before a migraine episode. Prodrome symptoms can include sensitivity to light and sound, changes in appetite, fatigue and yawning, malaise, mood changes, and food cravings. Auras are sensory disturbances that occur before the migraine attack in one in five patients. Positive auras include bright or shimmering light or shapes at the edge of the field of vision. Other positive aura experiences are zigzag lines or stars. Negative auras are dark holes, blind spots, or tunnel vision. Patients may have mixed positive and negative auras. Other neurologic symptoms that may occur at the same time as the aura include speech disturbances, tingling, numbness, or weakness in an arm or leg, perceptual disturbances such as space or size distortions, and confusion. A migraine attack usually lasts from 4 to 72 hours and typically produces throbbing pain on one side of the head, pain worsened by physical activity, nausea, visual symptoms, facial tingling or numbness, extreme sensitivity to light and noise, looking pale and feeling cold, and less commonly tearing and redness in one eye, swelling of the eyelid, and nasal congestion. During the attack the pain may migrate from one part of the head to another, and may radiate down the neck into the shoulder. Scalp tenderness occurs in the majority of patients during or after an attack. After a migraine attack, there is usually a postdrome phase, in which patients may feel exhausted, irritable, and/or be unable to concentrate. Other types of migraine include menstrual migraines, opthalmologic migraine, retinal migraine, basilar migraine, familial hemiplegic migraine, and status migrainosus.

It is theorized that persons prone to migraine have a reduced threshold for neuronal excitability, possibly due to reduced activity of the inhibitory neurotransmitter γ-aminobutyric acid (GABA). GABA normally inhibits the activity of the neurotransmitters serotonin (5-HT) and glutamate, both of which appear to be involved in migraine attacks. The excitatory neurotransmitter glutamate is implicated in an electrical phenomenon called cortical spreading depression, which can initiate a migraine attack, while serotonin is implicated in vascular changes that occur as the migraine progresses.

Migraine may be diagnosed by determining whether some of a person's recurrent headaches meet migraine criteria as disclosed in, for example, see The International Classification of Headache Disorders, 2nd edition, Headache Classification Committee of the International Headache Society, *Cephalalgia* 2004, 24 (suppl 1), 8-160.

The $GABA_B$ agonist baclofen has been found to be effective for prophylactic treatment of migraine at doses of 15 mg/day to 40 mg/day (Hering-Hanit, *Cephalalgia* 1999, 19(6), 589-91; and Hering-Hanit and Gadoth, *Headache* 2000, 40(1), 48-51).

A $GABA_B$ ligand of Formula (I) or a pharmaceutical composition thereof may be administered to a patient after initiation of the migraine. For example, a patient may be in the headache phase of the migraine or the postdrome phase before the prodrug or pharmaceutical composition is administered. Alternatively, a $GABA_B$ ligand of Formula (I) or pharmaceutical composition thereof may be administered to the patient before the migraine starts, such as once the patient senses that a migraine is developing or when the early symptoms of the migraine have begun. A $GABA_B$ ligand of Formula (I) may also be administered to a patient on an ongoing or chronic basis to treat recurrent or frequent occurrences of migraine episodes.

The efficacy of administering a compound of Formula (I) for treating migraine can be assessed using animal and human models of migraine and clinical studies. Animal and human models of migraine are known. For example, to delineate and assess the effectiveness of a $GABA_B$ ligand of Formula (I) for treating migraine, the frequency of migraine attacks, their severity and their accompanying symptoms may be recorded and measured at baseline, and at 3 months, and 6 months, etc., following initiation of treatment.

Pain includes nociceptive pain caused by injury to bodily tissues and neuropathic pain caused by abnormalities in nerves, spinal cord, and/or brain. Pain includes mechanical allodynia, thermal allodynia, hyperplasia, central pain, peripheral neuropathic pain, diabetic neuropathy, breakthrough pain, cancer pain, deafferentation pain, dysesthesia, fibromyalgia syndrome, hyperpathia, incident pain, movement-related pain, myofacial pain, and paresthesia. More generally, pain includes neuropathic pain and musculoskeletal pain. Pain may be acute or chronic.

Neuropathic pain involves an abnormal processing of sensory input usually occurring after direct injury or damage to nerve tissue. Neuropathic pain is a collection of disorders characterized by different etiologies including infection, inflammation, disease such as diabetes and multiple sclerosis, trauma or compression to major peripheral nerves, and chemical or irradiation-induced nerve damage. Neuropathic pain typically persists long after tissue injury has resolved.

An essential part of neuropathic pain is a loss (partial or complete) of afferent sensory function and the paradoxical presence of certain hyperphenomena in the painful area. The nerve tissue lesion may be found in the brain, spinal chord, or the peripheral nervous system. Symptoms vary depending on the condition but are usually the manifestations hyperalgesia (the lowering of pain threshold and an increased response to noxious stimuli), allodynia (the evocation of pain by non-noxious stimuli such as cold, warmth, or touch), hyperpathia (an explosive pain response that is suddenly evoked from cutaneous areas with increased sensory detection threshold when the stimulus intensity exceeds sensory threshold), paroxysms a type of evoked pain characterized by shooting, electric, shock like or stabbing pain that occur spontaneously, or following stimulation by an innocuous tactile stimulus or by a blunt pressure), paraesthesia (abnormal but non-painful sensations, which can be spontaneous or evoked, often described as pins and needles), dyesthesia (abnormal unpleasant but not necessarily painful sensation, which can be spontaneous or provoked by external stimuli), referred pain and abnormal pain radiation (abnormal spread of pain), and wind-up like pain and aftersensations (the persistence of pain long after termination of a painful stimulus). Patients with neuropathic pain typically describe burning, lancinating, stabbing, cramping, aching and sometimes vice-like pain. The pain can be paroxysmal or constant. Pathological changes to the peripheral nerve(s), spinal cord, and brain have been implicated in the induction and maintenance of chronic pain. Patients suffering from neuropathic pain typically endure chronic, debilitating episodes that are refractory to current pharmacotherapies and profoundly affect their quality of life.

There are several types of neuropathic pain. A classification that relates to the type of damage or related pathophysiology causing a painful neuropathy includes neuropathies associated with mechanical nerve injury such as carpal tunnel syndrome, vertebral disk herniation, entrapment neuropathies, ulnar neuropathy, and neurogentic thoracic outlet syndrome; metabolic disease associated neuropathies such as diabetic polyneuropathy; neuropathies associated with neurotropic viral disease such as herpes zoster and human immunodeficiency virus (HIV) disease; neuropathies associated with neurotoxicity such as chemotherapy of cancer or tuberculosis, radiation therapy, drug-induced neuropathy, and alcoholic neuropathy; neuropathies associated with inflammatory and/or immunologic mechanisms such as multiple sclerosis, anti-sulfatide antibody neuropathies, neuropathy associated with monoclonal gammopathy, Sjogren's disease, lupus, vasculitic neuropathy, polyclonal inflammatory neuropathies, Guillain-Barre syndrome, chronic inflammatory demyelinating neuropathy, multifocal motor neuropathy, paraneoplastic autonomic neuropathy, ganglinoic acetylcholine receptor antibody autonomic neuropathy, Lambert-Eaton myasthenic syndrome and myasthenia gravis; neuropathies associated with nervous system focal ischemia such as thalamic syndrome (anesthesia dolorosa); neuropathies associated with multiple neurotransmitter system dysfunction such as complex regional pain syndrome (CRPS); neuropathies associated with chronic/neuropathic pain such as osteoarthritis, lower back pain, fibromyalgia, cancer bone pain, chronic stump pain, phantom limb pain, and paraneoplastic neuropathies; neuropathies associated with neuropathic pain including peripheral neuropathies such as postherpetic neuralgia, toxic neuropathies (e.g., exposure to chemicals such as exposure to acrylamide, 3-chloropentane, carbamates, carbon disulfide, ethylene oxide, n-hexane, methyl n-butylketone, methyl bromide, organophosphates, polychlorinated biphenyls, pyriminil, trichlorethylene, or dichloroacetylene), focal traumatic neuropathies, phantom and stump pain, monoradiculopathy, and trigeminal neuralgia; and central neuropathies including ischemic cerebrovascular injury (stroke), multiple sclerosis, spinal cord injury, Parkinson's disease, amyotrophic lateral sclerosis, syringomyelia, neoplasms, arachnoiditis, and post-operative pain; mixed neuropathies such as diabetic neuropathies (including symmetric polyneuropathies such as sensory or sensorimotor polyneuropathy, selective small-fiber polyneuropathy, and autonomic neuropathy; focal and multifocal neuropathies such as cranial neuropathy, limb mononeuropathy, trunk mononeuropathy, mononeuropathy multiplex, and asymmetric lower limb motor neuropathy) and sympathetically maintained pain. Other neuropathies include focal neuropathy, glosopharyngeal neuralgia, ischemic pain, trigeminal neuralgia, atypical facial pain associated with Fabry's disease, Celiac disease, hereditary sensory neuropathy, or $B_{12}$-deficiency; mono-neuropathies, polyneuropathies, hereditary peripheral neuropathies such as Carcot-Marie-Tooth disease, Refsum's disease, Strumpell-Lorrain disease, and retinitis pigmentosa; acute polyradiculoneuropathy; and chronic polyradiculoneuropathy. Paraneoplastic neuropathies include paraneoplastic subacute sensory neuronopathy, paraneoplastic motor neuron disease, paraneoplastic neuromyotonia, paraneoplastic demyelinating neuropathies, paraneoplastic vasculitic neuropathy, and paraneoplastic autonomic insufficiency.

The $GABA_B$ agonist baclofen has long been known to have antinociceptive activity in models of acute pain and recent studies have shown that baclofen inhibits allodynia and hyperalgesia in the chronic constriction injury and spinal nerve ligation models of persistent neuropathic pain at doses lower than those required to produce sedation and impairment of motor activity (Hwang and Yaksh, *Pain* 1997, 70, 150-22; Smith et al., *Neuropharmacology* 1994, 33, 1103-1108; and Patel et al., *Pain* 2001, 90, 217-226; Hwang and Yaksh, *Pain* 1997, 70, 15-22; Patel et al., *Pain* 2001, 90, 217-226; Balerio and Rubio, *Pharmacol Res* 2002, 46, 281-286; and Reis and Duarte, *Br J Pharmacol* 2006, 149(6), 733-9). However, $GABA_B$ receptors are also located in the ventral horn of the spinal cord where they have an inhibitory effect on motor neurons resulting in muscle relaxation. Thus, in the absence of a clear analgesic therapeutic window, baclofen is primarily used clinically as a spasmolytic agent.

In clinical studies, intrathecal baclofen administration has been shown to be effective in treating neuropathic pain associated with spinal-cord injury and multiple sclerosis (Herman et al., *Clin J Pain* 1992, 12, 241-247; and Taira et al., *Stereotactic Funct Neurosurg* 1995, 65, 101-105), painful extremity paresthesias (Gatscher et al., *Acta Neurochir Suppl* 2002, 79, 75-76), sympathetically maintained pain (Van Hilten et al., *N Engl J Med* 2000, 343, 625-630; Becker et al., *J Clin Neurosci* 2000, 7, 316-319; and Zuniga et al., *Reg Anesth Pain Med* 2002, 27, 90-93). $GABA_B$ agonists such as baclofen have also been shown to be effective in treating trigeminal, glospharyngeal, vagoglossopharyngeal, and ophthalmic-postherpetic neuralgias (Bowsher, *Br Med Bull* 1991, 47, 655-66; Fromm et al., *Neurology* 1981, 31, 683-687; and Ringel and Roy, *Ann Neurol* 1987, 21, 514-515); and in patients with diabetic neuropathy (Anghinah et al., *Muscle Nerve* 1994, 958-59). Doses of baclofen from about 50 mg/day to about 60 mg/day have been shown to be effective in treating trigeminal neuralgia (Fromm et al., *Ann Neurol* 1984, 15, 240-244).

The efficacy of $GABA_B$ receptor ligands of Formula (I) for treating one or more types of neuropathic pain can be assessed in animal models of neuropathic pain and in clinical trials. Useful animal models of neuropathic pain include peripheral nerve injury by ligation or transection include dorsal rhizotomy; spinal nerve ligation; sciatic nerve; sciatic nerve cuff; partial nerve ligation; chronic constriction; rat spinal cord ischemia model; and spared nerve injury. Other animal models of neuropathies involving immune system activation, and metabolic and chemically induced neuropathies include sciatic cyroneurolysis; zymosan-induced neuritis; HIV gp120-induced pain model; photochemical ischemia; anti-ganglioside antibody; streptozotocin-neuropathy; DDI-induced myelinopathy; formalin phase 2 model of hyperalgesic pain; vincristine-induced pain model; paclitaxel-induced pain model; and cisplatin-induced pain model.

The efficacy of $GABA_B$ receptor ligands of Formula (I) for treating various types of neuropathic pain can also be assessed in clinical trials using, for example, randomized double-blind placebo controlled methods. End points used in clinical trials for neuropathic pain can be determined using validated neuropathic pain criteria such as the Brief Pain Inventory, Categorical Scale, Gracety Pain Scale, Likert Scale, Neuropathic Pain Scale, Numerical Pain Scale, Short Form McGill Pain Questionnaire, Verbal Pain Scale, Visual Analog Scale (VAS), VAS Pain Intensity Scale, and/or VAS Pain Relief Scale.

Musculoskeletal conditions causing tenderness and muscle spasms include fibromyalgia, tension headaches, myofascial pain syndrome, facet joint pain, internal disk disruption, somatic dysfunction, spinal fractures, vertebral osteomyelitis, polymyalgia rheumatica, atlantoaxial instability, atlanto-occipital joint pain, osteoporotic vertebral compression fracture, Scheuermann's disease, spondyloysis, spondylolisthesis, kissing spines, sacroiliac joint pain, sacral stress fracture, coccygodynia, failed back syndrome, and mechanical low back or neck pain (Meleger and Krivickas, *Neurol Clin* 2007, 25, 419-438). In these conditions, muscle spasm is related to local factors involving the affected muscle groups without the increased tone or reflex characteristic of spasticity. Muscle, tendon, ligament, intervertebral disc, articular cartilage, and bone can be involved in musculoskeletal pain. Disorders that can produce neck and back pain include muscle strain, ligament sprain, myofascial pain, fibromyalgia, facet joint pain, internal disc disruption, somatic dysfunction, spinal fracture, verterbral osteomyelitis, and polymyalgia rheumatica, atlantoaxial instability and atlanto-occipital joint pain.

$GABA_B$ agonists are known to induce muscle-relaxant effects when administered systemically or centrally (Malcangio and Bowery, *Trends Pharmacol Sci* 1996, 17, 457-462). Consequently, the use of $GABA_B$ agonists such as baclofen for treating spasticity associated with upper motor neuron syndromes is well established. Studies have also shown that $GABA_B$ agonists can be effective in treating muscular pain and/or spasms associated with peripheral musculoskeletal conditions. Baclofen has been shown effective in treating migraine (Hering-Hanit, *Cephalalgia* 1999, 19, 589-591; Hering-Hanit and Gadoth, *Headache* 2000, 40, 48-51) and specifically in tension-type headaches (Freitag, *CNS Drugs* 2003, 17(6), 373-381); and in low-back pain and radiculopathy (Zuniga et al., *Anesthesiology* 2000, 92, 876-880; Vatine et al., Pain Clin 1989, 2, 207-217; Dapas et al., *Spine* 1985, 10(4), 345-349; and Raphael et al., *BMC Musculoskeletal Disorders* 2002, 3(17), EPub June 20.

The efficacy of $GABA_B$ receptor ligands of Formula (I) for treating one or more types of musculoskeletal pain can be assessed in animal models of neuropathic pain and in clinical trials.

Low back pain generally occurs in the lumbar region of the back in the location of lumbar vertebrae L1-L5. Pain in the lower back can be caused by a sprain, strain, or spasm to one of the muscles, ligaments, facet joints, and/or sacroiliac joints in the back; spinal sprain or overcompression; or disc rupture or bulge. Low back pain may also reflect nerve or muscle irritation or bone lesions. Most low back pain follows injury or trauma to the back, but pain may also be caused by degenerative conditions such as arthritis or disc disease, osteoporosis, or other bone diseases, viral infections, irritation to joints and discs, or congenital abnormalities in the spine. Obesity, smoking, weight gain during pregnancy, stress, poor physical condition, posture inappropriate for the activity being performed, and poor sleeping position also may contribute to low back pain. Additionally, scar tissue created when the injured back heals itself does not have the strength or flexibility of normal tissue. Buildup of scar tissue from repeated injuries eventually weakens the back and can lead to more serious injury. Occasionally, low back pain may indicate a more serious medical problem. Pain accompanied by fever or loss of bowel or bladder control, pain when coughing, and progressive weakness in the legs may indicate a pinched nerve or other serious condition. People with diabetes may have severe back pain or pain radiating down the leg related to neuropathy. Low back pain can be caused by bulging disc (e.g., protruding, herniated, or ruptured disc), sciatica, spinal degeneration, spinal stenosis, osteoporosis, osteoarthritis, compression fractures, skeletal irregularities, fibromyalgia, spondylolysis and/or spondylolisthesis. Less common spinal conditions that can cause low back pain include ankylosing spondylitis, bacterial infections, osteomyelitis, spinal tumors, Paget's disease, and Scheuermann's disease.

Clinical results suggest that $GABA_B$ receptor agonists such as baclofen can be effective in treating low back pain (Dapas et al., *Spine* 1985, 10(4), 345-349; and Raphael et al., *BMC Musculoskeletal Disorders* 2002, 3917). For example doses of baclofen from about 20 mg/day to about 80/mg day have been shown to be effective in treating acute low back pain (Dapas et al., *Spine* 1985, 10(4), 345-9).

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors. One of the characteristic features of asthma is the propensity of the airways to respond to stimuli that are otherwise innocuous to healthy subjects, and the similarities in the mechanisms contributing to hyperalgesia and allodynia in clinical pain syndromes and bronchial hyperresponsiveness in asthma has been recognized.

$GABA_B$ receptor agonists have been shown to modulate the contraction of airway smooth muscle, and it has been suggested that dysfunction of $GABA_B$ receptors may underlie the airway obstruction characteristic of certain respiratory diseases such as asthma.

The efficacy of $GABA_B$ receptor ligands of Formula (I) for treating asthma can be assessed using animal models and in clinical trials.

$GABA_B$ receptor ligands of Formula (I) can act as full agonists, partial agonists, antagonists, inverse agonists, and/or allosteric modulators of $GABA_B$ receptors. Accordingly, $GABA_B$ receptor ligands of Formula (I) can be used to modulate $GABA_B$ receptor function in a patient.

$GABA_B$ receptor ligands of Formula (I) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical. Administration may be systemic or local. Various delivery systems are known, e.g., encapsulation in liposomes, microparticles, microcapsules, capsules, etc) that may be used to administer a compound and/or pharmaceutical composition.

In certain embodiments, it may be desirable to introduce $GABA_B$ receptor ligands of Formula (I) and pharmaceutical compositions thereof into the central nervous system, which may be by any suitable route, including intraventricular, intrathecal, and epidural injection. Intraventricular injection may be facilitated using an intraventricular catheter attached to a reservoir such as an Ommaya reservoir.

The amount of a $GABA_B$ receptor ligand of Formula (I) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a $GABA_B$ receptor ligand of Formula (I) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a $GABA_B$ receptor ligand of Formula (I) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a $GABA_B$ ligand may exhibit a high therapeutic index. The data obtained from these cell culture assays and animal studies may be used in formulating a dosage range that is not toxic for use in humans. A dose of a $GABA_B$ ligand provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Methods provided by the present disclosure may further comprise administering one or more pharmaceutically active compounds in addition to a $GABA_B$ receptor ligand of Formula (I). Such compounds may be provided to treat the same disease or a different disease than the disease being treated with the $GABA_B$ receptor ligand of Formula (I).

In certain embodiments, a $GABA_B$ ligand of Formula (I) may be used in combination with at least one other therapeutic agent. In certain embodiments, a $GABA_B$ receptor ligand of Formula (I) may be administered to a patient together with another compound for treating spasticity, gastro-esophageal reflux disease, emesis, cough, a substance abuse disorder, an attention disorder, an anxiety disorder, a mood disorder, a cognitive disorder, migraine, or pain. A $GABA_B$ receptor ligand of Formula (I) and the at least one other therapeutic agent may act additively or, in certain embodiments, synergistically. The at least one additional therapeutic agent may be included in the same dosage form as a $GABA_B$ receptor ligand of Formula (I) or may be in a separate dosage form. Methods provided by the present disclosure may further include, in addition to administering a $GABA_B$ receptor ligand of Formula (I), administering one or more therapeutic agents effective for treating the same or different disease than the disease being treated by a $GABA_B$ receptor ligand of Formula (I). Methods provided by the present disclosure include administration of a $GABA_B$ receptor ligand of Formula (I) and one or more other therapeutic agents provided that the combined administration does not inhibit the therapeutic efficacy of the $GABA_B$ receptor ligand of Formula (I) and/or does not produce adverse combination effects.

In certain embodiments, dosage forms comprising a $GABA_B$ receptor ligand of Formula (I) may be administered concurrently with the administration of another therapeutic agent, which may be part of the same dosage form as, or in a different dosage form than that comprising a $GABA_B$ ligand of Formula (I). A $GABA_B$ receptor ligand of Formula (I) may be administered prior or subsequent to administration of another therapeutic agent. In certain embodiments of combination therapy, the combination therapy may comprise alternating between administering a $GABA_B$ receptor ligand of Formula (I) and a composition comprising another therapeutic agent, e.g., to minimize adverse drug effects associated with a particular drug. When a $GABA_B$ receptor ligand of Formula (I) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a $GABA_B$ receptor ligand of Formula (I) may be administered with one or more substances to enhance, modulate and/or control release, bioavailability, therapeutic efficacy, therapeutic potency, stability, and the like of a $GABA_B$ receptor ligand of Formula (I). For example, to enhance the therapeutic efficacy of a $GABA_B$ receptor ligand of Formula (I), the $GABA_B$ receptor ligand of Formula (I) may be co-administered with or a dosage form comprising a $GABA_B$ receptor ligand of Formula (I) may comprise one or more active agents to increase the absorption or diffusion of a $GABA_B$ receptor ligand of Formula (I) from the gastrointestinal tract to the systemic circulation, or to inhibit degradation of the $GABA_B$ receptor ligand of Formula (I) in the blood of a patient. In certain embodiments, a $GABA_B$ receptor ligand of Formula (I) may be co-administered with an active agent having pharmacological effects that enhance the therapeutic efficacy of a $GABA_B$ receptor ligand of Formula (I).

Additionally, dosage forms provided by the present disclosure may be used in combination with other drugs that are themselves known to cause spasticity, gastro-esophageal reflux disease, emesis, cough, a substance abuse disorder, an attention disorder, an anxiety disorder, a mood disorder, a cognitive disorder, migraine, or pain, thereby preventing or reducing the occurrence of such adverse effects.

In certain embodiments, a $GABA_B$ receptor ligand of Formula (I) or a pharmaceutical composition thereof may be administered to a patient for treating spasticity in combination with a therapy or another therapeutic agent known or believed to be effective in treating spasticity. Examples of drugs useful for treating spasticity and which may be administered in conjunction with a $GABA_B$ ligand of Formula (I) include levodopa; gabapentin; mild sedatives such as benzodiazepines such as alprazolam, chlordiazepoxide, clonazepam, clorazepate, diazepam, lorazepam, dantrolene, and oxazepam; imidazolines such as clonidine and tizanidine; muscle relaxants such as baclofen; anticholinergic drugs such as trihexyphenidyl and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline; chemodenervation with local anesthetics such as lidocaine and xylocalne; type A botulinum toxin and type B botulinum toxin. Surgical treatments useful in treating spasticity include neurosurgery such as selective dorsal rhizotomy; and orthopedic operations such as contracture release, tendon or muscle lengthening, tendon transfer, osteotomy, and arthrodesis. Other therapies for treating spasticity include physical and occupational therapy such as functional based therapies, rehabilitation, facilitation such as neurodevelopmental therapy, proprioceptive neuromuscular facilitation, and sensory integration; biofeedback: electrical stimulation; and orthoses.

In certain embodiments, a $GABA_B$ receptor ligand of Formula (I) or a pharmaceutical composition thereof may be administered to a patient for treating gastro-esophageal reflux disease in combination with a therapy or another therapeutic agent known or believed to be effective in treating gastro-esophageal reflux disease. Examples of drugs for treating gastro-esophageal reflux disease and which may be administered in conjunction with a $GABA_B$ receptor ligand of Formula (I) include H2 inhibitors such as cimetidine, famotidine, nizatidine, and ranitidine; proton pump inhibitors such as omeprazole, lansoprazole, pantoprazole, rabeprazole, and exomeprazole; and prokinetics such as cisparide, bethanechol, and metoclopramide.

In certain embodiments, a $GABA_B$ receptor ligand of Formula (I) or a pharmaceutical composition thereof may be administered to a patient for treating emesis in combination with a therapy or another therapeutic agent known or believed to be effective in treating emesis. Examples of drugs for treating emesis (nausea and vomiting) and which may be administered in conjunction with a $GABA_B$ ligand of Formula (I) include benzamines such as metoclopramide; phenothiazines such as prochlorperazine, perphenazine, chlorpromazine, promethazine, and thiethylperazine; butyrophenones such as droperidol and haloperidol; dopamine 2 antagonists such as metoclorpamide; 5-HT3 antagonists such as ondansetron, granisetron, dolasetron, palonosetron; NK-1 receptor antagonists such as aprepitant, corticosteroids such as dexamethazone; antihistamines such as diphenhydramine and hydroxyzine; cannabinoids such as dronabinol; and benzodiazepines such as lorazepam, midazolam, alprazolam, and olanzapine. Examples of drugs useful for treating CINV include aprepitant, dexamethasone, dolasetron, dronabinol, granisetron, lorazepam, metoclopramide, ondonsetron, palonosetrondiphenhydramine, and prochlorperazine. Examples of drugs useful for treating breakthrough emesis such as prochlorperazine, thiethylperazine, metoclopramide, diphenhydramine, lorzepam, haloperidol, dronabinol, ondansetron, granisetron, dolasetron, dexamethasone, olanzapine, and promethazine. Examples of drugs useful for treating anticipatory emesis include alprazolam and lorazepam.

In certain embodiments, a $GABA_B$ ligand of Formula (I) or a pharmaceutical composition thereof may be administered to a patient for treating alcohol addiction or abuse in combination with a therapy or another therapeutic agent known or believed to be effective in treating alcohol addiction and abuse. Examples of drugs for treating alcohol addiction or abuse and which may be administered in conjunction with a $GABA_B$ ligand of Formula (I) include disulfuram, naltrexone, clonidine, methadone, 1-alpha-acetylmethadol, buprenorphine, and bupropion. Examples of drugs useful for treating alcohol dependency or alcohol abuse disorders include disulfuram, naltrexone, acamprosate, ondansetron, atenolol, chlordiazepoxide, clonidine, clorazepate, diazepam, oxazepam, methadone, topiramate, 1-α-acetylmethadol, buprenorphine, bupropion, and baclofen.

In certain embodiments, a $GABA_B$ ligand of Formula (I) or a pharmaceutical composition thereof may be administered to a patient for treating narcotic addiction or abuse in combination with a therapy or another therapeutic agent known or believed to be effective in treating narcotic addiction or abuse. Examples of drugs for treating narcotic addiction or abuse and which may be administered in conjunction with a $GABA_B$ ligand of Formula (I) include buprenorphine, tramadol, methadone, and naltrexone. Examples of drugs useful for treating opioid abuse disorders include buprenorphine, naloxone, tramadol, methadone, and naltrexone. Examples of drugs useful for treating cocaine abase disorders include disulfuram, modafinil, propranolol, baclofen, vigabatrin, and topiramate.

In certain embodiments, a $GABA_B$ ligand of Formula (I) or a pharmaceutical composition thereof may be administered to a patient for treating nicotine addiction or abuse in combination with a therapy or another therapeutic agent known or believed to be effective in treating nicotine addiction or abuse. Examples of drugs for treating nicotine addiction or abuse and which may be administered in conjunction with a $GABA_B$ receptor ligand of Formula (I) include bupropion, clonidine, rimonabant, varenicline, and nicotine.

In certain embodiments, a $GABA_B$ receptor ligand of Formula (I) or a pharmaceutical composition thereof may be administered to a patient for treating cough in combination with a therapy or another therapeutic agent known or believed to be effective in treating cough. Examples of drugs for treating cough and which may be administered in conjunction with a $GABA_B$ receptor ligand of Formula (I) include dextromethorphan, guaifenesin, hydrocodone, benzonatate, diphenhydramine, pseudoephedrine, acetaminophen, and carbinoxamine.

In certain embodiments, $GABA_B$ receptor ligands of Formula (I) or pharmaceutical compositions thereof may be administered to a patient for treating cough in combination with a therapy or another therapeutic agent known or believed to be effective in treating cough, or in certain embodiments, a disease, disorder, or condition associated with cough. Examples of drugs useful for treating cough include acetaminophen, benzonatate, carbetapentane, carbinoxamine, chlorpheniramine, codeine, dextromethorphan, diphehydramine, guaiacol sulfonate, guaifenesin, homatropine, homatropine methyl bromide, hydrocodone, hydromorphone, moguisteine, potassium iodide, promethazine, and pseudoephedrine. Other antitussive therapies include nocicpetin/orphanin, tachykinins, transient receptor potential vallinoid receptor-1 (TRPV-1) antagonists, postassium channel openers, diuretics, and methylxanthines.

In certain embodiments, $GABA_B$ receptor ligand of Formula (I) or pharmaceutical compositions thereof may be administered to a patient for treating various forms of urinary incontinence including overactive bladder. Urinary incontinence is any involuntary leakage of urine and can be categorized into five types based on the pattern of symptoms including urge incontinence, stress incontinence, overflow incontinence, functional incontinence, and mixed incontinence. Current pharmacological management of urinary incontinence includes muscarinic receptor antagonists such as oxybutynin, tolterodine, trospium, solifenacin, and darifenacin. Lam and Hilas, *Clinical Interventions in Aging* 2007, 2, 337-345. These anticholinergic drugs are contraindicated in patients with urinary retention, gastric retention, or uncontrolled narrow-angle glaucoma, and have possible anticholinergic side effects such as heat prostration, dry mouth, constipation, dry eyes, urinary retention, dizziness and blurred vision. In a double blind crossover trial baclofen administered at a dose of 5 mg four times per day was shown to significantly improve diurnal and nocturnal of frequency of micturition and the severity of incontinence in patients with unstable bladder syndrome. (Taylor and Bates, *British J Urology* 1979, 51, 504-505). In preclinical studies baclofen has been shown to inhibit the micturition reflex of rats in a bladder filling model and inhibited bladder overactivity caused by oxyhemoglobin (Pherson, et. al. *J. Urology* 2002, 168, 2700-2705.

In certain embodiments, $GABA_B$ receptor ligand of Formula (I) or pharmaceutical compositions thereof may be administered to a patient for treating asthma in combination with a therapy or another therapeutic agent known or believed to be effective in treating asthma, or in certain embodiments, a disease, disorder, or condition associated with asthma. Examples of drugs useful in treating asthma include albuterol, aminophylline, beclomethasone, bitolterol, budesonide, cromolyn, ephedrine, epinephrine, flunisolide, fluticasone, formoterol, hydrocortisone, isoproterenol, levalbuterol, methylprednisolone, prednisolone, prednisone, pirbuterol, metaproterenol, racepinephrine, omalizumab, oxytriphylline, mometusone, montelukast, nedocromil, oxtriphylline, pirbuterol, salmeterol, terbutaline, theophylline, triamcinolone, zafirlukast, and zileuton.

In certain embodiments, a $GABA_B$ receptor ligand of Formula (I) or a pharmaceutical composition thereof may be administered to a patient for treating an attention disorder in combination with a therapy or another therapeutic agent known or believed to be effective in treating an attention disorder. Examples of drugs for treating attention disorders and which may be administered in conjunction with a $GABA_B$ ligand of Formula (I) include dextroamphetamine, methylphenidate, pemoline, atomoxetine, bupropion, dexmethylphenidate, and lisdexamfetamine.

In certain embodiments, a $GABA_B$ receptor ligand of Formula (I) or a pharmaceutical composition thereof may be administered to a patient for treating an anxiety disorder in combination with a therapy or another therapeutic agent known or believed to be effective in treating an anxiety disorder. Examples of drugs for treating anxiety disorders and which may be administered in conjunction with a $GABA_B$ ligand of Formula (I) include alprazolam, atenolol, busipirone, chlordiazepoxide, clonidine, clorazepate, diazepam, doxepin, escitalopram, halazepam, hydroxyzine, lorazepam, nadolol, oxazepam, paroxetine, prochlorperazine, trifluoperazine, venlafaxine, amitriptyline, sertraline, citalopram, clomipramine, fluoxetine, fluvoxamine, and paroxetine.

In certain embodiments, a $GABA_B$ receptor ligand of Formula (I) or a pharmaceutical composition thereof may be administered to a patient for treating a mood disorder in combination with a therapy or another therapeutic agent known or believed to be effective in treating a mood disorder. Examples of drugs useful for treating bipolar disorder and which may be administered in conjunction with a $GABA_B$ ligand of Formula (I) include aripirprazole, verapamil, carbamazepine, clonidine, clonazepam, lamotrigine, olanzapine, quetiapine, fluoxetine, and ziprasidone. Examples of drugs useful for treating depression and which may be administered in conjunction with a $GABA_B$ ligand of Formula (I) include tricyclics such as amitriptyline, amoxapine, clomipramine, desipramine, doxepin, imipramine, maprotiline, nortryptyline, protryptyline, and trimipramine; tetracyclics such as maprotiline and mirtazapine; selective serotonin reuptake inhibitors (SSRI) such as citalopram, escitalopram, fluoxetine, fluvoxamine, paroxetine, and sertraline; serotonin and norepinephrine reuptake inhibitors (SNRI) such as venlafaxine and duloxetine; monoamine oxidase inhibitors such as isocarboxazid, phenelzine, selegiline, and tranylcypromine; psychostimulants such as dextroamphetamine and methylphenidate; and other drugs such as bupropion, mirtazapine, nefazodone, trazodone, lithium, and venlafaxine.

In certain embodiments, a $GABA_B$ receptor ligand of Formula (I) or a pharmaceutical composition thereof may be administered to a patient for treating a cognitive disorder in combination with a therapy or another therapeutic agent known or believed to be effective in treating a cognitive disorder. Examples of drugs for treating cognitive disorders and which may be administered in conjunction with a $GABA_B$ ligand of Formula (I) include risperidone; acetylcholinesterase inhibitors such as donepezil, rivastigmine, metrifonate, galantamine, physostigmine, tacrine, hyperzine A, and icopezil.

In certain embodiments, a $GABA_B$ receptor ligand of Formula (I) or a pharmaceutical composition thereof may be administered to a patient for treating migraine in combination with a therapy or another therapeutic agent known or believed to be effective in treating migraine. Drugs useful for treating migraine can prevent a migraine from occurring, abort a migraine that is beginning, or relieve pain during the migraine episode.

Prophylactic migraine treatments reduce the frequency of migraines and include non-steroidal anti-inflammatory agents (NSAIDs), adrenergic beta-blockers, calcium channel blockers, tricyclic antidepressants, selective serotonin reuptake inhibitors, anticonvulsants, NMDA receptor antagonists, angiotensin converting enzyme (ACE) inhibitors, angiotensin-receptor blockers (ARBs), leukotriene-antagonists, dopamine agonists, selective 5HT-1D agonists, selective 5HT-1F agonists, AMPA/KA antagonists, CGRP (calcitonin gene related peptide) antagonists, NOS (nitric oxide synthase) inhibitors, blockers of spreading cortical depression, and other therapy. Examples of NSAIDs useful for preventing migraine include aspirin, ibuprofen, fenoprofen, flurbiprofen, ketoprofen, mefenamic acid, and naproxen. Examples of adrenergic beta-blockers useful for preventing migraine include acebutolol, atenolol, imilol, metoprolol, nadolol, pindolol, propranolol, and timolol. Examples of calcium channel blockers useful for preventing migraine include amlodipine, diltiazem, dotarizine, felodipine, flunarizine, nicardipine, nifedipine, nimodipine, nisoldipine, and verapamil. Examples of tricyclic antidepressants useful for preventing migraine include amitriptyline, desipramine, doxepin, imipramine, nortriptyline, and protriptyline. Examples of selective serotonin reuptake inhibitors (SSRIs) useful for preventing migraine include fluoxetine, methysergide, nefazodone, paroxetine, sertraline, and venlafaxine. Examples of other antidepressants useful for preventing migraine include bupropion, nefazodone, norepinephrine, and trazodone.

Examples of anticonvulsants (antiepileptics) useful for preventing migraine include divalproex sodium, felbamate, gabapentin, lamotrigine, levetiracetam, oxcarbazepine, tiagabine, topiramate, valproate, and zonisamide. Examples of NMDA receptor antagonists useful for preventing migraine include dextromethorphan, magnesium, and ketamine. Examples of angiotensin converting enzyme (ACE) inhibitors useful for preventing migraine include lisinopril. Examples of angiotensin-receptor blockers (ARBs) useful for preventing migraine include candesartan. Examples of leukotriene-antagonists useful for preventing migraine include zileuton, zafirlukast, montelukast, and pranlukast. Examples of dopamine agonists useful for preventing migraine include α-dihydroergocryptine. Examples of other therapy useful for preventing migraine include botulinum toxin, magnesium, hormone therapy, riboflavin, methylergonovine, cyproheptadine, and phenelzine, and complementary therapies such as counseling/psychotherapy, relaxation training, progressive muscle relaxation, guided imagery, diaphragmatic breathing, biofeedback, acupuncture, and physical and massage therapy.

Acute migraine treatments intended to eliminate or reduce the severity of the headache and any associated symptoms after a migraine has begun include serotonin receptor agonists, such as triptans (5-hydroxytryptophan (5-HT) agonists) such as almotriptan, eletriptan, frovatriptan, naratriptan, rizatriptan, sumatriptan, and zolmitriptan; ergotamine-based compounds such as dihydroergotamine and ergotamine; antiemetics such as metoclopramide and prochlorperazine; and compounds that provide analgesic effects.

Other drugs used to treat migraine once started include, acetaminophen-aspirin, caffeine, cyproheptadine, methysergide, valproic acid, NSAIDs such as diclofenac, flurbiprofen, ketaprofen, ketorolac, ibuprofen, indomethacin, meclofenamate, and naproxen sodium, opioids such as codeine, meperidine, and oxycodone, and glucocorticoids including dexamethasone, prednisone and methylprednisolone.

In certain embodiments, a $GABA_B$ receptor ligand of Formula (I) or a pharmaceutical composition thereof may be administered to a patient for treating pain in combination with a therapy or another therapeutic agent known or believed to be effective in treating pain.

Examples of drugs for treating neuropathic pain and which may be administered in conjunction with a $GABA_B$ receptor ligand of Formula (I) include opioid analgesics such as morphine, codeine, fentanyl, meperidine, methadone, propoxyphene, levorphanol, hydromorphone, oxycodone, oxymorphone, tramadol and pentazocine; nonopioid analgesics such as aspirin, ibuprofen, ketoprofen, naproxen, and acetaminophen; non-steroidal anti-inflammatory drugs such as aspirin, choline magnesium trisalicylate, diflunisal, salsalate, celecoxib, rofecoxib, valdecoxib, diclofenac, etodolac, fenoprofen, flubiprofen, ibuprofen, indomethacin, ketoprofen, ketorolac, meclofanamate, mefenamic acid, meloxicam, nabumetone, naproxen, oxaprozin, piroxicam, sulindac, and tometin; antiepileptics such as gabapentin, pregabalin, carbamazepine, phenyloin, lamotrigine, and topiramate; antidepressants such as duloxetine, amitriptyline, venlafaxine, nortryptyline, imipramine, and desipramine; local anesthetics such as lidocaine, and mexiletine; NMDA receptor antagonists such as dextropethorphan, memantine, and ketamine; N-type calcium-channel blockers such as ziconotide; vanilloid receptor-1 modulators such as capsaicin; cannabinoid receptor modulators such as sativex; neurokinin receptor antagonists such as lanepitant; other analgesics such as neurotropin; and other drugs such as desipramine, clonazepam, divalproex, oxcarbazepine, divalproex, butorphanol, valdecoxib, vicoprofen, pentazocine, propoxyhene, fenoprofen, piroxicam, indometnacin, hydroxyzine, buprenorphine, benzocaine, clonidine, flurbiprofen, meperidine, lacosamide, desvenlafaxine, and bicifadine.

In certain embodiments, a drug useful for treating neuropathic pain is chosen from propoxyphene, meperidine, hydromorphone, hydrocodone, morphine, codeine, 2-piperidinol-1-alkanol, eliprodil, ifenprodil, rofecoxib, celecoxib, salicylic acid, diclofenac, piroxicam indomethacin, ibuprofen, naproxen, gabapentin, carbemazepine, pregabalin, topiramate, valproic acid, sumatriptan, elitriptan, rizatriptan, zolmitriptan, naratriptan, flexeril, carisoprodol, robaxisal, norgesic, dantrium, diazepam, chlordiazepoxide, alprazolam, lorazepam, acetaminophen, nitrous oxide, halothane, lidocaine, etidocaine, ropivacaine, chloroprocaine, sarapin, bupivacaine, capsicin, desipramine, amitriptyline, doxepin, perphenazine, protriptyline, tranylcypromine, baclofen, clonidine, mexelitine, diphenhydramine, hydroxyzine, caffeine, prednisone, methyl-prednisone, decadron, sertraline, paroxetine, fluoxetine, tramadol, levodopa, dextromethorphan, substance P antagonists, and botulinum toxin. In certain embodiments, a drug useful for treating neuropathic pain can be chosen from a nicotine receptor partial agonist. Non-pharmacological therapies for treating neuropathic pain include transcutaneous electrical nerve stimulation, percutaneous electrical nerve stimulation, and acupuncture.

In certain embodiments, a $GABA_B$ receptor ligand of Formula (I) or a pharmaceutical composition thereof may be administered to a patient for treating pain in combination with a therapy or another therapeutic agent known or believed to be effective in treating pain. Examples of drugs for treating musculoskeletal pain and which may be administered in conjunction with a $GABA_B$ receptor ligand of Formula (I) include cyclobenzaprine, dantrolene, methocarbamol, orphenadrine, tizanidrine, metaxalone, carisoprodol, chlorphenesin, chlorzoxazone, alprazolam, bromazepam, chlordiazepoxide, clorazepate, diazepam, flunitriazepam, lorazepam, medazepam, midazolam, oxazepam, prazepam, triazolam, temazepam, botulinum toxin, NSAIDs such as aspirin, naproxen, and ibuprofen; anticonvulsants, antidepressants such as amitriptyline and desipramine; and opioids such as codeine, oxycodone, hydrocodone, and morphine.

EXAMPLES

The following examples describe in detail the synthesis of $GABA_B$ receptor ligands of Formula (I), properties of $GABA_B$ receptor ligands of Formula (I), and uses of $GABA_B$ receptor ligands of Formula (I). It will be apparent to those skilled in the art that many modifications, both to materials and methods, may be practiced without departing from the scope of the disclosure.

General Synthetic Protocols

All reagents and solvents were purchased from commercial suppliers and used without further purification or manipulation prior to use.

Proton NMR spectra (400 MHz) were recorded on a Varian AS 400 NMR spectrometer equipped with an autosampler and data processing computation. DMSO-$d^6$ (99.9% D) or CDCl$_3$ (99.8% D) were used as solvents unless otherwise noted. The DMSO-$d^5$ or CHCl$_3$ solvent signal was used for calibration of the individual spectra. Analytical LC/MS was performed on a Waters 2790 separation module equipped with a Waters Micromass QZ mass spectrometer, a Waters 996 photodiode detector, and a Merck Chromolith UM2072-027 or Phenomenex Luna C-18 analytical column. Analytical thin layer chromatography (TLC) was performed using Whatman, Schleicher & Schuell TLC MK6F silica gel plates (2.5×7.5 cm, 250 µm layer thickness). Mass-guided preparative HPLC purification of titled compounds was performed on an instrument equipped with a Waters 600 controller, ZMD Micromass spectrometer, a Waters 2996 photodiode array detector, and a Waters 2700 Sample Manager. Acetonitrile/water gradients containing 0.05% formic acid were used as eluants in both analytical and preparative HPLC experiments unless noted otherwise.

Synthesis of Precursors of 2-Substituted Chlorophenol Derivatives (4R)-4-(3-Amino-6-bromo-4-chlorophenyl)pyrrolidin-2-one Seven and one-half (7.5) g (35.71 mmol) of (4R)-4-(3-amino-4-chlorophenyl)-pyrrolidin-2-one was dissolved in 170 mL chloroform (0.25 M) and 3 mL of acetic acid. To this solution, 6.3 g of solid N-bromosuccinimide was added portion-wise. The reaction was stirred overnight at room temperature. The reaction mixture was diluted with saturated ammonium chloride aqueous solution (50 mL). The aqueous solution was extracted with dichloromethane (2×50 mL), dried over $MgSO_4$ and the solvent evaporated to dryness. Water was added to the oil and the pH adjusted to 9 with 1N NaOH. The solid was filtered, washed consecutively with water, ether, and hexane and dried under a high vacuum to give 9.3 g of the title compound (88% yield).

The same method was used to prepare the iodo-substituted compound using N-iodosuccinimide. $^1$H-NMR (400 MHz, $CD_3OD$): δ 2.35-2.41 (dd, J=17.2, 5.2 Hz, 1H), 2.67-2.75 (dd, J=17.2, 9.2 Hz, 1H), 3.75-3.80 (dd, J=10.0, 4.0 Hz, 1H), 3.93-4.00 (m, 1H), 6.83 (s, 1H), 7.37 (s, 1H); MS (ESI) m/z 290.93 $(M+H)^+$.

(4R)-4-(2-Bromo-4-chlorophenyl)pyrrolidin-2-one (4R)-4-(3-Amino-6-bromo-4-chlorophenyl)pyrrolidin-2-one was dissolved in 32 mL of sulfuric acid aqueous solution (1M) and the heated at 55° C. for 20 min. The reaction mixture was cooled to 0° C. and 160 mL ethyl acetate/water added. To this mixture, 1.5 equivalent of $NaNO_2$ was added portion wise. The reaction was monitored by LCMS. After the starting material was consumed, the mixture was diluted with water and extracted with dichloromethane. The combined organic phases were washed with water and brine, and dried over sodium sulfate. The solvent was removed to provide the title compound as an off-white solid (4.7 g, 55% yield). $^1$H-NMR (400 MHz, $CD_3OD$): δ 2.38-2.44 (dd, J=17.2, 4.0 Hz, 1H), 2.73-2.80 (dd, J=17.2, 9.2 Hz, 1H), 3.33-3.37 (dd, J=10.0, 6 Hz, 5.6 Hz, 1H), 3.78-3.83 (dd, J=10.0, 8.0 Hz, 1H), 4.06-4.13 (m, 1H), 7.64-7.65 (m, 1H), 7.38 (m, 2H); MS (ESI) m/z 275.89 $(M+H)^+$.

(3R)-4-Amino-3-(2-bromo-4-chlorophenyl)butanoic acid hydrochloride

To a solution of (4R)-4-(3-amino-4-chlorophenyl)pyrrolidin-2-one (100 mg) in 0.2 mL of acetonitrile was added 1 mL of 6N HCl. The mixture was heated overnight at 90° C. The reaction mixture was then cooled to room temperature and the pH was adjusted to 5.0. Solvent was removed in vacuo. The residue was purified by HPLC to give 19.9 mg of the title compound. $^1$H-NMR (400 MHz, $CD_3OD$): δ 2.58-2.62 (dd, J=16.0, 4.0 Hz, 1H), 2.66-2.73 (dd, J=16.0, 12.0 Hz, 1H), 3.16-3.24 (dd, J=12.8, 6.0 Hz, 1H), 3.12-3.31 (m, 1H), 3.81-3.88 (m, 1H), 7.34 (s, 1H), 7.37-7.40 (d, J=2.0 Hz, 1H), 7.67 (d, J=2.0 Hz, 1H); MS (ESI) m/z 293.89 $(M+H)^+$.

(3R)-4-Amino-3-(4-chloro-2-iodophenyl)butanoic acid hydrochloride

Following the procedure and replacing N-bromosuccinimide with N-iodosuccinimide in the synthesis of (4R)-4-(3-amino-6-bromo-4-chlorophenyl)pyrrolidin-2-one afforded the title compound in good yield. $^1$H-NMR (400 MHz, $CD_3OD$): δ 2.66-2.72 (dd, J=16.8, 7.6 Hz, 1H), 2.75-2.81 (dd, J=16.8, 6.8 Hz, 1H), 3.22 (m, 1H), 3.30-3.33 (m, 1H), 3.81-3.88 (m, 1H), 7.35 (s, 1H), 7.43-7.45 (d, J=8.8 Hz, 1H), 7.93-7.94 (d, J=4, 2.4 Hz, 1H); MS (ESI) m/z 339.99 $(M+H)^+$.

General Synthetic Procedure for Sulfonamide Analogs

Step 1: N-(5-((3R)-5-Oxopyrrolidin-3-yl)-2-chlorophenyl)-2,2,2-trifluoroacetamide To a suspension of (4R)-4-(3-amino-4-chlorophenyl)-pyrrolidin-2-one (9 g, 43 mmol) in dichloromethane (50 mL) triethylamine (64.5 mmol, 1.5 eq) was added. The mixture was cooled to 0° C. and trifluoroacetic anhydride (43 mmol) was added dropwise. The reaction mixture was stirred overnight and monitored by TLC and LCMS, and then diluted with saturated ammonium chloride aqueous solution and extracted with dichloromethane (2×100 mL). The combined organic phases were washed with 1N HCl and brine, dried over sodium sulfate, and concentrated to dryness to provide 13.1 g (98% yield) of the title compound. $^1$H-NMR (400 MHz, $CD_3OD$): δ 2.42-2.48 (dd, J=16.0, 8.0 Hz, 1H), 2.69-2.75 (dd, J=16.0, 8.0 Hz, 1H), 3.37-3.39 (m, 1H), 3.74-3.80 (m, 2H), 7.27-7.30 (d, J=4.0 Hz, 1H), 7.47-7.49 (m, 2H); MS (ESI) m/z 307.05 $(M+H)^+$.

Step 2: N-(5-((3R)-5-Oxopyrrolidin-3-yl)-2-chloro-4-nitrophenyl)-2,2,2 trifluoroacetamide N-(5-((3R)-5-Oxopyrrolidin-3-yl)-2-chlorophenyl)-2,2,2-trifluoroacetamide (7.6 g, 24.83 mmol) was dissolved in 25 mL of concentrated $H_2SO_4$ (1M solution). The mixture was then cooled to 0° C. and guanidine nitrate (24.83 mmol) was added portion-wise. The reaction mixture was stirred at 0° C. for 30 min. The mixture was then poured into a solution of ice/water. The mixture was extracted with ethyl acetate (3×100 mL). The combined organic layers were washed with water and brine and dried over $MgSO_4$. The solvent was removed to give the title compound (8.7 g, 98% yield). $^1$H-NMR (400 MHz, $CD_3OD$): δ 2.42-2.48 (dd, J=16.8, 6.0 Hz, 1H), 2.69-2.75 (dd, J=16.8, 8.8 Hz, 1H), 3.37-3.39 (m, 1H), 3.74-3.80 (dd, J=10.4, 8.0 Hz, 1H), 7.89 (s, 1H), 8.13 (s, 1H); MS (ESI) m/z 352.03 $(M+H)^+$.

Step 3: (4R)-4-(3-Amino-4-chloro-6-nitrophenyl)pyrrolidin-2-one

To a solution of N-(5-((3R)-5-oxopyrrolidin-3-yl)-2-chloro-4-nitrophenyl)-2,2,2-trifluoroacetamide (8.7 g, 24.7 mmol) in 48 mL of ethanol was added 9 mL of 4N NaOH aqueous solution. The mixture was then heated to 50° C. for 3 h. The reaction mixture was diluted with ethyl acetate (100 mL) and water (50 mL). The layers were separated. The organic layer was dried over $Na_2SO_4$ and concentrated in vacuo to provide the title compound (3.5 g, 57% yield). MS (ESI) m/z 256.03 $(M+H)^+$.

Step 4: (4R)-4-(4-Chloro-2-nitrophenyl)pyrrolidin-2-one

A solution of (4R)-4-(3-amino-4-chloro-6-nitrophenyl) pyrrolidin-2-one (3.5 g, 13.7 mmol) in 12.6 mL of conc. $H_2SO_4$ was heated to 55° C. Sodium nitrite (16.94 mmol) was added in small portions. The reaction mixture turned from yellow to red, then dark red. After the mixture was stirred for additional 30 min at this temperature, the mixture was cooled to room temperature and water was added. The mixture was then extracted with ethyl acetate (3×30 mL). The combined organic phases were washed with water and brine, and dried over Na$_2$SO$_4$. The solvent was removed in vacuo to afford the title compound (2.5 g, 80% yield). $^1$H-NMR (400 MHz, CD$_3$OD): δ 2.45-2.51 (dd, J=17.2, 6.8 Hz, 1H), 2.77-2.84 (dd, J=17.2, 9.2 Hz, 1H), 3.41-3.44 (m, 1H), 3.80-3.85 (dd, J=10.4, 8.0 Hz, 1H), 4.03-4.05 (m, 1H), 7.61-7.63 (d, J=8.4 Hz, 1H), 7.67-7.70 (dd, J=8.4, 2.0 Hz, 1H), 7.91 (d, J=2.0 Hz, 1H); MS (ESI) m/z 241.01 (M+H)$^+$.

Step 5: (4R)-4-(2-Amino-4-chlorophenyl)pyrrolidin-2-one hydrochloride

To a solution of (4R)-4-(4-chloro-2-nitrophenyl)pyrrolidin-2-one (150 mg, 0.714 mmol) in diethyl ether (1 mL) was slowly added a solution of SnCl$_2$ (2 g, 3.21 mmol) in 2 mL of conc. hydrochloric acid. The reaction was vigorous. The reaction mixture was cooled to room temperature and a portion of ice/water was poured onto the reaction mixture. After a few minutes, the mixture was filtered. The solid was collected and washed with cold water to afford the title compound (170 mg, 90% yield). MS (ESI) m/z 211.06 (M+H)$^+$.

Step 6: Substituted (3R)-4-Amino-3-(2-{sulfonylamino}-4-chlorophenyl)butanoic acid hydrochloride To a cooled (0° C.) solution of (4R)-(2-amino-4-chlorophenyl)pyrrolidin-2-one (1.0 equivalent) in dichloromethane (0.45 M) was added triethylamine (1.2 equivalents) followed by 1.0 equivalent of an appropriate sulfonyl chloride. The reaction mixture was warmed to room temperature and stirred overnight. The mixture was then diluted with water and extracted with dichloromethane (2 times). The combined organic phases were washed with 1N HCl and brine, and dried over sodium sulfate. The solvent was removed in vacuo. The crude residue was treated overnight with 6N HCl aq./acetonitrile (10% v/v) at 95° C. The crude product was purified by HPLC purification. The compounds were treated with 1 equivalent of 1N HCl aq. before lyophilization to provide the corresponding substituted (3R)-4-amino-3-(2-{sulfonylamino}-4-chlorophenyl)butanoic acid hydrochloride.

Example 1

(3R)-4-Amino-3-(2-{[(3,4-dichlorophenyl)sulfonyl]amino}-4-chlorophenyl)butanoic acid hydrochloride (1)

The title compound (1) was synthesized according to the general procedure for sulfonamide analogs using 3,4-dichlorophenyl sulfonyl chloride in Step 6. $^1$H NMR (400 MHz, CD$_3$OD): δ 2.51-2.57 (dd, J=17.2, 6.0 Hz, 1H), 2.73-2.80 (dd, J=17.2, 8.0 Hz, 1H), 3.30 (m, 2H), 3.32-3.38 (m, 1H), 7.45 (m, 2H), 7.62-7.82 (m, 4H); (ESI) m/z 436.92 (M+H)$^+$.

General Synthetic Procedure for Amide Analogs

To a cooled (0° C.) solution of (4R)-4-(2-amino-4-chlorophenyl)pyrrolidin-2-one (see preparation of sulfonamide analogs, step 6) (1 equiv) in dichloromethane (0.3 M) was added triethylamine (1.3 eq) followed by an appropriate acid chloride (1.0 eq). The reaction mixture was warmed to room temperature and stirred overnight. The mixture was then diluted with 1N hydrochloric acid aqueous solution and extracted twice with dichloromethane. The combined organic phases were washed with brine and dried over Na$_2$SO$_4$. The solvent was removed in vacuo. The crude residue was then dissolved in 6N HCl aq. solution and heated 90° C. overnight. The final product was purified by HPLC. 1N HCl aqueous solution was added and the solution lyophilized to provide the corresponding substituted (3R)-4-amino-3-{2-(carbonylamino)-4-chlorophenyl}butanoic acid hydrochloride as a hydrochloride salt.

Example 2

(3R)-4-Amino-3-{2-[(3,4-dichlorophenyl)carbonylamino]-4-chlorophenyl}butanoic acid hydrochloride (2)

The title compound (2) was synthesized according to the general procedure for amide analogs using 3,4-dichlorobenzoyl chloride. $^1$H-NMR (400 MHz, CD$_3$OD): δ 2.61-2.67 (dd, J=16.0, 8.0 Hz, 1H), 2.76-2.82 (dd, J=16.0, 4.0 Hz, 1H), 3.24-3.34 (m, 2H), 3.59-3.66 (m, 1H), 7.44-7.50 (m, 3H), 7.69-7.71 (d, J=8.0 Hz, 1H), 7.93-7.96 (d, J=2.0 Hz, 1H), 8.20 (d, J=2.4 Hz, 1H); MS (ESI) m/z 402.97 (M+H)$^+$.

Example 3

(3R)-4-Amino-3-[4-chloro-2-(2-phenylethyl)phenyl]butanoic acid hydrochloride (3)

Step 1: 4-[2-((1E)-2-Phenylvinyl)-4-chlorophenyl](4R)pyrrolidin-2-one (3a)

To a solution of (4R)-4-(2-bromo-4-chlorophenyl)pyrrolidin-2-one (140 mg, 0.51 mmol), Pd(OAc)$_2$ (34 mg, 0.15 mmol) and triphenylphosphine (0.3 mmol) in DMF (1 mL) was added styrene (0.17 mL, 2 mmol) followed by diisopropylethylamine (0.17 mL, 1.02 mmol) under a N$_2$ atmosphere. The reaction mixture was heated to 90° C. overnight. The mixture was then cooled to room temperature and diluted with 1N HCl aq. solution (10 mL) and extracted with ethyl acetate (3×30 mL). The combined organic phases were washed with brine (3×30 mL) and dried over MgSO$_4$. The solvent was removed in vacuo to provide 4-[2-((1E)-2-phenylvinyl)-4-chlorophenyl](4R)pyrrolidin-2-one (3a) (120 mg). MS (ESI) m/z 284.02 (M+H)$^+$.

Step 2: (3R)-4-Amino-3-[4-chloro-2-(2-phenylethyl)phenyl]butanoic acid hydrochloride (3)

Crude 4-[2-((1E)-2-phenylvinyl)-4-chlorophenyl](4R)pyrrolidin-2-one (3a) was then stirred overnight with 5% PtO$_2$ in methanol under a hydrogen atmosphere (1 atm). The catalyst was filtered using Celite and filtrate concentrated to dryness. The crude product was treated overnight with 6N HCl aqueous solution at 90° C. and the title compound (3) purified by HPLC. $^1$H-NMR (400 MHz, CD$_3$OD): δ 2.36-2.41 (dd, J=16.0, 4.0 Hz, 1H), 2.69-2.75 (dd, J=16.0, 8.0 Hz, 1H), 2.88-3.00 (m, 4H), 3.05-3.12 (m, 1H), 3.17-3.24 (m, 1H), 3.65-3.69 (m, 1H), 7.14-7.22 (m, 8H); MS (ESI) m/z 318.09 (M+H)$^+$.

General Procedure for Palladium Catalyzed Suzuki Cross-Coupling Reactions Using (4R)-4-(2-Bromo-4-chlorophenyl)pyrrolidin-2-one A suspension of (4R)-4-(2-bromo-4-chlorophenyl)pyrrolidin-2-one (150 mg, 0.5 mmol), Pd(OAc)$_2$ (22 mg, 0.1 mmol), tetrabutylammonium bromide (64 mg, 0.1 mmol), K$_3$PO$_4$ (212 mg, 1 mmol) and an appropriate aryl- or heteroarylboronic acid (0.6 mmol) in DMF (1.5 mL) was heated overnight at 90° C. The reaction was diluted with water and extracted with ethyl acetate (3 times). The combined organic phases were washed with brine (3 times), dried over $MgSO_4$, and the solvent removed in vacuo to provide substituted (4R)-4-(4-chloro-2-phenylphenyl)pyrrolidin-2-one. The crude residue was heated overnight with a 6N HCl aq. solution at 90° C. The water was removed in vacuo. The crude product was purified by HPLC to provide the corresponding substituted (3R)-4-amino-3-(4-chloro-2-arylphenyl)butanoic acid.

Example 4

(3R)-4-Amino-3-[2-(3,4-dichlorophenyl)-4-chlorophenyl]butanoic acid hydrochloride (4)

The title compound (4) was synthesized according to the general procedure for palladium catalyzed Suzuki cross-coupling reactions using 3,4-dichlorophenyl boronic acid. $^1$H-NMR (400 MHz, $CD_3OD$): δ 2.73-2.75 (d, J=7.6 Hz, 2H), 3.05-3.16 (m, 2H), 3.44-3.49 (m, 1H), 7.26-7.31 (m, 2H), 7.45-7.46 (d, J=4.0 Hz, 2H), 7.59-7.61 (m, 2H); MS (ESI) m/z 360.03 $(M+H)^+$.

Example 5

4-{2-[(1R)-2-Amino-1-(carboxymethyl)ethyl]-5-chlorophenyl}benzoic acid hydrochloride (5)

The title compound (5) was synthesized according to the general procedure for palladium catalyzed Suzuki cross-coupling reactions using carboxymethylethyl boronic acid. $^1$H-NMR (400 MHz, $CD_3OD$): δ 2.72-2.74 (d, J=7.6 Hz, 2H), 3.12-3.14 (dd, J=8.0, 4.0 Hz, 2H), 3.30 (m, 1H), 3.46-3.52 (m, 1H), 7.27 (t, J=1.2 Hz, 1H), 7.47-7.45 (m, 4H), 8.09-8.11 (d, J=6.8 Hz, 2H); MS (ESI) m/z 334.08 $(M+H)^+$.

Example 6

(3R)-4-Amino-3-[4-chloro-2-(3-thienyl)phenyl]butanoic acid hydrochloride (6)

The title compound (6) was synthesized according to the general procedure for palladium catalyzed Suzuki cross-coupling reactions using 3-thienylphenyl boronic acid. $^1$H-NMR (400 MHz, $CD_3OD$): δ 2.72-2.74 (d, J=7.2 Hz, 1H), 3.08-3.19 (m, 2H), 3.68-3.72 (m, 1H), 7.53-7.55 (dd, J=8.0, 3.2 Hz, 2H), 7.17-7.19 (d, J=1.6 Hz, 1H), 7.28-7.29 (d, J=0.8 Hz, 1H), 7.40-7.43 (m, 3H); MS (ESI) m/z 296.03 $(M+H)^+$.

Example 7

(3R)-4-Amino-3-[4-chloro-2-(4-chlorophenyl)phenyl]butanoic acid hydrochloride (7)

The title compound (7) was synthesized according to the general procedure for palladium catalyzed Suzuki cross-coupling reactions using 4-chlorophenyl boronic acid. $^1$H-NMR (400 MHz, $CD_3OD$): δ 2.70-2.72 (d, J=7.2 Hz, 1H), 3.09-3.14 (m, 2H), 3.48-3.54 (m, 2H), 7.45-7.47 (s, 1H), 7.43 (d, J=8.0 Hz, 2H), 7.43-7.47 (m, 4H); MS (ESI) m/z 324.06 $(M+H)^+$.

Example 8

(3R)-4-Amino-3-[4-chloro-2-(3-pyridyl)phenyl]butanoic acid hydrochloride (8)

The title compound (8) was synthesized according to the general procedure for palladium catalyzed Suzuki cross-coupling reactions using 3-pyridylphenyl boronic acid. $^1$H-NMR (400 MHz, $CD_3OD$): δ 2.82-2.84 (m, 2H), 3.15-3.17 (d, J=7.6 Hz, 2H), 3.30-3.41 (m, 1H), 7.40-7.41 (m, 1H), 7.57 (s, 2H), 7.98-8.01 (m, 1H), 8.46-8.48 (d, J=8.4 Hz, 1H), 8.83-8.84 (d, J=4.0 Hz, 1H), 8.90 (s, 1H); MS (ESI) m/z 291.07 $(M+H)^+$.

General Procedure for Diaryl Ether Synthesis

To a mixture of (4R)-4-(2-bromo-4-chlorophenyl)pyrrolidin-2-one (0.2 g, 0.72 mmol), 2 mol % CuI (3 mg, 0.014 mmol), N,N-dimethylglycine (7.5 mol %), an appropriate substituted phenol (0.14 g, 0.93 mmol), and cesium carbonate (0.6 g, 1.8 mmol) was added 1.5 mL dioxane under a nitrogen atmosphere. The mixture was heated overnight at 90° C. The reaction mixture was then cooled to room temperature and diluted with water. The mixture was extracted with ethyl acetate (3 times), washed with a 1N HCl aq. solution, and brine (3 times), and dried over $Na_2SO_4$. The solvent was removed in vacuo. The corresponding substituted (4R)-4-(4-chloro-2-phenoxyphenyl)pyrrolidin-2-one was heated overnight at 90° C. in 6N HCl aq. solution. The product, substituted (3R)-4-amino-3-(4-chloro-2-phenoxyphenyl)butanoic acid, was purified by preparative HPLC.

Example 9

4-{3-[(1R)-2-Amino-1-(carboxymethyl)ethyl]-4-chlorophenoxy}benzoic acid hydrochloride (9)

The title compound (9) was synthesized according to the general procedure for diaryl ether synthesis using carboxymethylethyl phenol. $^1$H-NMR (400 MHz, $CD_3OD$): δ 2.78-2.82 (dd, J=16.4, 1.6 Hz, 4H), 3.74-3.76 (m, 1H), 6.92-6.93 (d, J=2.4 Hz, 1H), 7.11-7.13 (d, J=8.8 Hz, 2H), 7.12-7.24 (dd, J=8.4, 2.0 Hz, 1H), 7.41-7.43 (d, J=8.4 Hz, 1H), 8.05-8.07 (d, J=8.8 Hz, 2H); MS (ESI) m/z 349.98 $(M+H)^+$.

Example 10

(3R)-4-Amino-3-(4-chloro-2-phenoxyphenyl)butanoic acid hydrochloride (10)

The title compound (10) was synthesized according to the general procedure for diaryl ether synthesis using phenol. $^1$H-NMR (400 MHz, $CD_3OD$): δ 2.78-2.89 (m, 2H), 3.31-3.37 (m, 2H), 3.76-3.84 (m, 1H), 6.70-6.71 (d, J=2.0 Hz, 1H), 7.08-7.12 (m, 3H), 7.19-7.23 (m, 1H), 7.35-7.37 (d, J=8.4 Hz, 1H), 7.40-7.44 (t, J=7.6 Hz, 2H); MS (ESI) m/z 306.1 $(M+H)^+$.

Example 11

(3R)-4-Amino-3-[4-chloro-2-(phenylcarbonyl)phenyl]butanoic acid hydrochloride (11)

To a mixture of lithium wire (30 mg, 4.28 mmol), naphthalene (52 mg, 0.66 mmol), and $MnBr_2$ (0.64 g, 2.08 mmol) was cannulated anhydrous tetrahydrofuran (THF) under a nitrogen atmosphere. The mixture was stirred for 2 h at room temperature before (4R)-4-(2-bromo-4-chlorophenyl)pyrrolidin-2-one in anhydrous THF (2 mL) was added dropwise. After stirring for 1 h, the reaction mixture was cooled to 0° C. and 1,2-dibromoethane (0.3 mL, 1.89 mmol) was added. The reaction mixture was warmed to room temperature before a solution of CuI (11.4 mg, 0.06 mmol) in THF (1 mL) was introduced via cannulation. The mixture was then stirred for 5 min and benzoyl chloride (0.1 mL, 0.66 mmol) was added.

The reaction mixture was stirred overnight at room temperature. The reaction was diluted with water (1.5 mL) and extracted with ethyl acetate (3×5 mL). The combined organic phases were washed with brine and dried over MgSO$_4$. The solvent was removed in vacuo to provide (4R)-4-[4-chloro-2-(phenylcarbonyl)phenyl]pyrrolidin-2-one. The crude residue was treated with a 6N HCl aq. solution and heated overnight. The crude residue was purified by HPLC to afford the title compound (11). $^1$H-NMR (400 MHz, CD$_3$OD): δ 2.71-2.87 (m, 2H), 3.44-3.59 (m, 3H), 7.27 (s, 3H), 7.37-7.41 (m, 2H), 7.46-7.48 (m, 1H), 7.66-7.68 (m, 2H); MS (ESI) m/z 318.09 (M+H)$^+$.

Example 12

3-({2-[(1R)-2-Amino-1-(carboxymethyl)ethyl]-4-chlorophenyl}hydroxymethyl)benzoic acid hydrochloride (12)

To a suspension of Mg turnings (0.61 g, 2.5 mmol) in dry THF (5 mL) was added 1,2-dibromoethane (0.45 mL, 2.5 mmol), followed by washing with THF (2×4 mL). Then, a pale yellow solution of Li$_2$MnCl$_4$ (derived from MnCl$_2$ (0.94 g, 7.5 mmol) and LiCl (0.64 g, 15 mmol) in THF (2.0 mL) was added to the solid Mg with vigorous stirring. The reaction mixture turned dark black overnight and was stirred for 2 days under a N$_2$ atmosphere. To a solution of (4R)-4-(2-iodo-4-chlorophenyl)pyrrolidin-2-one in THF (2 mL) was added a solution of activated Mn(0) in THF (3 mL) at room temperature and the mixture stirred for 2 h followed by the dropwise addition of methyl 3-formylbenzoate (0.6 mL, 0.6 mmol). The reaction mixture was heated to reflux for 1 hr before being cooled to room temperature. The mixture was then diluted with water and extracted with ethyl acetate (3×20 mL). The combined organic phases were washed with brine, dried over MgSO$_4$, and concentrated in vacuo. The crude residue was heated overnight in a 6N HCl aq. solution at 90° C. and then cooled to room temperature and purified by HPLC purification to afford the title compound (12). $^1$H-NMR (400 MHz, CD$_3$OD): δ 2.65-2.79 (m, 2H), 3.01-3.05 (dd, J=10.0, 4.0 Hz, 1H), 3.43-3.51 (m, 1H), 3.80 (m, 1H), 4.48-4.49 (d, J=4 Hz, 1H), 7.31-7.38 (m, 3H), 7.43-7.45 (d, J=2.4 Hz, 1H), 7.84 (m, 1H), 7.94-7.95 (d, J=2.0 Hz, 1H); MS (ESI) m/z 364.09 (M+H)$^+$.

Synthesis of Intermediates of 3-Substituted Chlorophenol Derivatives (4R)-4-Amino-3-(4-chloro-2-vinylphenyl)butanoic acid hydrochloride To a solution of (4R)-4-(2-iodo-4-chlorophenyl)pyrrolidin-2-one (600 mg, 1.8 mmol), copper(I) iodide (36 mg, 0.18 mmol) and Pd(Ph$_3$P)$_4$ (103 mg, 0.09 mmol) in DMF (5 mL) under a nitrogen atmosphere was introduced vinyl tributyl tin (0.68 g, 2.16 mmol) followed by CsF (54 0 mg, 3.6 mmol). The reaction mixture was heated overnight at 100° C. After the reaction mixture was cooled to room temperature, it was diluted with water and extracted with ethyl ether (3×30 mL). The combined organic phases were washed with a 1N HCl aq. solution, a saturated sodium bicarbonate aqueous solution, and brine. The organic phase was then dried over sodium sulfate and concentrated in vacuo to provide (4R)-4-(4-chloro-2-vinylphenyl)pyrrolidin-2-one (0.35 g, 85% crude yield); MS (ESI) m/z 222.04 (M+H)$^+$. (4R)-4-(4-Chloro-2-vinylphenyl)pyrrolidin-2-one (75 mg, 0.33 mmol) was treated overnight with a 6N HCl aq. solution at 90° C. The product was purified by HPLC to provide the title compound. MS (ESI) m/z 240.06 (M+H)$^+$.

(3R)-4-Amino-3-[4-chloro-2-(hydroxymethyl)phenyl]butanoic acid hydrochloride

To a cooled (0° C.) solution of sodium periodate (607 mg, 2.85 mmol) in water (3.8 mL) was added a catalytic amount of RuCl$_3$(III) (27 mg, 0.13 mmol) followed by ethyl acetate (10 mL) and acetonitrile (10 mL). The reaction mixture was stirred for 5 min at 0° C. before (4R)-4-(4-chloro-2-vinylphenyl)pyrrolidin-2-one prepared as described above was added. After stirring for an additional two minutes, the reaction mixture was quenched with a Na$_2$S$_2$O$_3$ aq. solution (2 M, 10 mL). The layers were separated and the aqueous phase was extracted with ethyl acetated (4×20 mL). The combined organic phases were dried over MgSO$_4$ and concentrated in vacuo. The resulting crude (2-((3S)-5-oxopyrrolidin-3-yl)-5-chlorobenzaldehyde was dissolved in tetrahydrofuran/water (v/v 1:1, 4.5 mL) and sodium borohydride (70 mg, 1.85 mmol) was added. The mixture was stirred for 20 min at room temperature and then diluted with water (7 mL), extracted with dichloromethane (4×30 mL). The combined organic phases were dried over sodium sulfate and concentrated in vacuo. The crude residue was then treated with a 6N HCl aqueous solution (1.5 mL) and heated overnight at 90° C. The final product was purified by HPLC to provide the title compound. $^1$H-NMR (400 MHz, CD$_3$OD): δ 2.84-2.70 (m, 2H), 3.08-3.14 (m, 1H), 3.75-3.83 (m, 1H), 4.85 (s, 1H), 4.57-4.60 (d, J=12.0 Hz, 1H), 7.33-7.42 (m, 3H); MS (ESI) m/z 244.06 (M+H)$^+$.

General Procedure for the Synthesis of Precursors for 3-Substituted Analogs

Step 1: (4R)-4-(4-Chlorophenyl)pyrrolidin-2-one

To R-baclofen (50 g, 234.7 mmol) was added 235 mL of acetic acid. The reaction mixture was refluxed overnight. The following day, the mixture was cooled to room temperature, the acetic acid removed in vacuo and the resultant mixture treated with water (400 mL). An off-white product precipitated and was filtered, washed with hexane, and dried in vacuo to provide the title compound as a white solid (42.1 g, 92% yield). $^1$H-NMR (400 MHz, CD$_3$OD): δ7.22-7.33 m, 4H), 3.64-3.79 (m, 2H), 3.32-3.39 (m, 1H), 2.66-2.73 (dd, J=16.8, 8.8 Hz, 1H), 2.40-2.47 (dd, J=16.8, 8.8 Hz, 1H); MS (ESI) m/z 195.97 (M+H)$^+$.

Step 2: (4R)-4-(4-Chloro-3-nitrophenyl)pyrrolidin-2-one (4R)-4-(4-Chlorophenyl)pyrrolidin-2-one (44 g, 225.6 mmol) was treated with conc. sulfuric acid (220 mL). This solution was cooled in ice. Guanidine nitrate (27.5 g, 225.6 mmol) was added in portions. The reaction mixture was warmed to room temperature and stirred for 1 h. The mixture was then poured into ice. The product crashed out as a pale yellow solid and was filtered, washed with hexane, and dried to give the title compound (51 g, 95% yield). $^1$H-NMR (400 MHz, CD$_3$OD): δ7.12 d, J=8.4 Hz, 1H), 6.73-6.74 (d, J=4.0 Hz, 1H), 6.52-6.55 (m, 1H), 3.70-3.74 (m, 1H), 3.54-3.62 (m, 1H), 3.32-3.46 (m, 1H), 2.63-2.69 (dd, J=16.4, 8.8 Hz, 1H), 2.37-2.43 (dd, J=16.8, 8.8 Hz, 1H); MS (ESI) m/z 241.05 (M+H)$^+$.

Step 3: (4R)-4-(3-Amino-4-chlorophenyl)pyrrolidin-2-one (4R)-4-(4-Chloro-3-nitrophenyl)pyrrolidin-2-one (24 g, 100 mmol) was treated with acetic acid (100 mL) and warmed to 50° C. Iron(0) (19.5 g, 350 mmol) was added in portions. After the addition, the reaction mixture was stirred for 1 h at 50° C. The mixture was then cooled and filtered through Celite. The filtrate was diluted with water and extracted with ethyl acetate (3×100 mL). The combined ethyl acetate layers were washed with water (3 times), brine, and concentrated to provide the title compound as a yellow oil. (18.9 g, 90% yield). $^1$H-NMR (400 MHz, CD$_3$OD): δ 7.11-7.12 d, J=8.4 Hz, 1H), 6.73-6.74 (d, J=2.0 Hz, 1H), 6.52-6.55 (m, 1H), 3.70-3.74 (m, 1H), 3.54-3.62 (m, 1H), 3.29-3.34 (m, 1H), 2.63-2.69 (dd, J=16.4, 8.8 Hz, 1H), 2.37-2.43 (dd, J=16.4, 8.4 Hz, 1H); MS (ESI) m/z 211.07 (M+H)$^+$.

Step 4: (4R)-4-(3-Bromo-4-chlorophenyl)pyrrolidin-2-one (4R)-4-(3-Amino-4-chlorophenyl)pyrrolidin-2-one (12 g, 57.14 mmol) was added to a mixture of 75 mL of 48% HBr/water and 150 mL of water. The solution was cooled in ice. Sodium nitrite (4.33 g, 62.85 mmol) in 10 mL of water was added dropwise. The resulting mixture was stirred for 10 min. Copper(I) bromide (8.9 g, 62.85 mmol) was dissolved in a mixture of 75 mL of 48% HBr/water and 150 mL of water and added dropwise to the reaction mixture. The mixture was then stirred overnight at room temperature. Ethyl acetate (250 mL) was added to the reaction mixture and stirred for 10 min. The organic layer was separated and the aqueous layer was extracted with 200 mL of ethyl acetate. The combined ethyl acetate layers were washed with water (3 times), brine and then concentrated to give the desired product as a brownish yellow oil, which was purified by silica gel column chromatography eluting with methylene chloride/methanol to provide 7.2 g of the title compound (60% yield). $^1$H-NMR (400 MHz, CD$_3$OD): δ 7.62-7.63 d, J=2.0 Hz, 1H), 7.45-7.47 (m, 1H), 7.26-7.30 (m, 1H), 3.69-3.79 (m, 2H), 3.33-3.37 (m, 1H) 2.67-2.74 (dd, J=16.4, 8.8 Hz, 1H), 2.40-2.47 (dd, J=16.4, 8.4 Hz, 1H); MS (ESI) m/z 275.89 (M+H)$^+$.

(4R)-4-[4-Chloro-3-(4,4,5,5-tetramethyl(1,3,2-dioxaborolan-2-yl))phenyl]pyrrolidin-2-one (4R)-4-(3-Bromo-4-chlorophenyl)pyrrolidin-2-one (1.5 g, 5.5 mmol), bis(pinalcolato)diboron (1.8 g, 7.11 mmol), and 1,1,-bis(diphenyl)phosphino)ferrocene)-dichloro palladium (II) (220 mg, 0.275 mmol) were stirred in dioxane (11 mL). Potassium acetate (2.7 g, 27.5 mmol) was added and the mixture was stirred overnight at 90° C. The reaction mixture was cooled, diluted with ethyl acetate, washed with 10% HCl aqueous solution, brine. The ethyl acetate layer was then concentrated in vacuo. The compound was then purified by silica gel chromatography (biotage) to give the title compound. MS (ESI) m/z 322 (M+H)$^+$.

(3R)-4-Amino-3-(3-bromo-4-chlorophenyl)butanoic acid hydrochloride

To (4R)-4-(3-bromo-4-chlorophenyl)pyrrolidin-2-one (0.2 g, 0.73 mmol) was added 0.2 mL acetonitrile and 1 mL 6N HCl aqueous solution. The mixture was heated overnight at 95° C. The reaction mixture was then cooled to room temperature and neutralized with a 4N NaOH aqueous solution. The mixture was purified by reversed phase LC/MS to provide (3R)-4-amino-3-(3-bromo-4-chlorophenyl)butanoic acid (43 mg, 30% yield), which was then converted to the title compound as the hydrochloride salt by lyophilization from a 1N HCl aqueous solution. $^1$H-NMR (400 MHz, CD$_3$OD): δ 7.68-7.69 d, J=2.00 Hz, 1H), 7.51-7.53 (d, J=8.44 Hz, 1H), 7.30-7.33 (dd, J=8.4, 2.44 Hz, 1H), 3.32-3.40 (m, 2H), 3.15-3.21 (m, 1H), 2.77-2.83 (dd, J=16.8, 6.4, 4 Hz, 1H), 2.63-2.69 (dd, J=16.4, 7.66 Hz, 1H); MS (ESI) m/z 293.89 (M+H)$^+$.

(3R)-4-Amino-3-(3,4-dichlorophenyl)butanoic acid hydrochloride

Copper(II) chloride (0.183 g, 1.37 mmol) and tert-butyl nitrite (0.2 mL, 1.71 mmol) was stirred in acetonitrile (1 mL) at 0° C. (4R)-4-(3-Amino-4-chlorophenyl)pyrrolidin-2-one (0.24 g, 1.14 mmol) in acetonitrile (1 mL) was added dropwise. The mixture was warmed to 60° C. and stirred for 1 h. The reaction mixture was then cooled to room temperature, diluted with ethyl acetate, and washed with a 10% aqueous HCl solution, brine, and the ethyl acetate layers were concentrated. Hydrolysis of the resulting lactam with aqueous HCl as described for the preparation of (3R)-4-amino-3-(3-bromo-4-chlorophenyl)butanoic acid hydrochloride provided the title compound. $^1$H-NMR (400 MHz, CD$_3$OD): δ 7.53-7.54 (m, 1H), 7.51 (s, 1H), 7.26 (m, 1H), 3.28-3.41 (m, 2H), 3.15-3.21 (m, 1H), 2.77-2.83 (dd, J=16.4, 6.4 Hz, 1H) 2.63-2.69 (dd, J=16.8, 8.0 Hz, 1H); MS (ESI) m/z 247.99 (M+H)$^+$.

Example 13

2-({5-[(1R)-2-Amino-1-(carboxymethyl)ethyl]-2-chlorophenyl}amino)benzoic acid (13)

Step 1: Methyl 2-{[5-((3R)-5-Oxopyrrolidin-3-yl)-2-chlorophenyl]amino}benzoate (13a)

To a mixture of (4R)-4-(3-amino-4-chlorophenyl)pyrrolidin-2-one (0.18 g, 0.86 mmol), methyl 2-bromobenzoate (0.37 g, 1.72 mmol), palladium acetate (0.038 g, 0.172 mmol), and Buchwald's reagent (2-dicyclohexylphosphino-2',4',6'-triisopropylbiphenyl) (0.122 g, 0.256 mmol) was added dioxane (2 mL). The mixture was degassed by alternatively applying a vacuum and flushing with nitrogen for a few cycles. After 15 minutes, potassium carbonate (0.237 g, 1.72 mmol) was added. The mixture was stirred overnight at 100° C., and then cooled to room temperature and filtered through Celite. The filtrate was washed with an aqueous HCl solution and extracted with ethyl acetate (3 times). The ethyl acetate layers were then washed with brine and concentrated to give the title compound (13a) as a brown residue which was used directly in the next step. MS (ESI) m/z 345 (M+H)$^+$.

Step 2: 2-({5-[(1R)-2-Amino-1-(carboxymethyl)ethyl]-2-chlorophenyl}amino)benzoic acid (13)

To methyl 2-{([5-((3R)-5-oxopyrrolidin-3-yl)-2-chlorophenyl]amino}benzoate (13a) (0.25 g, 0.73 mmol) was added 0.2 mL acetonitrile and 1 mL of a 6N HCl aqueous solution. The mixture was heated overnight at 95° C. The following day, the reaction mixture was cooled to room temperature and neutralized with 4N NaOH. This was purified by reverse phase LC/MS to provide the title compound (13). $^1$H-NMR (400 MHz, CD$_3$OD): δ 7.92-7.95 (m, 1H), 7.31-7.48 (m, 4H), 6.81-6.89 (m, 2H), 3.25-3.29 (m, 2H), 3.04-

3.08 (m, 1H), 2.64-2.70 (dd, J=16.0, 7.6 Hz, 1H), 2.55-2.61 (dd, J=16.8, 6.0 Hz). MS (ESI) m/z 349.06 (M+H)+.

Example 14

3-({5-[(1R)-2-Amino-1-(carboxymethyl)ethyl]-2-chlorophenyl}amino)benzoic acid (14)

Following the procedure according to Example 13 and replacing methyl 2-bromobenzoate with methyl 3-bromobenzoate in Step 1 provided the title compound (14). MS (ESI) m/z 349.05 (M+H)+.

Example 15

4-({5-[(1R)-2-Amino-1-(carboxymethyl)ethyl]-2-chlorophenyl}amino)benzoic acid (15)

Following the procedure according to Example 13 and replacing methyl 2-bromobenzoate with methyl 4-bromobenzoate in Step 1 provided the title compound (15). $^1$H-NMR (400 MHz, CD$_3$OD): δ 7.87 (d, J=8.0 Hz, 2H), 7.4 (d, J=8.0 Hz 1H), 7.35 (d, J=2.0 Hz, 1H), 7.04 (d, J=8.8 Hz, 2H), 6.92-6.95 (m, 1H), 3.21-3.26 (m, 2H), 3.08-3.11 (m, 1H), 2.61-2.67 (dd, J=12.8, 7.6 Hz, 1H), 2.52-2.60 (dd, J=12, 5.6 Hz, 1H); MS (ESI) m/z 349.12 (M+H)+.

Example 16

(3R)-4-Amino-3-{4-chloro-3-[(4-methoxyphenyl)amino]phenyl}butanoic acid (16)

Following the procedure according to Example 13 and replacing methyl 2-bromobenzoate with 1-bromo-4-methoxybenzene in Step 1 provided the title compound (16). $^1$H-NMR (400 MHz, CD$_3$OD): δ 7.28-7.34 (m, 2H), 7.15 (d, J=2.0 Hz, 1H), 6.89-7.02 (m, 3H), 6.72-6.75 (m, 1H), 3.19-3.23 (m, 2H), 3.04-3.08 (m, 1H), 2.51-2.62 (m, 2H); MS (ESI) m/z 335.10 (M+H)+.

Example 17

(3R)-4-Amino-3-[4-chloro-3-(2-pyidylamino)phenyl]butanoic acid (17)

Following the procedure according to Example 13 and replacing methyl 2-bromobenzoate with 2-bromopyridine in Step 1 provided the title compound (17). MS (ESI) m/z 306.04 (M+H)+.

Example 18

(3R)-4-Amino-3-{3-[3,4-dichlorophenyl)amino]-4-chlorophenyl}butanoic acid (18)

Following the procedure according to Example 13 and using (4R)-4-(3-bromo-4-chlorophenyl)pyrrolidin-2-one and 3,4-dichlorophenylamine with the same reaction conditions gave the title compound (18). $^1$H-NMR (400 MHz, CD$_3$OD): δ 7.41 (m, 2H), 7.24 (d, J=2.4 Hz, 1H), 7.19 (d, J=2.4 Hz, 1H), 7.01 (m, 1H), 6.90 (m, 1H), 3.42-3.45 (m, 2H), 3.12-3.18 (m, 1H), 2.44-2.52 (m, 2H); MS (ESI) m/z 375.00 (M+H)+.

Example 19

(3R)-4-Amino-3-[4-chloro-3-(4-pyridylamino)phenyl]butanoic acid (19)

Following the procedure according to Example 13 and replacing methyl 2-bromobenzoate with 4-bromopyridine in Step 1 provided the title compound (19). $^1$H-NMR (400 MHz, CD$_3$OD): δ 8.20 (d, J=7.6 Hz, 2H), 7.63 (d, J=8.0 Hz, 1H), 7.51 (d, J=2.0 Hz, 1H), 7.39-7.42 (m, 1H), 7.03 (d, J=6.8 Hz, 2H), 3.41-3.50 (m, 1H), 3.22-3.37 (m, 2H), 2.82-2.88 (dd, J=16.4, 6 Hz, 1H), 2.67-2.73 (dd, J=16.4, 8.8 Hz, 1H); MS (ESI) m/z 306.04 (M+H)+.

Example 20

4-Amino-3-[4-chloro-3-(phenylamino)phenyl]butanoic acid hydrochloride (20)

Following the procedure according to Example 13 and replacing methyl 2-bromobenzoate with iodobenzene in Step 1 provided the title compound (20). $^1$H-NMR (400 MHz, CD$_3$OD): δ7.35-7.37 m, 1H), 7.26-7.30 (m, 2H), 7.14-7.19 (m, 3H), 6.95-6.99 (m, 1H), 6.75-6.78 (m, 1H), 3.23-3.34 (m, 2H), 3.08-3.11 (m, 1H), 2.69-2.75 (dd, J=16.4, 6.4 Hz, 1H), 2.57-2.63 (dd, J=16.4, 8.0 Hz, 1H); MS (ESI) m/z 306.09 (M+H)+.

Example 21

(3R)-4-Amino-3-(3-{[(3,4-dichlorophenyl)sulfonyl]amino}-4-chlorophenyl)butanoic acid (21)

(4R)-4-(3-Amino-4-chlorophenyl)pyrrolidin-2-one (0.105 g, 0.5 mmol) was dissolved in 2 mL of methylene chloride (2 mL). Diisopropylethylamine (0.14 mL, 0.75 mmol) was added followed by 3,4-dichlorobenzenesulfonyl chloride (0.134 g, 0.55 mmol) and a catalytic amount of DMAP (0.05 mmol). The mixture was stirred overnight at room temperature. The mixture was then diluted with methylene chloride (50 mL), washed with water, then brine, and concentrated to give the product, which was treated with HCl as described for the preparation of (3R)-4-amino-3-(3-bromo-4-chlorophenyl)butanoic acid hydrochloride to provide the title compound (21). MS (ESI) m/z 438.89 (M+H)+.

Example 22

3-{5-[(1R)-2-Amino-1-(carboxymethyl)ethyl]-2-chlorophenoxy}benzoic acid (22)

To a mixture of (4R)-4-(3-bromo-4-chlorophenyl)pyrrolidin-2-one (0.1 g, 0.36 mmol) and methyl 3-hydroxybenzoate (0.055 g, 0.36 mmol) in dioxane (1 mL) was added N,N-dimethylglycine (0.011 g, 0.11 mmol), copper(I) iodide (0.02 g, 0.11 mmol) and cesium carbonate (0.23 g, 0.72 mmol). The mixture was stirred overnight at 100° C. The mixture was then diluted with ethyl acetate (50 mL), washed with a 10% aq. HCl solution then brine, and concentrated to give 3-[5-((3R)-5-oxopyrrolidin-3-yl)-2-chlorophenoxy]benzoic acid, which was treated with HCl as described for the preparation of (3R)-4-amino-3-(3-bromo-4-chlorophenyl)butanoic acid hydrochloride to provide the title compound (22). MS (ESI) m/z 350.07 (M+H)$^+$.

Example 23

(3R)-4-Amino-3-(4-chloro-3-phenoxyphenyl)butanoic acid (23)

To a mixture of (4R)-4-(3-bromo-4-chlorophenyl)pyrrolidin-2-one (0.1 g, 0.36 mmol) and phenol (0.034 g, 0.36 mmol) in dioxane (2 mL) was added N,N-dimethylglycine (0.011 g, 0.11 mmol) and copper(I) iodide (0.02 g, 0.11 mmol) and cesium carbonate (0.23 g, 0.72 mmol). The mixture was stirred at 100° C. overnight. The following day, the mixture was diluted with ethyl acetate, washed with 10% aq. HCl solution, brine and concentrated to give (4R)-4-(4-chloro-3-phenoxphenyl)pyrrolidin-2-one, which was treated with HCl as described for the preparation of (3R)-4-amino-3-(3-bromo-4-chlorophenyl)butanoic acid hydrochloride to provide the title compound (23). MS (ESI) m/z 306.04 (M+H)$^+$.

Example 24

4-{5-[(1R)-2-Amino-1-(carboxymethyl)ethyl]-2-chlorophenyl}benzoic acid hydrochloride (24)

(4R)-4-(3-Bromo-4-chlorophenyl)pyrrolidin-2-one (0.5 g, 0.55 mmol) and 4-methoxycarbonylphenyl boronic acid (0.144 g, 0.55 mmol) were mixed in DMF (2 mL). The mixture was degassed by alternately applying a vacuum and flushing with nitrogen gas. Palladium acetate (0.025 g, 0.11 mmol) and tetrabutylammonium bromide (0.053 g, 0.165 mmol) were added followed by potassium phosphate (0.35 g, 1.65 mmol). The mixture was stirred overnight at 90° C. The reaction mixture was cooled to room temperature, diluted with ethyl acetate (50 mL), washed with 10% aqueous HCl solution then brine, and concentrated in vacuo to provide 4-[5-((3R)-5-oxopyrrolidin-3-yl)-2-chlorophenyl]benzoic acid. 4-[5-((3R)-5-Oxopyrrolidin-3-yl)-2-chlorophenyl]benzoic acid was then treated with HCl as described for the preparation of (3R)-4-amino-3-(3-bromo-4-chlorophenyl) butanoic acid hydrochloride to provide the title compound (24). MS (ESI) m/z 334.07 (M+H)$^+$.

Example 25

3-{5-[(1R)-2-Amino-1-(carboxymethyl)ethyl]-2-chlorophenyl}benzoic acid hydrochloride (25)

(4R)-4-(3-Bromo-4-chlorophenyl)pyrrolidin-2-one (0.5 g, 0.55 mmol) and 3-methoxycarbonylphenyl boronic acid (0.144 g, 0.55 mmol) were mixed with DMF (2 mL). The mixture was degassed by alternately applying a vacuum and flushing with nitrogen. Palladium acetate (0.025 g, 0.11 mmol) and tetrabutylammonium bromide (0.053 g, 0.165 mmol) were added followed by potassium phosphate (0.35 g, 1.65 mmol). The mixture was stirred overnight at 90° C., then cooled to room temperature, diluted with ethyl acetate (30 mL), washed with a 10% aqueous HCl solution then brine, and concentrated in vacuo. The product, 3-[5-((3R)-5-oxopyrrolidin-3-yl)-2-chlorophenyl]benzoic acid, was then treated with HCl as described for the preparation of (3R)-4-amino-3-(3-bromo-4-chlorophenyl)butanoic acid hydrochloride to provide the title compound (25). $^1$H-NMR (400 MHz, CD$_3$OD): δ8.03-8.06 m, 2H), 7.65-7.68 (m, 2H), 7.55-7.57 (m, 1H), 7.33-7.37 (m, 2H), 3.42-3.49 (m, 1H), 3.2-3.26 (m, 2H), 2.77-2.83 (dd, J=16.8, 6.4 Hz, 1H), 2.63-2.69 (dd, J=16.4, 7.6 Hz, 1H); MS (ESI) m/z 333.98 (M+H)$^+$.

Example 26

(3R)-4-Amino-3-(3-benzimidazol-6-yl-4-chlorophenyl)butanoic acid hydrochloride (26)

Following the procedure according to Example 25 using 6-bromo-N-Boc-benzimidazole and (4R)-4-[4-chloro-3-(4,4,5,5-tetramethyl(1,3,2-dioxaborolan-2-yl))phenyl]pyrrolidin-2-one provided the title compound (26). $^1$H-NMR (400 MHz, CD$_3$OD): δ 8.23 (s, 1H), 7.64-7.66 (m, 2H), 7.49-7.52 (m, 1H), 7.28-7.39 (m, 3H), 3.29-3.40 (m, 2), 3.18-3.23 (m, 1H), 2.73-2.79 (dd, J=16.0, 7.6 Hz, 1H), 2.63-2.69 (dd, J=16.4, 8.0 Hz, 1H); MS (ESI) m/z 328.12 (M+H)$^+$.

Example 27

4-{5-[(1R)-2-Amino-1-(carboxymethyl)ethyl]-2-chlorophenyl}thiophene-2-carboxylic acid hydrochloride (27)

Following the procedure according to Example 25 using 2-carboxythiophene-4-boronic acid and (4R)-4-(3-bromo-4-chlorophenyl)pyrrolidin-2-one provided the title compound (27). $^1$H-NMR (400 MHz, CD$_3$OD): δ 7.96 s, 1H), 7.86 (s, 1H), 7.46-7.54 (m, 2H), 7.32 (m, 1H), 3.40-3.45 (m, 1H), 3.20-3.37 (m, 2H), 2.80-2.86 (dd, J=16.4, 6.8 Hz, 1H), 2.68-2.75 (dd, J=16.4, 7.6 Hz, 1H); MS (ESI) m/z 339.90 (M+H)$^+$.

Example 28

(3R)-4-Amino-3-{4-chloro-3-[3-(hydroxymethyl) phenyl]phenyl}butanoic acid hydrochloride (28)

Following the procedure according to Example 25 using 3-(hydroxymethyl)phenylboronic acid and (4R)-4-(3-bromo-4-chlorophenyl)pyrrolidin-2-one provided the title compound (28). $^1$H-NMR (400 MHz, CD$_3$OD): δ 7.48-7.50 m, 1H), 7.28-7.41 (m, 6H), 4.65 (s, 2H), 3.32-3.39 (m, 2H), 3.17-3.22 (m, 1H), 2.75-2.81 (dd, J=16.4, 7.2 Hz, 1H), 2.63-2.69 (dd, J=16.0, 7.2 Hz, 1H); MS (ESI) m/z 320.00 (M+H)$^+$.

Example 29

(3R)-4-Amino-3-[4-chloro-3-(5-cyano-2-thienyl)) phenyl]butanoic acid hydrochloride (29)

Following the procedure according to Example 25 using 5-cyanothiophene 2-boronic acid and (4R)-4-(3-bromo-4-chlorophenyl)pyrrolidin-2-one provided the title compound (29). $^1$H-NMR (400 MHz, CD$_3$OD): δ☐☐☐d, J=4.0 Hz, 1H), 7.57-7.60 (m, 2H), 7.46 (d, J=4.0 Hz, 1H), 7.41 (m, J, 1H), 3.43-3.47 (m, 1H), 3.21-3.38 (m, 2H), 2.81-2.87 (dd, J=16.4, 6.4 Hz, 1H), 2.68-2.74 (dd, J=16.4, 8.0 Hz, 1H); MS (ESI) m/z 320.94 (M+H)$^+$.

Example 30

(3R)-4-Amino-3-[4-chloro-3-(2-methylpyrimidin-5-yl)phenyl]butanoic acid hydrochloride (30)

Following the procedure according to Example 25 using 2-methylpyrimidin-5-yl boronic acid and (4R)-4-(3-bromo-4-chlorophenyl)pyrrolidin-2-one provided the title compound (30). ¹H-NMR (400 MHz, CD₃OD): δ☐☐☐s, 2H), 7.61-7.63 (m, 1H), 7.46-7.51 (m, 2H), 3.45-3.51 (m, 1H), 3.35-3.40 (m, 1H), 3.24-3.27 (m, 1H), 2.83-2.88 (dd, J=16.4, 6.4 Hz, 1H), 2.83 (s, 3H), 2.70-2.77 (dd, J=16.8, 7.6 Hz, 1H). MS (ESI) m/z 305.98 (M+H)⁺.

Example 31

(3R)-4-Amino-3-{4-chloro-3-[3-(ethoxycarbonyl)phenyl]phenyl}butanoic acid hydrochloride (31)

Following the cross-coupling procedure according to Example 25 using 3-ethoxycarbonylphenyl boronic acid and (4R)-4-(3-bromo-4-chlorophenyl)pyrrolidin-2-one followed by basic hydrolysis provided the title compound (31). ¹H-NMR (400 MHz, CD₃OD): δ 1.37-1.40 (t, J=4.8 Hz, 3H), 2.70-2.76 (dd, J=16.0, 8.0 Hz, 1H), 2.59-2.65 (dd, J=16.0, 6.0 Hz, 1H), 3.16-3.20 (dd, J=12.4, 8.0 Hz, 1H), 3.32-3.41 (m, 2H), 4.35-4.40 (q, J=16.0 Hz, 2H), 7.30-7.31 (m, 2H), 7.50-7.56 (m, 2H), 7.65-7.67 (d, J=1.2 Hz, 1H), 8.01-8.06 (m, 2H); MS (ESI) m/z 362.15 (M+H)⁺.

Example 32

(3R)-4-Amino-3-(4-chloro-3-(3-pyridyl)phenyl)butanoic acid hydrochloride (32)

Following the cross-coupling procedure according to Example 25 using 3-pyridyl boronic acid and (4R)-4-(3-bromo-4-chlorophenyl)pyrrolidin-2-one provided the title compound (32). ¹H-NMR (400 MHz, CD₃OD): δ 2.71-2.77 (dd, J=16.8, 6.8 Hz, 1H), 2.84-2.89 (dd, J=16.4, 8.4 Hz, 1H), 3.30 (m, 1H), 3.31-3.40 (dd, J=12.0, 3.6 Hz, 1H), 3.48-3.56 (m, 1H), 7.51-7.65 (m, 3H), 8.08-8.12 (dd, J=13.6, 5.6 Hz, 1H), 8.67-8.68 (m, 1H), 8.86-8.87 (d, J=5.6 Hz, 1H), 9.01 (s, 1H); MS (ESI) m/z 291.12 (M+H)⁺.

Example 33

(3R)-4-Amino-3-[4-chloro-3-(3-cyanophenyl)phenyl]butanoic acid hydrochloride (33)

Following the cross-coupling procedure according to Example 25 using 3-cyanophenylboronic acid and (4R)-4-(3-bromo-4-chlorophenyl)pyrrolidin-2-one followed by basic hydrolysis provided the title compound (33). ¹H-NMR (400 MHz, CD₃OD): δ 2.68-2.75 (dd, J=16.4, 6.8 Hz, 1H), 2.80-2.86 (dd, J=16.4, 8 Hz, 1H), 3.22-3.27 (m, 1H), 3.33-3.39 (m, 1H), 3.42-3.49 (m, 1H), 7.38-7.81 (m, 7H); MS (ESI) m/z 315.11 (M+H).

Example 34

(3R)-4-Amino-3-[4-chloro-3-(3-hydroxyphenyl)phenyl]butanoic acid hydrochloride (34)

Following the cross-coupling procedure according to Example 25 using 3-methoxyphenyl boronic acid and (4R)-4-(3-bromo-4-chlorophenyl)pyrrolidin-2-one followed by hydrolysis of the methyl ether using 48% HBr provided the title compound (34). ¹H-NMR (400 MHz, CD₃OD): δ 2.67-2.73 (dd, J=16.4, 6.4 Hz, 1H), 2.80-2.85 (dd, J=16.4, 7.6 Hz, 1H), 3.19-3.25 (dd, J=12.4, 12.0 Hz, 1H), 3.32-3.37 (m, 1H), 3.39-3.47 (m, 1H), 6.79-6.81 (m, 1H), 6.85-6.87 (m, 2H), 7.21-7.25 (m, 1H), 7.28-7.33 (m, 2H), 7.48-7.50 (d, J=8 Hz, 1H); MS (ESI) m/z 306.14 (M+H)⁺.

Example 35

(3R)-4-Amino-3-[4-chloro-3-(3-methoxyphenyl)phenyl]butanoic acid hydrochloride (35)

Following the cross-coupling procedure according to Example 25 using 3-methoxyphenylboronic acid and (4R)-4-(3-bromo-4-chlorophenyl)pyrrolidin-2-one provided the title compound (35). ¹H-NMR (400 MHz, CD₃OD): δ 2.68-2.74 (dd, J=16.0, 8.0 Hz, 1H), 2.81-2.86 (dd, J=16.8, 6.8 Hz, 1H), 1H), 3.20-3.26 (m, 1H), 3.33-3.38 (m, 1H), 3.41-3.48 (m, 1H), 3.84 (s, 3H), 6.94-6.99 (m, 3H), 7.31-7.36 (m, 3H), 7.49-7.51 (m, 1H); MS (ESI) m/z 320.13 (M+H)⁺.

Example 36

(3R)-4-Amino-3-[4-chloro-3-(4-cyanophenyl)phenyl]butanoic acid hydrochloride (36)

Following the cross-coupling procedure according to Example 25 using 4-cyanophenylboronic acid and (4R)-4-(3-bromo-4-chlorophenyl)pyrrolidin-2-one provided the title compound (36). ¹H-NMR (400 MHz, CD₃OD): δ 2.61-2.67 (dd, J=15.2, 7.2 Hz, 1H), 2.73-2.79 (dd, J=16.4, 7.6 Hz, 1H), 3.17-3.22 (dd, J=21.2, 8.8 Hz, 1H), 3.32-3.42 (m, 2H), 7.35-7.37 (m, 2H), 7.52-7.54 (m, 1H), 7.61-7.63 (m, 2H), 7.79-7.82 (m, 2H); MS (ESI) m/z 314.97 (M+H)⁺.

Example 37

(3R)-4-Amino-3-[4-chloro-3-(3-nitrophenyl)phenyl]butanoic acid hydrochloride (37)

Following the cross-coupling procedure according to Example 25 using 3-nitrophenylboronic acid and (4R)-4-(3-bromo-4-chlorophenyl)pyrrolidin-2-one provided the title compound (37). ¹H-NMR (400 MHz, CD₃OD): δ 2.69-2.75 (dd, J=16.0, 8.0 Hz, 1H), 2.81-2.87 (dd, J=16.0, 8.0 Hz, 1H), 3.22-3.27 (m, 1H), 3.34-3.50 (m, 2H), 7.39-7.43 (m, 2H), 7.56-7.58 (m, 1H), 7.70 (t, J=7.6 Hz, 1H), 7.85-7.87 (m, 1H), 8.26-8.31 (m, 2H); MS (ESI) m/z 334.96 (M+H)⁺.

Example 38

(3R)-4-Amino-3-[4-chloro-3-(3-methylthiophenyl)phenyl]butanoic acid hydrochloride (38)

Following the cross-coupling procedure according to Example 25 using 3-methylthiophenylboronic acid and (4R)-4-(3-bromo-4-chlorophenyl)pyrrolidin-2-one provided the title compound (38). ¹H-NMR (400 MHz, CD₃OD): δ 2.49 (s, 3H), 2.67-2.73 (dd, J=16.4, 8.0 Hz, 1H), 2.80-2.85 (dd, J=16.8, 6.8 Hz, 1H), 3.19-3.25 (m, 1H), 3.32-3.46 (m, 2H), 7.17-7.19 (m, 1H), 7.26-7.37 (m, 5H), 7.49-7.51 (m, 1H); MS (ESI) m/z 335.98 (M+H)⁺.

Example 39

(3R)-4-Amino-3-(4-chloro-3-phenyl-phenyl)butanoic acid hydrochloride (39)

Following the cross coupling procedure according to Example 25 using 3-phenylboronic acid and (4R)-4-(3-bromo-4-chlorophenyl)pyrrolidin-2-one provided the title compound (39). ¹H-NMR (400 MHz, CD₃OD): δ 2.67-2.73 (dd, J=16.4, 7.6 Hz, 1H), 2.79-2.85 (dd, J=16.4, 6.8 Hz, 1H), 3.19-3.25 (m, 1H), 3.32-3.37 (m, 1H), 3.40-3.47 (m, 1H), 7.30-7.40 (m, 3H), 7.41-7.42 (m, 4H), 7.49-7.51 (m, 1H); MS (ESI) m/z 290.00 (M+H)$^+$.

Example 40

3-{5-[(1R)-2-Amino-1-(carboxymethyl)ethyl]-2-chlorophenyl}-5-nitrobenzoic acid hydrochloride (40)

Following the cross-coupling procedure according to Example 25 using 3-carboxy-5-nitrophenyl boronic acid and (4R)-4-(3-bromo-4-chlorophenyl)pyrrolidin-2-one provided the title compound (40). $^1$H-NMR (400 MHz, CD$_3$OD): δ 2.71-2.77 (dd, J=16.4, 8 Hz, 1H), 2.82-2.88 (dd, J=16.0, 6.8 Hz, 1H), 3.23-3.29 (m, 1H), 3.35-3.40 (m, 1H) 3.45-3.50 (m, 1H), 7.43-7.48 (m, 2H), 7.59-7.61 (d, J=8.4 Hz, 1H), 8.44 (s, 1H), 8.51-8.52 (m, 1H), 8.80-8.81 (t, J=1.2 Hz, 1H); MS (ESI) m/z 378.97 (M+H)$^+$.

Example 41

(3R)-4-Amino-3-{3-[3-(dimethylamino)phenyl]-4-chlorophenyl}butanoic acid hydrochloride (41)

Following above cross-coupling procedure according to Example 36 using 3-bromo-N,N-dimethylaniline and (4R)-4-[4-chloro-3-(4,4,5,5-tetramethyl(1,3,2-dioxaborolan-2-yl))phenyl]pyrrolidin-2-one provided the title compound (41). $^1$H-NMR (400 MHz, CD$_3$OD): δ 2.61-2.67 (dd, J=16.8, 6.8 Hz, 1H), 2.72-2.78 (dd, J=16.4, 8.0 Hz, 1H), 2.94 (s, 6H), 3.15-3.21 (dd, J=21.2, 8.8 Hz, 1H), 3.30-3.34 (m, 1H), 3.34-3.40 (m, 1H), 6.70-6.73 (m, 1H), 6.76-6.80 (m, 2H), 7.21-7.31 (m, 2H), 7.31-7.32 (d, J=2.4 Hz, 1H), 7.45-7.47 (d, J=8.4, 1H); MS (ESI) m/z 333.06 (M+H)$^+$.

Example 42

Methyl (3R)-4-amino-3-[4-chloro-3-(3-cyanophenyl)phenyl]butanoate hydrochloride (42)

Seventy (70) mg (0.22 mmol) of Boc-(3R)-4-N-Boc-amino-3-[4-chloro-3-(3-cyanophenyl)phenyl]butanoic acid (70 mg, 0.22 mmol) was dissolved in 1 mL of a mixture of dichloromethane and methanol (v/v 9:1). The solution was cooled to 0° C. and 1.0 equivalent of a 2M solution of trimethylsilyldiazomethane in hexane (0.15 mL, 0.22 mmol of trimethylsilyl diazomethane-hexane) (2M) was added. The resulting mixture was stirred for 30 minutes before it was concentrated in vacuo. The crude residue was treated with 20% trifluoroacetic acid in dichloromethane at room temperature for 1 h. The mixture was then concentrated to dryness and purified by HPLC to provide the title compound (42). $^1$H-NMR (400 MHz, CD$_3$OD): δ 2.73-2.79 (dd, J=16.4, 7.6 Hz, 1H), 2.84-2.89 (dd, J=16.0, 7.8 Hz, 1H), 3.21-3.28 (m, 1H), 3.32-3.37 (m, 1H), 3.42-3.51 (m, 1H), 3.60 (s, 3H), 7.36-7.38 (m, 2H), 7.53-7.55 (m, 1H), 7.61-7.65 (m, 1H), 7.75-7.78 (m, 2H), 7.79-7.80 (m, 1H); MS (ESI) m/z 329.00 (M+H)$^+$.

Example 43

(3R)-4-Amino-3-{3-[3-(carboxymethyl)phenyl]-4-chlorophenyl}butanoic acid hydrochloride (43)

Step 1: tert-Butyl-(4R)-4-(3-iodo-4-chlorophenyl)-2-oxopyrrolidinecarboxylate (43a)

To (4R)-4-(3-Amino-4-chlorophenyl)pyrrolidin-2-one (10 g, 47.62 mmol) was added a mixture of 12N HCl (30 mL) and ice cold water (20 mL) and cooled in ice. Sodium nitrite (3.7 g, 52.4 mmol) in 20 mL water was added dropwise. The mixture was stirred for 30 minutes. Potassium iodide (67.5 g, 404.8 mmol) in 100 mL of water was added dropwise at 0° C. The mixture was stirred for 1 h at 0° C. and then for 45 min at room temperature. One-hundred (100) mL of 20% IPA/DCM was added. The organic phase was separated and washed with 10% sodium thiosulfate, followed by water and brine. The combined organic layers were then evaporated in vacuo to give a reddish yellow oil, which was purified by silica gel chromatography (biotage) eluting with methylene chloride/methanol to provide 17.4 g (75% yield) of (4R)-4-(4-chloro-3-iodophenyl)pyrrolidin-2-one.

To (4R)-4-(4-chloro-3-iodophenyl)pyrrolidin-2-one (17.4 g, 54.4 mmol) was added 50 mL DCM. The solution was cooled to 0° C. Triethylamine (9.1 mL, 65.25 mmol) was added followed by di-tert butyl carbonate (13.1 g, 59.04 mmol) in 60 mL of DCM. A catalytic amount of DMAP was added, the mixture warmed to room temperature, and then stirred overnight at room temperature. A 5% solution of HCl (50 mL) was added and the organic phase separated. The DCM layers were then washed with brine and evaporated to give the title compound (43a) as a yellowish solid (18.3 g, 80% yield). $^1$H-NMR (400 MHz, CD$_3$OD): δ 7.83-7.84 d, J=2 Hz, 1H), 7.35-7.46 (m, 1H), 7.31-7.33 (m, 1H), 4.11-4.15 (m, 1H), 3.62-3.67 (m, 2H), 3.45-3.61 (m, 1H), 2.80-2.84 (m, 1H), 2.69-2.74 (m, 1H) 1.52 (s, 9H); MS (ESI) m/z 443.86 (M+Na)$^+$.

Step 2: tert-Butyl-(4R)-4-[4-Chloro-3-(4,4,5,5-tetramethyl(1,3,2-dioxaborolan-2-yl)phenyl]-2-oxopyrrolidinecarboxylate (43b)

To a solution of bis(pinacolato)diboron (6.38 g, 25.2 mmol), 1,1-bis(diphenyl)phosphino)ferrocene)dichloro palladium(II) (1.64 g, 2.0 mmol) and potassium acetate (7.91 g, 80.8 mmol) (pre-dried overnight in an oven at 80° C.) in DMF (25 mL) was added a solution of tert-butyl-(4R)-4-(3-iodo-4-chlorophenyl)-2-oxopyrrolidincarboxylate (43a) (8.5 g, 20.2 mmol) in DMF (25 mL). The reaction mixture was stirred for a few minutes at room temperature before being heated overnight at 85° C. under a nitrogen atmosphere. The reaction mixture was then cooled to room temperature, diluted with ethyl acetate (100 mL), and the layers separated. The organic layer was washed with a 10% aq. HCl solution then brine, and dried over MgSO$_4$. The crude product was purified by silica gel chromatography (eluting with DCM/1% MeOH) to provide the title compound (43b) as a light yellow solid (6.6 g, 78% yield). $^1$H-NMR (400 MHz, CD$_3$OD): δ 7.57 (d, J=2.4 Hz, 1H), 7.34-7.35 (m, 2H), 4.11-4.15 (m, 1H), 3.56-3.69 (m, 2H), 2.81-2.88 (dd, J=16.8, 8.8 Hz, 1H), 2.67-2.74 (dd, J=17.2, 9.6 Hz, 1H), 1.52 s, 9H), 1.36 (s, 9H), 1.23 (s, 3H); MS (ESI) m/z 422.05 (M+H)$^+$.

Step 3: (3R)-4-Amino-3-{3-[3-(carboxymethyl)phenyl]-4-chlorophenyl}butanoic acid hydrochloride (43)

tert-Butyl-(4R)-4-[4-chloro-3-(4,4,5,5-tetramethyl(1,3,2-dioxaborolan-2-yl)phenyl]-2-oxopyrrolidinecarboxylate (43b) (0.16 g, 0.38 mmol) and 4-bromo-phenylacetate (95 mg, 0.41 mmol) were dissolved in DMF (1 mL). The mixture was degassed by alternately applying a vacuum and flushing with nitrogen gas. Palladium acetate (17 mg, 0.076 mmol) and tetrabutylammonium bromide (24 mg, 0.076 mmol) were added followed by potassium phosphate (241 mg, 1.14 mmol). The mixture was stirred overnight at 90° C. The reaction mixture was cooled to room temperature, diluted with ethyl acetate (30 mL), washed with 10% HCl aqueous solution, then brine, and concentrated in vacuo. The product, 2-(3-{5-[(3R)-5-oxo-1-(tert-butyl)pyrrolidin-3-yl]-2-chlorophenyl}phenyl)acetic acid, was then dissolved in a 6N HCl aq. solution and heated overnight at 90° C. The crude product was purified by HPLC to provide the title compound (43). $^1$H-NMR (400 MHz, CD$_3$OD): δ 2.67-2.73 (dd, J=16.4, 7.6 Hz, 1H), 2.78-2.84 (dd, J=16.4, 6.8 Hz, 1H), 3.19-3.24 (dd, J=22.0, 1.2 Hz, 1H), 3.32-3.49 (m, 2H), 3.66 (s, 2H), 7.28-7.40 (m, 6H), 7.49-7.51 (m, 1H); MS (ESI) m/z 348.12 (M+H)$^+$.

Example 44

4-{5-[(1R)-2-Amino-1-(carboxymethyl)ethyl]-2-chlorophenyl}-3-chlorobenzoic acid hydrochloride (44)

Following the cross-coupling procedure according to Example 43 and replacing 4-bromo-phenylacetate with 4-bromo-3-chlorobenzoic acid provided the title compound (44). $^1$H-NMR (400 MHz, CD$_3$OD): δ 2.67-2.73 (m, 1H), 2.75-2.81 (m, 1H), 3.12-3.21 (m, 3H), 7.20-7.22 (m, 1H), 7.43-7.53 (m, 3H), 7.99-8.06 (m, 1H), 8.12-8.16 (m, 1H); MS (ESI) m/z 367.96 (M+H)$^+$.

Example 45

3-{5-[(1R)-2-Amino-1-(carboxymethyl)ethyl]-2-chlorophenyl}-5-chlorobenzoic acid hydrochloride (45)

Following the cross coupling procedure according to Example 43 and replacing 4-bromo-phenylacetate with 3-bromo-5-chlorobenzoate provided the title compound (45). $^1$H-NMR (400 MHz, CD$_3$OD): δ 2.75-2.69 (dd, J=16.0, 7.6 Hz, 1H), 2.80-2.86 (dd, J=16.0, 6.8 Hz, 1H), 3.21-3.27 (m, 2H), 3.34-3.47 (m, 1H), 7.38-7.40 (m, 2H), 7.55-7.57 (m, 1H), 7.68-7.69 (t, J=1.6 Hz, 1H), 8.00-8.02 (m, 2H); MS (ESI) m/z 368.09.

Example 46

3-{5-[(1R)-2-Amino-1-(carboxymethyl)ethyl]-2-chlorophenyl}-4-chlorobenzoic acid hydrochloride (46)

Following the cross-coupling procedure according to Example 43 and replacing 4-bromo-phenylacetate with 3-bromo-4-chlorobenzoate provided the title compound (46). $^1$H-NMR (400 MHz, CD$_3$OD): δ 2.66-2.73 (m, 1H), 2.78-2.86 (m, 1H), 3.20-3.26 (m, 1H), 3.32-3.46 (m, 2H), 7.28-7.32 (m, 1H), 7.38-7.43 (m, 1H), 7.54 (t, J=7.6 Hz, 1H), 7.60-7.63 (d, J=8.4 Hz, 1H), 7.90-7.92 (m, 1H) 8.00-8.03 (m, 1H); MS (ESI) m/z 367.94 (M+H)$^+$.

Example 47

(3R)-4-Amino-3-[4-chloro-3-(4-nitrophenyl)phenyl] butanoic acid hydrochloride (47)

Following the cross coupling procedure according to Example 43 and replacing 4-bromo-phenylacetate with 1-bromo-4-nitrobenzene provided the title compound (47). $^1$H-NMR (400 MHz, CD$_3$OD): δ 2.57-2.63 (dd, J=15.6, 6.4 Hz, 1H), 2.68-2.74 (dd, J=16.0, 7.6 Hz, 1H), 3.16-3.21 (dd, J=20.0, 7.6 Hz, 1H), 3.31-3.40 (m, 2H), 7.35-7.37 (m, 2H), 7.52-7.54 (d, J=8.8 Hz, 1H), 7.67-7.70 (m, 2H), 8.29-8.32 (m, 2H); MS (ESI) m/z 334.96 (M+H)$^+$.

Example 48

5-{5-[(1R)-2-Amino-1-(carboxymethyl)ethyl]-2-chlorophenyl}pyridine-3-carboxylic acid hydrochloride (48)

Following the cross coupling procedure according to Example 43 and replacing 4-bromo-phenylacetate with 5-bromo-nicotinic acid provided the title compound (48). $^1$H-NMR (400 MHz, CD$_3$OD): δ 2.68-2.74 (dd, J=16.4, 8.0 Hz, 1H), 2.79-2.85 (dd, J=16.4, 6.8 Hz, 1H), 3.22-3.27 (dd, J=22.4, 9.6 Hz, 1H), 3.33-3.48 (m, 2H), 7.41-7.44 (m, 2H), 7.57-7.59 (m, 1H), 8.43 (t, J=2.0 Hz, 1H), 8.76-8.76 (d, J=2.4 Hz, 1H), 9.11-9.11 (d, J=2.0 Hz, 1H); MS (ESI) m/z 334.96 (M+H)$^+$.

Example 49

(3R)-4-Amino-3-[4-chloro-3-(4-chloro-3-cyanophenyl)phenyl]butanoic acid hydrochloride (49)

Following the cross coupling procedure according to Example 43 and replacing 4-bromo-phenylacetate with 5-bromo-2-chlorobenzonitrile provided the title compound (49). $^1$H-NMR (400 MHz, CD$_3$OD): δ 2.69-2.71 (dd, J=16.4, 7.6 Hz, 1H), 2.77-2.82 (dd, J=16.4, 7.2 Hz, 1H), 3.19-3.28 (m, 1H), 3.30-3.46 (m, 2H), 7.37-7.39 (m, 2H), 7.53-7.55 (m, 1H), 7.76-7.77 (m, 2H), 7.88-7.89 (d, J=2.0 Hz, 1H); MS (ESI) m/z 348.9 8 (M+H)$^+$.

Example 50

3-{5-[(1R)-2-Amino-1-(carboxymethyl)ethyl]-2-chlorophenyl}-5-fluorobenzoic acid hydrochloride (50)

Following the cross coupling procedure according to Example 43 and replacing 4-bromo-phenylacetate with 3-bromo-5-fluorobenzoate provided the title compound (50). $^1$H-NMR (400 MHz, CD$_3$OD): δ 2.78-2.84 (m, 1H), 2.67-2.73 (m, 1H), 3.20-3.26 (d, J=12.4, 9.2 Hz, 1H), 3.34-3.37 (m, 1H), 3.42-3.47 (m, 1H), 7.89-7.90 (t, J=1.2 Hz, 1H), 7.71-7.74 (d, J=4.0, 1.6 Hz, 1H), 7.54-7.56 (m, 1H), 7.42-7.44 (dd, J=2.4, 1.6 Hz, 1H), 7.36-7.39 (m, 2H); MS (ESI) m/z 352.02 (M+H)$^+$.

Example 51

3-{3-[(1R)-2-Amino-1-(carboxymethyl)ethyl] phenyl}benzoic acid hydrochloride (51)

To solid 5% Pd/C (5 mg) was added a solution of 3-{5-[(1R)-2-amino-1-(carboxymethyl)ethyl]-2-chlorophenyl}butanoic acid prepared according to Example 43 (17 mg, 0.05 mmol) in 1 mL of methanol under nitrogen atmosphere. The mixture was flushed with nitrogen gas and vacuum three times before hydrogen gas (1 atm) was introduced via balloon. After 2 hrs, the hydrogen was removed via vacuum and the mixture filtered through a pad of Celite. The Celite was rinsed twice with methanol and the solvent was removed in vacuo. The crude residue was purified by HPLC to provide the title compound (51) (5.3 mg, 33% yield). $^1$H-NMR (400 MHz, CD$_3$OD): δ 2.73-2.79 (dd, J=16.4, 7.6

Hz, 1H), 2.85-2.90 (dd, J=16.4, 6.8 Hz, 1H), 3.36-3.42 (dd, J=12.8, 7.2 Hz, 1H), 3.47-3.54 (m, 1H), 7.36-7.38 (m, 1H), 7.49-7.53 (t, J=7.6 Hz, 1H), 7.54-7.58 (t, J=7.6 Hz, 1H), 7.60-7.63 (m, 2H), 7.86-7.89 (m, 1H), 8.00-8.02 (t, J=1.2 Hz, 1H), 8.27-8.28 (t, J=1.6 Hz, 1H); MS (ESI) m/z 300.14 (M+H)+.

Example 52

(3R)-4-Amino-3-[3-(3-carbamoylphenyl)-4-chlorophenyl]butanoic acid hydrochloride (52)

Boc-(3R)-4-amino-3-[4-chloro-3-(3-cyanophenyl)phenyl]butanoic acid (52a) was synthesized using the general Suzuki cross coupling procedure. Crude Boc-(3R)-4-amino-3-[4-chloro-3-(3-cyanophenyl)phenyl]butanoic acid (52a) (130 mg, 0.32 mmol) was treated with 1 mL of trifluoroacetic acid/conc. sulfuric acid (4:1) and stirred for 1 h at room temperature. Trifluoroacetic acid was removed in vacuo. The crude residue was purified by preparative HPLC to provide the title compound (52) as a white solid. $^1$H-NMR (400 MHz, CD$_3$OD): δ 2.78-2.83 (m, 1H), 2.65-2.71 (m, 1H), 3.19-3.25 (dd, J=22.0, 9.2 Hz, 1H), 3.32-3.47 (m, 2H), 7.92-7.93 (m, 1H), 7.87-7.89 (d, J=7.6, 1 Hz), 7.62-7.64 (d, J=7.6 Hz, 1H), 7.51-7.54 (m, 2H), 7.32-7.38 (m, 2H); MS (ESI) m/z 333.00 (M+H)+.

Example 53

3-{5-[(1R)-1-(Aminomethyl)-3-hydroxypropyl]-2-chlorophenyl}benzenecarbonitrile hydrochloride (53)

Two-hundred (200) mg (0.48 mmol) of Boc-(3R)-4-amino-3-[4-chloro-3-(3-cyanophenyl)phenyl]butanoic acid (52a) (200 mg, 0.48 mmol) was dissolved in 1 mL of tetrahydrofuran (THF). The reaction mixture was cooled to 0° C. and 3 equivalents of 2M borane/THF solution was added. The mixture was warmed to room temperature and stirred for 3 days. The reaction mixture was then carefully quenched with excess methanol. After stirring for 15 min, 2 mL of 1N NaOH was added and the mixture stirred for one hour. The mixture was extracted with ethyl acetate (3×10 mL), the aqueous solution acidified to pH 3, and then extracted two additional times with ethyl acetate. The combined organic layers were dried over Na$_2$SO$_4$ and concentrated in vacuo. The crude residue was purified by HPLC to provide the title compound (53) (4.3 mg, 10% yield). $^1$H-NMR (400 MHz, CD$_3$OD): δ 1.93-2.01 (m, 1H), 1.81-1.88 (m, 1H), 3.22-3.27 (dd, J=22.4, 9.6 Hz, 1H), 3.14-3.19 (m, 1H), 3.30-3.39 (m, 1H), 3.52-3.57 (m, 1H), 7.54-7.56 (m, 1H), 7.33-7.36 (m, 2H), 7.61-7.65 (m, 1H), 7.75-7.78 (m, 1H), 7.80-7.81 (m, 1H); MS (ESI) m/z 301.04 (M+H)+.

Example 54

(3R)-4-Amino-3-{4-chloro-3-[3-(methylsulfonyl)phenyl]phenyl}butanoic acid hydrochloride (54)

(4S)-4-[4-Chloro-3-(3-methylthiophenyl)phenyl]-1-tert-butyl pyrrolidin-2-one (54a) was synthesized according to the general Suzuki cross coupling procedure. To a solution of (45)-4-[4-chloro-3-(3-methylthiophenyl)phenyl]-1-tert-butyl pyrrolidin-2-one (54a) (240 mg, 0.57 mmol) in dichloromethane was added m-chlorobenzoic acid (mCPBA) (387 mg, 1.7 mmol) at room temperature. The resulting mixture was stirred for 2 h at room temperature. The mixture was then diluted with water and extracted with ethyl acetate (3×20 mL). The organic phases were dried over MgSO$_4$ and concentrated in vacuo. The crude residue was heated for 5 h at 90° C. in a 6N HCl aq. solution and purified by preparative HPLC to provide the title compound (54). $^1$H-NMR (400 MHz, CD$_3$OD): δ 2.77-2.83 (m, 1H), 2.66-2.71 (m, 1H), 3.20-3.25 (dd, J=21.6, 12.8 Hz, 1H), 3.16 (s, 3H), 3.40-3.44 (m, 2H), 3.32-3.37 (m, 1H), 7.98-8.01 (m, 1H), 7.79-7.81 (m, 1H), 7.70-7.73 (t, J=7.6 Hz, 1H), 7.54-7.56 (d, J=8.0 Hz, 1H), 7.36-7.40 (m, 2H); MS (ESI) m/z 368.00 (M+H)+.

Example 55

(3R)-4-Amino-3-(3-{[((2,4-dichlorophenyl)methyl]amino}-4-chlorophenyl)butanoic acid hydrochloride (55)

(4R)-4-(3-Amino-4-chlorophenyl)pyrrolidin-2-one (0.21 g, 1.0 mmol) and 2,4-dicholorobenzaldehyde (0.17 mL, 1 mmol) were dissolved in methanol (2 mL). Sodium cyanoborohydride (0.075 g, 1.2 mmol) was added followed by acetic acid (0.1 mL). The mixture was stirred overnight at 70° C. The reaction mixture was cooled to room temperature, diluted with ethyl acetate (30 mL), washed with 10% HCl aqueous solution then brine, and concentrated. The product was then subjected to acidic hydrolysis as described for the preparation of (3R)-4-amino-3-(3-bromo-4-chlorophenyl)butanoic acid hydrochloride to provide the title compound (55). $^1$H-NMR (400MHz, CD$_3$OD): δ 7.47 (d, J=2.4 Hz, 1H), 7.30-7.32 (m, 1H), 7.23-7.26 (m, 2H), 6.54-6.56 (m, 1H), 6.39 (d, J=2.4 Hz, 1H), 4.52 (s, 2H), 3.08-3.21 (m, 2H), 2.98-3.08 (m, 1H), 2.59-2.66 (dd, J=16.0, 7.2 Hz, 1H), 2.47-2.53 (dd, 16.4, 6.8 Hz); MS (ESI) m/z 388.98 (M+H)+.

Example 56

(3R)-4-Amino-3-(4-chloro-3-{[(3-phenoxyphenyl)methyl]amino}phenyl)butanoic acid hydrochloride (56)

Following the procedure according to Example 55 and replacing 2,4-dicholorobenzaldehyde with 3-phenoxy-benzaldehyde provided the title compound (56). $^1$H-NMR (400 MHz, CD$_3$OD): δ 7.26-7.31 (m, 3H), 7.20 (d, J=8.0 Hz, 1H), 7.05-7.11 (m, 2H), 6.96-6.97 (m, 1H), 6.91-6.93 (m, 2H), 6.81-6.83 (m, 1H), 6.47-6.52 (m, 2H), 4.43 (s, 2H), 3.13-3.22 (m, 2H), 2.98-3.02 (m, 1H), 2.57-2.63 (dd, J=16.4, 7.6 Hz, 1H), 2.46-251 (dd, J=16.0, 5.6 Hz); MS (ESI) m/z 411.15 (M+H)+.

Example 57

(3R)-4-Amino-3-{4-chloro-3-[(4-pyridylmethyl)amino]phenyl}butanoic acid hydrochloride (57)

Following the procedure according to Example 55 and replacing 2,4-dicholorobenzaldehyde with 4-pyridine carboxaldehyde provided the title compound (57). $^1$H-NMR (400 MHz, CD$_3$OD): δ 8.47 (d, J=5.6 Hz, 2H), 7.50 (d, J=5.6 Hz, 2H), 7.25 (d, J=8.0 Hz, 1H), 6.55-6.58 (dd, J=8.4, 2.4 Hz, 1H), 6.40 (d, J=1.6 Hz, 1H), 4.60 (s, 2H), 3.15-3.21 (m, 2H), 2.90-3.20 (m, 1H), 2.60-2.67 (dd, J=16.4, 6.8 Hz, 1H), 2.45-2.51 (dd, J=16.4, 7.2 Hz, 1H); MS (ESI) m/z 320.06 (M+H)+.

Example 58

(3R)-4-Amino-3-{(4-chloro-3-[(2-pyridylmethyl) amino]phenyl}butanoic acid hydrochloride (58)

Following the procedure according to Example 55 and replacing 2,4-dicholorobenzaldehyde with 2-pyridine carboxaldehyde provided the title compound (58). $^1$H-NMR (400 MHz, CD$_3$OD): δ 8.58-8.60 (m, 1H), 8.08-8.12 (m, 1H), 7.69 (d, J=8.0 Hz, 1H), 7.57 (t, J=6.4 Hz, 1H), 7.26 (d, J=8.0 Hz, 1H), 6.61 (d, J=2.0 Hz, 1H), 6.59 (d, J=2.0 Hz, 1H), 6.54 (s, 1H), 4.67 (s, 2H), 3.21-3.25 (m, 2H), 3.04-3.20 (m, 2H), 2.63-2.69 (dd, J=16.0, 8.0 Hz, 1H), 2.48-2.54 (dd, J=16.4, 7.2 Hz, 1H); MS (ESI) m/z 320.19 (M+H)$^+$.

Example 59

(3R)-4-Amino-3-(4-chloro-3-{[(1-methylimidazol-5-yl)methyl]amino}phenyl)butanoic acid (59)

Following the procedure according to Example 55 and replacing 2,4-dicholorobenzaldehyde with 1-methyl-1H-imidazole-5-carboxaldehyde provided the title compound (59). $^1$H-NMR (400 MHz, CD$_3$OD): δ 8.35 (s, 1H), 7.81 (s, 1H), 7.22 (d, J=8.0 Hz, 1H), 7.07 (s, 1H), 6.74 (d, J=2.4 Hz, 1H), 6.57 (m, 1H), 4.51 (s, 2H), 3.76 (s, 3H), 3.23-3.27 (m, 2H), 3.07-3.09 (m, 1H), 2.48-2.63 (m, 2H); MS (ESI) m/z 323.15 (M+H)$^+$.

Example 60

(3R)-4-Amino-3-{4-chloro-3-[(imidazol-5-ylmethyl) amino]phenyl}butanoic acid hydrochloride (60)

Following the procedure according to Example 55 and replacing 2,4-dicholorobenzaldehyde with 1H-imidazole-5-carboxaldehyde provided the title compound (60). $^1$H-NMR (400 MHz, CD$_3$OD): —8.42 (d, J=2.0 Hz, 1H), 7.33 (s, 1H), 7.22 (d, J=8.0 Hz, 1H), 6.71 (d, J=2.0 Hz, 1H), 6.57 (m, 1H), 4.51 (s, 2H), 3.23-3.27 (m, 2H), 3.07-3.09 (m, 1H), 2.46-2.63 (m, 2H). MS (ESI) m/z 309.11 (M+H)$^+$.

Example 61

(3R)-4-Amino-3-[3-({[3-(3,4-dichlorophenoxy)phenyl]methyl}amino)-4-chlorophenyl]butanoic acid hydrochloride (61)

Following the procedure according to Example 55 and replacing 2, 4-dicholorobenzaldehyde with 3-(3,4-dichlorophenoxybenzaldehyde) provided the title compound (61). $^1$H-NMR (400 MHz, CD$_3$OD): δ 2.42-2.47 (dd, J=16.0, 4.8 Hz, 1H), 2.53-2.57 (dd, J=16.0, 8.8 Hz, 1H), 2.95-2.99 (dd, J=11.6, 8.0 Hz, 1H), 3.00-3.18 (m, 2H), 4.46 (s, 2H), 6.49-6.51 (d, J=2 Hz, 1H), 6.81-6.84 (d, J=2.8 Hz, 1H), 6.87-6.89 (m, 1H), 6.99-7.00 (m, 1H), 7.05-7.06 (d, J=3.2 Hz, 1H), 7.17-7.19 (s, 2H), 7.32-7.36 (t, J=7.6 Hz, 1H), 7.40-7.42 (d, J=8.8 Hz, 1H); MS (ESI) m/z 481.00 (M+H)$^+$.

Example 62

(3R)-4-Amino-3-(4-chloro-3-{[(2-fluorophenyl)methyl]amino}phenyl)butanoic acid hydrochloride (62)

Following the procedure according to Example 55 and replacing 2,4-dicholorobenzaldehyde with 2-fluorobenzaldehyde provided the title compound (62). $^1$H-NMR (400 MHz, CD$_3$OD): δ 2.45-2.62 (m, 2H), 2.97-3.02 (m, 1H), 3.11-3.21 (m, 2H), 4.51 (s, 2H), 6.50-6.53 (m, 2H), 7.04-7.11 (m, 2H), 7.18-7.27 (m, 2H), 7.32-7.36 (m, 1H); MS (ESI) m/z 337.06 (M+H)$^+$.

Example 63

4-[({5-[(1R)-2-Amino-1-(carboxymethyl)ethyl]-2-chlorophenyl}amino)methyl]benzoic acid hydrochloride (63)

Following the procedure according to Example 55 and replacing 2, 4-dicholorobenzaldehyde with 4-carboxybenzaldehyde provided the title compound (63). $^1$H-NMR (400 MHz, CD$_3$OD): δ 2.44-2.50 (dd, J=16.4, 6.0 Hz, 1H), 2.54-2.60 (dd, J=16.4, 8.4 Hz, 2H), 2.92-2.96 (m, 1H), 3.09-3.24 (m, 2H), 4.53 (s, 2H), 6.42-6.43 (d, J=2.4 Hz, 1H), 6.49-6.51 (d, J=2.0 Hz, 1H), 7.20-7.22 (d, J=1.6 Hz, 1H), 7.42-7.44 (d, J=8.4 Hz, 2H), 7.93-7.95 (m, 2H); MS (ESI) m/z 363.06 (M+H)$^+$.

Example 64

(3R)-4-Amino-3-{4-chloro-3-[(3-furylmethyl) amino]phenyl}butanoic acid hydrochloride (64)

Following the procedure according to Example 55 and replacing 2, 4-dicholorobenzaldehyde with 3-furaldehyde provided the title compound (64). $^1$H-NMR (400 MHz, CD$_3$OD): δ 2.60-2.66 (dd, J=16.4, 7.6 Hz, 1H), 2.75-2.80 (dd, J=16.4, 6.4 Hz, 1H), 3.11-3.27 (dd, J=12.4, 9.2 Hz, 2 Hz, 1H), 3.31-3.37 (m, 1H), 4.38 (s, 2H), 6.45 (t, J=0.4 Hz, 1H), 6.90-6.92 (d, J=2.0 Hz, 1H), 7.00-7.01 (d, J=2.0 Hz, 1H), 7.36-7.38 (s, 1H), 7.46-7.47 (t, J=1.6 Hz, 1.6 Hz, 1H), 7.52-7.53 (t, J=1.2 Hz, 1H); MS (ESI) m/z 309.11 (M+H)$^+$.

Example 65

(3R)-4-Amino-3-(4-chloro-3-(phenylcarbonylamino) phenyl]butanoic acid (65)

Step 1: Methyl (3R)-3-(4-chloro-3-nitrophenyl)-4-(2,2,2-trifluoroacetylamino)butanoate (65a)

Methyl (3R)-4-amino-3-(4-chlorophenyl)butanoate hydrochloric acid salt (3.0 g, 11.4 mmol) and triethylamine (3.2 mL, 22.8 mmol) were dissolved in 60 mL dichloromethane. The reaction mixture was cooled to 0° C. and trifluoroacetic anhydride (2.37 mL, 17.1 mmol) was slowly added. The reaction mixture was stirred for 1 hour at room temperature. The reaction mixture was partitioned twice with 10 mL 1N hydrochloric acid and the organic layer was further washed with 20 mL saturated sodium bicarbonate solution. The organic layer was dried over sodium sulfate and the solvent removed under reduced pressure. The residue, methyl (3R)-3-(4-chlorophenyl)-4-(2,2,2-trifluoroacetylamino)butanoate, was dissolved in 40 mL concentrated sulfuric acid, the resulting solution cooled to 0° C., and nitric acid (0° C., 0.75 mL, 13.7 mmol) was slowly added to the solution. After stirring the mixture at room temperature for 1 hour, the solution was poured into 200 g of ice. The aqueous solution was extracted with 100 mL of ether (2 times), the ether layer dried over sodium sulfate, and the solvent was removed under reduced pressure to provide 3.26 g of methyl (3R)-3-(4-chloro-3-nitrophenyl)-4-(2,2,2-trifluoroacetylamino)butanoate (65a) as a white solid.

Step 2: Methyl (3R)-3-(3-amino-4-chlorophenyl)-4-(2,2,2-trifluoroacetylamino)butanoate (65b)

Methyl (3R)-3-(4-chloro-3-nitrophenyl)-4-(2,2,2-trifluoroacetylamino)butanoate (65a) (3 g, 8.15 mmol) was dissolved in 4 mL of acetic acid and 60 mL of water. At 50° C., iron powder (2.5° C., 2.74 g, 40.75 mmol) was added and the reaction mixture was stirred for 1 h at 50° C. The mixture was cooled to room temperature and then extracted with 100 mL of ethyl acetate. The ethyl acetate solution was washed with 30 mL of water, and the water extraction repeated another ten times to remove the acetic acid. The organic layer was dried over sodium sulfate and the solvent removed under reduced pressure to provide 2.1 g of methyl (3R)-3-(3-amino-4-chlorophenyl)-4-(2,2,2-trifluoroacetylamino)butanoate (65b).

Step 3: (3R)-4-Amino-3-(3-amino-4-chlorophenyl)butanoic acid (65c)

Two-hundred (200) mg of methyl (3R)-3-(3-amino-4-chlorophenyl)-4-(2,2,2-trifluoroacetylamino)butanoate (65b) was dissolved in 2.5 mL of methanol and 0.2 mL of 2N sodium hydroxide, the reaction mixture was stirred at room temperature for 16 hours, the solvent was removed under reduced pressure, and the residue purified by preparative HPLC to provide 90 mg of the title compound (65c). $^1$H NMR (400 MHz, CD$_3$OD): δ 7.21 (d, J=8.0 Hz, 1H), 6.83 (s, 1H), 6.65 (d, J=8.0 Hz, 1H), 3.30-3.26 (m, 2H), 3.15-3.11 (m, 1H), 2.74 (dd, J=16.4, 6.4 Hz, 1H), 2.62 (dd, J=16.4, 6.4 Hz, 1H); MS (ESI) m/z 229.0 (M+H)$^+$.

Step 4: (3R)-4-Amino-3-(4-chloro-3-(phenylcarbonylamino)phenyl]butanoic acid (65)

At 0° C., 0.65 mmol of benzoyl chloride was slowly added to (3R)-3-(3-amino-4-chlorophenyl)-4-(2,2,2-trifluoroacetylamino)butanoate (200 mg, 0.59 mmol) (65b), the diisopropylethylamine (1.13 mL, 0.65 mmol) of (3R)-3-(3-amino-4-chlorophenyl)-4-(2,2,2-trifluoroacetylamino)butanoate, and 113 mL (0.65 mmol) of diisopropylethyl amine in 15 mL of dichloromethane. The reaction solution was stirred for 3 h at room temperature. The reaction mixture was then washed with 1N HCl and saturated sodium bicarbonate solution. The solvent was removed under reduced pressure. The residue, methyl (3R)-3-[3-(acetylamino)-4-chlorophenyl]-4-(2,2,2-trifluoroacetylamino)butanoate, was dissolved in 2.5 mL of methanol and 0.2 mL 2N sodium hydroxide. The solution was stirred at room temperature for 16 h. The solvent was removed under reduced pressure. The residue was purified by preparative HPLC to provide the title compound (65). $^1$H NMR (400 MHz, CD$_3$OD): δ7.97 (d, J=8.0 Hz, 2H), 7.69 (s, 1H), 7.63-7.59 (m, 1H), 7.55-7.50 (m, 2H), 7.27 (d, J=8.0 Hz, 1H), 3.47-3.18 (m, 3H), 2.81 (dd, J=16.0, 8.0 Hz, 1H), 2.70 (dd, J=16.0, 8.0 Hz, 1H); MS (ESI) m/z 333.1 (M+H)$^+$.

Example 66

(3R)-4-Amino-3-{4-chloro-3-[(3-chlorophenylcarbonylamino]phenyl}butanoic acid (66)

Following the procedure according to Example 65 and replacing benzoyl chloride with 3-chlorobenzoyl chloride provided the title compound (66). $^1$H NMR (400 MHz, CD$_3$OD): δ 7.98 (s, 1H), 7.91 (d, J=8.0 Hz, 1H), 7.65-7.50 (m, 3H), 7.28 (d, J=8.0 Hz, 1H), 3.47-3.18 (m, 3H), 2.84-2.67 (m, 2H); MS (ESI) m/z 367.0 (M+H)$^+$, 365.0 (M−H)$^−$.

Example 67

5-{5-[(1R)-2-Amino-1-(carboxymethyl)ethyl]-2-chlorophenyl}thiophene-2-carboxylic acid hydrochloride (67)

Following the procedure according to Example 25 and replacing 3-methoxycarbonylphenyl boronic acid with 5-(dihydroxyboryl)-2-thiophenecarboxylic acid provided the title compound (67). $^1$H-NMR (400 MHz, CD$_3$OD): δ7.75 d, J=3.6 Hz, 1H), 7.55-7.58 (m, 2H), 7.40 (d, J=4.8 Hz, 1H), 7.35-7.38 (dd, J=8.8, 4.0 Hz, 1H), 3.41-3.47 (m, 1H), 3.33-3.38 (m, 1H), 3.21-3.26 (m, 1H), 2.67-2.86 (dd, J=16.4, 6.8 Hz, 2H); MS (ESI) m/z 339.97 (M+H)$^+$.

Example 68

(3R)-4-Amino-3-[4-chloro-3-(4-pyridylmethoxy)phenyl]butanoic acid hydrochloride (68)

Step 1: Tert-butyl (4R)-4-(4-chloro-3-hydroxyphenyl)-2-oxopyrrolidinecarboxylate (68a)

One an one-half (1.5 g, 3.56 mmol) of (4R)-tert-butyl-4-[4-chloro-3-(4,4,5,5-tetramethyl(1,3,2-dioxaborolan-2yl))phenyl]-2-oxopyrrolidinecarboxylate was dissolved in 10 mL dichloromethane. To this solution, 3 equiv. of 35% hydrogen peroxide (10.68 mmol) was added dropwise. The reaction mixture was stirred overnight at room temperature. The mixture was diluted with saturated ammonium chloride aqueous solution and extracted with dichloromethane (3 times). The combined organic layers were dried over Na$_2$SO$_4$ and concentrated to dryness to provide tert-butyl (4R)-4-(4-chloro-3-hydroxyphenyl)-2-oxopyrrolidinecarboxylate (68a) as a clear oil (1.2 g, 95% yield). $^1$H-NMR (400 MHz, CD$_3$OD): δ 2.63-2.69 (dd, J=17.2, 9.2 Hz, 1H), 2.80-2.87 (dd, J=17.2, 8.4 Hz, 1H), 3.47-3.54 (m, 1H), 3.61-3.66 (m, 1H), 4.12-4.11 (t, J=2.4 Hz, 1H), 7.24-7.22 (d, J=8.0 Hz, 1H), 6.82-6.82 (d, J=2.0 Hz, 1H), 6.73-6.75 (d, J=2.0 Hz, 1H); MS (ESI) m/z 334.01 (M+Na)$^+$.

Step 2: (3R)-4-Amino-3-[4-chloro-3-(4-pyridylmethoxy)phenyl]butanoic acid hydrochloride (68)

To a solution of tert-butyl (4R)-4-(4-chloro-3-hydroxyphenyl)-2-oxopyrrolidinecarboxylate (68a) (1.0 equiv.) in ethanol (0.4M) was added K$_2$CO$_3$ (2 equiv.) followed by an appropriate electrophile (1.5 equiv., e.g. 4-bromomethylpyridine hydrobromide). The reaction mixture was heated overnight at 90° C. The mixture was cooled to room temperature and the solvent removed. The crude residue was treated with a 6N HCl aqueous solution (0.1M) and heated for 3 h at 90° C. The title compound (68) was obtained following purification by HPLC purification. $^1$H-NMR (400 MHz, CD$_3$OD): δ 2.60-2.66 (dd, J=16.4, 7.6 Hz, 1H), 2.74-2.78 (dd, J=16.4, 7.2 Hz, 1H), 3.17-3.24 (m, 1H), 5.28 (s, 2H), 8.53-8.54 (d, J=4.0 Hz, 1H), 7.56-7.57 (d, J=4 Hz, 1H), 7.40 (d, J=8.0 Hz, 1H), 7.09-7.09 (d, J=2.0 Hz, 1H), 6.92-6.95 (d, J=4.0 Hz, 1H); MS (ESI) m/z 321.01 (M+H)$^+$.

Example 69

2-{5-[(1R)-2-Amino-1-(carboxymethyl)ethyl]-2-chlorophenyl}-1,3-thiazole-4-carboxylic acid hydrochloride (69)

Following the procedure according to Example 25 and replacing 3-methoxycarbonylphenyl boronic acid with methyl-2-bromothiazole carboxylate provided the title compound (69). $^1$H-NMR (400 MHz, CD$_3$OD): δ 8.51 (s, 1H), 8.28-8.29 (d, J=2.4 Hz, 1H), 7.58-7.60 (d, J=8.4 Hz, 1H), 7.44-7.47 (dd, J=2.4, 2.0 Hz, 1H), 3.44-3.49 (m, 1H), 3.27-3.41 (m, 2H), 2.82-2.88 (dd, J=6.8, 6.4 Hz, 1H), 2.71-2.75 (dd, J=6.8, 6.4 Hz, 1H); MS (ESI) m/z 340.99 (M+H)$^+$.

Example 70

2-{5-[(1R)-2-Amino-1-(carboxymethyl)ethyl]-2-chlorophenyl}-1,3-oxazole-4-carboxylic acid hydrochloride (70)

Following the procedure according to Example 25 and replacing 3-methoxycarbonylphenyl boronic acid with ethyl 2-bromo-oxazole carboxylate provided the title compound (70). $^1$H-NMR (400 MHz, CD$_3$OD): δ 8.65 s, 1H), 7.96-7.97 (d, J=2.4 Hz, 1H), 7.59-7.61 (d, J=7.6 Hz, 1H), 7.49-7.52 (dd, J=2.4, 2.4 Hz, 1H), 3.44-3.52 (m, 1H), 3.22-3.40 (m, 2H), 2.80-2.86 (dd, J=6.8, 6.4 Hz, 1H), 2.68-2.74 (dd, J=6.8, 6.4 Hz, 1H); MS (ESI) m/z 325.01 (M+H)$^+$.

Example 71

4-{5-[(1R)-2-Amino-1-(carboxymethyl)ethyl]-2-chlorophenyl}-1,3-thiazole-2-carboxylic acid hydrochloride (71)

Following the procedure according to Example 25 and replacing 3-methoxycarbonylphenyl boronic acid with methyl-4-bromothiazole carboxylate provided the title compound (71). $^1$H-NMR (400 MHz, CD$_3$OD): δ 8.31 s, 1H), 7.88-7.89 (d, J=4 Hz, 1H), 7.54-7.56 (d, J=8.4 Hz, 1H), 7.35-7.38 (dd, J=2.0, 2.4 Hz, 1H), 3.44-3.49 (m, 1H), 3.25-3.39 (m, 2H), 2.79-2.85 (dd, J=7.6, 6.8 Hz, 1H), 2.68-2.75 (dd, J=7.6, 6.8 Hz, 1H); MS (ESI) m/z 340.99 (M+H)$^+$.

Example 72

2-{5-[(1R)-2-Amino-1-(carboxymethyl)ethyl]-2-chlorophenyl}-4-methyl-1,3-thiazole-5-carboxylic acid hydrochloride (72)

Following the procedure according to Example 25 and replacing 3-methoxycarbonylphenyl boronic acid with methyl 2-bromo-4-methylthiazole carboxylate provided the title compound (72). $^1$H-NMR (400 MHz, CD$_3$OD): δ 8.18-8.19 d, J=2.4 Hz, 1H), 7.60-7.62 (d, J=8.0 Hz, 1H), 7.45-7.48 (dd, J=2.4, 2.4 Hz, 1H), 3.46-3.52 (m, 1H), 3.22-3.40 (m, 2H), 2.82-2.87 (dd, J=6.8, 6.8 Hz, 1H), 2.76 (s, 3H), 2.70-2.75 (dd, J=6.8, 6.8 Hz, 1H); MS (ESI) m/z 355.01 (M+H)$^+$.

Example 73

(3R)-4-((2S)-2-Aminopropanoylamino)-3-[4-chloro-3-(4-pyridylmethoxy)phenyl]butanoic acid hydrochloride (73)

Boc-alanine (0.37 mmol, 1 eq), N,N'-dicyclohexylcarbodiimide (0.47 mmol, 1.2 eq), and N-hydroxysuccinimide (0.47 mmol, 1.2 eq) were dissolved in 2 mL acetonitrile. The mixture was stirred at room temperature for 2 hr. The solid was filtered and added to (3R)-4-amino-3-[4-chloro-3-(4-pyridylmethoxy)phenyl]butanoic acid hydrochloride (68) and sodium bicarbonate (NaHCO$_3$) (1.5 eq) in 1 mL water. The reaction was stirred at room temperature overnight. The solvent was then evaporated and treated with trifluoroacetic acid (TFA). The trifluoroacetic acid (TFA) was evaporated and purified by HPLC to provide the title compound (73). $^1$H-NMR (400 MHz, CD$_3$OD): δ 8.53 (d, J=6.0 Hz, 2H), 7.57 (d, J=6.0 Hz, 2H), 7.30 (d, J=8.0 Hz, 1H), 7.05 (d, J=1.6 Hz, 1H), 6.87 (d, J=2 Hz, 1H), 5.26 (s, 2H), 3.69-3.74 (q, J=6.8 Hz, 1H), 3.56-3.61 (dd, J=8.4, 13.2 Hz, 1H), 3.28-3.39 (m, 1H), 2.55-2.61 (dd, J=16.0, 8.0 Hz, 1H), 2.44-2.50 (dd, J=15.2, 8.0 Hz, 1H), 1.23 (d, J=6.8, 3H); MS (ESI) m/z 391.87 (M+H)$^+$.

Example 74

(3R)-4-(2S)-2-Amino-3-methylbutanoylamino)-3-[4-chloro-3-(4-pyridylmethoxy)phenyl]butanoic acid, hydrochloride (74)

Using the procedure according to Example 73, and replacing Boc-alanine with Boc-valine provided the title compound (74). $^1$H-NMR (400 MHz, CD$_3$OD): δ 8.68 (d, J=6.0 Hz, 2H), 7.83 (d, J=5.6 Hz, 2H), 7.33 (d, J=8.4 Hz, 1H), 7.11 (d, J=4.0 Hz, 1H), 6.92 (d, J=1.6 Hz, 1H), 5.26 (s, 2H), 3.72-3.78 (m, 1H), 3.49 (d, J=5.2 Hz, 1H), 3.33-3.37 (m, 2H), 2.68-2.73 (dd, J=15.6, 8.0 Hz, 1H), 2.54-2.60 (dd, J=16.4, 8.0 Hz, 1H), 1.88-1.98 (m, 1H), 1.23 (d, J=6.8, 3H), 0.80 (d, J=6.8, 3H), 0.69 (d, J=7.2, 3H); MS (ESI) m/z 421.70 (M+H)$^+$.

Example 75

3-{5-[2-Amino-1-((hydrohydroxyphosphoryl)methyl)ethyl]-2-chlorophenyl}benzoic acid hydrochloride (75)

Step 1: 1-(4-Chloro-3-nitrophenyl)-2-nitroethene (75a)

A solution of 4-chloro-3-nitro-benzaldehyde (5 g) and ammonium acetate (3.5 g) in nitromethane (4.5 mL) and acetic acid (20 mL) was heated to reflux for 3 hr, and then cooled to room temperature in an ice bath. The product precipitated as a dark solid. The dark solid was washed with water then ether/hexane (1:1) and dried overnight under vacuum to give 3.5 g of the title compound (75a) as a bright-red solid.

Step 2: (1,1-Diethoxyethyl) [2-(4-chloro-3-nitrophenyl)-3-nitropropyl]ethoxyphosphino-1-one (75b)

A solution of (1,1-diethyloxyethyl)ethoxymethylphosphino-1-one (4.1 mL) was dissolved in 20 mL tetrahydrofuran (THF), and cooled to −78° C. One (1.0) eq of n-BuLi was slowly added to the solution via a syringe under a nitrogen atmosphere. The reaction was stirred at −78° C. for 30 min. 1-(4-Chloro-3-nitrophenyl)-2-nitroethene (75a) (3.5 g) was dissolved in 20 mL tetrahydrofuran (THF) under a nitrogen atmosphere and cooled to −78° C. The solution of (1,1-diethyloxyethyl)ethoxymethylphosphino-1-one in 20 mL THF was added over 2 min by cannula under nitrogen. The reactants were stirred at −78° C. for another 30 min and then at 0° C. for 30 min. The reaction was monitored by TLC and LCMS. The reaction was quenched with an ammonium chloride (NH$_4$Cl) solution at 0° C. The product was extracted with ethyl acetate and the organic layer dried with sodium sulfate (Na$_2$SO$_4$). The solvent was evaporated to provide 7.0 g of the crude product. The crude product was purified by silica gel chromatography using ethyl acetate/hexane to give 3.0 g (38% yield) of the title compound (75b)

Step 3: [3-Amino-2-(3-amino-4-chlorophenyl)propyl](1,1-diethoxyethyl)ethoxyphosphino-1-one (75c)

Three (3) g of (1,1-diethoxyethyl) [2-(4-chloro-3-nitrophenyl)-3-nitropropyl]ethoxyphosphino-1-one (75b) was reduced overnight using activated Raney nickel in 50 mL ethanol under hydrogenation with a pressure of 50 psi. The Raney nickel was filtered off and the solvent removed by evaporation to provide 2.7 g (90% yield) of the title compound (75c).

Step 4: [3-(tert-Butoxy)carbonyl-amino-2-(3-amino-4-chlorophenyl)propyl](1,1-diethoxyethyl)ethoxyphosphino-1-one (75d)

A solution of [3-amino-2-(3-amino-4-chlorophenyl)propyl](1,1-diethoxyethyl)ethoxyphosphino-1-one (75c) (2.7 g, 6.88 mmol) in 20 mL of dichloromethane (DCM) was cooled to 0° C. Triethylamine (TEA) (1.2 eq, 1.1 mL) and 1.05 eq of $Boc_2O$ (1.57 g, 7.2 mmol) was added dropwise followed by addition of a catalytic amount of 4-dimethylaminopyridine (DMAP). The reactants were stirred from 0° C. to room temperature overnight. The reaction was monitored by LCMS. The crude product was extracted with ethyl acetate (50 mL) and ammonium chloride ($NH_4Cl$) (10 mL). The aqueous layer was then extracted twice with ethyl acetate and dried over $Na_2SO_4$. The solvents were evaporated to provide 2.8 g of the title compound (75d).

Step 5: [3-(tert-Butoxy)carbonyl-amino-2-(3-iodo-4-chlorophenyl)propyl](1,1-diethoxyethyl)ethoxyphosphino-1-one (75e)

pTsOH $H_2O$ (2.75 g, 14.49 mmol) was dissolved in 10 mL acetonitrile (can). [3-(Tert-butoxy)carbonyl-amino-2-(3-amino-4-chlorophenyl)propyl](1,1-diethoxyethyl)ethoxyphosphino-1-one (75d) (2.38 g) in 5 mL acetonitrile (ACN) was added while stirring. The reaction mixture was cooled to 0° C. and a solution of 0.667 g of sodium nitrite ($NaNO_2$) and 2 g of potassium iodide (KI) in 4 mL $H_2O$ was added at 10° C. The reaction was stirred at 10° C. for 2 hr. The mixture as extracted with dichloromethane (DCM) and ammonium chloride ($NH_4Cl$) and dried over sodium sulfate ($Na_2SO_4$) to give 3.4 g of product as a crude oil. The crude product was purified by silica gel chromatography using ethyl acetate/hexane to provide 840 mg (28% yield) of the title compound (75e).

Step 6: (1,1-Diethoxyethyl)-4-[(tert-butoxy)carbonylamino]-3-{4-chloro-3-[3-(methoxycarbonyl)phenyl]phenyl}ethoxyphosphino-1-one (75f)

[3-(tert-Butoxy)carbonyl-amino-2-(3-iodo-4-chlorophenyl)propyl](1,1-diethoxyethyl)ethoxyphosphino-1-one (75e) (0.63 mmol, 1 eq) and $Pd(PPh_3)_4$ (0.15 eq) were dissolved in 2 mL toluene. The mixture was bubbled with nitrogen and purged under vacuum for few minutes. The reaction mixture was stirred for 20 min. Methyl 3-(dimethoxy)boramethyl benzoate in ethanol was added and the reaction mixture stirred for 20 min followed by the addition of 2.2 eq of 2M potassium carbonate ($K_2CO_3$) (0.75 mL, 1.53 mmol). The mixture was reacted at 90° C. overnight. The mixture was then partitioned with ethyl acetate and 1N HCl and dried over sodium sulfate ($Na_2SO_4$). The solvent was evaporated to provide the title compound (f) as a yellow oil (200 mg, 40% yield).

Step 7: 3-{5-[2-Amino-1-((hydrohydroxyphosphoryl)methyl)ethyl]-2-chlorophenyl}benzoic acid, chloride (75)

(1,1-Diethoxyethyl)-4-[(tert-butoxy)carbonylamino]-3-{4-chloro-3-[3-(methoxycarbonyl)phenyl]phenyl}ethoxyphosphino-1-one (75f) was dissolved in 3N HCl and heated at 80° C. overnight. Following work-up and purification by HPLC, 32 mg of the title compound (75) was obtained. $^1$H-NMR (400 MHz, $D_2O$): δ 7.94 (s, 1H), 7.91 (d, J=8 Hz, 1H), 7.62 (d, J=8 Hz, 1H), 7.42-7.48 (m, 2H), 7.22-7.25 (m, 2.5H), 5.91 (m, 0.5H), 3.06-3.26 (m, 3H), 1.75-1.94 (m, 2H); MS (ESI) m/z 354.06 (M+H)$^+$.

Example 80

5-(5-{(1R)-1-[2S-Amino-4-carbamoylbutanoylamino)methyl]-2-carboxyethyl}-2-chlorophenyl)thiophene-2-carboxylic acid hydrochloride (80)

To a solution of methyl-(3R)-4-amino-3-(4-chloro-3-[5-(methoxycarbonyl)(2-thienyl)]phenyl}butanoate (0.7 mmol, 0.273 g) and Boc-glutamine (0.7 mmol, 0.2 g) in 2 mL of dichloromethane was added N-(3-dimethylaminopropyl)-N'-ethylcarbodiimde hydrochloride (1.05 mmol, 0.2 g). A catalytic amount of 4-dimethylaminopyridine (DMAP) was added and the reaction was stirred at room temperature overnight. The mixture was diluted with dichloromethane, washed with 1N HCl and brine and dried over sodium sulfate ($Na_2SO_4$). The solvent was removed in vacuo. The crude residue was treated with NaOH/water/THF/methanol and stirred at room temperature for 2 hours. The crude product was purified by HPLC purification. 1N HCl aqueous solution was added and the solution lyophilized to provide the title compound (80) as the hydrochloride salt. $^1$H-NMR (400 MHz, $CD_3OD$): δ 7.76-7.77 (d, J=4 Hz, 1H), 7.54-7.55 (d, J=4 Hz, 1H), 7.48-7.51 (m, 1H), 7.40-7.41 (d, J=3.6 Hz, 1H), 7.32-7.35 (m, 1H), 3.79-3.82 (t, J=8 Hz, 1H), 3.67-3.74 (m, 1H), 3.35-3.49 (m, 2H), 2.75-2.80 (dd, J=16.4, 8.8 Hz, 1H), 2.61-2.67 (dd, J=16.8, 8.4 Hz, 1H), 2.16-2.20 (m, 2H), 1.86-1.91 (m, 2H). MS (ESI) m/z 468.02 (M+H)$^+$.

Example 81

(3R)-3-{4-Chloro-3-{5-methoxycarbonyl)(2-thienyl)}phenyl}-4-{[(2-methylpropanoyloxy)ethoxy]carbonylamino}butanoic acid (81)

To a solution of (3R)-4-amino-3-{4-chloro-3-[5-(methoxycarbonyl)(2-thienyl)]phenyl}butanoic acid (1 mmol, 0.382 g) and 1-({[2,5-dioxopyrrolidin-1-yl)oxy}carbonyl}-oxy)ethyl 2-methylpropanoate (1 mmol, 0.273 mg) in 4 mL of 1:1 acetonitrile and water was added sodium bicarbonate (1 mmol, 0.084 mg). The reaction mixture was stirred overnight at room temperature. The mixture was then filtered, purified by HPLC and lyophilized to give the title compound (81). $^1$H-NMR (400 MHz, $CD_3OD$): δ 7.76-7.77 d, J=4 Hz, 1H), 7.43-7.48 (m, 2H), 7.37-7.38 (d, J=4.4 Hz, 1H), 7.26-7.29 (m, 1H), 6.63-6.67 (q, J=10.8 Hz, 1H), 3.88 (s, 3H), 3.31-3.39 (m, 2H), 2.71-2.76 (m, 1H), 2.57-2.64 (m, 1H), 2.39-2.49 (m, 1H), 1.36-1.38 (t, J=5.2 Hz, 3H), 1.08-1.10 (d, J=6.8 Hz, 3H), 1.03-1.07 (m, 3H). MS (ESI) m/z 512.03 (M+H)$^+$.

Example 82

2-{4-Chloro-3-(4-pyridylmethoxy)phenyl]-3-(hydrohydroxyphosphoryl)propylamine (82)

Step 1: Methyl 4-chloro-3-hydroxy benzoate (82a)

Commercially available 2-chloro-5-(methoxycarbonyl)phenylboronic acid (14.01 mmol, 3 g) was dissolved in 30 mL of 1:1 dichloromethane and water. Thirty-percent (30%) v/v hydrogen peroxide (28.02 mmol, 1.59 mL) was added and the reaction mixture was stirred at room temperature overnight. The two layers were separated and the dichloromethane layers were evaporated in vacuo to give the title compound (82a) in 92% yield.

Step 2: Methyl 4-chloro-3-(phenylmethoxy)benzoate (82b)

Methyl 4-chloro-3-hydroxy benzoate (82a) (12.9 mmol, 2.4 g) was dissolved in 25 mL acetone. Benzyl bromide (12.9 mmol, 1.53 mL) was added to this solution. Cesium carbonate (15.48 mmol, 5.03 g) was added to the reaction mixture and heated to reflux overnight. The mixture was cooled to room temperature, acetone was removed by rotovap, and diluted with 50 mL of ethyl acetate. The ethyl acetate layer was washed with water, 5% HCl and brine and dried over anhydrous sodium sulfate. The solvent was concentrated to dryness to give the title compound (82b) in 91% yield.

Step 3: 4-Chloro-3-(phenylmethoxy)phenyl methan-1-ol (82c)

Methyl 4-chloro-3-(phenylmethoxy)benzoate (82b) (3.4 g, 11.9 mmol) was dissolved in 20 mL tetrahydrofuran (THF). The solution was cooled to 0° C. A 2M solution of lithium aluminum hydride in THF (5.9 mL, 11.9 mmol) was added dropwise. The reaction mixture was warmed to room temperature and stirred overnight. The reaction mixture was quenched at 0° C. using a small amount of water until hydrogen evolution ceased. The white precipitate was dissolved using 5% HCl and the solution diluted with ethyl acetate. The ethyl acetate layers were washed with water, brine, dried over sodium sulfate ($Na_2SO_4$) and concentrated to dryness to provide 2.74 g (93% yield) of the title compound (82c).

Step 4: 4-Chloro-3-(phenylmethoxy)benzaldehyde (82d)

4-Chloro-3-(phenylmethoxy)phenyl methan-1-ol (82c) (2.74 g, 11.06 mmol) was dissolved in 25 mL ether. Triethylamine (TEA) (7.74 mL, 55.3 mmol) was added and the mixture was cooled to 0° C. A suspension of sulfur trioxide-pyridine (5.27 g, 22.18 mmol) and dimethylsulfoxide (6.3 mL, 88.48 mmol) was added dropwise. The reaction mixture was warmed to room temperature and stirred for 1 hour. The reaction mixture was then diluted with dichloromethane, washed with 1N hydrochloric acid, sodium bicarbonate and brine and concentrated to dryness. The crude product was purified by preparative HPLC using hexane/ethyl acetate to give the 1.9 g (71% yield) of the title compound (82d).

Step 5: 4-Nitrovinyl-1-chloro-2-(phenylmethoxy)benzene (82e)

4-Chloro-3-(phenylmethoxy)benzaldehyde (82d) (1.9 g, 7.7 mmol) was dissolved in 12 mL of acetic acid. To this was added 1.7 g of ammonium acetate and 2.5 mL of nitromethane. The reaction mixture was refluxed for 3 hours. The solution was cooled to room temperature and poured into ice. A green-yellow solid precipitated. The precipitate was filtered, washed with water, and hexane, and vacuum dried to give the 1.6 g (72% yield) of the title compound (82e).

Step 6: (1,1-Diethoxyethyl){2-[4-chloro-3-(phenylmethoxy)phenyl]-3-nitropropyl}ethoxyphosphino-1-one (82f)

A solution of (1,1-diethyloxyethyl)ethoxymethylphosphino-1-one (5.5 mmol, 1.2 mL) was dissolved in 10 mL tetrahydrofuran (THF) and cooled to −78° C. 1.0 eq of n-BuLi was slowly added to the solution via a syringe under a nitrogen atmosphere. The reaction mixture was stirred at −78° C. for 30 min. 4-Nitrovinyl-1-chloro-2-(phenylmethoxy)benzene (82e) (5.5 mmol, 1.6 g) was dissolved in 10 mL tetrahydrofuran (THF) and cooled to −78° C. The phosphino compound was slowly added via a cannula to the nitro compound. The reaction mixture was stirred at −78° C. for another 30 min and then at 0° C. for 30 min. The reaction was quenched with saturated ammonium chloride solution and diluted with ethyl acetate. The ethyl acetate layer was washed with brine and concentrated to dryness. The crude product was then purified by using ethyl acetate/hexane to give 1.47 g (52% yield) of the title compound (82f).

Step 7: {3-Amino-2-[4-chloro-3-(phenylmethoxy)phenyl]propyl}(1,1-diethyloxoethyl)ethoxyphosphino-1-one (82 g)

(1,1-Diethoxyethyl){2-[4-chloro-3-(phenylmethoxy)phenyl]-3-nitropropyl}ethoxyphosphino-1-one (82f) was dissolved in 25 mL of ethanol. Activated Raney nickel was added and the reaction was carried out overnight in a Parr shaker under hydrogen at 50 psi. The Raney nickel was then filtered and the solvent evaporated under a vacuum to give 1.13 g (82% yield) of title compound (82 g).

Step 8: Boc-{3-Amino-2-[4-chloro-3-(phenylmethoxy)phenyl]propyl}(1,1-diethyloxoethyl)ethoxyphosphino-1-one (82 h)

{3-Amino-2-[4-chloro-3-(phenylmethoxy)phenyl]propyl}(1,1-diethyl)ethoxyphosphino-1-one (82 g) (1.1 g, 2.35 mmol) was dissolved in 5 mL of dichloromethane (DCM) cooled to 0° C. To this was added triethylamine (TEA) (2.58 mmol, 0.36 mL) and di-tert-butyl carbonate (2.47 mmol, 0.54 g) dropwise followed by addition of a catalytic amount of 4-dimethylamino pyridine (DMAP). The reaction mixture was then stirred at room temperature overnight. The reaction mixture was then diluted with dichloromethane and washed with 10 mL ammonium chloride ($NH_4Cl$), dried over sodium sulfate ($Na_2SO_4$), and concentrated to dryness to give 1.26 g (82% yield) of the title compound (82 h).

Step 9: N-{3-[(1,1-Diethoxyethyl)ethoxyphosphino-1-one]-2-(4-chloro-3-hydroxyphenyl)propyl}(tert-butoxy)carboxamide (82i)

Boc-{3-Amino-2-[4-chloro-3-(phenylmethoxy)phenyl]propyl}(1,1-diethyl)ethoxyphosphino-1-one (82 h) (1.2 g, 2.05 mmol) was dissolved in ethanol. About 100 mg of 10% w/w palladium on charcoal was added and the reaction mixture transferred to a Parr shaker and stirred overnight in a 50 psi hydrogen atmosphere. The reaction was filtered with silica to remove the palladium and the ethanol layer was concentrated to dryness to give 0.94 g (78% yield) of the title compound (82i).

Step 10: N-{3-[(1,1-Diethoxyethyl)ethoxyphosphino-1-one]-2-(4-chloro-3-(4-pyridylmethoxy)phenyl]propyl}(tert-butoxy)carboxamide (82j)

N-{3-[(1,1-Diethoxyethyl)ethoxyphosphino-1-one]-2-(4-chloro-3-hydroxyphenyl)propyl}(tert-butoxy)carboxamide (82i) (0.9 g, 1.82 mmol) was dissolved in 4 mL of acetonitrile. 4-(Bromomethyl)-pyridine hydrogen bromide (2.73 mmol, 0.69 g) and cesium carbonate (5.46 mmol, 1.78 g) were added to the solution, which was then heated to 80° C. overnight. The reaction mixture was cooled to room temperature, filtered to remove the excess cesium carbonate, and diluted with ethyl acetate. The ethyl acetate layer was washed with water, brine and concentrated to dryness. The crude product was then purified by normal phase using dichloromethane and methanol to give 0.45 g of the title compound (82j).

Step 11: 2-{4-Chloro-3-(4-pyridylmethoxy)phenyl]-3-(hydrohydroxyphosphoryl)propylamine (82)

N-{3-[(1,1-Diethoxyethyl)ethoxyphosphino-1-one]-2-(4-chloro-3-hydroxyphenyl)propyl}(tert-butoxy)carboxamide (82j) was treated with 3 mL of a 1:1 mixture of 6N HCl and acetonitrile/water and heated to 80° C. for 2 hours to remove the protecting groups. The reaction was cooled to room temperature, neutralized with sodium hydroxide solution, and purified by reverse phase HPLC to give 50 mg of the title compound (82). $^1$H-NMR (400 MHz, CD$_3$OD): δ 8.66-8.67 d, J=4 Hz, 2H), 7.78-7.80 (d, J=8 Hz, 2H), 7.51 (s, 0.5H), 7.42-7.44 (d, J=8 Hz, 2H), 7.13 (s, 1H), 6.96-6.97 (d, J=4 Hz, 1H), 6.24 (s, 2H), 3.29-3.33 (m, 2H), 3.11-3.14 (m, 1H), 1.89-1.94 (m, 2H). MS (ESI) m/z 341.12 (M+H)$^+$.

Example 83

GABA$_B$ Receptor Binding Assay

An assay using rat cerebral cortex membranes was used to determine the affinity of GABA$_B$ receptor ligands for the GABA$_B$ receptor.

An assay buffer of 50 mM Tris pH 7.4 was prepared with 100 μM of isoguvacine, to block GABA$_A$ interactions. The assay buffer with isoguvacine was used for dilution of membranes, compounds, and radiolabel.

Rat cerebral cortex membranes were diluted in assay buffer at 1 mg/mL and aliquoted into a 96-well plate at 900 μL/well. Buffer or test compound were added at 20-times final concentration in the buffer at 50 μL/well. Membranes and test compounds or buffer were incubated for 10 min. at room temperature. Radiolableled [S—(R*,R*)]-[3-[[1-(3,4-dichlorophenyl)ethyl]amino]-2-hydroxypropyl](cyclohexylmethyl) phosphinic acid (CGP54626) was then added at 50 μL/well in the buffer at 1-10 nM concentration in 50 μl. The mixture was incubated for 15 min. at room temperature. The assay mixture was filtered using Brandell filtration apparatus and GFB filters, washed twice with 3 mL of 4° C., 50 mM Tris pH 7.4, buffer without isoguvacine. The filters were then dried at room temperature and the dried filters punched out and placed in individual vials. Three (3) mL of scintillation fluid was added to each vial and the radiolabel counted on the scintillation counter. The inverse amount of radiolabel was indicative of binding of a test compound to the GABA$_B$ receptor.

Example 84 cAMP Assay for Determining GABA$_B$ Receptor Agonist Activity

The following procedure was used to determine the level of intracellular cAMP. Recombinant HEK cells expressing the GABA$_B$ R1a2 receptor were used in the experiments. cAMP levels were measured using a cAMP XS$^+$ HitHunter™ Chemiluminescence Assay Kit (90-0075-02, GE Healthcare Biosciences Corp.). Cells were seeded overnight at 5,000 cells per well, in black, clear bottom 96-well plates. The following morning, cells were washed twice with 100 μL PBS per well. Forskolin was weighed out and dissolved in DMSO to a final concentration 100 mM. One-hundred (100) μM forskolin solutions were prepared in PBS with and without test compound at 1-times final concentration. Thirty (30) μL of the test solutions were added to the wells and incubated for 1 h at room temperature. The cAMP concentration was determined according to the protocol described in the cAMP assay kit, maintaining the plate at room temperature and in the dark. Two hours after the final kit reagent was added, the plate bottom was covered with black tape, and the plate read using a 1450 MicroBeta Trilux microplate scintillation and luminescence counter (PerkinElmer, Waltham, Mass.). Each well was read for 6 seconds. The untransformed data was then analyzed.

Example 85

Ca$^{2+}$ Assay for Determining GABA$_B$ Receptor Agonist Activity

The following procedure was used to determine the GABA$_B$ receptor agonist activity of a compound as reflected by activation of Ca$^{2+}$ signaling. HEK TREx cells expressing GABA$_B$R1a2 under tetracycline induction control, and Gqi chimeric protein (expressed constitutively), allowing GABA$_B$R coupling through the Ca$^{2+}$ signaling pathway were used in the experiments.

Cells were seeded in media containing tetracycline overnight at 100,000 cells/well, in black, clear-bottom, 96-well plates. The following morning, cells were washed twice with 100 μL HBSS buffer per well. Fluorescent Ca$^{2+}$ indicator dye was prepared using the materials and procedure described in the F362056 Fluo-4 NW Calcium Assay Kit (Invitrogen, Carlsbad, Calif.). Ten (10) mL of kit buffer and 100 μl of kit Probenecid were added to individual kit dye vials, and rolled back and forth several times to dissolve the dye. Cells were then loaded into the dye solution at 50 μL per well. The cells and dye were incubated for 30 min at 37° C., and then incubated for an additional 30 min at room temperature in the dark. Test compounds are dissolved in HBSS buffer at twice final concentration. Duplicate wells were used for each unique condition. Solution containing the test compound was added to the wells using a FLEXStation II (Molecular Devices, Sunnyvale, Calif.). Using the instrument in kinetic mode in which each well was read every 2 sec over a total collection time of 50 sec fluorescence was measured using an excitation wavelength 494 nm and a detection wavelength of 516 nm. A normalized fluorescence value for each well was calculated using the following procedure. The difference in fluorescence at 35 sec (usually representing maximal response) and at 15 sec (a time point prior to addition of test compounds) was calculated, divided by the fluorescence at 15 sec, and the result multiplied by 100. The final value represented the percent increase in fluorescence relative to the fluorescence at 15 sec. Data was analyzed using standard procedures.

Example 86

Electrophysiology Assay for Determining GABA$_B$ Receptor Agonist Activity

GABA$_B$ receptor agonist activity was determined using an electrophysiological method employing inward rectification of G-protein-coupled K$^+$ channels (GIRK1/4) in *Xenopus laevis* oocytes expressing the GABA$_B$ receptor (GABA$_B$R 1a/2).

Expression of GABA$_B$R/GIRK in *Xenopus laevis* oocytes was accomplished using the following procedure. Oocytes were removed from mature, anesthetized, HCG-injected female *Xenopus laevis* and washed in 0 mM CaCl$_2$ ND96 buffer (90 mM NaCl, 10 mM hemi-Na HEPES, 2 mM KCl, 1 mM MgCl$_2$). Oocytes were then shaken in collagenase solution for 1 h at room temperature. The oocytes were then washed thoroughly and sorted according to desired maturity and morphology. Selected oocytes were injected with a mixture of cRNA encoding for hGBBR1a+2 and rGIRK1+4. Final volume ratios of the GIRK1/4 and GBBR1a/2 RNA were about 1:10 and about 1:5, respectively. Forty-six (46) nL of the RNA mixture was injected into each oocyte. Uninjected oocytes were used as controls. Oocytes were incubated at 16-18° C. in 0.9 mM CaCl$_2$ ND96 buffer pH 7.4 (90 mM NaCl$_2$, 10 mM hemi-Na HEPES, 2 mM KCl, 1 mM MgCl$_2$, 0.9 mM CaCl$_2$) containing Pen/Strep (SV30010, Hyclone) for 1-2 days.

Electrophysiology measurements were made using a 2-electrode voltage clamp recording instrument (GeneClamp 500B amplifier/Clampex8.2/Clampfit8, Axon Instruments, Union City, Calif.) and standard analysis software (Chart4, ADInstruments, Mountain View, Calif.).

Dose response curves of test compound GABA$_B$ agonist activity and pEC$_{50}$ values were determined as follows. Test compounds were weighed and dissolved in an appropriate solvent. Serial dilution curves were made in 100 mM KCl ND96 buffer (90 mM NaCl$_2$, 10 mM hemi-Na HEPES, 1 mM MgCl$_2$, 1.8 mM CaCl$_2$, 100 mM KCl). The highest concentration of a test compound was typically 1 mM, with 1:5 or 1:4 serial dilutions to provide a 5- or 6-point curve over a concentration range to 0.01 µM. Currents were measured with oocytes clamped at a holding potential between −15 mV to −40 mV, depending on the health and/or the receptor expression level of individual oocytes. Baseline currents at this holding potential were allowed to reach a steady state before compound addition and recording.

Prior to and between each series of test compound dilutions, a sub-maximal concentration of a known agonist (4 µM GABA) was used as a control. Currents were measured by manually adding 650 µL of diluted test compound to a clamped oocyte in the holding chamber. Currents were allowed to saturate before activating the system vacuum/bath perfusion to wash away the test compound. If a test compound appeared to have agonist activity, it was also tested in the presence of a known GABA$_B$R inhibitor, (2S)-3-[[(1S)-1-(3, 4-dichlorophenyl)ethyl]amino-2-hydroxypropyl](phenylmethyl)phosphinic acid (CGP55845). Serial dilutions of the test compound were made in 100 mM KCl ND96 buffer containing 10 µM CGP55845. As another control, the test compound was also tested in uninjected oocytes at a single concentration of 100 µM.

For analysis of the dose response curves, currents generated from each test dilution were calculated as a percentage of the current generated by the control compound. The curve traces were then graphed using GraphPad (Prism, San Diego, Calif.) and pEC$_{50}$ values generated.

Example 87

Assay for Determining GABA$_B$ Receptor Antagonist Activity

Any of the in vitro assays used to determine GABA$_B$ receptor agonist activity according to Examples 83-86 can be adapted to determine GABA$_B$ receptor antagonist activity. For example, adapting the electrophysiology assay described in Example 86, serial dilutions of a test compound were made in 100 mM KCl ND96 buffer containing GABA, a known GABA$_B$R agonist, and the ability of the test compound to attenuate the activity of GABA measured.

GABA$_B$ receptor antagonist activity can also be assessed using a method described by Ong et al., *Eur J Pharmacology* 1999, 374, 351-4. Rat neocortical slices are prepared from halothane anaesthetized rats (250-350 g), which are decapitated. The brains are rapidly dissected and immersed for 30 min in ice-cold oxygenated Krebs solution gassed with 95% O$_2$:5% CO$_2$ (pH 7.4) of the following composition: 118 mM NaCl, 2.1 mM KCl, 1.2 mM KH$_2$PO$_4$, 2.5 mM CaCl$_2$, 25 mM NaHCO$_3$, 11 mM glucose, and 1.3 mM MgSO$_4$. Cerebral cortical slices (400 µM thick) are prepared by cutting coronal sections and a radial wedge is cut from each side of the dorsal mid-line to yield slices of cingulate cortex and corpus callosum 2-3 mm wide. The slices are subsequently equilibrated in gassed Krebs solution at room temperature (20-30° C.) for 60 min prior to experimentation.

Slices from the neocortex are superfused with gassed Mg$^{2+}$-free Krebs medium at 25° C. DC potentials between the cingulate cortex and corpus callosum are monitored. The neocortical slices develop spontaneous paroxysmal discharges after equilibration in Mg$^{2+}$-free Krebs medium for 15 min. The GABA$_B$ receptor agonist baclofen, added to the superfusing medium, is applied to the cortical side of the tissue for 2 min and the preparation is allowed 30 min recovery between drug applications. The antagonist is first superfused for 2 min and then added together with the agonist.

Results are quantified by counting the number of spontaneous discharges in 10 min epochs, in the absence and presence of test compounds, and the values expressed as a percentage depression of the average control discharge rate during the 10 min immediately before the addition of drugs. Concentration-response curves for the agonist are constructed, in the absence and presence of the antagonist. Antagonist activity is indicated by the ability to prevent the baclofen-induced suppression of spontaneous discharges.

Example 88

Bioavailability Following Oral Administration of Prodrugs of GABA$_B$ Ligands and Prodrugs Thereof to Rats Rats were obtained commercially and were pre-cannulated in the jugular vein. Animals were conscious at the time of the experiment. All animals were fasted overnight and until 4 hours post-dosing of a compound.

Rat blood samples (0.3 mL/sample) were collected from all animals prior to dosing and at different time-points up to 24 h post-dose into tubes containing EDTA. Two aliquots (100 µL each) were quenched with 300 µL methanol and stored at −20° C. prior to analysis.

To prepare analysis standards, 90 µL of rat blood was quenched with 300 µL methanol followed by 10 µL of spiking standard and/or 20 µL of internal standard. The sample tubes were vortexed for at least 2 min and then centrifuged at 3400 rpm for 20 min. The supernatant was then transferred to an injection vial or plate for analysis by LC-MS-MS.

To prepare samples for analysis, 20 µL of internal standard was added to each quenched sample tube. The sample tubes were vortexed for at least 2 min and then centrifuged at 3400 rpm for 20 min. The supernatant was then transferred to an injection vial or plate for analysis by LC-MS-MS.

LC/MS/MS analysis was performed using an API 2000 or API 4000 mass spectrometer equipped with a Shimadzu and or Agilent HPLC system are used for determination concentration of compounds in rat blood. A Varian Polaris C18, 3μ 50×4.6 mm column was used. 0.1% Formic acid in water and acetonitrile were applied as the mobile phase. Runs were 4.0 min. MS detection was done in positive in mode The ion monitored for (67) was m/z 339.98/305.00; for (3R)-3-{4-chloro-3-{5-methoxycarbonyl)(2-thienyl)}phenyl}-4-{[(2-methylpropanoyloxy)ethoxy]carbonylamino}butanoic acid was m/z 512.31/380.10; for 5-(5-{(1R)-1-[2S-amino-4-carbamoylbutanoylamino)methyl]-2-carboxyethyl}-2-chlorophenyl)thiophene-2-carboxylic acid hydrochloride was m/z 468.10/433.08; for (68) was m/z 321.06/93.00; for (3R)-4-(2S)-2-aminopropanoylamino)-3-[4-chloro-3-(4-pyridylmethoxy)phenyl]butanoic acid hydrochloride was m/z 392.02/93.20; and for (3R)-4-((2S)-2-amino-3-methylbutanoylamino)-3-[4-chloro-3-(4-pyridylmethoxy)phenyl]butanoic acid, hydrochloride was m/z 420.15/320.90. L-4-Chlorophenylalanine was used as an internal standard at m/z 200.00/154.00.

Non-compartmental analysis was performed using WinNonlin software (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

The oral bioavailability (F %) of a compound was determined by comparing the area under the compound concentration vs time curve (AUC) following oral administration of a prodrug of a $GABA_B$ ligand with the AUC of the compound concentration vs time curve following intravenous administration of the $GABA_B$ ligand on a dose normalized basis. Compounds (3R)-3-{4-chloro-3-{5-methoxycarbonyl)(2-thienyl)}phenyl}-4-{[(2-methylpropanoyloxy)ethoxy]carbonylamino}butanoic acid, 5-(5-{(1R)-14-2S-amino-4-carbamoylbutanoylamino)methyl]-2-carboxyethyl}-2-chlorophenyl)thiophene-2-carboxylic acid hydrochloride, (68), (3R)-4-(2S)-2-aminopropanoylamino)-3-[4-chloro-3-(4-pyridylmethoxy)phenyl]butanoic acid hydrochloride was m/z 392.02/93.20, and (3R)-4-(2S)-2-amino-3-methylbutanoylamino)-3-[4-chloro-3-(4-pyridylmethoxy)phenyl]butanoic acid, hydrochloride exhibited an oral bioavailability of greater than about 10%.

Example 89

Hypothermia Model of $GABA_B$ Agonist Activity

The method described by Quéva et al., *Br. J. Pharmacology* 2003, 140, 315-322, can be used to assess the in vivo $GABA_B$ agonist activity of a compound.

Age matched, C57B16/129Sv F1 hybrid $GABA_{B(1)}^{+/+}$, $GABA_{B(1)}^{+/-}$ and $GABA_{B(1)}^{-/-}$ mice are used. The mice are maintained in Perspex cages at an ambient temperature between 21° C. and 23° C. and a relative humidity between 52% and 56%. A thermosensitive chip is implated in the interscapular region under brief isoflurane anesthesia, and the animals are allowed to recover for at least 1 day. The animals have free access to food and water, except for during the experiment. On the experimental day, the mice are place in individual cages between 0900 and 1000, and the ambient temperature is 20.5±1.0° C. After 30 min, three basal temperature recordings are made using a transponder communicating with a computer for data acquisition. In preliminary experiments, the system is evaluated in mice by measuring the interscapular temperature and rectal temperature at the same time. The thermosensitive chips are calibrated by the producer in the range from 32° C. to 43° C., and they are calibrated against a thermistor in a water bath before implantation. The resolution of the chips is 0.1° C. Test compound or control are injected subcutaneously at an appropriate dose after the last measurement. The doses are chosen based on pilot experiments in which they are found to produce a significant hypothermia. Measurements are then made at regular intervals. Behavioral scoring is made at each time point, and the behavioral data is presented as the maximal effect. The following definitions are used for behavioral effects: (1) no effect; (2) exophthalmus, slight motor impairment; (2) more pronounced motor impairment; (3) immobile with intact righting reflex; (4) no righting reflex, disturbed respiration, occasional seizures, detectable but very low muscle tonus; and (5) paralysed, no muscle tonus, moribund (killed for ethical reasons). The behavior is scored by the same experienced observer in all experiments. The doses used are obtained from pilot dose-response experiments. The data obtained is analyzed using appropriate statistical methods.

In this method, baclofen (9.6 mg/kg), a $GABA_B$ agonist, produces a marked hypothermia in $GABA_{B(1)}^{+/-}$ and $GABA_{B(1)}^{+/+}$ but not $GABA_{B(1)}^{-/-}$ mice, which reaches its minimum at 60-80 min after administration, and subsequently returns towards baseline levels. The minimum temperature is about 3° C. less than the temperature of $GABA_{B(1)}^{-/-}$ mice. Behavioral effects are also observed following the administration of baclofen to $GABA_{B(1)}^{+/-}$ and $GABA_{B(1)}^{+/+}$ but not $GABA_{B(1)}^{-/-}$ mice.

Example 90

Spinal Nerve Ligation Pain Model

The efficacy of compounds provided by the present disclosure for treating pain was evaluated using the rat spinal nerve ligation model as described in Chaplan et al., *J Neurosci Methods* 1994, 53, 55-63; Dixon, *Ann Rev Pharmacol Toxicol* 1980, 20, 441-462; and Kim et al., *Pain* 1992, 50, 355-363.

Rats weighed between 130 and 190 g on the day of surgery.

Rats were anesthetized under 2.5% isoflurane, and the mid-lower back area shaved. The skin was sterilized with 70% ethanol, followed by a Providone Iodine swab, and finally wiped with 70% ethanol. The left paraspinal muscle was separated from the spinous processes at the L4-S2 levels using a sterile #10 surgical blade. The L6 transverse process was carefully removed with extra fine rongeurs to expose the L4 and L5 spinal nerves. The L5 nerve was separated from L4 using a glass rod and the nerve tightly ligated with a double knot using 4-0 silk. A glass rod was then gently inserted under the hip bone (being careful not to grab L4/L5) to expose L6. L6 was also tightly ligated with 4-0 silk. After confirming complete hemostasis, the muscle was sutured in layers with two 4-0 silk sutures. Animals were administered Rimadyl (5-10 mg/kg s.c.) to alleviate post-operative pain and 200 μL lactated Ringer's solution. The rats were then allowed to recover in their cages, which contained fresh soft white bedding.

Pre-surgery allodynia testing was done 1-2 days prior to surgery using an up-down method.

Behavioral testing was performed during the day portion of the circadian cycle only (7:00-19:00). Rats were placed in a leucite box on top of a metal mesh stand, which allowed full access to the paws. Behavioral accommodation was allowed for approximately 15 min until cage exploration and major grooming activities ceased. The area tested was the front plantar region of the left hind paw. The paw was touched with 1 of a series of 8 von Frey hairs with logarithmically incremental stiffness (0.4, 1, 1.2, 2, 4, 6, 8, 15 g). The von Frey hair was presented perpendicular to the plantar surface with sufficient force to cause slight buckling against the paw, and held for approximately 6-8 s. Stimuli were presented at intervals of several seconds, allowing for apparent resolution of any behavioral responses to previous stimuli. A positive response was noted if the paw was sharply withdrawn. Flinching immediately upon removal of the hair was also considered a positive response. Ambulation was considered an ambiguous response and in such cases, the stimulus was repeated. Based on observations on normal, un-operated rats, the cut-off of 15 g hair (~10% of the body weight) was selected as the upper limit for testing as stiffer hairs tended to raise the entire limb rather than to buckle.

The 50% withdrawal threshold was determined using the up-down method. In this paradigm, testing was initiated with the 2 g hair, in the middle of the series. Stimuli were always presented in a consecutive fashion, whether ascending or descending. In the absence of a paw withdrawal response to the initially selected hair, a stronger stimulus is presented. In the event of paw withdrawal, the next weaker stimulus was chosen. According to Dixon, optimal threshold calculation by this method requires 6 responses in the immediate vicinity of the 50% threshold. Since the threshold is not known, strings of similar responses may be generated as the threshold is approached from either direction. Accordingly, although all responses are noted, counting of the critical 6 data points did not begin until the response threshold is first crossed at which time the 2 responses straddling the threshold are retrospectively designated as the first 2 responses of the series of 6. Four additional responses to the continued presentation of stimuli that are varied sequentially up or down, based on the rat's response, constitute the remainder of the series. Thus, the number of actual responses collected using this paradigm can vary from a minimum of 4 (in the case of paw withdrawal sequentially to the 4 hairs in the descending range: 2-0.4 g: threshold lies below the range of actual stimuli) to a maximum of 9 (in the case of the first withdrawal occurring on the fifth ascending stimulus presentation at 15 g followed by elicitation of 4 additional responses, assuming that withdrawal continued to occur at or below 15 g). In cases in which continuous positive or negative responses were observed to the exhaustion of the stimulus set, values of 15 g and 0.25 g were assigned, respectively. The resulting pattern of positive and negative responses were tabulated using the convention "x"=withdrawal; "o"=no withdrawal.

Testing of compound was performed 7-9 days post-surgery with the pre-dose baseline occurring on the same morning prior to dosing. After testing for allodynia, animals were euthanized using $CO_2$.

The $EC_{50}$ (μmol/kg) for efficacy in the spinal nerve ligation model of pain 1 hour following administration of baclofen, (3R)-4-amino-3-[4-chloro-3-(4-pyridylmethoxy)phenyl]butanoic acid hydrochloride (68), 4-{5-[(1R)-2-amino-1-(carboxymethyl)ethyl]-2-chlorophenyl}thiophene-2-carboxylic acid hydrochloride (27), or 5-{5-[(1R)-2-amino-1-(carboxymethyl)ethyl]-2-chlorophenyl}thiophene-3-carboxylic acid hydrochloride, to rats was less than 100 μmol/kg. The results demonstrate that the tested $GABA_B$ receptor ligands pass through the blood brain barrier and show efficacy in treating pain.

Example 91

Sedative Effects of $GABA_B$ Ligands

Male Sprague-Dawley rats weighing 100-200 g were used to evaluate the sedative effects of compounds provided by the present disclosure. The animals were acclimated to the housing facility for a minimum of 3 days prior to the study.

On the day of the study, test compounds were formulated in appropriate buffers. Animals were placed in clean translucent boxes. The animals were dosed either IP or PO. For PO dosing, the rats were fasted for at least 15 h prior to dosing, and food was provided immediately after dosing. The IP and PO dos volumes were either 2 mL/kg or 4 mL/kg depending on the solubility of the test compound in the buffer.

Following dosing, the rats were observed and the sedation score recorded at 1, 2, and 4 hours post dosing using the following scale: 100% (Score 5) asleep, eyes fully closed, body relaxed; 80% (Score 4) heavy sedation, eyes mostly closed, loss of righting reflex; 60% (Score 3) moderate sedation, head mostly or completely down, eyes partly closed, flattened posture, no spontaneous movement; 40% (Score 2) mild sedation, eyes partly closed, head somewhat down, impaired locomotion including abnormal posture, use of only some limbs, dragging and stumbling; 20% (Score 1) awake, inactive, eyes fully open, head up, little to no locomotion, rearing or grooming, normal posture; 0% (Score 0) awake, active, engaged in locomotion, rearing, head movements, or grooming (Chuck et al., *Life Sciences* 2006, 79, 154-164). At each time point the rat being studied was placed in a clean translucent box and settled for 1-2 min prior to scoring. The animals were not touched during scoring except when tested for the righting reflex.

Data was presented as percent sedation vs. time according to treatment group.

The $EC_{50}$ (μmol/kg) for sedation 1 hour following administration of baclofen, (3R)-4-amino-3-[4-chloro-3-(4-pyridylmethoxy)phenyl]butanoic acid hydrochloride (68), 4-{5-[(1R)-2-amino-1-(carboxymethyl)ethyl]-2-chlorophenyl}thiophene-2-carboxylic acid hydrochloride (27), 3-{5-[(1R)-2-amino-1-(carboxymethyl)ethyl]-2-chlorophenyl}-4-chlorobenzoic acid hydrochloride (46), 5-{5-[(1R)-2-amino-1-(carboxymethyl)ethyl]-2-chlorophenyl}thiophene-2-carboxylic acid (67), or 5-{5-[(1R)-2-amino-1-(carboxymethyl)ethyl]-2-chlorophenyl}thiophene-3-carboxylic acid hydrochloride to rats was less than 100 μmol/kg. The results demonstrate that the tested $GABA_B$ receptor ligands pass through the blood-brain-barrier and interact with $GABA_B$ receptors in the brain.

Example 92

Use of Clinical Trials to Assess the Efficacy of $GABA_B$ Ligands for Maintaining Abstinence from Alcohol Alcohol dependence (DSM-IV 303.90) is defined with respect to substance dependence (pages 192-198). For example, the efficacy of a $GABA_B$ receptor ligand of Formula (I) for treating alcoholism can be assessed using a randomized, double-blind, double-dummy, placebo-controlled trial. Patients aged 18 to 65 years meeting DSM IV criteria for alcohol dependence and having a history of alcohol dependence for at least 12 months are selected for the study. Patients are required to have undergone detoxification and have had five or more days of abstinence from alcohol before commencing treatment. Patients receive an appropriate dose of a compound of Formula (I) or placebo.

Primary and secondary outcome measures include commonly accepted subjective measures (based mainly on self-reported data) of continuous abstinence rate (CAR, i.e., the percentage of pateints completely abstinent throughout the entire treatment and/or follow-up period), cumulative abstinence duration (CAD), the proportion of the total time that CAD represented (CADP, i.e. CAD as a proportion of the total treatment duration) and/or time to first drink (TFD). Surrogate biologcial markers of relapse such as γ-glutamyl transferase, carbohydrate-deficient transferrin, AST and ALT levels, and mean corpuscular volume can also be determined. Efficacy of $GABA_B$ receptor ligands of Formula (I) in the maintenance of abstinence in patients with alcohol dependence is reflected in an increased CAR, CADP, and TFD compared to patients recieving placebo.

Example 93

Use of Animal Models to Assess the Efficacy of $GABA_B$ Receptor Ligands for Treating Alcohol Withdrawal Therapeutic efficacy of $GABA_B$ receptor ligands of Formula (I) for maintaining abstinence in patients with alcohol dependence can be assessed using animal models (Scott et al., *CNS Drugs* 2005, 19(5), 445-464; and Mason et al., *J Psychiatric Res* 2006, 40, 383-393). Withdrawal Seizure-Prone (WSP) and Withdrawal Seizure-Resistant (WSR) mice are used to assess the efficacy of a $GABA_B$ receptor ligand of Formula (I) for treating alcohol withdrawal. Mice are made dependent on ethanol via 72 h of chronic ethanol vapor inhalation. On day 1, mice are weighed, injected with a loading dose of ethanol and pyrazole HCl (Pyr), an alcohol dehydrogenase inhibitor, and placed into ethanol vapor chambers. Controls are placed into air chambers and receive Pyr only. At 24 and 48 h, Pyr boosters are administered to both the experimental and control groups. Blood ethanol concentrations (BECs) for ethanol groups are measured and the ethanol vapor concentrations adjusted to equate ethanol exposure between lines. Mean BECs are maintained between approximately 1.0-2.0 mg/mL, depending upon the effects of the test compound being studied. After 72 h, all mice are removed from the chanbers to initiate withdrawal, and ethanol treated mice have blood samples drawn for BEC determinations. Ethanol concentration can be determined by gas chromatography.

Following removal from the ethanol or air chambers, mice are scored hourly for handling-induced convulsion (HIC). Scoring is initiated 1 h after removal from ethanol and hourly over the next 12-15 h and again at 24 h. If animals do not return to baseline HIC levels by 25 h, an additional score is obtained at 48 h. The scale described by Crabbe et al. infra is used (0—NO convulsion after a gently 180° spin; 1—only facial grimace after gentle 180° spin; 2—tonic convulsion elicited by gently 180° spin; 3—tonic-clonic convulsion after 180° spin; 4—tonic convulsion when lifted by tail, no spin; 5—tonic-clonic convulsion when lifted by tail, no spin; 6—severe tonic-clonic convulsion when lifted by tail, no spin; and 7—severe tonic-clonic convulsion elicited before lifting by the tail). The area under the curve is calculated and used to quantitatively evaluate withdrawal severity. An additional index of withdrawal severity is the peak HIC score, calculated by identifying the highest HIC for each individual mouse and averaging this score with the two adjacent scores. Data are analyzed by appropriate statistical methods.

Example 94

Clinical Trial for Assessing Efficacy in Treating Asthma

Adult subjects (nonsmokers) with stable mild-to-moderate asthma are enrolled (Van Schoor and Pauwels, *Eur Respir J* 2002, 19, 997-1002). A randomized, double-blind, placebo-controlled, two-period crossover design is used. On screening day 1, patients undergo a methacholine challenge (<8 mg/mL). The baseline forced expiratory volume in one second (FEV1) prior to each subsequent challenge must be within 15% of the screening baseline FEV1 obtained at the first visit. A neurokinin challenge ($1\times10^{-6}$ mol/mL) on screening day 2 is performed 24-72 h later. Study-period one commences within 10 days after visit two. First, a methacholine and a neurokinin-A (NKA) challenge is performed on days 1 and 0, respectively. At visit four, test compound is administered at an appropriate dose and for an appropriate period of time. On the last 2 days of the treatment period, methacholine and NKA challenges are repeated. Following treatment-period one, there is a washout period of about 5 weeks, following which the patients crossed over to another medication or placebo in study period two, which is identical to period one. Pulmonary function tests are performed using a spirometer. The metacholine challenge is performed by inhaling doubling concentrations of methacholine until the FEV1 falls by more than 20% of the postdiluent baseline FEV1 of that day. NKA challenge is performed by inhaling increasing concentrations of NKA. The effect of a treatment on airway responsiveness is determined using appropriate statistical methods.

Example 95

Methods for Assessing Therapeutic Efficacy of $GABA_B$ Receptor Ligands for Treating Cough Animal Model Male guinea pigs are individually placed into a sealed perspex exposure chamber and allowed to acclimatize prior to administration of tussive stimuli or test compound by aerosol. Cough responses are induced by exposure to an aerosol of either citric acid (20%, 10 min) or capsaicin (15 μM, 4 min) at flow rates of 2 L/min and 3 L/min, respectively. An observer continuously monitors the animals, and the number of coughs counted over a 15 min period from commencement of the aerosol administration of the tussive stimuli. Guinea pigs are then randomly allocated to receive either test compound or control, and exposure to the tussive stimuli repeated and the number of coughs recorded.

Human Model

Healthy, nonsmoking subjects who do not experience symptoms of respiratory tract infection or seasonal allergy for at least 4 weeks prior to evaluation and who demonstrate normal pulmonary function are enrolled. Subjects inhale single breaths of capsaicin solution (ranging from 0.98 μmol/L to 1,000 μmol/L) from a compressed-air driven nebulizer controlled by a dosimeter. Single breaths of capsaicin solution are given in ascending order, with inhalations of saline solution randomly interspersed to increase challenge blindness, until the concentration inducing five or more coughs is reached. Breaths are delivered at 1-min intervals.

The number of coughs in response to each concentration of capsaicin during the 1-min period immediately after each inhalation is recorded by a blinded observer. Subjects are unaware that the end point of the study is the number of coughs induced. After undergoing baseline capsaicin cough challenge, subjects are randomly assigned, in a double-blind manner, and administered a test compound at an appropriate dose or placebo, after which the cough challenge is repeated. A significant response can be defined as a fourfold or greater increment in the capsaicin concentration required to elicit five or more coughs.

Example 96

Animal Model for Assessing Therapeutic Efficacy of $GABA_B$ Receptor Ligands for Treating Emesis

*S. murinus* (house musk shrew) has been used to investigate mechanisms in the control of emesis.

Female *S. murinus* weighing between 30 and 45 g are used in the studies. On the day of an experiment, the animals are transferred to clear Perspex observation chambers (21×14×13 cm) where they are allowed 30 min to adapt before being presented with about 10 g of cat food. A $GABA_B$ receptor agonist or vehicle are administered in an appropriate amount and regimen. Emetic challenges are nicotine (5 mg·kg, s.c.), copper sulfate pentahydrate (120 mg/kg, intragstric), and linear reciprocating motion (4 cm horizontal displacement, delivered at 1 Hz). A trained observer that is blind to the treatment groups then records animal behavior for 30 min in experiments involving nicotine and copper sulphate, and for 5 min for those experiments involving motion. Episodes of emesis are characterized by rhythmic abdominal contractions that are either associated with the oral expulsion of solid or liquid material from the gastrointestinal tract (i.e. vomiting), or not associated with the passage of material (i.e. retching movements). Two consecutive episodes of retching and/or vomiting are considered separate when an animal changes its location in the observation chamber, or when the interval between retches and/or vomits exceeds 2 s. Data is analyzed using appropriate statistical methods. An antiemetic effect manifests as a reduced number of retching and/or vomiting episodes. For example, using this model, the $GABA_B$ receptor agonist, baclofen, reduces the number of emetic episodes from about 23 to about 13 when administered subcutaneously 30 minutes prior to challenge at doses of 1, 3, and 10 mg/kg (Chan et al., *Eur J Pharmacology* 2007, 559, 196-201).

Example 97

Animal Model for Assessing Therapeutic Efficacy of $GABA_B$ Receptor Ligands for Treating Spasticity The mutant spastic mouse is a homozygous mouse that carries an autosomal recessive trait of genetic spasticity characterized by a deficit of glycine receptors throughout the central nervous system (Chai et al., *Proc. Soc. Exptl. Biol. Med.* 1962, 109, 491). The mouse is normal at birth and subsequently develops a coarse tremor, abnormal gait, skeletal muscle rigidity, and abnormal righting reflexes at two to three weeks of age. Assessment of spasticity in the mutant spastic mouse can be performed using electrophysiological measurements or by measuring the righting reflex (any righting reflex over one second is considered abnormal), tremor (holding mice by their tails and subjectively rating tremor), and flexibility.

Models of acute spasticity include the acute decerebrate rat, the acute or chronic spinally transected rat, and the chronically spinal cord-lesioned rat.

The Irwin Test is used to detect physiological, behavioral, and toxic effects of a test substance, and indicates a range of doses that can be used for later experiments. Typically, rats (three per group) are administered the test substance and are then observed in comparison with a control group given vehicle. Behavioral modifications, symptoms of neurotoxicity, pupil diameter, and rectal temperature are recorded according to a standardized observation grid derived from that of Irwin. The grid contains the following items: mortality, sedation, excitation, aggressiveness, Straub tail; writhes, convulsions, tremor, exopthalmos, salivation, lacrimation, piloerection, defecation, fear, traction, reactivity to touch, loss of righting reflexes, sleep, motor incoordination, muscle tone, stereotypes, head-weaving, catalepsy, grasping, ptosis, respiration, corneal reflex, analgesia, abnormal gait, forepaw treading, loss of balance, head twitches, rectal temperature, and pupil diameter. Observations are performed at 15, 30, 60, 120, and 180 minutes following administration of a test compound, and also 24 hours later.

In the Rotarod Test rats or mice are placed on a rod rotating at a speed of eight turns per minute. The number of animals that drop from the rod before three minutes is counted and the drop-off times are recorded (maximum: 180 sec). Diazepam, a benzodiazepine, can be administered at 8 mg/kg, i.p., as a reference substance.

Example 98

Animal Models to Assess the Efficacy of $GABA_B$ Receptor Ligands for Treating Migraine Therapeutic activity of a $GABA_B$ receptor ligand of Formula (I) may be determined in various animal models of neuropathic pain or in clinically relevant studies of different types of neuropathic pain. Animal models for neuropathic pain are known in the art and include animal models that determine analgesic activity or compounds that act on the CNS to reduce the phenomenon of central sensitization that results in pain from nonpainful or normoxious stimuli. Other animal models that are known in the art, such as hot plate tests, model acute pain and are useful for determining analgesic properties of compounds that are effective when painful or noxious stimuli are present. The progression of migraines is believed to be similar to the progression of epilepsy (because an episodic phenomenon underlies the initiation of the epileptic episode) and, as such, it is believed that epilepsy animal models may be useful in determining efficacy in treating migraine.

The following test can be used to evaluate the analgesic activity of a $GABA_B$ receptor ligand of Formula (I). Test compound is administered orally to mice. Morphine is administered as a reference substance at 64 mg/kg to mice under the same experimental conditions. A vehicle is administered to mice as a control substance under the same experimental conditions. Test compound, morphine, or vehicle is administered to the mice in a blind study. Sixty minutes after the test compound, morphine, or vehicle is administered, the mice are placed onto a hot metal plate maintained at 54° C. and surrounded by a Plexiglass cylinder. The time taken for the mice to lick their feet is an index of analgesic activity. Effective analgesics increase the latency or amount of time to licking. Latency to the first foot lick is measured, up to a maximum time of 30 sec to prevent tissue damage to the mice.

Hyperreflexia and Flexor Reflex Tests

Assessment of hyperreflexia, pain, and muscle tone in chronic spinally transected rats is performed using male albino Holtzman-derived rats weighing 270-530 gm. The rats are housed independently and have continuous access to food and water throughout the experiments. Animals are anesthetized. Rats are placed in a stereotaxic frame and anesthesia is maintained. An incision is made so that the paraspinal muscles can be retracted and a laminectomy performed between T6-T9. A one- to two-millimeter portion of the spinal cord is removed by evacuation and replaced with gel foam to reduce bleeding, after which the incision is closed in layers.

Following the transection, rats are placed in a room in which the ambient temperature is raised to about 27° C. to maintain body temperature. On the following morning post-surgery, the hindquarters of the spinalized rats are bathed and their urine expressed manually by applying pressure to their bladders. Experiments are conducted between 21 and 28 days after surgery. For the first two weeks post-surgery, 0.25 mL of an antibiotic is administered to the rats to prevent bladder infection. A topical antibiotic is applied to any part of the skin that shows signs of decubitus lesions. Within approximately two weeks, all animals regain bladder control and are no longer given antibiotic treatment. Assessment of hyperreflexia and flexor reflex is performed before and after treatment with test compound so that each animal serves as its own control.

Initial assessment of hyperreflexia is performed by rating the hyperreflexia response elicited with an innocuous stimulus, such as a metal probe. A metal probe is pressed against the lower abdomen at four specific sites. The response is evaluated for each of four trials using a scale ranging from zero (no response in all four trials) to four (a maximum, tonic-clonic reaction elicited in all four trials). All scores, pre- and post-treatment, are transformed to indicate the percent of hyperreflexia, pain, or muscle tone. The data is analyzed using appropriate statistical methods.

After determining hyperreflexia before drug treatment, test compound is administered to the rats.

Polysynaptic flexor-reflex responses, elicited by stimuli that activate high-threshold afferents, are recorded as EMG activity from the ipsilateral hamstring muscle. Supramaximal electric shocks are applied to the hindpaw and recording electrodes are placed in the biceps femoris semitendinosus muscle. Five sets of stimuli are made at each time point. The flexor reflex is recorded, in periods with and without test compound, every 30 min once a stable baseline response is achieved. The data at time zero represent pre-treatment control values. The responses are determined in spinalized rats by observing the flexor-reflex response before treatment and at each of 30, 60, 90, and 120 min following administration of test compound, baclofen (10 mg/kg s.c.), or vehicle (water, 12 mL/kg p.o.). Efficacy is indicated when a test compound is shown to reduce the magnitude of the flexor-reflex responses in a chronic spinalized rat at all time points with similar efficacy to baclofen, the positive control.

Cutaneous Hypersensitivity Tests

The effects of a test compound on nociceptive activation of the trigeminovascular system is determined using the migraine model described in Goadsby et al., *Brain* 2002, 125, 1392-1401. A pharmaceutical composition comprising a test compound is administered to cats. To serve as positive and negative controls, a vehicle control is administered to the cats. Efficacy is indicated for compounds that inhibit trigeminovascular activation compared to the trigeminovascular activation in the cats that receive the vehicle.

Yawning

Yawning is a behavior that has been linked to activation of dopaminergic neurotransmission. Yawning is part of a behavioral syndrome occurring in most patients during a migraine attack. Blockage of quinipirole-induced yawning in rats has been used as an animal model to study the potential antagonism of migraine symptoms.

Male Sprague Dawley rats are acclimatized for 12 days before testing and at the time of the study. The rats are housed in standard size steel cages with four animals per cage and are maintained on a 12 h light/dark schedule. Test compound or vehicle is administered 15 min before the dopamine D2 agonist quinipirole in vehicle or the vehicle alone is administered to the animals. The animals are then placed individually in a 6×6 $in^2$ plexiglass observation cages and the number of yawns is counted for the subsequent 30 min. The data is analyzed by an appropriate statistical method.

The dopamine D2 agonist quinipirole can produce an average of 13-15 yawns per 30 min while no yawning behavior is typically observed in vehicle treated animals. Compounds that inhibit quinipirole-induced yawning may be efficacious in treating migraine.

Animal Model of Dural Protein Extravasation

The following animal model can be employed to determine the ability of a $GABA_B$ receptor ligand of Formula (I) to inhibit protein extravasation, an exemplary functional assay of the neuronal mechanism of migraine.

Rats or guinea pigs are anesthetized and placed in a stereotaxic frame with the incisor bar set at −3.5 mm for rats or −4.0 mm for guinea pigs. Following a midline sagittal scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, with all coordinates referenced to bregma). Pairs of stainless steel stimulating electrodes, insulated except at the tips are lowered through the holes in both hemispheres to a depth of 9 mm (rats) or 10.5 mm (guinea pigs) from dura.

The femoral vein is exposed and a dose of a test compound is administered. About 7 min later a fluorescent dye (e.g., Evans Blue) is administered. The fluorescent dye complexes with proteins in the blood and functions as a marker for protein extravasation. Ten (10) min post-injection of the test compound, the left trigeminal ganglion is stimulated for 3 minutes at a current intensity of 1.0 mA (5 Hz, 4 msec duration) with a potentiostat/galvanostat. Fifteen minutes following stimulation, the animals are killed and exsanguinated with 20 mL of saline. The top of the skull is removed to facilitate collection of the dural membranes. Dural membrane samples are removed from both hemispheres, rinsed with water, and spread flat on microscopic slides. Once dried, the tissues are coverslipped with a 70% glycerol/water solution. A fluorescence microscope equipped with a grating monochromator and a spectrophotometer is used to quantify the amount of fluorescent dye in each sample.

The extravasation induced by the electrical stimulation of the trigeminal ganglion is an ipsilateral effect (i.e. occurs only on the side of the dura in which the trigeminal ganglion is stimulated). This allows the other (unstimulated) half of the dura to be used as a control. The ratio of the amount of extravasation in the dura from the stimulated side, over the amount of extravasation in the unstimulated side, is calculated. Control animals dosed with only saline, yield, for example, a ratio of about 2.0 in rats and about 1.8 in guinea pigs. In contrast, a compound that effectively prevents the extravasation in the dura from the stimulated side yields a ratio of about 1.0. Dose-response curves can be generated for a test compound and the dose that inhibits the extravasation by 50% ($ID_{50}$) or 100% ($ID_{100}$) can be determined.

Amygdala Kindling Model

A relationship has been reported between migraine, affective illness and epilepsy. Although the three disorders are distinct, they all are paroxysmal dysregulations of the nervous system that partially overlap in their pharmacology. The kindling model for complex-partial seizures is based on the progressive development of seizures combined with electroencephalographic (EEG) paroxysmal patterns induced by repeated initially subconvulsive electrical stimulation of limbic structures, e.g., the basolateral nucleus of the amygdala. Once established, the phenomenon persists for months. Since the amygdala-kindled seizures in animals share numerous characteristics with complex-partial seizures in humans, it is a useful animal model of complex partial seizures. An advantage of using the amygdala kindling model is that both behavioral and EEG parameters of the partial and generalized seizures can be measured. Furthermore, the amygdala kindling model is reported to be appropriate for studying diseases such as migraine, affective illness, and epilepsy which increase in severity over time and in a manner which is related to the number of symptomatic episodes.

Rats are obtained at an age of 11-12 weeks (body weight 180-200 gm). Rats are maintained separately in plastic cages at controlled temperature (23° C.) and humidity (about 50% RH) with a 12-h light cycle. The rats receive standard diet and tap water ad libitum.

For implantation of stimulation and recording electrodes, rats are anesthetized and receive stereotaxic implantation of one bipolar electrode in the right basolateral amygdala. Coordinates for electrode implantation are AP-2.2 mm, L-4.8 mm, V-8.5 mm. All coordinates are measured from bregma. Skull screws serve as the reference electrode. The electrode assembly is attached to the skull by dental acrylic cement. After a postoperative period of 2 weeks, constant current stimulations (500 μA, 1 ms, monophasic square-wave pulses, 50/sec for 1 sec) are delivered to the amygdala at intervals of 1/day until ten stage 5 seizures are elicited. The electrical susceptibility of the stimulated region (threshold for induction of afterdischarges) is recorded on the first day of the experiment (initial afterdischarge threshold) as well as after kindling acquisition (with an interval of at least 4 days after the tenth stage 5 seizure) using an ascending staircase procedure. The initial current intensity is 1 μA, and the current intensity is increased in steps of about 20% of the previous current at intervals of 1 min until an afterdischarge of at least 3 sec duration is elicited. In addition to afterdischarge threshold, the following parameters of kindled seizures are measured in fully-kindled rats after stimulation with the afterdischarge threshold current: seizure severity is classified as follows: 1—immobility, eye closure, twitching of vibrissae, sniffing, facial clonus; 2—head nodding associated with more severe facial clonus; 3—clonus of one forelimb; 4—rearing, often accompanied by bilateral forelimb clonus; and 5—rearing with loss of balance and falling accompanied by generalized clonic seizures. Seizure duration 1 is the duration of limbic (stage 1-2) and/or motor seizures (stage 3-5). Seizure duration 2 includes the time of limbic and/or motor seizures plus the adjacent time of immobility. Afterdischarge duration 1 (ADD 1) is the time of spikes in the EEG recorded from the site of stimulation with a frequency of at least 1/sec. Afterdischarge duration 2 (ADD 2) is the total time of spikes occurring in the EEG including those, which followed the ADD 1 with lower frequency and amplitude.

Test compound is administered to the prepared animals. Control experiments are performed 2-3 days before each test compound experiment. For control determinations, rats receive vehicle (e.g., saline) with the pretreatment time of the respective test compound experiment. For all test compound experiments, at least 4 days are interposed between successive administrations in order to avoid alterations in drug potency due to cumulation or tolerance. Data is analyzed using appropriate statistical methods.

In addition to recordings of anticonvulsant parameters, kindled rats can be observed for adverse effects in order to estimate a therapeutic index. Tests include open field observations, rotarod test, and body temperature. Tests used to evaluate adverse effects are performed in the same manner in control and test compound experiments at two different times, immediately before application of a test compound or vehicle and 13 min after application.

The rotarod test is carried out with a rod of 6 cm diameter and rotation speed of 8 rpm. Neurological deficit is indicated by inability of the animals to maintain their equilibrium for at least 1 min on the rotating rod. Rats are trained prior to the rotarod evaluation to maintain their balance on the rod. After treatment with a test compound or vehicle, rats that are not able to maintain their equilibrium on the rod for three subsequent 1 min attempts are considered to exhibit neurological deficit.

In addition to these quantitative estimations of neurological deficit, behavioral alterations after administration of test compound are noted in the cage and after placing the animals in an open field of 90-100 cm diameter. Muscle tone is estimated by palpation of the abdomen. The extent of deficits in behavior after administration of a test compound is determined by a rating system. Animals are taken out of the cage, placed in an open field, observed for about 1 minute and rated separately for ataxia, abducted hindlimbs, reduced righting, flat body posture, circling, Straub tail, piloerection, hypolocomotion and hyperlocomotion (abdominal muscle tone is evaluated by palpation at the end of the period of observation). All other parameters except ataxia are scored from 0 to 3: 0—absent; 1-equivocal; 2—present; 3—intense. For ataxia: 1—slight ataxia in hind-legs (tottering of the hind quarters); 2—more pronounced ataxia with dragging of hind legs; 3—further increase of ataxia and more pronounced dragging of hind legs; 4—marked ataxia, animals lose balance during forward locomotion; 5—very marked ataxia with frequent loss of balance during forward locomotion; and 6—permanent loss of righting reflexes, but animal still attempts to move forward. Rectal body temperature is measured. Body weight of the animals is recorded once daily before a test compound is administered. Data is analyzed by an appropriate statistical method. The ability of a test compound to increase the electrical threshold for induction of after discharges, decrease the severity of seizures, reduce seizure duration, and reduce total afterdischarge duration indicates efficacy in treating migraine.

Example 99

Animal Model for Assessing Therapeutic Efficacy of $GABA_B$ Receptor Ligands for Treating Anxiety A method for assessing the effects of test compounds on anxiety described by Pellow and File, *Pharmacol Biochem Behav* 1986, 24, 524-529, i.e., the elevated plus-maze test, is used. A plus-maze is consists of two open arms (50×10 $cm^2$) and two closed arms (50×10×40 $cm^3$). The arms extend from a central platform (10×10 $cm^2$) and are raised 50 cm. Each mouse is placed at the center of the maze facing a closed arm and is allowed to explore the maze for 5 min. The time spent in the open arms and the time spent in the closed arms is monitored, and the percent of time spent in the open arms determined. Increased time spent in the open arms indicates an anxiolytic effect for the test condition. A test that measures spontaneous locomotor activity such as measurement in an activity cage can be used to determine whether the test compound also affects locomotor activity. It is desirable that a compound exhibiting an anxiolytic effect not decrease locomotor activity.

Example 100

Animal Models of Depression

Forced Swim Test in Rats

Male Wistar rats weighting 230-270 g are acclimated to the colony room for a minimum of 1 week, handled daily for at least 4 days and habituated to saline injections for 2 days before the experiments.

Two glass cylinders (20 cm dia×40 cm height) are separated by black opaque partitions and filled with water at about 24° C. to a depth of 30 cm. At this depth a rat cannot stand on the cylinder bottom. The water level is 10 cm from the top. Water is changed before each animal is placed into the water tank. An experimental session consists of two trials. During the conditioning trial, rats are gently placed into the cylinders for 15 min. After the trial, rats are dried and placed into a warm cage with the paper towels for 10-15 min before being returned to their home cages. Twenty-four hours later, for the test trial, animals are placed again into the cylinders for a 5-min test session. Tests are video taped for subsequent quantitative behavioral analysis. The frequency and/or total duration are calculated for each of the following categories: passive/immobile behavior (floating is scored when an animal remains in the water with all four limbs motionless, except for occasional alternate movements of paws and tail necessary to prevent sinking and to keep head/nose above the water); active/mobile behaviors (swimming characterized by rigorous movements with all four legs; paddling characterized by floating with rhythmical simultaneous kicks and occasional pushes off the wall to give speed and direction to the drift), including escape-oriented behaviors (climbing characterized by intense movements with all four limbs, with the two forepaws breaking the surface of the water and being directed against the walls of the cylinder; diving characterized by movements towards the bottom of the cylinder with the head below its hind limbs), and self-directed behaviors (headshakes, vigorous headshakes to get water off the snout and eyes; wiping, rubbing water away from the snout). In addition, at the end of each test trial, fecal boli are counted. A test compound, control, or positive control (e.g., imipramine) is administered prior to the test.

Tail Suspension Test in Mice

Mice are housed in standard laboratory cages and acclimated. Mice are moved from the housing room to the testing area in their home cages and allowed to adapt to the new environment for at least 1 h before testing. Immobility is induced by tail suspension. Mice are hung individually on a paper adhesive tape, 65 cm above a tabletop. Tape is placed approximately 1 cm from the tip of the tail. Animals are allowed to hang for 6 min and the duration of immobility is recorded. Mice are considered immobile only when hanging passively and completely motionless. Mice from these experiments are used one week later in locomotor activity studies. A test compound, control, or positive control (e.g., imipramine) is administered prior to the test.

Locomotor Activity

The spontaneous locomotor activity of mice is measured in photoresistor actometers (circular cages, 25 cm in dia, 15 cm high, two light sources, two photoresistors), wherein the animals are placed individually 1 h after injection of a test compound. The number of crossings of light beams is measured during the first 30 min of the experimental session. The first measurement is performed 6 min after placing an animal into the actometer.

The spontaneous locomotor activity of rats is measured in photoresistor actometers (40×40×25 cm, two light sources, two photoresistors), where the animals are placed after administration of a test compound. The number of crossings of light beams is measured during the first 30 min of an experimental session. The first measurement is performed 5 min after placing an animal in the actometer.

Example 101

Animal Models of Neuropathic Pain

Inflammatory Pain—Formalin Test

A formalin assessment test is performed according to the procedure described by Dubuisson and Dennis, *Pain* 1977, 4, 161-174. Fifty (50) µL of a 5% formalin solution is injected subcutaneously into the dorsal aspect of the right hind paw and the rats are then individually placed into clear observation cages. Rats are observed for a continuous period of 60 min or for periods of time corresponding to phase I (from 0 to 10 min following formalin injection) and phase II (from 30 to 50 min following formalin injection) of the formalin test. The number of flinching behaviors of the injected paw is recorded using a sampling technique in which each animal is observed for one 60-sec period during each 5-min interval. Test compound is administered 30 min or other appropriate interval prior to formalin injection.

Inflammatory Pain—Carrageenan-Induced Acute Thermal Hyperalgesia and Edema

Paw edema and acute thermal hyperalgesia are induced by injecting 100 µL of a 1% solution of λ-carrageenan in physiological saline into the plantar surface of the right hind paw. Thermal hyperalgesia is determined 2 h following carrageenan injection, using a thermal paw stimulator. Rats are placed into plastic cubicles mounted on a glass surface maintained at 30° C. and a thermal stimulus in the form of radiant heat emitted from a focused projection bulb is then applied to the plantar surface of each hind paw. The stimulus current is maintained at about 4.5 Amp, and the maximum time of exposure is set at about 20 s to limit possible tissue damage. The elapsed time until a brisk withdrawal of the hind paw from the thermal stimulus is recorded automatically using photodiode motion sensors. The right and left hind paw of each rat is tested in three sequential trials at about 5-min intervals. Carrageenan-induced thermal hyperalgesia of paw withdrawal latency ($PWL_{thermal}$) is calculated as the mean of the two shortest latencies. Test compound is administered 30 min before assessment of thermal hyperalgesia.

The volume of paw edema is measured using water displacement with a plethysmometer 2 h following carrageenan injection by submerging the paw up to the ankle hairline (approx. 1.5 cm). The displacement of the volume is measured by a transducer and recorded. Test compound is administered at an appropriate time following carrageenan injection, such as for example, 30 min or 90 min.

Visceral Pain

Thirty (30) min following administration of test compound, mice receive an injection of 0.6% acetic acid in sterile water (10 mL/kg, i.p.). Mice are then placed in table-top Plexiglass observation cylinders (60 cm high×40 cm diameter) and the number of constrictions/writhes (a wave of mild constriction and elongation passing caudally along the abdominal wall, accompanied by a slight twisting of the trunk and followed by bilateral extension of the hind limbs) is recorded during the 5-20 min following acetic acid injection for a continuous observation period of 15 min.

Neuropathic Pain—Chronic Constriction Injury of the Sciatic Nerve

A model of chronic constriction injury of the sciatic nerve-induced neuropathic pain according to the method of Bennett and Xie, *Pain* 1988, 33, 87-107, is used. The right common sciatic nerve is isolated at mid-thigh level and loosely ligated by four chromic gut (4-0) ties separated by an interval of 1 mm. Control rats undergo the same procedure but without sciatic nerve constriction. All animals are allowed to recover for at least 2 weeks and for no more than 5 weeks prior to testing of mechanical allodynia. Allodynic PWT is assessed in the animals as described for animals with spinal nerve ligation. Only rats with a PWT≦5.0 g are considered allodynic and utilized to evaluate the analgesic activity of a test compound. Test compound is administered 30 min or other appropriate time prior to the assessment of mechanical allodynia.

Neuropathic Pain—Vincristine-Induced Mechanical Allodynia

A model of chemotherapy-induced neuropathic pain is produced by continuous intravenous vincristine infusion. Anesthetized rats undergo a surgical procedure in which the jugular vein is catheterized and a vincristine-primed pump is implanted subcutaneously. Fourteen days of intravenous infusion of vincristine (30 μg/kg/day) results in systemic neuropathic pain of the animal. Control animals undergo the same surgical procedure, with physiological saline infusion. PWT of the left paw is assessed in the animals 14 days post-implantation as described for the spinal nerve ligation model. Test compound is administered 30 min prior to the test for mechanical allodynia in rats with PWT≦5.00 g before treatment.

Post-Operative Pain

A model of post-operative pain is performed in rats as described by Brennan et al., *Pain* 1996, 64, 493-501. The plantar aspect of the left hind paw is exposed through a hole in a sterile plastic drape, and a 1-cm longitudinal incision is made through the skin and fascia, starting 0.5 cm from the proximal edge of the heel and extending towards the toes. The plantaris muscle is elevated and incised longitudinally leaving the muscle origin and insertion points intact. After hemostasis by application of gently pressure, the skin is apposed with two mattress sutures using 5-0 nylon. Animals are then allowed to recover for 2 h following surgery, at which time mechanical allodynia and thermal hyperalgesia are assessed.

Effects of test compound on mechanical allodynia are assessed 30 min following administration, with PWT being examined in these animals for both the injured and non-injured paw as described for the spinal nerve ligation model with the von Frey filament systematically pointing towards the medial side of the incision. In a separate experiment, the effects of test compound on thermal hyperalgesia are assessed 30 min following administration of test compound, with $PWL_{thermal}$ being determined as described for the carrageenan-induced thermal hyperalgesia model with the thermal stimulus applied to the center of the incision of the paw planter aspect.

Example 102

Animal Models of Gastroesophageal Reflux Disease

The method described by Stakeberg and Lehmann, *Neurogastroenterol. Mot.* 1999, 11, 125-132, can be used to evaluate the efficacy of gamma-aminobutyric acid derivatives provided by the present disclosure in reducing transient lower esophageal sphincter relaxations (TLESRs) and thereby in treating GERD.

Adult Labrador retrievers are equipped with an oesophagostomy. After recovery, the animals are intubated with a water-perfused multi-lumen Dentsleeve assembly to record pressure of the oesophagus, lower oesophageal sphincter and stomach. An antimony pH catheter is placed next to the manometric assembly to measure reflux episodes. A thin air-perfused catheter is placed retrogradely in the hypopharynx to measure swallows. Only pharyngeal contractions followed by a peristaltic wave are included in the analysis. TLESRs are stimulated by infusion of an acidified nutritious soup followed by insufflation of air. The data are related to the average of the control experiments in each dog, and every fourth experiment is designated as a control. Test compound is administered intragastrically through the assembly at an appropriate dose and interval before infusion of soup.

Example 103

Animal Model of Overactive Bladder

Effects of Test Compounds on Volume-Induced Rhythmic Bladder Voiding Contractions in Anaesthetized Rats Female Sprague Dawley rats weighing 225-275 g are used. The animals are housed with free access to food and water and maintained on a 12 h alternating light-dark cycle at 22-24° C. for at least one week, except during the experiment. The activity on the rhythmic bladder voiding contractions is evaluated according to the method of Dray, *J. Pharmacol. Methods* 13:157, 1985), with some modifications as in Guarneri, *Pharmacol. Res.* 27: 173, 1993. Briefly, rats are anesthetized by subcutaneous injection of 1.25 g/kg (5 ml/kg) urethane, after which the urinary bladder is catheterized via the urethra using PE 50 polyethylene tubing filled with physiological saline. The catheter is then tied in place with a ligature around the external urethral orifice and connected to a conventional pressure transducer. The intravesical pressure is displayed continuously on a chart recorder. The bladder is then filled via the recording catheter with incremental volumes of warm (37° C.) saline until reflex bladder voiding contractions occur. After 15 min, solutions of the test compounds according to the invention are administered by intravenous (i.v.) route into the jugular vein.

Bioactivity is assessed in individual animals (using 6-10 rats per dose) by measuring the duration of bladder quiescence (i.e., the duration of time during which no contractions occurred) over a 60 min period. Effective doses that prevent bladder contraction for 10 minutes are evaluated by linear regression analysis to compare the potency of the tested compounds in inhibiting the bladder voiding contractions. Potency of test compounds is compared to a known inhibitor of voiding contractions in this assay, such as morphine, which is used as a positive control.

Finally it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

What is claimed is:

1. A compound of Formula (I):

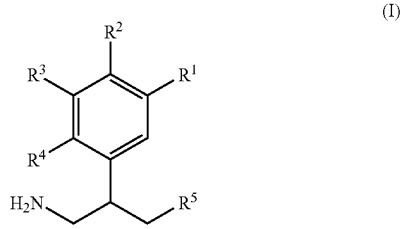

or a pharmaceutically acceptable salt thereof, wherein:
$R^1$ is chosen from hydrogen and halogen;
$R^2$ is halogen;
one of $R^3$ and $R^4$ is —X—Y, and the other of $R^3$ and $R^4$ is hydrogen, wherein:
X is chosen from a covalent bond, $C_{1-3}$ alkyldiyl, substituted $C_{1-3}$ alkyldiyl, $C_{1-3}$ heteroalkyldiyl, and substituted $C_{1-3}$ heteroalkyldiyl; and
Y is chosen from $C_{6-12}$ aryl, substituted $C_{6-12}$ aryl, $C_{5-12}$ heteroaryl, and substituted $C_{5-12}$ heteroaryl; and
$R^5$ is chosen from —COOH, —SOOH, and —P(O)(OH)$R^8$ wherein $R^8$ is chosen from hydrogen and $C_{1-4}$ alkyl.

2. The compound of claim 1, wherein the compound is of Formula (II):

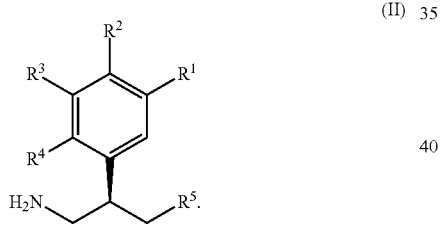

3. The compound of claim 1, wherein $R^1$ and $R^2$ are independently chosen from halogen.

4. The compound of claim 1, wherein:
$R^1$ is hydrogen; and
$R^2$ is chloro.

5. The compound of claim 1, wherein:
$R^3$ is —X—Y; and
$R^4$ is hydrogen.

6. The compound of claim 1, wherein:
$R^3$ is hydrogen; and
$R^4$ is —X—Y.

7. The compound of claim 1, wherein X is $C_{1-3}$ heteroalkyldiyl and is chosen from —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl.

8. The compound of claim 1, wherein X is chosen from substituted $C_{1-3}$ alkyldiyl and substituted $C_{1-3}$ heteroalkyldiyl, wherein each of the one or more substituents is independently chosen from —OH, —NH$_2$, $C_{1-4}$ alkyl, $C_{1-4}$ alkoxy, and =O.

9. The compound of claim 1, wherein Y is chosen from substituted $C_{6-12}$ aryl and substituted $C_{5-12}$ heteroaryl, wherein each of the one or more substituents is independently chosen from halogen, —OH, —NH$_2$, —NO$_2$, —CN, —COOH, —CF$_3$, —OCF$_3$, $C_{1-4}$ alkyl, substituted $C_{1-4}$ alkyl, $C_{1-4}$ heteroalkyl, and substituted $C_{1-4}$ heteroalkyl.

10. The compound of claim 9, wherein: each of the one or more substituents of substituted $C_{1-4}$ alkyl is chosen from —OH, =O, —OCH$_3$, —SCH$_3$, —N(CH$_3$)$_2$, and —OCH$_2$CH$_3$; and substituted $C_{1-4}$ heteroalkyl is chosen from —C(O)NH$_2$, —CH$_2$COOH, —COOCH$_3$, —COOCH$_2$CH$_3$, and —SO$_2$CH$_3$.

11. The compound of claim 1, wherein Y is chosen from phenyl, substituted phenyl, $C_5$ heteroaryl, substituted $C_5$ heteroaryl, $C_6$ heteroaryl, and substituted $C_6$ heteroaryl.

12. The compound of claim 1, wherein Y is chosen from phenyl, substituted phenyl, thienyl, substituted thienyl, furyl, substituted furyl, imidazolyl, substituted imidazolyl, thiazole, substituted thiazole, oxazole, substituted oxazole, thiazolidine, substituted thiazolidine, oxazolidine, substituted oxazolidine, oxadiazole, substituted oxadiazole, thiadiazole, substituted thiadiazole, pyridyl, substituted pyridyl, indazolyl, substituted indazolyl, isoquinolyl, and substituted isoquinolyl.

13. The compound of claim 2, wherein:
$R^1$ is hydrogen;
$R^2$ is chloro;
$R^3$ is hydrogen; and
$R^4$ is —X—Y wherein:
X is chosen from a covalent bond, $C_{1-3}$ alkyldiyl, substituted $C_{1-13}$ alkyldiyl, —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl; and
Y is chosen from phenyl, substituted phenyl, $C_5$ heteroaryl, substituted $C_5$ heteroaryl, $C_6$ heteroaryl, and substituted $C_6$ heteroaryl.

14. The compound of claim 13, wherein Y is chosen from phenyl, substituted phenyl, thienyl, substituted thienyl, furyl, substituted furyl, imidazolyl, substituted imidazolyl, thiazole, substituted thiazole, oxazole, substituted oxazole, thiazolidine, substituted thiazolidine, oxazolidine, substituted oxazolidine, oxadiazole, substituted oxadiazole, thiadiazole, substituted thiadiazole, pyridyl, and substituted pyridyl wherein:
each of the one or more substituent groups is independently chosen from halogen, —OH, —NH$_2$, —NO$_2$, —CN, —COOH, —CF$_3$, —OCF$_3$, $C_{1-4}$ alkyl, substituted $C_{1-4}$ alkyl, $C_{1-4}$ heteroalkyl, and substituted $C_{1-4}$ heteroalkyl.

15. The compound of claim 2, wherein:
$R^1$ is hydrogen;
$R^2$ is chloro;
$R^3$ is —X—Y wherein:
X is chosen from a covalent bond, $C_{1-13}$ alkyldiyl, substituted $C_{1-13}$ alkyldiyl, —NH(CHR$^7$)$_n$—, —O(CHR$^7$)$_n$—, and —NH—SO$_2$—; wherein n is chosen from 0, 1, and 2; and each $R^7$ is independently chosen from hydrogen and $C_{1-4}$ alkyl; and
Y is chosen from phenyl, substituted phenyl, $C_5$ heteroaryl, substituted $C_5$ heteroaryl, $C_6$ heteroaryl, and substituted $C_6$ heteroaryl; and
$R^4$ is hydrogen.

16. The compound of claim 15, wherein Y is chosen from phenyl, substituted phenyl, thienyl, substituted thienyl, furyl, substituted furyl, imidazolyl, substituted imidazolyl, thiazole, substituted thiazole, oxazole, substituted oxazole, thiazolidine, substituted thiazolidine, oxazolidine, substituted oxazolidine, oxadiazole, substituted oxadiazole, thiadiazole, substituted thiadiazole, pyridyl, and substituted pyridyl; wherein:

each of the one or more substituent groups is independently chosen from halogen, —OH, —NH$_2$, —NO$_2$, —CN, —COOH, —CF$_3$, —OCF$_3$, C$_{1-4}$ alkyl, substituted C$_{1-4}$ alkyl, C$_{1-4}$ heteroalkyl, and substituted C$_{1-4}$ heteroalkyl.

17. The compound of claim 1, wherein the compound is chosen from:

(3R)-4-amino-3-[4-chloro-3-(phenylcarbonylamino)phenyl]butanoic acid;
(3R)-4-amino-3-[2-(3,4-dichlorophenyl)-4-chlorophenyl]butanoic acid;
4-{2-[(1R)-2-amino-1-(carboxymethyl)ethyl]-5-chlorophenyl}benzoic acid;
(3R)-4-amino-3-(4-chloro-2-(3-thienyl)phenyl)butanoic acid;
(3R)-4-amino-3-[4-chloro-2-(4-chlorophenyl)phenyl]butanoic acid;
2-({5-[(1R)-2-amino-1-(carboxymethyl)ethyl]-2-chlorophenyl}amino)benzoic acid;
3-({5-[(1R)-2-amino-1-(carboxymethyl)ethyl]-2-chlorophenyl}amino)benzoic acid;
4-({5-[(1R)-2-amino-1-(carboxymethyl)ethyl]-2-chlorophenyl}amino)benzoic acid;
(3R)-4-amino-3-(4-chloro-2-(3-pyridyl)phenyl)butanoic acid;
(3R)-4-amino-3-(4-chloro-2-phenoxyphenyl)butanoic acid;
(3R)-4-amino-3-{3-[(3,4-dichlorophenyl)amino]-4-chlorophenyl}butanoic acid;
(3R)-4-amino-3-[4-chloro-2-(phenylcarbonyl)phenyl]butanoic acid;
(3R)-4-amino-3-[4-chloro-2-(2-phenylethyl)phenyl]butanoic acid;
(3R)-4-amino-3-[3-({[3-(3,4-dichlorophenoxy)phenyl]methyl}amino)-4-chlorophenyl]butanoic acid;
(3R)-4-amino-3-{4-chloro-3-[(2-pyridylmethyl)amino]phenyl}butanoic acid;
(3R)-4-amino-3-(4-chloro-3-{[(2-fluorophenyl)methyl]amino}phenyl)butanoic acid;
(3R)-4-amino-3-(3-{[(2,4-dichlorophenyl)methyl]amino}-4-chlorophenyl)butanoic acid;
(3R)-4-amino-3-(4-chloro-3-{[(3-phenoxyphenyl)methyl]amino}phenyl)butanoic acid;
4-amino-3-[4-chloro-3-(phenylamino)phenyl]butanoic acid;
(3R)-4-amino-3-{4-chloro-3-[(3-furylmethyl)amino]phenyl}butanoic acid;
(3R)-4-amino-3-{4-chloro-3-[(imidazol-5-ylmethyl)amino]phenyl}butanoic acid;
3-{5-[(1R)-2-amino-1-(carboxymethyl)ethyl]-2-chlorophenyl}benzoic acid;
(3R)-4-amino-3-{4-chloro-3-[3-(ethoxycarbonyl)phenyl]phenyl}butanoic acid;
(3R)-4-amino-3-(4-chloro-3-(3-pyridyl)phenyl)butanoic acid;
(3R)-4-amino-3-[4-chloro-3-(3-cyanophenyl)phenyl]butanoic acid;
(3R)-4-amino-3-{3-[3-(carboxymethyl)phenyl]-4-chlorophenyl}butanoic acid;
(3R)-4-amino-3-[4-chloro-3-(3-hydroxyphenyl)phenyl]butanoic acid;
3-{3-[(1R)-2-amino-1-(carboxymethyl)ethyl]phenyl}benzoic acid;
(3R)-4-amino-3-[4-chloro-3-(3-methoxyphenyl)phenyl]butanoic acid;
(3R)-4-amino-3-(3-benzimidazol-6-yl-4-chlorophenyl)butanoic acid;
(3R)-4-amino-3-[4-chloro-3-(4-cyanophenyl)phenyl]butanoic acid;
(3R)-4-amino-3-[3-(3-carbamoylphenyl)-4-chlorophenyl]butanoic acid;
(3R)-4-amino-3-{4-chloro-3-[3-(hydroxymethyl)phenyl]phenyl}butanoic acid;
3-{5-[(1R)-2-amino-1-(carboxymethyl)ethyl]-2-chlorophenyl}-4-chlorobenzoic acid;
(3R)-4-amino-3-[4-chloro-3-(3-nitrophenyl)phenyl]butanoic acid;
(3R)-4-amino-3-[4-chloro-3-(4-nitrophenyl)phenyl]butanoic acid;
5-{5-[(1R)-2-amino-1-(carboxymethyl)ethyl]-2-chlorophenyl}pyridine-3-carboxylic acid;
3-{5-[(1R)-1-(aminomethyl)-3-hydroxypropyl]-2-chlorophenyl}benzenecarbonitrile;
4-{5-[(1R)-2-amino-1-(carboxymethyl)ethyl]-2-chlorophenyl}thiophene-2-carboxylic acid;
(3R)-4-amino-3-{4-chloro-3-[(4-pyridylmethyl)amino]phenyl}butanoic acid;
(3R)-4-amino-3-[4-chloro-3-(3-methylthiophenyl)phenyl]butanoic acid;
(3R)-4-amino-3-{4-chloro-3-[3-(methylsulfonyl)phenyl]phenyl}butanoic acid;
5-{5-[(1R)-2-amino-1-(carboxymethyl)ethyl]-2-chlorophenyl}thiophene-2-carboxylic acid;
(3R)-4-amino-3-(4-chloro-3-phenylphenyl)butanoic acid;
3-{5-[(1R)-2-amino-1-(carboxymethyl)ethyl]-2-chlorophenyl}-5-nitrobenzoic acid;
(3R)-4-amino-3-[4-chloro-3-(4-chloro-3-cyanophenyl)phenyl]butanoic acid;
(3R)-4-amino-3-{3-[3-(dimethylamino)phenyl]-4-chlorophenyl}butanoic acid;
3-{5-[(1R)-2-amino-1-(carboxymethyl)ethyl]-2-chlorophenyl}-5-fluorobenzoic acid;
4-{5-[(1R)-2-amino-1-(carboxymethyl)ethyl]-2-chlorophenyl}-3-chlorobenzoic acid;
(3R)-4-amino-3-[4-chloro-3-(4-pyridylmethoxy)phenyl]butanoic acid;
(3R)-4-amino-3-{4-chloro-3-[(3-chlorophenyl)carbonylamino]phenyl}butanoic acid;
(3R)-4-amino-3-(2-{[(3,4-dichlorophenyl)sulfonyl]amino}-4-chlorophenyl)butanoic acid;
(3R)-4-amino-3-{2-[(3,4-dichlorophenyl)carbonylamino]-4-chlorophenyl}butanoic acid;
(3R)-4-amino-3-[4-chloro-3-(2-pyridylamino)phenyl]butanoic acid;
(3R)-4-amino-3-{4-chloro-3-[(4-methoxyphenyl)amino]phenyl}butanoic acid;
(3R)-4-amino-3-[4-chloro-3-(4-pyridylamino)phenyl]butanoic acid;
4-{3-[(1R)-2-amino-1-(carboxymethyl)ethyl]-4-chlorophenoxy}benzoic acid;
3-{5-[(1R)-2-amino-1-(carboxymethyl)ethyl]-2-chlorophenoxy}benzoic acid;
(3R)-4-amino-3-(4-chloro-3-phenoxyphenyl)butanoic acid;
(3R)-4-amino-3-(3-{[(3,4-dichlorophenyl)sulfonyl]amino}-4-chlorophenyl)butanoic acid;
4-{5-[(1R)-2-amino-1-(carboxymethyl)ethyl]-2-chlorophenyl}benzoic acid;
3-({2-[(1R)-2-amino-1-(carboxymethyl)ethyl]-4-chlorophenyl}hydroxymethyl)benzoic acid;
4-[({5-[(1R)-2-amino-1-(carboxymethyl)ethyl]-2-chlorophenyl}amino)methyl]benzoic acid;

(3R)-4-amino-3-(4-chloro-3-{[(1-methylimidazol-5-yl)methyl]amino}phenyl) butanoic acid;
(3R)-4-amino-3-[4-chloro-3-(5-cyano(2-thienyl))phenyl]butanoic acid;
(3R)-4-amino-3-[4-chloro-3-(2-methylpyrimidin-5-yl)phenyl]butanoic acid;
5-{5-[(1R)-2-amino-1-(carboxymethyl)ethyl]-2-chlorophenyl}-2-fluorobenzoic acid;
(3R)-4-amino-3-[4-chloro-3-(3-cyano-6-methylphenyl)phenyl]butanoic acid;
(3R)-4-amino-3-[4-chloro-3-(3-cyano-5-fluorophenyl)phenyl]butanoic acid;
(3R)-4-amino-3-[4-chloro-3-(4-methyl(3-pyridyl))phenyl]butanoic acid;
(3R)-4-amino-3-[4-chloro-3-(3-cyano-6-fluorophenyl)phenyl]butanoic acid;
(3R)-4-amino-3-[4-chloro-3-(6-chloro-3-cyanophenyl)phenyl]butanoic acid; methyl (3R)-4-amino-3-[4-chloro-3-(4-pyridylmethoxy)phenyl]butanoate;
(3R)-4-amino-3-[4-chloro-3-(3-pyridylmethoxy)phenyl]butanoic acid;
5-{5-[(1R)-2-amino-1-(carboxymethyl)ethyl]-2-chlorophenyl}furan-3-carboxylic acid;
(3R)-4-amino-3-[4-chloro-3-(2-(4-pyridyl)ethoxy)phenyl]butanoic acid;
(3R)-4-amino-3-[4-chloro-3-(4-pyridylethoxy)phenyl]butanoic acid;
(3R)-3-[3-((1R)-1-(4-pyridyl)ethoxy)-4-chlorophenyl]-4-aminobutanoic acid;
(3R)-4-amino-3-[4-chloro-3-(5-cyano(3-thienyl))phenyl]butanoic acid;
(3R)-4-amino-3-{4-chloro-3-[(2-methyl(4-pyridyl))methoxy]phenyl}butanoic acid;
(3R)-4-amino-3-{4-chloro-3-[(3-chloro(4-pyridyl))methoxy]phenyl}butanoic acid;
5-{5-[(1R)-2-amino-1-(carboxymethyl)ethyl]-2-chlorophenyl}thiophene-3-carboxylic acid;
(3R)-4-amino-3-[4-chloro-3-(2-(4-pyridyl)ethyl)phenyl]butanoic acid;
(3R)-4-amino-3-[4-chloro-3-(1,3-thiazol-5-ylmethoxy)phenyl]butanoic acid;
(3R)-4-amino-3-{3-[5-(N,N-dimethylcarbamoyl)(2-thienyl)]-4-chlorophenyl}butanoic acid;
2-{4-Chloro-3-(4-pyridylmethoxy)phenyl]-3-(hydrohydroxyphosphoryl)propylamine;
3-{5-[2-amino-1-((hydrohydroxyphosphoryl)methyl)ethyl]-2-chlorophenyl}benzoic acid;
(3R)-4-amino-3-{4-chloro-3-[5-(ethoxycarbonyl)(2-thienyl)]phenyl}butanoic acid; and
a pharmaceutically acceptable salt of any of the foregoing.

18. The compound of claim 1, wherein the compound is chosen from:
3-({5-[(1R)-2-amino-1-(carboxymethyl)ethyl]-2-chlorophenyl}amino)benzoic acid;
3-{5-[(1R)-2-Amino-1-(carboxymethyl)ethyl]-2-chlorophenyl}benzoic acid;
(3R)-4-amino-3-{4-chloro-3-[(imidazol-5-ylmethyl)amino]phenyl}butanoic acid;
(3R)-4-amino-3-(4-chloro-3-(3-pyridyl)phenyl)butanoic acid;
(3R)-4-amino-3-[4-chloro-3-(3-cyanophenyl)phenyl]butanoic acid;
(3R)-4-amino-3-[3-(3-carbamoylphenyl)-4-chlorophenyl]butanoic acid;
3-{5-[(1R)-2-amino-1-(carboxymethyl)ethyl]-2-chlorophenyl}-4-chlorobenzoic acid;
(3R)-4-amino-3-[4-chloro-3-(3-nitrophenyl)phenyl]butanoic acid;
4-{5-[(1R)-2-amino-1-(carboxymethyl)ethyl]-2-chlorophenyl}thiophene-2-carboxylic acid
(3R)-4-amino-3-{4-chloro-3-[(4-pyridylmethyl)amino]phenyl}butanoic acid;
5-{5-[(1R)-2-amino-1-(carboxymethyl)ethyl]-2-chlorophenyl}thiophene-2-carboxylic acid;
3-{5-[(1R)-2-amino-1-(carboxymethyl)ethyl]-2-chlorophenyl}-5-fluorobenzoic acid;
(3R)-4-amino-3-[4-chloro-3-(4-pyridylmethoxy)phenyl]butanoic acid;
(3R)-4-amino-3-[4-chloro-3-(5-cyano(2-thienyl))phenyl]butanoic acid;
5-{5-[(1R)-2-amino-1-(carboxymethyl)ethyl]-2-chlorophenyl}-2-fluorobenzoic acid;
(3R)-4-amino-3-[4-chloro-3-(3-cyano-6-methylphenyl)phenyl]butanoic acid;
(3R)-4-amino-3-[4-chloro-3-(3-cyano-5-fluorophenyl)phenyl]butanoic acid;
(3R)-4-amino-3-[4-chloro-3-(4-methyl(3-pyridyl))phenyl]butanoic acid;
(3R)-4-amino-3-[4-chloro-3-(3-cyano-6-fluorophenyl)phenyl]butanoic acid;
(3R)-4-amino-3-[4-chloro-3-(6-chloro-3-cyanophenyl)phenyl]butanoic acid;
methyl (3R)-4-amino-3-[4-chloro-3-(4-pyridylmethoxy)phenyl]butanoate;
(3R)-4-amino-3-[4-chloro-3-(3-pyridylmethoxy)phenyl]butanoic acid;
5-{5-[(1R)-2-amino-1-(carboxymethyl)ethyl]-2-chlorophenyl}furan-3-carboxylic acid;
(3R)-4-amino-3-[4-chloro-3-(2-(4-pyridyl)ethoxy)phenyl]butanoic acid;
(3R)-4-amino-3-[4-chloro-3-(4-pyridylethoxy)phenyl]butanoic acid;
(3R)-3-[3-((1R)-1-(4-pyridyl)ethoxy)-4-chlorophenyl]-4-aminobutanoic acid;
(3R)-4-amino-3-[4-chloro-3-(5-cyano(3-thienyl))phenyl]butanoic acid;
(3R)-4-amino-3-{4-chloro-3-[(2-methyl(4-pyridyl))methoxy]phenyl}butanoic acid;
(3R)-4-amino-3-{4-chloro-3-[(3-chloro(4-pyridyl))methoxy]phenyl}butanoic acid;
5-{5-[(1R)-2-amino-1-(carboxymethyl)ethyl]-2-chlorophenyl}thiophene-3-carboxylic acid;
(3R)-4-amino-3-[4-chloro-3-(2-(4-pyridyl)ethyl)phenyl]butanoic acid;
(3R)-4-amino-3-[4-chloro-3-(1,3-thiazol-5-ylmethoxy)phenyl]butanoic acid;
(3R)-4-amino-3-{3-[5-(N,N-dimethylcarbamoyl)(2-thienyl)]-4-chlorophenyl}butanoic acid;
2-{chloro-3-(4-pyridylmethoxy)phenyl]-3-(hydrohydroxyphosphoryl)propylamine; and
a pharmaceutically acceptable salt of any of the foregoing.

19. The compound of claim 1, wherein the compound exhibits GABA$_B$ receptor agonist activity.

20. The compound of claim 1, wherein the compound exhibits GABA$_B$ receptor partial agonist activity.

21. The compound of claim 1, wherein the compound exhibits GABA$_B$ receptor antagonist activity.

22. A pharmaceutical composition comprising a therapeutically effective amount of a compound of claim 1 and a pharmaceutically acceptable vehicle.

23. The pharmaceutical composition of claim 22, wherein the amount is effective for the treatment of a disease chosen from spasticity, gastro-esophageal reflux disease, emesis, cough, overactive bladder, a substance abuse disorder, an attention disorder, an anxiety disorder, a mood disorder, a cognitive disorder, migraine, and pain.

24. A method of treating a disease in a patient comprising administering to a patient in need of such treatment the pharmaceutical composition of claim 22, wherein the disease is chosen from spasticity, gastro-esophageal reflux disease, emesis, cough, overactive bladder, a substance abuse disorder, an attention disorder, an anxiety disorder, a mood disorder, a cognitive disorder, migraine, and pain.

25. A method of modulating $GABA_B$ receptor function in a patient comprising administering to a patient a compound of claim 1.

26. The compound (3R)-4-amino-3-[4-chloro-3-(4-pyridylmethoxy)phenyl]butanoic acid or a pharmaceutically acceptable salt thereof.

27. The compound 4-{5-[(1R)-2-amino-1-(carboxymethyl)ethyl]-2-chlorophenyl}thiophene-2-carboxylic acid or a pharmaceutically acceptable salt thereof.

28. The compound 5-15- R1R)-2-amino-1-(carboxymethyl)ethyl]-2-chlorophenyl}thiophene-3-carboxylic acid or a pharmaceutically acceptable salt thereof.

* * * * *